(12) United States Patent
Lynch et al.

(10) Patent No.: US 11,279,956 B2
(45) Date of Patent: *Mar. 22, 2022

(54) COMPOSITIONS AND METHODS FOR ROBUST DYNAMIC METABOLIC CONTROL OF MEVALONATE PRODUCTION

(71) Applicant: DUKE UNIVERSITY, Durham, NC (US)

(72) Inventors: Michael David Lynch, Durham, NC (US); Zhixia Ye, Raleigh, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/661,065

(22) Filed: Oct. 23, 2019

(65) Prior Publication Data

US 2020/0248212 A1    Aug. 6, 2020

Related U.S. Application Data

(63) Continuation of application No. 16/487,542, filed as application No. PCT/US2018/019040 on Feb. 21, 2018.

(60) Provisional application No. 62/461,436, filed on Feb. 21, 2017.

(51) Int. Cl.
| | |
|---|---|
| *C12P 7/42* | (2006.01) |
| *C12N 9/04* | (2006.01) |
| *C12N 9/02* | (2006.01) |
| *C12N 9/06* | (2006.01) |
| *C12N 9/10* | (2006.01) |
| *C12N 15/74* | (2006.01) |
| *C12P 13/06* | (2006.01) |

(52) U.S. Cl.
CPC ............. *C12P 7/42* (2013.01); *C12N 9/001* (2013.01); *C12N 9/0006* (2013.01); *C12N 9/0008* (2013.01); *C12N 9/0016* (2013.01); *C12N 9/0051* (2013.01); *C12N 9/1025* (2013.01); *C12N 15/746* (2013.01); *C12P 13/06* (2013.01)

(58) Field of Classification Search
None
See application file for complete search history.

(56) References Cited

U.S. PATENT DOCUMENTS

| | | | |
|---|---|---|---|
| 8,916,358 B2 | 12/2014 | Swartz | |
| 10,036,001 B2 | 7/2018 | Swartz | |
| 10,087,453 B2 | 10/2018 | Duchateau et al. | |
| 10,196,644 B2 | 2/2019 | Lee et al. | |
| 10,385,367 B2 | 8/2019 | Way et al. | |
| 10,662,426 B2 * | 5/2020 | Lynch ................ | C12N 15/1137 |
| 2011/0125118 A1 | 5/2011 | Lynch | |
| 2011/0244575 A1 | 10/2011 | Lipscomb | |
| 2012/0214170 A1 | 8/2012 | Moore | |
| 2013/0171328 A1* | 7/2013 | Kishore ......... | C12Y 402/03019 426/658 |
| 2015/0072399 A1 | 3/2015 | Lynch et al. | |
| 2017/0121707 A1* | 5/2017 | Lynch .................... | C12N 15/70 |

FOREIGN PATENT DOCUMENTS

| | | |
|---|---|---|
| EP | 2842542 A1 | 3/2015 |
| WO | 2012129450 A1 | 9/2012 |
| WO | 2013176772 A1 | 11/2013 |
| WO | 2014160025 A1 | 10/2014 |
| WO | 2015191638 A1 | 12/2015 |
| WO | 2018156646 A1 | 8/2018 |

OTHER PUBLICATIONS

Tabata et al. Biotechnology Letters 26: 1487-1491, 2004 (Year: 2004).*
Lynch. Standardized two-stage bioprocess development using synthetic metabolic valves and dynamic metabolic control, Abstract of Papers: ACS National Meeting & Exposition; 249th National Meeting and Exposition of the American-Chemical-Society (ACS), vol. 249, p. BIOT418. Mar. 22-26, 2015. (Year: 2015).*
Lynch. Into new territory: improved microbial synthesis through engineering of the essential metabolic network. Curr Opin Biotechnol. Apr. 2016;38:106-11. Epub Feb. 10, 2016. (Year: 2016).*
Zhao. Global metabolic response of *Escherichia coli* to gnd or zwf gene-knockout, based on 13C-labeling experiments and the measurement of enzyme activities. Appl Microbiol Biotechnol. Mar. 2004;64(1):91-8. (Year: 2004).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Quandt et al. eLife. 2015; 4: e09696. Published online Oct. 14, 2015. (Year: 2015).*
Vick et al. Appl Environ Microbiol. Feb. 2015; 81(4): 1406-1416. (Year: 2015).*
Jan et al. Biotechnol Prog. Sep.-Oct. 2013;29(5):1124-30. (Year: 2013).*
Wang et al. J Ind Microbiol Biotechnol. Dec. 2013;40(12):1449-60 (Year: 2013).*
Luo et al. Nucleic Acids Res. Jan. 9, 2015; 43(1): 674-681 (Year: 2015).*

(Continued)

*Primary Examiner* — Christian L Fronda
(74) *Attorney, Agent, or Firm* — Benesch, Friedlander, Coplan & Aronoff LLP

(57) ABSTRACT

The present disclosure provides compositions and methods for rapid production of chemicals in genetically engineered microorganisms in a large scale. Also provided herein is a high-throughput metabolic engineering platform enabling the rapid optimization of microbial production strains. The platform, which bridges a gap between current in vivo and in vitro bio-production approaches, relies on dynamic minimization of the active metabolic network.

16 Claims, 117 Drawing Sheets

Specification includes a Sequence Listing.

(56) References Cited

OTHER PUBLICATIONS

Rath et al. Nucleic Acids Res. Jan. 9, 2015; 43(1): 237-246. (Year: 2015).*

Yuki Soma et al: "Metabolic flux redirection from a central metabolic pathway toward a synthetic pathway using a metabolic toggle switch", Metabolic Engineering, vol. 23, May 1, 2014, pp. 175-184.

Kathleen E. Mcginness et al: "Engineering Controllable Protein Degradation", Molecular Cell., vol. 22, No. 5, Jun. 1, 2006, pp. 701-707.

Levchenko Igor et al: "A specificity-enhancing factor for the CIpXP degradation machine", Science, vol. 289, No. 5488, Sep. 29, 2000, pp. 2354-2356.

Lynch et al., "Standarized two-stage bioprocess development using synthetic metabolic valves and dynamic metabolic control", Abstracts of Papers ; ACS National Meeting & Exposition; 249th National Meeting and Exposition of the American-Chemical-Society (ACS), vol. 249, p. BIOT418.

Brockman et al., "Dynamic knockdown of *E. coli* central metabolism for redirecting fluxes of primary metabolites", Metabolic Engineering, vol. 28., pp. 104-113.

Kim et al., "A genetic strategy to identify targets for the development of drugs that prevent bacterial persistence", Proc. Natl. Acad. Sci. USA (2013); vol. 110, pp. 19095-19100.

Qi et al, "Repurposing CRISPR as an RNA-guided platform for sequence-specific control of gene expression," Cell (2013); vol. 152, pp. 1173-1183.

* cited by examiner

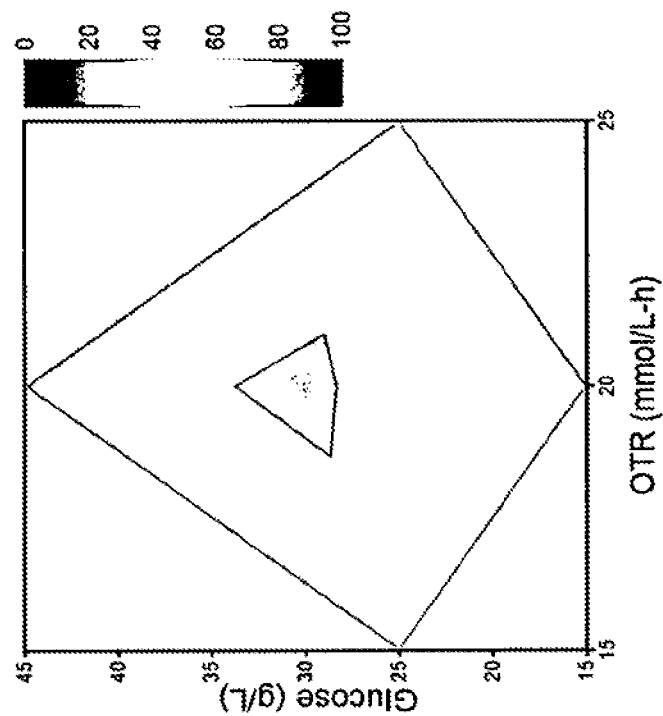
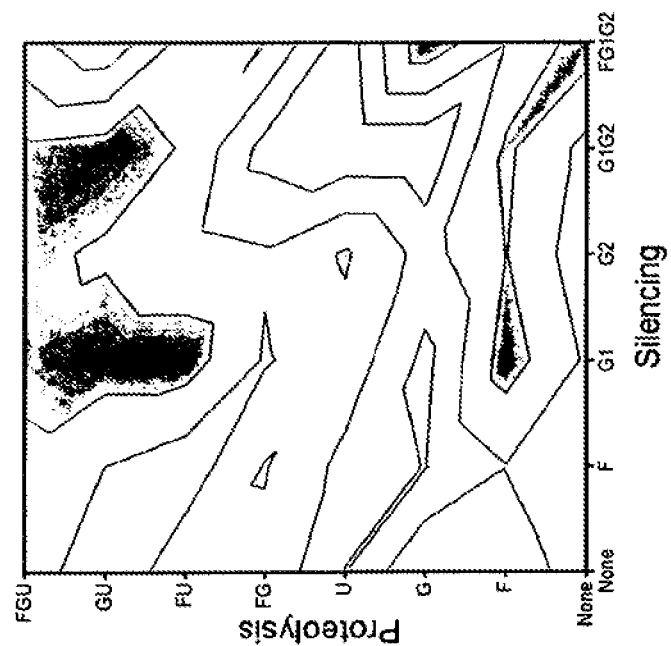
FIGURE 3K
FIGURE 3J

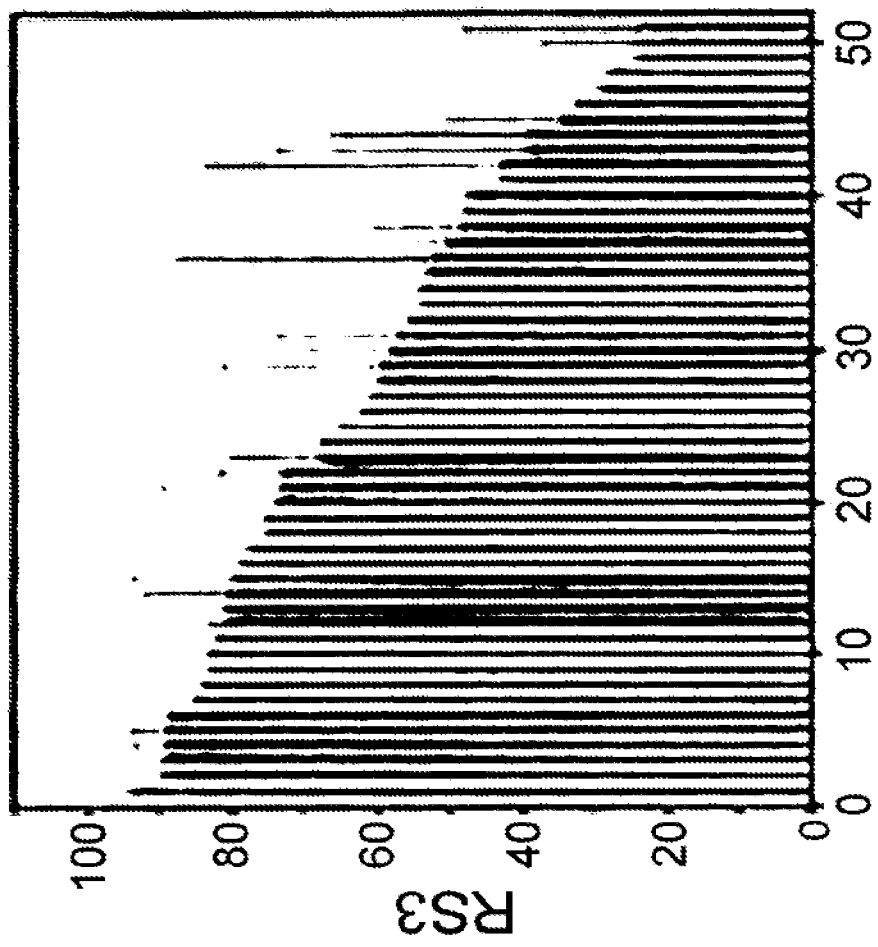

```
SEQUENCE LISTING

<160> NUMBER OF SEQ ID NOS: 204

<210> SEQ ID NO 1
<211> LENGTH: 114
<212> TYPE: DNA
<213> ORGANISM: Escherichia coli

<400> SEQUENCE: 1
tctttctgac accttactat cttacaaatg taacaaaaaa gttatttttc tgtaattcga      60
gcatgtcatg ttaccccgcg agcataaaac gcgtgtgtag gaggataatc tatg          114

<210> SEQ ID NO 2
<211> LENGTH: 160
<212> TYPE: DNA
<213> ORGANISM: Escherichia coli

<400> SEQUENCE: 2
gtgcgtaatt gtgctgatct cttatatagc tgctctcatt atctctctac cctgaagtga      60
ctctctcacc tgtaaaaata atatctcaca ggcttaatag tttcttaata caaagcctgt     120
aaaacgtcag gataacttct gtgtaggagg ataatctatg                           160

<210> SEQ ID NO 3
<211> LENGTH: 174
<212> TYPE: DNA
<213> ORGANISM: Escherichia coli

<400> SEQUENCE: 3
cgattacgta aagaagttat tgaagcatcc tcgtcagtaa aaagttaatc ttttcaacag      60
ctgtcataaa gttgtcacgg ccgagactta tagtcgcttt gttttttattt tttaatgtat    120 ttgtagtgta ggaggataat ctatggctag caaaggagaa gaactttca catg           174

<210> SEQ ID NO 4
<211> LENGTH: 154
<212> TYPE: DNA
<213> ORGANISM: Escherichia coli

<400> SEQUENCE: 4
```

```
gccacggaaa tcaataacct gaagatatgt gcgacgagct tttcataaat ctgtcataaa      60
tctgacgcat aatgacgtcg cattaatgat cgcaacctat ttattgtgta ggaggataat     120
ctatggctag caaaggagaa gaacttttca catg                                 154
```

<210> SEQ ID NO 5
<211> LENGTH: 120
<212> TYPE: DNA
<213> ORGANISM: Escherichia coli

<400> SEQUENCE: 5

```
agacagtcaa cgcgcttgat agcctggcga agatcatccg atcttcgcct tacacttttg      60
tttcacattt ctgtgacata ctatcggatg tgcggtaatt gtataggagg ataatctatg     120
```

<210> SEQ ID NO 6
<211> LENGTH: 125
<212> TYPE: DNA
<213> ORGANISM: Escherichia coli

<400> SEQUENCE: 6

```
gctatgccgg actgaatgtc caccgtcagt aattttttata cccggcgtaa ctgccgggtt     60
attgcttgtc acaaaaaagt ggtagactca tgcagttaac tcactgtgta ggaggataat    120
ctatg                                                                125
```

<210> SEQ ID NO 7
<211> LENGTH: 206
<212> TYPE: DNA
<213> ORGANISM: Escherichia coli

<400> SEQUENCE: 7

```
catccataaa ttttgcataa ttaatgtaaa gaccaggctc gccagtaacg ctaaattcat      60
ttggctgtaa gcgcggtgtc atccgcgtca ggaaaattaa acagttactt taaaaaatga    120
aaacgtaaaa aggttgggtt tcgatgtatt gacgggtaaa ctttgtcgcc cgctaaacat    180
ttgtttgtgt aggaggataa tctatg                                         206
```

<210> SEQ ID NO 8
<211> LENGTH: 184
<212> TYPE: DNA
<213> ORGANISM: Escherichia coli

<400> SEQUENCE: 8

```
aatcctgctg aaagcacaca gcttttttca tcactgtcat cactctgtca tctttccagt     60
agaaactaat gtcactgaaa tggtgtttta tagttaaata taagtaaata tattgttgca    120
ataaatgcga gatctgttgt acttattaag tagcagcgga agttcgtgta ggaggataat    180
ctat                                                                184
```

<210> SEQ ID NO 9
<211> LENGTH: 359
<212> TYPE: DNA
<213> ORGANISM: Escherichia coli

<400> SEQUENCE: 9

```
ctacagagat gacgtgtaga aaatagttac cgatataaat agttacagct aaacgcctga     60
aattacatgt cgagggcact atttaaaaca attttgagga tttccttata ttggtggtta    120
gtacgcatgc aattaaaaat gaaattccgc gaccacaagc caaaataaca aacggcaagg    180
```

```
agacaaaaat aagcacaaat agccaacacg tcctctgttc actttaaagg gaatcgctga      240
aaaatacgct ctgtttaagg ggattcacct ttctcagaaa gctattccgc ccttttcctg      300
ctgagaaatc gccacattcg gcatgacaac attgtgaaag tgtaggagga taatctatg      359
```

<210> SEQ ID NO 10
<211> LENGTH: 156
<212> TYPE: DNA
<213> ORGANISM: Escherichia coli

<400> SEQUENCE: 10

```
accgaactga agcaggatta caccgtggtg atcgtcaccc acaacatgca gcaggctgcg      60
cgttgttccg accacacggc gtttatgtac ctgggcgaat tgattgagtt cagcaacacg     120
gacgatctgt tcaccagtgt aggaggataa tctatg                               156
```

<210> SEQ ID NO 11
<211> LENGTH: 151
<212> TYPE: DNA
<213> ORGANISM: Escherichia coli

<400> SEQUENCE: 11

```
aagactttat ctctctgtca taaaactgtc atattcctta catataactg tcacctgttt      60
gtcctatttt gcttctcgta gccaacaaac aatgctttat gagtgtagga ggataatcta     120
tggctagcaa aggagaagaa cttttcacat g                                    151
```

<210> SEQ ID NO 12
<211> LENGTH: 186
<212> TYPE: DNA
<213> ORGANISM: Escherichia coli

<400> SEQUENCE: 12

```
agcatggcgt tttgttgcgc gggatcagca agcctagcgg cagttgttta cgcttttatt      60
acagatttaa taaattacca cattttaaga atattattaa tctgtaatat atctttaaca     120
atctcaggtt aaaaactttc ctgttttcaa cgggactctc ccgctggtgt aggaggataa     180
tctatg                                                                186
```

<210> SEQ ID NO 13
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
ccaggcatca ataaaacga aaggctcagt cgaaagactg ggcctttcgt tttatctgtt       60
gtttgtcggt gaacgctctc tactagagtc acactggctc accttcgggt gggcctttct     120
gcgtttatac acagctaaca ccacgtcgtc cctatctgct gccctaggtc tatgagtggt     180
tgctggataa cgtgcgtaat tgtgctgatc tcttatatag ctgctctcat tatctctcta     240
ccctgaagtg actctctcac ctgtaaaaat aatatctcac aggcttaata gtttcttaat     300
acaaagcctg taaacgtca ggataacttc tatattcagg gagaccacaa cggtttccct      360
ctacaaataa ttttgtttaa cttt                                            384
```

<210> SEQ ID NO 14
<211> LENGTH: 284
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 14

```
cgcaaaaaac cccgcttcgg cggggttttt tcgcacgtct ccatcgcttg cccaagttgt      60
gaagcacagc taacaccacg tcgtccctat ctgctgccct aggtctatga gtggttgctg     120
gataacgcca cggaaatcaa taacctgaag atatgtgcga cgagcttttc ataaatctgt     180
cataaatctg acgcataatg acgtcgcatt aatgatcgca acctatttat tatattcagg     240
gagaccacaa cggtttccct ctacaaataa ttttgtttaa cttt                      284
```

<210> SEQ ID NO 15
<211> LENGTH: 365
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
cgccgaaaac cccgcttcgg cggggttttg ccgcacgtct ccatcgcttg cccaagttgt      60
gaagcacagc taacaccacg tcgtccctat ctgctgccct aggtctatga gtggttgctg     120
gataaccatc cataaatttt gcataattaa tgtaaagacc aggctcgcca gtaacgctaa     180
attcatttgg ctgtaagcgc ggtgtcatcc gcgtcaggaa aattaaacag ttactttaaa     240
aaatgaaaac gtaaaaggt tgggtttcga tgtattgacg ggtaaacttt gtcgcccgct      300
aaacatttgt ttatattcag ggagaccaca acggtttccc tctacaaata attttgttta     360
acttt                                                                  365
```

<210> SEQ ID NO 16
<211> LENGTH: 320
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
aaaaaaaaac cccgcccctg acagggcggg gttttttta cgtctccatc gcttgcccaa      60
gttgtgaagc acagctaaca ccacgtcgtc cctatctgct gccctaggtc tatgagtggt     120
tgctggataa caccgaactg aagcaggatt acaccgtggt gatcgtcacc cacaacatgc     180
agcaggctgc gcgttgttcc gaccacacgg cgtttatgta cctgggcgaa ttgattgagt     240
tcagcaacac ggacgatctg ttcaccaata ttcagggaga ccacaacggt ttccctctac     300
aaataatttt gtttaacttt                                                  320
```

<210> SEQ ID NO 17
<211> LENGTH: 350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
cgccgcaaac cccgcccctg acagggcggg gtttcgccgc acgtctccat cgcttgccca      60
agttgtgaag cacagctaac accacgtcgt ccctatctgc tgccctaggt ctatgagtgg     120
```

```
ttgctggata acaatcctgc tgaaagcaca cagcttttt catcactgtc atcactctgt      180
catctttcca gtagaaacta atgtcactga aatggtgttt tatagttaaa tataagtaaa      240
tatattgttg caataaatgc gagatctgtt gtacttatta agtagcagcg gaagttcata      300
ttcagggaga ccacaacggt ttccctctac aaataatttt gtttaacttt                 350
```

<210> SEQ ID NO 18
<211> LENGTH: 208
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
cgccgaaaac cccgcttcgg cggggttttg ccgcacgtct ccatcgcttg cccaagttgt       60
gaagcacagc taacaccacg tcgtccctat ctgctgccct aggtctatga gtggttgctg      120
gataacttta cgggcatgca taaggctcgt aggctatatt cagggagacc acaacggttt      180
ccctctacaa ataattttgt ttaactttt                                         208
```

<210> SEQ ID NO 19
<211> LENGTH: 213
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
aaaaaaaaac cccgcccctg acagggcggg gtttttttta cgtctccatc gcttgcccaa       60
gttgtgaagc acagctaaca ccacgtcgtc cctatctgct gccctaggtc tatgagtggt      120
tgctggataa cttacgggc atgcataagg ctcgtaatat atattcaggg agaccacaac      180
ggtttccctc tacaaataat tttgtttaac ttt                                    213
```

<210> SEQ ID NO 20
<211> LENGTH: 214
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
cgccgcaaac cccgcccctg acagggcggg gtttcgccgc acgtctccat cgcttgccca       60
agttgtgaag cacagctaac accacgtcgt ccctatctgc tgccctaggt ctatgagtgg      120
ttgctggata actttacggg catgcataag gctcgtatga tatattcagg gagaccacaa      180
cggtttccct ctacaaataa ttttgtttaa cttt                                   214
```

<210> SEQ ID NO 21
<211> LENGTH: 208
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
cgcaaaaaac cccgcttcgg cggggttttt tcgcacgtct ccatcgcttg cccaagttgt       60
```

```
gaagcacagc taacaccacg tcgtccctat ctgctgccct aggtctatga gtggttgctg    120
gataacttta cgggcatgca taaggctcgt ataatatatt cagggagacc acaacggttt    180
ccctctacaa ataattttgt ttaacttt                                       208
```

<210> SEQ ID NO 22
<211> LENGTH: 429
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 22

```
ccaggcatca aataaaacga aaggctcagt cgaaagactg ggcctttcgt tttatctgtt    60
gtttgtcggt gaacgctctc tactagagtc acactggctc accttcgggt gggccttttct  120 gcgtttatac acagctaaca ccacgtcgtc cctatctgct gccctaggtc tatgagtggt   180
tgctggataa cctccttcac agattcccaa tctcttgtta aataacgaaa aagcatcaat   240 taaaaccat gtctttctat attccagcaa tgttttatag gggacatatt gatgaagatg    300
ggtatcacct tagtgaattg ctataagctg ctcttttttg ttcgtgatat actgataaat   360
tgaattttca cacttcatat tcagggagac cacaacggtt tccctctaca aataattttg   420
tttaacttt                                                            429
```

<210> SEQ ID NO 23
<211> LENGTH: 76
<212> TYPE: DNA
<213> ORGANISM: Artificial Sequence
<220> FEATURE:
<223> OTHER INFORMATION: Description of Artificial Sequence: Synthetic
      primer <400> SEQUENCE: 23

```
taacaataaa aatgaaaatg atttccacga tacagaaaaa agagactgtc atcctaatttt   60 ttgttgacac tctatc                                                    76
```

<210> SEQ ID NO 24
<211> LENGTH: 75
<212> TYPE: DNA
<213> ORGANISM: Artificial Sequence
<220> FEATURE:
<223> OTHER INFORMATION: Description of Artificial Sequence: Synthetic
      primer <400> SEQUENCE: 24

```
tgccactcag gtatgatggg cagaatattg cctctgcccg ccagaaaaag atcaaaggga    60
aaactgtcca tatgc                                                     75
```

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide <400> SEQUENCE: 25

```
ccgacaggga ttccatctg                                                 19
```

<210> SEQ ID NO 26
<211> LENGTH: 26

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tatgacgacc attttgtcta cagttc                                              26

<210> SEQ ID NO 27
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggacttttgt acttcctgtt tcgatttagt tggcaattta ggtagcaaac tcctaattt         60 tgttgacact ctatc                                                          75

<210> SEQ ID NO 28
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ataaaaacgg cgctaaaaag cgccgttttt tttgacggtg gtaaagccga atcaaaggga         60
aaactgtcca tatgc                                                          75

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cctgactgta ctaacggttg ag                                                  22

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30 tgactttat ggcgttcttt gtttttg                                              27

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctggtacacg ctgatgaaca cc                                                  22
```

```
<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctggtcattg ccatttgtgc c                                              21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gaatcagagc gttccgaccc                                                20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtacgcagtt tgccaacgtg                                                20

<210> SEQ ID NO 35
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aatagcccgc tgatatcatc gataatacta aaaaaacagg gaggctatta tcctaatttt    60
tgttgacact ctatc                                                     75

<210> SEQ ID NO 36
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tacagggatc cagttatcaa taagcaaatt catttgttct ccttcatatg atcaaaggga    60
aaactgtcca tatgc                                                     75

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
```
caagacatgt gtatatcact gtaattc                                          27

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gcgattgcag atttatgatt tgg                                              23

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcaaaatgct ggctcattg                                                   19

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gaactgaatg gcaaactgac tg                                               22

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tggggatgat cgaccaca                                                    18

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tatcatcctg aaagcgatgg                                                  20

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
atctcaccgt gtgatcgg                                                18

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
caaaagagat tctgggtatt cact                                         24

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ctgctggaaa ccatgcg                                                 17

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
agagcatgtc gttataggag gtgat                                        25

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
agtactcaac caagtcattc tg                                           22

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gagcatggtg atcttctcag t                                            21

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gcgatgaatg tcttactacg ga                                           22

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gtcgctgggt aatctgcaa                                                    19

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
atcaacgcat atagcgctag cag                                               23

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
actgaagccc agacgatc                                                     18

<210> SEQ ID NO 53
<211> LENGTH: 3527
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
tcctaatttt tgttgacact ctatcattga tagagttatt ttaccactcc ctatcagtga        60
tagagaaaag tgaaatgaat agttcgacaa agatcgcatt ggtaattacg ttactcgatg       120
ccatggggat tggccttatc atgccagtct tgccaacgtt attacgtgaa tttattgctt       180
cggaagatat cgctaaccac tttggcgtat tgcttgcact ttatgcgtta atgcaggtta       240
tctttgctcc ttggcttgga aaaatgtctg accgatttgg tcggcgccca gtgctgttgt       300
tgtcattaat aggcgcatcg ctggattact tattgctggc tttttcaagt gcgctttgga       360
tgctgtattt aggccgtttg ctttcaggga tcacaggagc tactggggct gtcgcggcat       420
cggtcattgc cgataccacc tcagcttctc aacgcgtgaa gtggttcggt tggttagggg       480
caagttttgg gcttggttta atagcggggc ctattattgg tggttttgca ggagagattt       540
caccgcatag tcccttttt atcgctgcgt tgctaaatat tgtcactttc cttgtggtta       600
tgttttggtt ccgtgaaacc aaaaatacac gtgataatac agataccgaa gtaggggttg       660
agacgcaatc gaattcggta tacatcactt tatttaaaac gatgcccatt tgttgatta       720 tttatttttc agcgcaattg ataggccaaa ttcccgcaac ggtgtgggtg ctatttaccg       780
aaaatcgttt tggatggaat agcatgatgg ttggctttc attagcgggt cttggtctt       840

```
tacactcagt attccaagcc tttgtggcag gaagaatagc cactaaatgg ggcgaaaaaa    900
cggcagtact gctcggattt attgcagata gtagtgcatt tgcctttta gcgtttatat    960
ctgaaggttg gttagttttc cctgttttaa ttttattggc tggtggtggg atcgctttac   1020
ctgcattaca gggagtgatg tctatccaaa caaagagtca tcagcaaggt gctttacagg   1080
gattattggt gagccttacc aatgcaaccg gtgttattgg cccattactg tttgctgtta   1140
tttataatca ttcactacca atttgggatg gctggatttg gattattggt ttagcgtttt   1200
actgtattat tatcctgcta tcgatgacct tcatgttaac ccctcaagct caggggagta   1260
aacaggagac aagtgcttag ttatttcgtc accaaatgat gttattccgc gaaatataat   1320
gaccctcttg ataacccaag agcatcacat atacctgccg ttcactatta tttagtgaaa   1380
tgagatatta tgatattttc tgaattgtga ttaaaaaggc aactttatgc ccatgcaaca   1440
gaaactataa aaaatacaga gaatgaaaag aaacagatag atttttttagt tctttaggcc   1500
cgtagtctgc aaatcctttt atgattttct atcaaacaaa agaggaaaat agaccagttg   1560
caatccaaac gagagtctaa tagaatgagg tcgaaaagta aatcgcgcgg gtttgttact   1620
gataaagcag gcaagaccta aaatgtgtaa agggcaaagt gtatactttg gcgtcaccccc   1680
ttacatattt taggtcttttt tttattgtgc gtaactaact tgccatcttc aaacaggagg   1740
gctggaagaa gcagaccgct aacacagtac ataaaaaagg agacatgaac gatgaacatc   1800
aaaaagttg caaaacaagc aacagtatta acctttacta ccgcactgct ggcaggaggc   1860
gcaactcaag cgtttgcgaa agaaacgaac caaaagccat aaggaaac atacggcatt    1920
tcccatatta cacgccatga tatgctgcaa atccctgaac agcaaaaaaa tgaaaaatat   1980
caagttcctg agttcgattc gtccacaatt aaaaatatct cttctgcaaa aggcctggac   2040
gtttgggaca gctggccatt acaaaacgct gacggcactg tcgcaaacta tcacggctac   2100
cacatcgtct ttgcattagc cggagatcct aaaaatgcgg atgacacatc gatttacatg   2160
ttctatcaaa aagtcggcga aacttctatt gacagctgga aaaacgctgg ccgcgtcttt   2220
aaagacagcg acaaattcga tgcaaatgat tctatcctaa aagaccaaac acaagaatgg   2280
tcaggttcag ccacatttac atctgacgga aaaatccgtt tattctacac tgatttctcc   2340
ggtaaacatt acggcaaaca aacactgaca actgcacaag ttaacgtatc agcatcagac   2400
agctcttttga acatcaacgg tgtagaggat tataaatcaa tctttgacgg tgacggaaaa   2460
acgtatcaaa atgtacagca gttcatcgat gaaggcaact acagctcagg cgacaaccat   2520
acgctgagag atcctcacta cgtagaagat aaaggccaca atacttagt atttgaagca   2580
aacactggaa ctgaagatgg ctaccaaggc gaagaatctt tatttaacaa agcatactat   2640
ggcaaaagca catcattctt ccgtcaagaa agtcaaaaac ttctgcaaag cgataaaaaa   2700
cgcacggctg agttagcaaa cggcgctctc ggtatgattg agctaaacga tgattacaca   2760
ctgaaaaaag tgatgaaacc gctgattgca tctaacacag taacagatga aattgaacgc   2820
gcgaacgtct ttaaaatgaa cggcaaatgg tacctgttca ctgactcccg cggatcaaaa   2880
atgacgattg acggcattac gtctaacgat atttacatgc ttggttatgt ttctaattct   2940
ttaactggcc catacaagcc gctgaacaaa actggccttg tgttaaaaat ggatcttgat   3000
cctaacgatg taacctttac ttactcacac ttcgctgtac ctcaagcgaa aggaaacaat   3060
gtcgtgatta caagctatat gacaaacaga ggattctacg cagacaaaca atcaacgttt   3120
gcgccaagct tcctgctgaa catcaaaggc aagaaaacat ctgttgtcaa agacagcatc   3180
cttgaacaag gacaattaac agttaacaaa taaaaacgca aagaaaatg ccgatattga   3240
```

-continued

```
ctaccggaag cagtgtgacc gtgtgcttct caaatgcctg attcaggctg tctatgtgtg    3300
actgttgagc tgtaacaagt tgtctcaggt gttcaatttc atgttctagt tgctttgttt    3360
tactggtttc acctgttcta ttaggtgtta catgctgttc atctgttaca ttgtcgatct    3420
gttcatggtg aacagcttta aatgcaccaa aaactcgtaa aagctctgat gtatctatct    3480
tttttacacc gttttcatct gtgcatatgg acagttttcc ctttgat                 3527
```

<210> SEQ ID NO 54
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54

```
aaatgatttc cacgatacag aaaaaagaga ctgtcatggg cagaatattg cctctgcccg    60
ccagaaaaag                                                          70
```

<210> SEQ ID NO 55
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55

```
ctgtttcgat ttagttggca atttaggtag caaactcggc tttaccaccg tcaaaaaaaa    60
cggcgctttt                                                          70
```

<210> SEQ ID NO 56
<211> LENGTH: 476
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
caagacatgt gtatatcact gtaattcgat atttatgagc agcatcgaaa aatagcccgc    60
tgatatcatc gataatacta aaaaaacagg gaggctatta ccaggcatca ataaaaacga   120
aaggctcagt cgaaagactg gccctttcgt tttatctgtt gtttgtcggt gaacgctctc   180
tactagagtc acactggctc accttcgggt gggcctttct gcgtttatat ctttctgaca   240
ccttactatc ttacaaatgt aacaaaaaag ttatttttct gtaattcgag catgtcatgt   300
taccccgcga gcataaaacg cgtgtgtagg aggataatct ttgacggcta gctcagtcct   360
aggtacagtg ctagccatat gaaggagaac aaatgaattt gcttattgat aactggatcc   420
ctgtacgccc gcgaaacggg gggaaagtcc aaatcataaa tctgcaatcg ctatac       476
```

<210> SEQ ID NO 57
<211> LENGTH: 974
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
caagacatgt gtatatcact gtaattcgat atttatgagc agcatcgaaa aatagcccgc    60
tgatatcatc gataatacta aaaaaacagg gaggctatta ccaggcatca aataaaacga   120
aaggctcagt cgaaagactg ggcctttcgt tttatctgtt gtttgtcggt gaacgctctc   180
tactagagtc acactggctc accttcgggt gggcctttct gcgtttatat ctttctgaca   240
ccttactatc ttacaaatgt aacaaaaaag ttattttct gtaattcgag catgtcatgt   300
taccccgcga gcataaaacg cgtgtgtagg aggataatct atggatttgt cacagctaac   360
accacgtcgt ccctatctgc tgcgtgcatt ctatgagtgg ttgctggata accagctcac   420
gccgcacctg gtggtggatg tgacgctccc tggcgtgcag gttcctatgg aatatgcgcg   480
tgacgggcaa atcgtactca acattgcgcc gcgtgctgtc ggcaatctgg aactggcgaa   540
tgatgaggtg cgctttaacg cgcgctttgg tggcattccg cgtcaggttt ctgtgccgct   600
ggctgccgtg ctggctatct acgcccgtga aatggcgca ggcacgatgt tgagcctga    660 agctgcctac gatgaagata ccagcatcat gaatgatgaa gaggcatcgg cagacaacga   720
aaccgttatg tcggttattg atggcgacaa gccagatcac gatgatgaca ctcatcctga   780
cgatgaacct ccgcagccac cacgcggtgg tcgaccggca ttacgcgttg tgaagtaatt   840
gacggctagc tcagtcctag gtacagtgct agccatatga aggagaacaa atgaatttgc   900
ttattgataa ctggatccct gtacgcccgc gaaacggggg gaaagtccaa atcataaatc   960
tgcaatcgct atac                                                    974

<210> SEQ ID NO 58
<211> LENGTH: 970
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
ctattgaaga tgtgggtaac tctgcggcat tcctgtgctc cgatctctct gccggtatct    60
ccggtgaagt ggtccacgtt gacggcggtt tcagcattgc tgcaatgaac gaactcgaac   120
tgaaagcggc caacgatgaa aactattctg aaaactatgc ggatgcgtct taataggaag   180
ttcctattct ctagaaagta taggaacttc cgaatccatg tgggagttta ttcttgacac   240
agatatttat gatataataa ctgagtaagc ttaacataag gaggaaaaac atatgttacg   300
cagcagcaac gatgttacgc agcagggcag tcgccctaaa acaaagttag gtggctcaag   360
tatgggcatc attcgcacat gtaggctcgg ccctgaccaa gtcaaatcca tgcgggctgc   420
tcttgatctt ttcggtcgtg agttcggaga cgtagccacc tactcccaac atcagccgga   480
ctccgattac ctcgggaact tgctccgtag taagacattc atcgcgcttg ctgccttcga   540
ccaagaagcg gttgttggcg ctctcgcggc ttacgttctg cccaagtttg agcagccgcg   600
tagtgagatc tatatctatg atctcgcagt ctccggcgag caccggaggc agggcattgc   660
caccgcgctc atcaatctcc tcaagcatga ggccaacgcg cttggtgctt atgtgatcta   720
cgtgcaagca gattacggtg acgatcccgc agtggctctc tatacaaagt tgggcatacg   780
ggaagaagtg atgcactttg atatcgaccc aagtaccgcc acctaagaag ttcctattct   840
ctagaaagta taggaacttc cgttctgttg gtaaagatgg gcggcgttct gccgcccgtt   900
atctctgtta taccttctg atatttgtta tcgccgatcc gtctttctcc ccttcccgcc   960
ttgcgtcagg                                                         970
```

<210> SEQ ID NO 59
<211> LENGTH: 2000
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59

```
tctccaaagc ggccaacgat gaaaactatt ctgaaaacta tgcggatgcg tcttgattga      60
cagctagctc agtcctaggt ataatgctag caactttaaa attaagagg tatatattaa     120
tgactaagca atataagaat tacgtaaatg gggagtggaa gctttcggag aatgaaatta    180
agatctatga accagccagt ggggcggaat tggggtcagt cccggcaatg tccactgaag    240
aagttgacta tgtctacgcc tcggccaaaa aagcgcagcc agcatggcgc tcgctttcct    300
atattgagcg tgcggcttat ttgcacaaag tcgcagacat cctgatgcgt gacaaggaga    360
aaattggagc ggtattgtcc aaggaagtag cgaaaggcta caaatccgca gtatcggagg    420
tcgtccgcac cgccgagatt attaattatg cggccgaaga agggcttcgc atggagggtg    480
aggtcttgga gggcggcagt tttgaggcgg catccaagaa aaaaatcgct gtcgtccgtc    540
gcgagccggt gggacttgtg cttgctatta gtccgttcaa ttaccccgtg aatctggccg    600
gctccaagat tgcccctgca ctgatcgcgg gcaatgtaat cgcttttaaa ccaccgaccc    660
aaggatcgat tagtggactt cttttagcgg aggcgtttgc ggaggcaggt cttccagccg    720
gcgtattcaa taccatcacg gggcgtggaa gtgaaatcgg ggattacatc gtggagcacc    780
aggcagtaaa tttcatcaac ttcacgggtt ccacggggat cggggagcgt atcggtaaga    840
tggctgggat gcgtccgatc atgttggaac ttggcggcaa ggatagtgcg attgtgctgg    900
aagacgcaga cttggaattg acagctaaaa acattatcgc tggagccttc gggtatagtg    960
gtcaacgttg cacggcagtt aagcgcgttc ttgttatgga aagtgtcgcg gatgaattgg   1020
tcgagaagat tcgcgagaaa gtgttagctc ttacgattgg aaatccagag gacgatgctg   1080
acatcactcc attgatcgac acgaaatccg cggattacgt cgaggggctg atcaacgacg   1140
cgaacgataa gggagcagcg gctttgaccg agatcaaacg cgaggggaac ctgatctgcc   1200
cgattctttt tgacaaagtc acaactgaca tgcgcttggc atgggaagaa cccttcggcc   1260
cagtcttgcc tattatccgc gttactagcg tagaggaagc aattgaaatt ccaataaat    1320
ccgaatatgg gttgcaagcg agtatcttta ctaacgattt tccacgtgcc tttggtattg   1380
cggaacagtt agaagtcggg acagttcaca tcaacaacaa gacgcagcgc gggacagata   1440
acttcccctt tttgggagca aagaagtctg ggctggaat ccaaggggtg aaatactcca    1500
tcgaagccat gacgacggtg aagagcgttg tttttgacat caagtaaaac ataaggagga   1560
aaaacagatg gcgaaactga cctcggcggt tccggttctg acggcacgtg atgtggcggg   1620
cgcggttgaa ttttggacgg atcgtctggg cttcagtcgt gattttgtgg aagatgactt   1680
cgcaggcgtg gttcgcgatg acgtcaccct gtttatttcc gcagttcagg atcaagtcgt   1740
gccggacaac acgctggctt gggtgtgggt tcgtggcctg gatgaactgt atgcggaatg   1800
gagcgaagtt gtctctacca atttccgtga cgcgagcggt ccggccatga cggaaatcgg   1860
cgaacagccg tggggtcgcg aatttgctct gcgtgacccg gctggcaact gtgtccattt   1920
cgtggctgaa gaacaagatt gagttgagat gacactgtga tctaaaaga gcgacttcgg   1980
tcgctctttt ttttacctga                                               2000
```

<210> SEQ ID NO 60
<211> LENGTH: 2000
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60

| | | | | |
|---|---|---|---|---|
| acgaaaccgg | ttactccaac | aaagttctgg | acctgatcgc | tcacatctcc | aaatgattga | 60 |
| cagctagctc | agtcctaggt | ataatgctag | caactttaaa | attaaagagg | tatatattaa | 120 |
| tgactaagca | atataagaat | tacgtaaatg | gggagtggaa | gctttcggag | aatgaaatta | 180 |
| agatctatga | accagccagt | ggggcggaat | tggggtcagt | cccggcaatg | tccactgaag | 240 |
| aagttgacta | tgtctacgcc | tcggccaaaa | aagcgcagcc | agcatggcgc | tgctttcct | 300 |
| atattgagcg | tgcggcttat | ttgcacaaag | tcgcagacat | cctgatgcgt | gacaaggaga | 360 |
| aaattggagc | ggtattgtcc | aaggaagtag | cgaaaggcta | caaatccgca | gtatcggagg | 420 |
| tcgtccgcac | cgccgagatt | attaattatg | cggccgaaga | agggcttcgc | atggagggtg | 480 |
| aggtcttgga | gggcggcagt | tttgaggcgg | catccaagaa | aaaaatcgct | gtcgtccgtc | 540 |
| gcgagccggt | gggacttgtg | cttgctatta | gtccgttcaa | ttaccccgtg | aatctggccg | 600 |
| gctccaagat | tgcccctgca | ctgatcgcgg | gcaatgtaat | cgcttttaaa | ccaccgaccc | 660 |
| aaggatcgat | tagtggactt | cttttagcgg | aggcgtttgc | ggaggcaggt | cttccagccg | 720 |
| gcgtattcaa | taccatcacg | gggcgtggaa | gtgaaatcgg | ggattacatc | gtggagcacc | 780 |
| aggcagtaaa | tttcatcaac | ttcacggggtt | ccacggggat | cggggagcgt | atcggtaaga | 840 |
| tggctgggat | gcgtccgatc | atgttggaac | ttggcggcaa | ggatagtgcg | attgtgctgg | 900 |
| aagacgcaga | cttggaattg | acagctaaaa | acattatcgc | tggagccttc | gggtatagtg | 960 |
| gtcaacgttg | cacggcagtt | aagcgcgttc | ttgttatgga | aagtgtcgcg | gatgaattgg | 1020 |
| tcgagaagat | tcgcgagaaa | gtgttagctc | ttacgattgg | aaatccagag | gacgatgctg | 1080 |
| acatcactcc | attgatcgac | acgaaatccg | cggattacgt | cgaggggctg | atcaacgacg | 1140 |
| cgaacgataa | gggagcagcg | gctttgaccg | agatcaaacg | cgaggggaac | ctgatctgcc | 1200 |
| cgattctttt | tgacaaagtc | acaactgaca | tgcgcttggc | atgggaagaa | cccttcggcc | 1260 |
| cagtcttgcc | tattatccgc | gttactagcg | tagaggaagc | aattgaaatt | tccaataaat | 1320 |
| ccgaatatgg | gttgcaagcg | agtatcttta | ctaacgattt | tccacgtgcc | tttggtattg | 1380 |
| cggaacagtt | agaagtcggg | acagttcaca | tcaacaacaa | gacgcagcgc | gggacagata | 1440 |
| acttccccctt | tttgggagca | agaagtctg | ggctggaat | ccaaggggtg | aaatactcca | 1500 |
| tcgaagccat | gacgacggtg | aagagcgttg | tttttgacat | caagtaaaac | ataaggagga | 1560 |
| aaaacagatg | gcgaaactga | cctcggcggt | tccggttctg | acggcacgtg | atgtggcggg | 1620 |
| cgcggttgaa | ttttggacgg | atcgtctggg | cttcagtcgt | gattttgtgg | aagatgactt | 1680 |
| cgcaggcgtg | gttcgcgatg | acgtcaccct | gtttatttcc | gcagttcagg | atcaagtcgt | 1740 |
| gccggacaac | acgctggctt | gggtgtgggt | tcgtggcctg | gatgaactgt | atgcggaatg | 1800 |
| gagcgaagtt | gtctctacca | atttccgtga | cgcgagcggt | ccggccatga | cggaaatcgg | 1860 |
| cgaacagccg | tggggtcgcg | aatttgctct | gcgtgacccg | gctggcaact | gtgtccattt | 1920 |
| cgtggctgaa | gaacaagatt | gagttgagat | gacactgtga | tctaaaaaga | gcgacttcgg | 1980 |
| tcgctctttt | ttttacctga | | | | | 2000 |

<210> SEQ ID NO 61
<211> LENGTH: 907
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
tctaccgatt tcaacggcga agtttgcact tccgtgttcg atgctaaagc tggtatcgct      60
ctgaacgaca acttcgtgaa actggtatcc tggtacgaca acgaaaccgg ttactccaac     120
aaagttctgg acctgatcgc tcacatctcc aaagcggcca acgatgaaaa ctattctgaa     180
aactatgcgg atgcgtcttg atcctgacgg atggcctttt tgcgtttcta caaactcttt     240
ttgtttattt ttctaaatac attcaaatat gtatccgctc atgagacaat aaccctgata     300
aatgcttcaa taatattgaa aaaggaagag taatggcgaa actgacctcg gcggttccgg     360
ttctgacggc acgtgatgtg gcgggcgcgg ttgaattttg gacggatcgt ctgggcttca     420
gtcgtgattt tgtggaagat gacttcgcag gcgtggttcg cgatgacgtc accctgttta     480
tttccgcagt tcaggatcaa gtcgtgccgg acaacacgct ggcttgggtg tgggttcgtg     540
gcctggatga actgtatgcg gaatggagcg aagttgtctc taccaatttc cgtgacgcga     600
gcggtccggc catgacggaa atcggcgaac agccgtgggg tcgcgaattt gctctgcgtg     660
acccggctgg caactgtgtc catttcgtgg ctgaagaaca agattgagtt gagatgacac     720
tgtgatctaa aaagagcgac ttcggtcgct cttttttta cctgataaaa tgaagttaaa     780
ggactgcgtc atgattaaga aaattttgc ccttccggtc atcgaacaaa tctcccctgt      840
cctctcccgt cgtaaactgg atgaactgga cctcattgtg gtcgatcatc cccaggtaaa     900
agcctct                                                               907
```

<210> SEQ ID NO 62
<211> LENGTH: 1421
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
gtattccgtc ttccatgttc accgtcattt tcgcaatggc acgtaccgtt ggctggatcg      60
cccactggag cgaaatgcac agtgacggta tgaagattgc ccgtccgcgt cagctgtata     120
caggatatga aaacgcgac tttaaaagcg atatcaagcg tgcggccaac gatgaaaact      180
attctgaaaa ctatgcggat gcgtcttaat agtcctgacg gatggccttt tgcgtttct      240 acaaactctt tttgtttatt tttctaaata cattcaaata tgtatccgct catgagacaa     300
taaccctgat aaatgcttca ataatattga aaaaggaaga gtatgagtat tcaacatttc     360
cgtgtcgccc ttattccctt ttttgcggca ttttgccttc ctgtttttgc tcacccagaa     420
acgctggtga agtaaaaga tgctgaagat cagttgggtg cacgagtggg ttacatcgaa      480
ctggatctca acagcggtaa gatccttgag agttttcgcc ccgaagaacg ttttccaatg     540
atgagcactt ttaaagttct gctatgtggc gcggtattat cccgtgttga cgccgggcaa     600
gagcaactcg gtcgccgcat acactattct cagaatgact tggttgagta ctcaccagtc     660
acagaaaagc atcttacgga tggcatgaca gtaagagaat tatgcagtgc tgccataacc     720
atgagtgata acactgcggc caacttactt ctgacaacga tcggaggacc gaaggagcta     780
```

```
accgctttt  tgcacaacat  gggggatcat  gtaactcgcc  ttgatcgttg  ggaaccggag      840
ctgaatgaag  ccataccaaa  cgacgagcgt  gacaccacga  tgcctacagc  aatggcaaca      900
acgttgcgca  aactattaac  tggcgaacta  cttactctag  cttcccggca  acaattaata      960
gactggatgg  aggcgataaa  agttgcagga  ccacttctgc  gctcggccct  tccggctggc     1020
tggtttattg  ctgataaatc  tggagccggt  gagcgtgggt  ctcgcggtat  cattgcagca     1080
ctggggccag  atggtaagcc  ctcccgtatc  gtagttatct  acacgacggg  gagtcaggca     1140
actatggatg  aacgaaatag  acagatcgct  gagataggtg  cctcactgat  taagcattgg     1200
taactgtcag  actaatggtt  gattgctaag  ttgtaaatat  tttaacccgc  cgttcatatg     1260
gcgggttgat  ttttatatgc  ctaaacacaa  aaaattgtaa  aaataaaatc  cattaacaga     1320
cctatataga  tatttaaaaa  gaatagaaca  gctcaaatta  tcagcaaccc  aatactttca     1380
attaaaaact  tcatggtagt  cgcatttata  accctatgaa  a                          1421

<210>  SEQ ID NO 63
<211>  LENGTH: 1078
<212>  TYPE: DNA
<213>  ORGANISM: Artificial Sequence
<220>  FEATURE:
<223>  OTHER INFORMATION: Description of Artificial Sequence: Synthetic
       polynucleotide

<400>  SEQUENCE: 63 accgtcattt  tcgcaatggc  acgtaccgtt  ggctggatcg  cccactggag  cgaaatgcac       60
agtgacggta  tgaagattgc  ccgtccgcgt  cagctgtata  caggatatga  aaaacgcgac      120
tttaaaagcg  atatcaagcg  tgcggccaac  gatgaaaact  attctgaaaa  ctatgcggat      180
gcgtcttaat  cctgacggat  ggccttttg  cgtttctaca  aactcttttt  gtttattttt      240
ctaaatacat  tcaaatatgt  atccgctcat  gagacaataa  ccctgataaa  tgcttcaata      300
atattgaaaa  aggaagagta  tgactgaata  caagcccacg  gtacgcttgg  cgacgcgcga      360
cgatgttccc  cgcgctgttc  gtacattagc  tgcggccttt  gcagattacc  cagcgacgcg      420
ccatacggtc  gatccggacc  gccatatcga  gcgtgtcaca  gaattgcagg  aacttttctt      480
aactcgcgtg  ggccttgaca  tcggaaaggt  ctgggtggct  gacgatggcg  ctgcagtggc      540 tgtttgacc  actccggaga  gtgtagaggc  tggtgcagtg  ttcgccgaaa  ttggtcctcg      600
tatggccgaa  ttaagtggaa  gtcgtctggc  agcccaacaa  caaatggaag  ggttgcttgc      660
gccccaccgt  ccgaaagaac  ccgcgtggtt  ccttgccacc  gttggagtaa  gcccagatca      720
ccaggggaag  ggtttaggat  ctgccgtagt  tttaccaggt  gtggaggcag  cagaacgtgc      780
gggagttccg  gccttccttg  agacgtcggc  gccgcgcaat  ttaccgtttt  acgaacgtct      840
tggattcacc  gttacggcgg  acgtggaggt  gccggaggga  ccccgtactt  ggtgtatgac      900
tcgtaaaccg  ggagcctgat  aatggttgat  tgctaagttg  taaatatttt  aacccgccgt      960
tcatatggcg  ggttgatttt  tatatgccta  aacacaaaaa  attgtaaaaa  taaaatccat     1020
taacagacct  atatagatat  ttaaaaagaa  tagaacagct  caaattatca  gcaaccca      1078

<210>  SEQ ID NO 64
<211>  LENGTH: 869
<212>  TYPE: DNA
<213>  ORGANISM: Artificial Sequence
<220>  FEATURE:
<223>  OTHER INFORMATION: Description of Artificial Sequence: Synthetic
       polynucleotide
```

<400> SEQUENCE: 64

```
gtattccgtc ttccatgttc accgtcattt tcgcaatggc acgtaccgtt ggctggatcg    60
cccactggag cgaaatgcac agtgacggta tgaagattgc ccgtccgcgt cagctgtata   120
caggatatga aaacgcgac tttaaaagcg atatcaagcg tgcggccaac gatgaaaact   180
attctgaaaa ctatgcggat gcgtcttaat agttgacaat taatcatcgg catagtatat   240
cggcatagta taatcgact cactatagga gggccatcat ggccaagttg accagtgccg   300
ttccggtgct caccgcgcgc gacgtcgccg agcggtcga gttctggacc gaccggctcg   360
ggttctcccg ggacttcgtg gaggacgact tcgccggtgt ggtccgggac gacgtgaccc   420
tgttcatcag cgcggtccag gaccaggtgg tgccggacaa caccctggcc tgggtgtggg   480
tgcgcggcct ggacgagctg tacgccgagt ggtcggaggt cgtgtccacg aacttccggg   540
acgcctccgg gccggccatg accgagatcg gcgagcagcc gtggggcgg gagttcgccc   600
tgcgcgaccc ggccggcaac tgcgtgcact ttgtggcaga ggagcaggac tgaggataag   660
taatggttga ttgctaagtt gtaaatattt taacccgccg ttcatatggc gggttgattt   720
ttatatgcct aaacacaaaa aattgtaaaa ataaaatcca ttaacagacc tatatagata   780
tttaaaaaga atagaacagc tcaaattatc agcaacccaa tactttcaat taaaaacttc   840
atggtagtcg catttataac cctatgaaa                                      869
```

<210> SEQ ID NO 65
<211> LENGTH: 1000
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

```
gcggcgagct gctgggtgaa atcggcctgg caatcgaaat gggttgtgat gctgaagaca    60
tcgcactgac catccacgcg cacccgactc tgcacgagtc tgtgggcctg gcggcagaag   120
tgttcgaagg tagcattacc gacctgccga cccgaaagc gaagaagaag gcggccaacg   180
atgaaaacta ttctgaaaac tatgcggatg cgtcttaata gcgaatccat gtgggagttt   240
attcttgaca cagatattta tgatataata actgagtaag cttaacataa ggaggaaaaa   300
catatgttac gcagcagcaa cgatgttacg cagcagggca gtcgccctaa aacaaagtta   360
ggtggctcaa gtatgggcat cattcgcaca tgtaggctcg cccctgacca agtcaaatcc   420
atgcgggctg ctcttgatct tttcggtcgt gagttcggag acgtagccac ctactcccaa   480
catcagccgg actccgatta cctcgggaac ttgctccgta gtaagacatt catcgcgctt   540
gctgccttcg accaagaagc ggttgttggc gctctcgcgg cttacgttct gcccaagttt   600
gagcagccgc gtagtgagat ctatatctat gatctcgcag tctccggcga gcaccggagg   660
cagggcattg ccaccgcgct catcaatctc ctcaagcatg aggccaacgc gcttggtgct   720
tatgtgatct acgtgcaagc agattacggt gacgatcccg cagtggctct ctatacaaag   780
ttgggcatac gggaagaagt gatgcacttt gatatcgacc caagtaccgc cacctaattt   840
ttcgtttgcc ggaacatccg gcaattaaaa aagcggctaa ccacgccgct ttttttacgt   900
ctgcaattta cctttccagt cttcttgctc cacgttcaga gagacgttcg catactgctg   960
accgttgctc gttattcagc ctgacagtat ggttactgtc                         1000
```

<210> SEQ ID NO 66

```
<211> LENGTH: 852
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
tctgggtatt cactgctttg gcgagcgcgc tgccgaaatt attcatatcg gtcaggcgat      60
tatggaacag aaaggtggcg gcaacactat tgagtacttc gtcaacacca cctttaacta    120
cccgacgatg gcggaagcct atcgggtagc tgcgttaaac ggtttaaacc gcctgtttgc    180
ggccaacgat gaaaactatt ctgaaaacta tgcggatgcg tcttaatagt tgacaattaa    240
tcatcggcat agtatatcgg catagtataa tacgactcac tataggaggg ccatcatgaa    300
gaccttcaac atctctcagc aggatctgga gctggtggag gtcgccactg agaagatcac    360
catgctctat gaggacaaca agcaccatgt cggggcggcc atcaggacca agactgggga    420
gatcatctct gctgtccaca ttgaggccta cattggcagg gtcactgtct gtgctgaagc    480
cattgccatt gggtctgctg tgagcaacgg gcagaaggac tttgacacca ttgtggctgt    540
caggcacccc tactctgatg aggtggacag atccatcagg gtggtcagcc cctgtggcat    600
gtgcagagag ctcatctctg actatgctcc tgactgcttt gtgctcattg agatgaatgg    660
caagctggtc aaaaccacca ttgaggaact catccccctc aagtacacca ggaactaaag    720
taaaacttta tcgaaatggc catccattct tgcgcggatg gcctctgcca gctgctcata    780
gcggctgcgc agcggtgagc caggacgata aaccaggcca atagtgcggc gtggttccgg    840
cttaatgcac gg                                                        852

<210> SEQ ID NO 67
<211> LENGTH: 898
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
gaagtggaag aagcctggaa atgggtagac tccattactg aggcgtgggc gatggacaat      60
gatgcgccga aaccgtatca ggccggaacc tggggacccg ttgcctcggt ggcgatgatt    120
acccgtgatg gtcgttcctg gaatgagttt gaggcggcca acgatgaaaa ctattctgaa    180
aactatgcgg atgcgtctta atagttgaca attaatcatc ggcatagtat atcggcatag    240
tataatacga ctcactatag gagggccatc atgaagacct tcaacatctc tcagcaggat    300
ctggagctgg tggaggtcgc cactgagaag atcaccatgc tctatgagga caacaagcac    360
catgtcgggg cggccatcag gaccaagact ggggagatca tctctgctgt ccacattgag    420
gcctacattg gcagggtcac tgtctgtgct gaagccattg ccattgggtc tgctgtgagc    480
aacgggcaga aggactttga caccattgtg gctgtcaggc accccactc tgatgaggtg    540 gacagatcca tcagggtggt cagcccctgt ggcatgtgca gagagctcat ctctgactat    600
gctcctgact gctttgtgct cattgagatg aatggcaagc tggtcaaaac caccattgag    660
gaactcatcc ccctcaagta caccaggaac taaagtaata tctgcgctta tcctttatgg    720
ttattttacc ggtaacatga tcttgcgcag attgtgaac aatttttaca ctttcaggcc    780
tcgtgcggat tcacccacga ggcttttttt attacactga ctgaaacgtt tttgccctat    840
gagctccggt tacaggcgtt tcagtcataa atcctctgaa tgaaacgcgt tgtgaatc     898
```

<210> SEQ ID NO 68
<211> LENGTH: 1181
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

```
gcgtgcgcac catgacggtg gggaccgtct cgatggatat gctagcggtc gatttaacgc      60
cttgcccgca ggcgggtatt ggtacgccgg ttgagctgtg gggcaaggag atcaaaattg     120
atgatgtcgc cgccgctgcc ggaacggtgg gctatgagtt gatgtgcgcg ctggcgctac     180
gcgtcccggt tgtgacggtg gcggccaacg atgaaaacta ttctgaaaac tatgcggatg     240
cgtcttaatc ctgacggatg gccttttttgc gtttctacaa actcttttg tttattttc     300
taaatacatt caaatatgta tccgctcatg agacaataac cctgataaat gcttcaataa     360
tattgaaaaa ggaagagtat gactgaatac aagcccacgg tacgcttggc gacgcgcgac     420
gatgttcccc gcgctgttcg tacattagct gcggcctttg cagattaccc agcgacgcgc     480
catacggtcg atccggaccg ccatatcgag cgtgtcacag aattgcagga acttttctta     540
actcgcgtgg gccttgacat cggaaaggtc tgggtggctg acgatggcgc tgcagtggct     600
gtttggacca ctccggagag tgtagaggct ggtgcagtgt tcgccgaaat tggtcctcgt     660
atggccgaat taagtggaag tcgtctggca gcccaacaac aaatggaagg gttgcttgcg     720
ccccaccgtc cgaaagaacc cgcgtggttc cttgccaccg ttggagtaag cccagatcac     780
caggggaagg gtttaggatc tgccgtagtt ttaccaggtg tggaggcagc agaacgtgcg     840
ggagttccgg ccttccttga gacgtcgcg ccgcgcaatt taccgttta cgaacgtctt     900
ggattcaccg ttacggcgga cgtggaggtg ccggagggac cccgtacttg gtgtatgact     960
cgtaaaccgg gagcctgata acttgttgta agcggatcg gaggcaacgt cttctgggtg    1020
caaaaaaatc atccatccgg ctggtcagca actgtagttg ttaatgtgac agagccattg    1080
cccatgatag tgtccattaa aaggatggac actatttccc cggaacctga actcaccgca    1140
caggcgttct acataaaacg cttacgcttc attgttgact c                       1181
```

<210> SEQ ID NO 69
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69

```
tcgagttccc cgcgccagcg gggataaacc gttgattata ataccgtttt atctgttcgt      60
atcgagttcc ccgcgccagc ggggataaac cg                                    92
```

<210> SEQ ID NO 70
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70

```
gtttatctgt tcgtatcgag ttccccgcgc cagcggggat aaaccgaaaa aaaaaccccc      59
```

<210> SEQ ID NO 71
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ggttattata atcaacggtt tatccccgct ggcgcgggga actcgaggtg gtaccagatc    60

<210> SEQ ID NO 72
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tcgagttccc cgcgccagcg gggataaacc ggttttttgta atttttacagg caaccttttta    60 ttcgagttcc ccgcgccagc ggggataaac cg                                   92

<210> SEQ ID NO 73
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
caggcaacct tttattcgag ttccccgcgc cagcggggat aaaccgaaaa aaaaacccc      59

<210> SEQ ID NO 74
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
taaaattaca aaaccggtt tatccccgct ggcgcgggga actcgaggtg gtaccagatc     60

<210> SEQ ID NO 75
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tcgagttccc cgcgccagcg gggataaacc gaaaagcata taatgcgtaa aagttatgaa    60
gttcgagttc cccgcgccag cggggataaa ccg                                 93

<210> SEQ ID NO 76
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gcgtaaaagt tatgaagttc gagttccccg cgccagcggg gataaaccga aaaaaaaacc    60
cc                                                                  62

<210> SEQ ID NO 77
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
attatatgct tttcggttta tccccgctgg cgcggggaac tcgaggtggt accagatct     59

<210> SEQ ID NO 78
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
tcgagttccc cgcgccagcg gggataaacc gtattgacca attcattcgg gacagttatt    60
agttcgagtt ccccgcgcca gcggggataa accg                               94

<210> SEQ ID NO 79
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gggacagtta ttagttcgag ttccccgcgc cagcgggat aaaccgaaaa aaaaacccc      59

<210> SEQ ID NO 80
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gaatgaattg gtcaatacgg tttatccccg ctggcgcggg gaactcgagg tggtaccaga    60
tct                                                                 63

<210> SEQ ID NO 81
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tcgagttccc cgcgccagcg gggataaacc gagtggttgc tggataactt tacgggcatg    60
ctcgagttcc ccgcgccagc ggggataaac cg                                  92

<210> SEQ ID NO 82

```
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
aactttacgg gcatgctcga gttccccgcg ccagcgggga taaaccgaaa aaaaaacccc      60

<210> SEQ ID NO 83
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
atccagcaac cactcggttt atccccgctg gcgcggggaa ctcgaggtgg taccagatct      60

<210> SEQ ID NO 84
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tcgagttccc cgcgccagcg gggataaaacc gttaccattc tgttgctttt atgtataaga    60
atcgagttcc ccgcgccagc ggggataaac cg                                   92

<210> SEQ ID NO 85
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ttttatgtat aagaatcgag ttccccgcgc cagcggggat aaaccgaaaa aaaaacccc      59

<210> SEQ ID NO 86
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gcaacagaat ggtaacggtt tatccccgct ggcgcgggga actcgaggtg gtaccagatc     60

<210> SEQ ID NO 87
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
tcgagttccc cgcgccagcg gggataaacc gctcgtaaaa gcagtacagt gcaccgtaag     60
atcgagttcc ccgcgccagc ggggataaac cg                                   92
```

<210> SEQ ID NO 88
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
cagtgcaccg taagatcgag ttccccgcgc cagcggggat aaaccgaaaa aaaaacccc      59

<210> SEQ ID NO 89
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
tactgctttt acgagcggtt tatccccgct ggcgcgggga actcgaggtg gtaccagatc     60

<210> SEQ ID NO 90
<211> LENGTH: 154
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
tcgagttccc cgcgccagcg gggataaacc gttgattata ataaccgttt atctgttcgt     60
atcgagttcc ccgcgccagc ggggataaac cgaaaagcat ataatgcgta aaagttatga    120
agttcgagtt ccccgcgcca gcggggataa accg                                154

<210> SEQ ID NO 91
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gcgccagcgg ggataaaccg aaaagcatat aatgcg                               36

<210> SEQ ID NO 92
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
cttgcccgcc tgatgaatgc tcatccgg                                        28

<210> SEQ ID NO 93
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ccggatgagc attcatcagg cgggcaag                                          28

<210> SEQ ID NO 94
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
cggtttatcc ccgctggcgc ggggaactcg atacgaacag ataaacggtt attataatc       59

<210> SEQ ID NO 95
<211> LENGTH: 155
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
tcgagttccc cgcgccagcg gggataaacc gttgattata ataaccgttt atctgttcgt       60
atcgagttcc ccgcgccagc ggggataaac cgtattgacc aattcattcg ggacagttat      120
tagttcgagt tccccgcgcc agcggggata aaccg                                 155

<210> SEQ ID NO 96
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gcgccagcgg ggataaaccg tattgaccaa ttcattc                                37

<210> SEQ ID NO 97
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
cttgcccgcc tgatgaatgc tcatccgg                                          28

<210> SEQ ID NO 98
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ccggatgagc attcatcagg cgggcaag                                          28

<210> SEQ ID NO 99
<211> LENGTH: 59
<212> TYPE: DNA
<213> ORGANISM: Artificial Sequence
<220> FEATURE:

<223> OTHER INFORMATION: Description of Artificial Sequence: Synthetic
primer

<400> SEQUENCE: 99
cggtttatcc ccgctggcgc ggggaactcg atacgaacag ataaacggtt attataatc    59

<210> SEQ ID NO 100
<211> LENGTH: 153
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 100
tcgagttccc cgcgccagcg gggataaacc gttgattata ataccgtttt atctgttcgt    60
atcgagttcc ccgcgccagc ggggataaac cgttaccatt ctgttgcttt tatgtataag   120
aatcgagttc cccgcgccag cggggataaa ccg                                153

<210> SEQ ID NO 101
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 101
gcgccagcgg ggataaaccg ttaccattct gttg                               34

<210> SEQ ID NO 102
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 102
cttgcccgcc tgatgaatgc tcatccgg                                      28

<210> SEQ ID NO 103
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 103
ccggatgagc attcatcagg cgggcaag                                      28

<210> SEQ ID NO 104
<211> LENGTH: 59
<212> TYPE: DNA
<213> ORGANISM: Artificial Sequence
<220> FEATURE:
<223> OTHER INFORMATION: Description of Artificial Sequence: Synthetic
primer

<400> SEQUENCE: 104
cggtttatcc ccgctggcgc ggggaactcg atacgaacag ataaacggtt attataatc    59

<210> SEQ ID NO 105
<211> LENGTH: 153

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
tcgagttccc cgcgccagcg gggataaacc gttgattata ataaccgttt atctgttcgt    60
atcgagttcc ccgcgccagc ggggataaac cgctcgtaaa agcagtacag tgcaccgtaa   120
gatcgagttc cccgcgccag cggggataaa ccg                                153

<210> SEQ ID NO 106
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
gcgccagcgg ggataaaccg ctcgtaaaag                                     30

<210> SEQ ID NO 107
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
cttgcccgcc tgatgaatgc tcatccgg                                       28

<210> SEQ ID NO 108
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ccggatgagc attcatcagg cgggcaag                                       28

<210> SEQ ID NO 109
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
cggtttatcc ccgctggcgc ggggaactcg atacgaacag ataaacggtt attataatc    59

<210> SEQ ID NO 110
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
tcgagttccc cgcgccagcg gggataaacc gaaaagcata taatgcgtaa aagttatgaa    60
```

```
gttcgagttc ccgcgccag cggggataaa ccgtattgac caattcattc gggacagtta      120
ttagttcgag ttccccgcgc cagcggggat aaaccg                               156
```

<210> SEQ ID NO 111
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111

```
gcgccagcgg ggataaaccg tattgaccaa ttcattc                               37
```

<210> SEQ ID NO 112
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112

```
cttgcccgcc tgatgaatgc tcatccgg                                         28
```

<210> SEQ ID NO 113
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113

```
ccggatgagc attcatcagg cgggcaag                                         28
```

<210> SEQ ID NO 114
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114

```
cggtttatcc ccgctggcgc ggggaactcg aacttcataa cttttac                    47
```

<210> SEQ ID NO 115
<211> LENGTH: 154
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

```
tcgagttccc cgcgccagcg ggataaacc gaaaagcata taatgcgtaa aagttatgaa       60
gttcgagttc cccgcgccag cggggataaa ccgttaccat tctgttgctt ttatgtataa     120
gaatcgagtt ccccgcgcca gcggggataa accg                                 154
```

<210> SEQ ID NO 116
<211> LENGTH: 34
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 116
gcgccagcgg ggataaaccg ttaccattct gttg                            34

<210> SEQ ID NO 117
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
cttgcccgcc tgatgaatgc tcatccgg                                   28

<210> SEQ ID NO 118
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
ccggatgagc attcatcagg cgggcaag                                   28

<210> SEQ ID NO 119
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
cggtttatcc ccgctggcgc ggggaactcg aacttcataa cttttac              47

<210> SEQ ID NO 120
<211> LENGTH: 154
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120
tcgagttccc cgcgccagcg gggataaacc gaaaagcata taatgcgtaa aagttatgaa    60
gttcgagttc cccgcgccag cggggataaa ccgctcgtaa aagcagtaca gtgcaccgta   120
agatcgagtt ccccgcgcca gcggggataa accg                              154

<210> SEQ ID NO 121
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gcgccagcgg ggataaaccg ctcgtaaaag                                  30

<210> SEQ ID NO 122
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
cttgcccgcc tgatgaatgc tcatccgg                                         28

<210> SEQ ID NO 123
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
ccggatgagc attcatcagg cgggcaag                                         28

<210> SEQ ID NO 124
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
cggtttatcc ccgctggcgc ggggaactcg aacttcataa cttttac                    47

<210> SEQ ID NO 125
<211> LENGTH: 155
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
tcgagttccc cgcgccagcg gggataaacc gtattgacca attcattcgg gacagttatt      60
agttcgagtt ccccgcgcca gcggggataa accgttacca ttctgttgct tttatgtata     120
agaatcgagt tccccgcgcc agcggggata aaccg                                155

<210> SEQ ID NO 126
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gcgccagcgg ggataaaccg ttaccattct gttg                                  34

<210> SEQ ID NO 127
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
cttgcccgcc tgatgaatgc tcatccgg                                         28
```

<210> SEQ ID NO 128
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
ccggatgagc attcatcagg cgggcaag                                          28

<210> SEQ ID NO 129
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
cggtttatcc ccgctggcgc ggggaactcg aactaataac tgtc                        44

<210> SEQ ID NO 130
<211> LENGTH: 155
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
tcgagttccc cgcgccagcg gggataaacc gtattgacca attcattcgg gacagttatt       60
agttcgagtt ccccgcgcca gcggggataa accgctcgta aaagcagtac agtgcaccgt       120
aagatcgagt tccccgcgcc agcggggata accg                                   155

<210> SEQ ID NO 131
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gcgccagcgg ggataaaccg ctcgtaaaag                                        30

<210> SEQ ID NO 132
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
cttgcccgcc tgatgaatgc tcatccgg                                          28

<210> SEQ ID NO 133
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ccggatgagc attcatcagg cgggcaag                                            28

<210> SEQ ID NO 134
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
cggtttatcc ccgctggcgc ggggaactcg aactaataac tgtc                          44

<210> SEQ ID NO 135
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135
tcgagttccc cgcgccagcg gggataaacc gttaccattc tgttgctttt atgtataaga         60
atcgagttcc ccgcgccagc ggggataaac cgctcgtaaa agcagtacag tgcaccgtaa        120
gatcgagttc cccgcgccag cggggataaa ccg                                    153

<210> SEQ ID NO 136
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gcgccagcgg ggataaaccg ctcgtaaaag                                          30

<210> SEQ ID NO 137
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
cttgcccgcc tgatgaatgc tcatccgg                                            28

<210> SEQ ID NO 138
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ccggatgagc attcatcagg cgggcaag                                            28

<210> SEQ ID NO 139
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 139
cggtttatcc ccgctggcgc ggggaactcg attcttatac ataaaagc                48

<210> SEQ ID NO 140
<211> LENGTH: 217
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
tcgagttccc cgcgccagcg gggataaacc gttgattata ataaccgttt atctgttcgt    60
atcgagttcc ccgcgccagc gggataaaac cgaaaagcat ataatgcgta aaagttatga   120
agttcgagtt ccccgcgcca gcggggataa accgtattga ccaattcatt cgggacagtt   180
attagttcga gttccccgcg ccagcgggga taaaccg                            217

<210> SEQ ID NO 141
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
gcgccagcgg ggataaaccg tattgaccaa ttcattc                             37

<210> SEQ ID NO 142
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
cttgcccgcc tgatgaatgc tcatccgg                                       28

<210> SEQ ID NO 143
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
ccggatgagc attcatcagg cgggcaag                                       28

<210> SEQ ID NO 144
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
cggtttatcc ccgctggcgc ggggaactcg aacttcataa cttttac                  47

<210> SEQ ID NO 145

```
<211> LENGTH: 217
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
tcgagttccc cgcgccagcg gggataaacc gaaaagcata taatgcgtaa aagttatgaa      60
gttcgagttc cccgcgccag cggggataaa ccgtattgac caattcattc gggacagtta     120
ttagttcgag ttccccgcgc cagcggggat aaaccggttt ttgtaatttt acaggcaacc     180
ttttattcga gttccccgcg ccagcgggga taaaccg                              217

<210> SEQ ID NO 146
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
gcgccagcgg ggataaaccg gttttttgtaa ttttacaggc                           40

<210> SEQ ID NO 147
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
cttgcccgcc tgatgaatgc tcatccgg                                         28

<210> SEQ ID NO 148
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ccggatgagc attcatcagg cgggcaag                                         28

<210> SEQ ID NO 149
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cggtttatcc ccgctggcgc ggggaactcg aactaataac tgtc                       44

<210> SEQ ID NO 150
<211> LENGTH: 217
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150
```

```
tcgagttccc cgcgccagcg gggataaacc gaaaagcata taatgcgtaa aagttatgaa      60
gttcgagttc cccgcgccag cggggataaa ccgtattgac caattcattc gggacagtta     120
ttagttcgag ttccccgcgc cagcggggat aaaccgttac cattctgttg cttttatgta     180
taagaatcga gttccccgcg ccagcgggga taaaccg                              217
```

<210> SEQ ID NO 151  
<211> LENGTH: 34  
<212> TYPE: DNA  
<213> ORGANISM: Artificial Sequence  
<220> FEATURE:  
<223> OTHER INFORMATION: Description of Artificial Sequence: Synthetic primer

<400> SEQUENCE: 151

```
gcgccagcgg ggataaaccg ttaccattct gttg                                  34
```

<210> SEQ ID NO 152  
<211> LENGTH: 28  
<212> TYPE: DNA  
<213> ORGANISM: Artificial Sequence  
<220> FEATURE:  
<223> OTHER INFORMATION: Description of Artificial Sequence: Synthetic primer

<400> SEQUENCE: 152

```
cttgcccgcc tgatgaatgc tcatccgg                                         28
```

<210> SEQ ID NO 153  
<211> LENGTH: 28  
<212> TYPE: DNA  
<213> ORGANISM: Artificial Sequence  
<220> FEATURE:  
<223> OTHER INFORMATION: Description of Artificial Sequence: Synthetic primer

<400> SEQUENCE: 153

```
ccggatgagc attcatcagg cgggcaag                                         28
```

<210> SEQ ID NO 154  
<211> LENGTH: 44  
<212> TYPE: DNA  
<213> ORGANISM: Artificial Sequence  
<220> FEATURE:  
<223> OTHER INFORMATION: Description of Artificial Sequence: Synthetic primer

<400> SEQUENCE: 154

```
cggtttatcc ccgctggcgc ggggaactcg aactaataac tgtc                       44
```

<210> SEQ ID NO 155  
<211> LENGTH: 217  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 155

```
tcgagttccc cgcgccagcg gggataaacc gaaaagcata taatgcgtaa aagttatgaa      60
gttcgagttc cccgcgccag cggggataaa ccgtattgac caattcattc gggacagtta     120
ttagttcgag ttccccgcgc cagcggggat aaaccgctcg taaaagcagt acagtgcacc     180
gtaagatcga gttccccgcg ccagcgggga taaaccg                              217
```

<210> SEQ ID NO 156
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
gcgccagcgg ggataaaccg ctcgtaaaag                                         30

<210> SEQ ID NO 157
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
cttgcccgcc tgatgaatgc tcatccgg                                           28

<210> SEQ ID NO 158
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
ccggatgagc attcatcagg cgggcaag                                           28

<210> SEQ ID NO 159
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
cggtttatcc ccgctggcgc ggggaactcg aactaataac tgtc                         44

<210> SEQ ID NO 160
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160
tcgagttccc cgcgccagcg ggataaaacc gttgattata ataaccgttt atctgttcgt        60
atcgagttcc ccgcgccagc ggggataaac cgaaaagcat ataatgcgta aaagttatga       120
agttcgagtt ccccgcgcca gcggggataa accgtattga ccaattcatt cgggacagtt       180
attagttcga gttccccgcg ccagcgggga taaaccggtt tttgtaattt tacaggcaac       240
cttttattcg agttccccgc gccagcgggg ataaaccg                              278

<210> SEQ ID NO 161
<211> LENGTH: 40
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 161
gcgccagcgg ggataaaccg gttttttgtaa ttttacaggc                              40

<210> SEQ ID NO 162
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
cttgcccgcc tgatgaatgc tcatccgg                                           28

<210> SEQ ID NO 163
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
ccggatgagc attcatcagg cgggcaag                                           28

<210> SEQ ID NO 164
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
cggtttatcc ccgctggcgc ggggaactcg aactaataac tgtc                         44

<210> SEQ ID NO 165
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 165
tcgagttccc cgcgccagcg ggataaaacc gttgattata ataaccgttt atctgttcgt        60
atcgagttcc ccgcgccagc ggggataaac cgaaaagcat ataatgcgta aaagttatga       120
agttcgagtt ccccgcgcca gcggggataa accgtattga ccaattcatt cgggacagtt       180
attagttcga gttccccgcg ccagcgggga taaaccgtta ccattctgtt gcttttatgt       240
ataagaatcg agttccccgc gccagcgggg ataaaccg                               278

<210> SEQ ID NO 166
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
```
gcgccagcgg ggataaaccg tattgaccaa ttcattc                                37

<210> SEQ ID NO 167
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
cttgcccgcc tgatgaatgc tcatccgg                                         28

<210> SEQ ID NO 168
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
ccggatgagc attcatcagg cgggcaag                                         28

<210> SEQ ID NO 169
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
cggtttatcc ccgctggcgc ggggaactcg aacttcataa cttttac                    47

<210> SEQ ID NO 170
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 170
tcgagttccc cgcgccagcg gggataaacc gttgattata ataaccgttt atctgttcgt      60
atcgagttcc ccgcgccagc ggggataaac cgaaaagcat ataatgcgta aaagttatga    120
agttcgagtt ccccgcgcca gcggggataa accgtattga ccaattcatt cgggacagtt   180
attagttcga gttccccgcg ccagcgggga taaaccgctc gtaaaagcag tacagtgcac   240
cgtaagatcg agttccccgc gccagcgggg ataaaccg                            278

<210> SEQ ID NO 171
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
gcgccagcgg ggataaaccg tattgaccaa ttcattc                               37

<210> SEQ ID NO 172
<211> LENGTH: 28
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 172
cttgcccgcc tgatgaatgc tcatccgg                                          28

<210> SEQ ID NO 173
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
ccggatgagc attcatcagg cgggcaag                                          28

<210> SEQ ID NO 174
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
cggtttatcc ccgctggcgc ggggaactcg aacttcataa cttttac                     47

<210> SEQ ID NO 175
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 175
tcgagttccc cgcgccagcg gggataaacc gaaaagcata taatgcgtaa aagttatgaa       60
gttcgagttc cccgcgccag cggggataaa ccgtattgac caattcattc gggacagtta      120
ttagttcgag ttccccgcgc cagcggggat aaaccgttac cattctgttg cttttatgta      180
taagaatcga gttccccgcg ccagcgggga taaaccggtt tttgtaattt tacaggcaac      240
cttttattcg agttccccgc gccagcgggg ataaaccg                              278

<210> SEQ ID NO 176
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gcgccagcgg ggataaaccg gtttttgtaa ttttacaggc                             40

<210> SEQ ID NO 177
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
```
cttgcccgcc tgatgaatgc tcatccgg                                                28

<210> SEQ ID NO 178
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
ccggatgagc attcatcagg cgggcaag                                                28

<210> SEQ ID NO 179
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
cggtttatcc ccgctggcgc ggggaactcg attcttatac ataaaagc                          48

<210> SEQ ID NO 180
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180
tcgagttccc cgcgccagcg gggataaacc gaaaagcata taatgcgtaa aagttatgaa             60
gttcgagttc cccgcgccag cggggataaa ccgtattgac caattcattc gggacagtta            120
ttagttcgag ttccccgcgc cagcgggat aaaccgttac cattctgttg cttttatgta             180
taagaatcga gttccccgcg ccagcgggga taaaccgctc gtaaaagcag tacagtgcac            240
cgtaagatcg agttccccgc gccagcgggg ataaaccg                                    278

<210> SEQ ID NO 181
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
gcgccagcgg ggataaaccg ctcgtaaaag                                              30

<210> SEQ ID NO 182
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
cttgcccgcc tgatgaatgc tcatccgg                                                28

<210> SEQ ID NO 183
<211> LENGTH: 28

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
ccggatgagc attcatcagg cgggcaag                                           28

<210> SEQ ID NO 184
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
cggtttatcc ccgctggcgc ggggaactcg attcttatac ataaaagc                     48

<210> SEQ ID NO 185
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185
tcgagttccc cgcgccagcg gggataaacc gttgattata ataaccgttt atctgttcgt        60
atcgagttcc ccgcgccagc ggggataaac cgaaaagcat ataatgcgta aaagttatga      120
agttcgagtt ccccgcgcca gcggggataa accgtattga ccaattcatt cgggacagtt     180
attagttcga gttccccgcg ccagcgggga taaaccgtta ccattctgtt gcttttatgt     240
ataagaatcg agttccccgc gccagcgggg ataaaccggt ttttgtaatt ttacaggcaa     300 cctttttattc gagttccccg cgccagcggg gataaaccg                            339

<210> SEQ ID NO 186
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
gcgccagcgg ggataaaccg gttttgtaa ttttacaggc                               40

<210> SEQ ID NO 187
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
cttgcccgcc tgatgaatgc tcatccgg                                           28

<210> SEQ ID NO 188
<211> LENGTH: 28
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 188
ccggatgagc attcatcagg cgggcaag                                        28

<210> SEQ ID NO 189
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
cggtttatcc ccgctggcgc ggggaactcg attcttatac ataaaagc                  48

<210> SEQ ID NO 190
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 190
tcgagttccc cgcgccagcg gggataaacc gttgattata ataaccgttt atctgttcgt     60
atcgagttcc ccgcgccagc ggggataaac cgaaaagcat ataatgcgta aaagttatga   120
agttcgagtt ccccgcgcca gcggggataa accgtattga ccaattcatt cgggacagtt   180
attagttcga gttccccgcg ccagcgggga taaaccgtta ccattctgtt gcttttatgt   240
ataagaatcg agttccccgc gccagcgggg ataaaccgct cgtaaaagca gtacagtgca   300
ccgtaagatc gagttccccg cgccagcggg gataaaccg                          339

<210> SEQ ID NO 191
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
gcgccagcgg ggataaaccg ctcgtaaaag                                      30

<210> SEQ ID NO 192
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
cttgcccgcc tgatgaatgc tcatccgg                                        28

<210> SEQ ID NO 193
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
```
ccggatgagc attcatcagg cgggcaag 28

<210> SEQ ID NO 194
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
cggtttatcc ccgctggcgc ggggaactcg attcttatac ataaaagc 48

<210> SEQ ID NO 195
<211> LENGTH: 400
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 195
tcgagttccc cgcgccagcg gggataaacc gttgattata ataaccgttt atctgttcgt       60
atcgagttcc ccgcgccagc ggggataaac cgaaaagcat ataatgcgta aaagttatga      120
agttcgagtt ccccgcgcca gcggggataa accgtattga ccaattcatt cgggacagtt      180
attagttcga gttccccgcg ccagcgggga taaaccgtta ccattctgtt gcttttatgt      240
ataagaatcg agttccccgc gccagcgggg ataaaccgct cgtaaaagca gtacagtgca      300
ccgtaagatc gagttccccg cgccagcggg gataaaccgg ttttttgtaat tttacaggca    360
acctttttatt cgagttcccc gcgccagcgg ggataaaccg                          400

<210> SEQ ID NO 196
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gcgccagcgg ggataaaccg gttttttgtaa ttttacaggc 40

<210> SEQ ID NO 197
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
cttgcccgcc tgatgaatgc tcatccgg 28

<210> SEQ ID NO 198
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
ccggatgagc attcatcagg cgggcaag 28

<210> SEQ ID NO 199
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
cggtttatcc ccgctggcgc ggggaactcg atcttacggt gcactgtac                49

<210> SEQ ID NO 200
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 200
tcgagttccc cgcgccagcg gggataaacc gttaccattc tgttgctttt atgtataaga    60
atcgagttcc ccgcgccagc ggggataaac cgctcgtaaa agcagtacag tgcaccgtaa   120
gatcgagttc cccgcgccag cggggataaa ccg                                153

<210> SEQ ID NO 201
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
gcgccagcgg ggataaaccg ctcgtaaaag                                     30

<210> SEQ ID NO 202
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
cttgcccgcc tgatgaatgc tcatccgg                                       28

<210> SEQ ID NO 203
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
ccggatgagc attcatcagg cgggcaag                                       28

<210> SEQ ID NO 204
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 204
cggtttatcc ccgctggcgc ggggaactcg attcttatac ataaaagc                    48
```

COMPOSITIONS AND METHODS FOR ROBUST DYNAMIC METABOLIC CONTROL OF MEVALONATE PRODUCTION

CROSS-REFERENCE

This application is a continuation of U.S. application Ser. No. 16/487,542, filed Aug. 21, 2019, which is a National Stage Entry of PCT/US 18/19040. filed Feb. 21, 2018 which claims the benefit of U.S. Provisional Application No. 62/461,436, filed Feb. 21, 2017, which application is incorporated herein by reference in its entirety.

STATEMENT AS TO FEDERALLY SPONSORED RESEARCH

This invention was made with Government support under Federal Grant Nos. HR0011-14-C-0075 awarded by DOD/DARPA, 12043956 and N00014-16-1-2558 awarded by NAVY/ONR, and 1445726 awarded by NSF. The Government has certain rights to this invention.

REFERENCE TO A SEQUENCE LISTING

The instant application contains a Sequence Listing which has been filed electronically in ASCII format and is hereby incorporated by reference in its entirety. Said ASCII copy, created on Feb. 21, 2018, is named 52240_702_601_SL.txt and is 81,697 bytes in size.

BACKGROUND OF THE INVENTION

Biotechnology-based fermentation processes have been successfully developed to produce everything from biologics and small molecule therapies to specialty, bulk and commodity chemicals, and even next generation biofuels. These processes have made rapid advancements in recent years due to technology developments in the fields of fermentation science and synthetic biology, as well as metabolic and enzyme engineering. Despite these substantial advances, most successful examples of rational and directed engineering approaches have also greatly relied on numerous and often lengthy cycles of trial and error. The present disclosure provides a strategy that simultaneously reduces the complexity of the problem (as well as the size of the relevant design space), while also minimizing metabolic responses to environmental conditions, increasing robustness and scalability of engineered strains.

SUMMARY OF THE INVENTION

The present disclosure provides, in part, a high-throughput engineering platform that enables the rapid development of microbial production strains.

In one aspect, the present disclosure provides a cell for generating a product, wherein the cell comprises: a heterologous polynucleotide for controlled reduction of expression of an enzyme of a metabolic pathway, wherein the controlled reduction of expression of the enzyme induces a stationary phase of the cell; and a heterologous production polynucleotide for mediating controlled increase in expression of a production enzyme for generation of the product; wherein a rate of production of the product during the stationary phase is reduced less in response to a change of an environmental condition as compared to a cell lacking the enzyme.

In some embodiments, the heterologous polynucleotide reduces flux through the metabolic pathway. In some embodiments, the enzyme is selected from the group consisting of enoyl-ACP/CoA reductase, glucose-6-phosphate dehydrogenase, lipoamide dehydrogenase, citrate synthase, soluble transhydrogenase, and NADH-dependent glyceraldehyde-3-phosphate dehydrogenase. In some embodiments, the production enzyme is selected from the group consisting of NADPH-dependent alanine dehydrogenase, an alanine exporter, and NADPH-dependent glyceraldehyde-3-phosphate dehydrogenase. In some embodiments, the change of an environmental condition comprises increasing or decreasing a concentration of a sugar in a culture medium contacting the cell. In some embodiments, the sugar is glucose. In some embodiments, the change of an environmental condition comprises increasing or decreasing oxygenation of a culture medium contacting the cell. In some embodiments, the product comprises 3-hydroxypropionic acid.

In some embodiments, the product comprises an amino acid. In some aspects, the amino acid comprises alanine. In some aspects, the cell is grown in a culture, and a rate of production of the alanine by the culture is at least 0.5 g/L/hour. In some aspects, the rate of production of the alanine is at least 1.0 g/L/hour. In some aspects, the rate of production of the alanine is at least 1.5 g/L/hour. In some aspects, the rate of production of the alanine is at least 1.6 g/L/hour. In some aspects, the culture produces at least 80 g/L of the alanine. In some aspects, the culture produces at least 100 g/L of the alanine. In some aspects, the culture produces at least 120 g/L of the alanine. In some aspects, the culture produces at least 140 g/L of the alanine. In some aspects, the production polynucleotide encodes an alanine exporter. In some aspects, the alanine exporter is alaE.

In some embodiments, the product comprises mevalonic acid. In some embodiments, the cell is grown in a culture, and a rate of production of the mevalonic acid by the culture is at least 0.5 g/L/hour. In some embodiments, the rate of production of the mevalonic acid is at least 1.0 g/L/hour. In some embodiments, the rate of production of the mevalonic acid is at least 1.2 g/L/hour. In some embodiments, the rate of production of the mevalonic acid is at least 1.25 g/L/hour. In some aspects, the cell is grown in a culture, and the culture produces at least 50 g/L of the mevalonic acid. In some embodiments, the culture produces at least 70 g/L of the mevalonic acid. In some embodiments, the culture produces at least 90 g/L of the mevalonic acid. In some embodiments, the culture produces at least 95 g/L of the mevalonic acid. In some embodiments, the heterologous polynucleotide is selected from the group consisting of: a silencing polynucleotide for repressing transcription of a gene encoding the enzyme; and a degradation polynucleotide for mediating cellular degradation of the enzyme.

In some aspects, the heterologous polynucleotide comprises a silencing polynucleotide, and the silencing polynucleotide comprises a guide RNA (gRNA) comprising a gRNA sequence that recognizes a promoter of a gene encoding the enzyme. In some aspects, the heterologous polynucleotide encodes a CRISPR enzyme, and the CRISPR enzyme specifically binds to the promoter sequence when bound to the gRNA. In some aspects, the CRISPR enzyme is catalytically inactive. In some aspects, the heterologous polynucleotide comprises a degradation polynucleotide, wherein the degradation polynucleotide comprises a sequence encoding a degradation tag, wherein the degradation tag mediates degradation of the enzyme. In some embodiments, expression of the heterologous polynucleotide is regulated by phosphate availability in the cell. In some embodiments, expression of the production polynucleotide is regulated by phosphate availability in the cell. In some embodiments, the cell is an *E. coli* cell.

In another aspect, disclosed herein is a method comprising: culturing independently a plurality of strains of a cell, wherein each strain comprises (i) a heterologous polynucleotide for mediating controlled reduction of expression of an enzyme of a metabolic pathway, wherein the controlled reduction of expression of the enzyme induces a stationary phase of the cell; and (ii) a heterologous production polynucleotide for mediating controlled increase in expression of a production enzyme for generation of the product; wherein each strain of the plurality of strains differs from another strain in a sequence of at least one of the heterologous polynucleotide or the heterologous production polynucleotide; growing the plurality of strains to stationary phase; and selecting a strain of the plurality of strains based on a level of the product produced by the selected strain during the stationary phase.

In some embodiments, the method comprises determining the level of the product. In some embodiments, the method comprises growing the selected strain. In some embodiments, the selected strain is grown in a bioreactor. In some embodiments, a culture medium comprising the selected strain has a volume of at least 500 ml. In some embodiments, the culture medium has a volume of at least 1 L. In some embodiments, the heterologous polynucleotide is selected from the group consisting of: a silencing polynucleotide for repressing transcription of a gene encoding the enzyme; and a degradation polynucleotide for mediating cellular degradation of the enzyme. In some embodiments, a first and second strain of the plurality of strains comprises a silencing polynucleotide. In some embodiments, the silencing polynucleotide comprises a guide RNA (gRNA) comprising a gRNA sequence that recognizes a promoter sequence of a gene encoding the enzyme. In some embodiments, the gRNA sequence differs between the first and second strains. In some embodiments, the first and second strain of the plurality of strains comprise a degradation polynucleotide. In some embodiments, the degradation polynucleotide differs between the first and second strains. In some embodiments, the enzyme is selected from the group consisting of enoyl-ACP/CoA reductase, glucose-6-phosphate dehydrogenase, lipoamide dehydrogenase, citrate synthase, soluble transhydrogenase, and NADH-dependent glyceraldehyde-3-phosphate dehydrogenase. In some embodiments, the production enzyme is selected from the group consisting of NADPH-dependent alanine dehydrogenase, an alanine exporter, and NADPH-dependent glyceraldehyde-3-phosphate dehydrogenase. In some embodiments, the product is selected from the group consisting of mevalonic acid, 3-hydroxypropionic acid, and an amino acid.

In some embodiments, the product is an amino acid and the amino acid is alanine. In some embodiments, the cell of the selected strain a rate of production of the product during the stationary phase is reduced less in response to a change of an environmental condition as compared to a cell lacking the heterologous polynucleotide. In some embodiments, the change of an environmental condition comprises a change in concentration of a sugar of a culture medium contacting the cell. In some embodiments, the change of an environmental condition comprises a change in oxygenation of a culture medium contacting the cell.

In another aspect, disclosed herein is a method of generating a cellular product comprising: culturing a heterologous cell in a culture medium, wherein the heterologous cell comprises: (i) a heterologous polynucleotide for mediating controlled reduction of expression of an enzyme of a metabolic pathway, wherein the controlled reduction of expression of the enzyme induces a stationary phase of the cell; and (ii) a heterologous production polynucleotide for mediating controlled increase in expression of a production enzyme for generation of the product; wherein a rate of production of the product during the stationary phase is reduced less in response to a change of an environmental condition as compared to a cell lacking the enzyme.

In one embodiment, the method further comprises changing the environmental condition. In one embodiment, the environmental condition comprises a concentration of a sugar of the culture medium, and changing the environmental condition comprises increasing or decreasing the concentration. In some embodiments, the sugar is glucose. In some embodiments, the environmental condition comprises an oxygen concentration of the culture medium, and changing the environmental condition comprises increasing or decreasing the oxygen concentration. In some embodiments, the culturing is performed in a bioreactor. In some embodiments, the culture medium has a volume of at least 500 ml. In some embodiments, the culture medium has a volume of at least 1 L. In some embodiments, the product comprises 3-hydroxypropionic acid. In some embodiments, the product comprises an amino acid. In some embodiments, the amino acid comprises alanine. In some embodiments, the rate of production of the alanine is at least 0.5 g/L/hour. In some embodiments, the rate of production of the alanine is at least 1.0 g/L/hour. In some embodiments, the rate of production of the alanine is at least 1.5 g/L/hour. In some embodiments, the rate of production of the alanine is at least 1.6 g/L/hour. In some embodiments, the production polynucleotide encodes an alanine exporter. In some embodiments, the alanine exporter is alaE.

In some embodiments, the product comprises mevalonic acid. In some embodiments, the rate of production of the mevalonic acid is at least 0.5 g/L/hour. In some embodiments, the rate of production of the mevalonic acid is at least 1.0 g/L/hour. In some embodiments, the rate of production of the mevalonic acid is at least 1.2 g/L/hour. In some embodiments, the rate of production of the mevalonic acid is at least 1.25 g/L/hour. In some embodiments, the heterologous polynucleotide is selected from the group consisting of: a silencing polynucleotide for repressing transcription of a gene encoding the enzyme; and a degradation polynucleotide for mediating cellular degradation of the enzyme. In some embodiments, the heterologous polynucleotide comprises a silencing polynucleotide, and the silencing polynucleotide comprises a guide RNA (gRNA) comprising a gRNA sequence that recognizes a promoter sequence of a gene encoding the enzyme. In some embodiments, the heterologous polynucleotide encodes a CRISPR enzyme, wherein the CRISPR enzyme specifically binds to the promoter sequence when bound to the gRNA. In some embodiments, the CRISPR enzyme is catalytically inactive. In some embodiments, the heterologous polynucleotide comprises a degradation polynucleotide, wherein the degradation polynucleotide comprises a sequence encoding a degradation tag, wherein the degradation tag mediates degradation of the enzyme. In some embodiments, the expression of the heterologous polynucleotide is regulated by phosphate availability in the cell. In some embodiments, the expression of the production polynucleotide is regulated by phosphate availability in the cell. In some embodiments, the cell is an *E. coli* cell.

In another aspect, disclosed herein is a cell for production of alanine, wherein the cell comprises: (i) a heterologous polynucleotide for controlled reduction of expression of an enzyme of a metabolic pathway, wherein the enzyme is selected from the group consisting of enoyl-ACP/CoA reductase, glucose-6-phosphate dehydrogenase, lipoamide dehydrogenase (lpd), citrate synthase (gltA), soluble transhydrogenase, and NADH-dependent glyceraldehyde-3-phosphate dehydrogenase; and (ii) an alanine exporter, wherein the alanine exporter is expressed at increased levels as compared to a wildtype cell.

In some embodiments, the alanine exporter is encoded by an alaE gene. In some embodiments, the controlled reduction of expression of the enzyme induces a stationary phase of the cell. In some embodiments, the cell further comprises a heterologous production polynucleotide for controlled increase in expression of a production enzyme for generation of the alanine. In some embodiments, the production enzyme is selected from the group consisting of NADPH-dependent alanine dehydrogenase and NADPH-dependent glyceraldehyde-3-phosphate dehydrogenase. In some embodiments, the heterologous polynucleotide is selected from the group consisting of: a silencing polynucleotide for mediating transcriptional repression of a gene encoding the enzyme; and a degradation polynucleotide for mediating cellular degradation of the enzyme. In some embodiments, the heterologous polynucleotide comprises a silencing polynucleotide, and the silencing polynucleotide comprises a guide RNA (gRNA) comprising a gRNA sequence that recognizes a promoter sequence of a gene encoding the enzyme. In some embodiments, the polynucleotide further encodes a CRISPR enzyme, wherein the CRISPR enzyme specifically binds to the promoter sequence when bound to the gRNA. In some embodiments, the CRISPR enzyme is catalytically inactive. In some embodiments, the heterologous polynucleotide comprises a degradation polynucleotide, wherein the degradation polynucleotide comprises a sequence encoding a degradation tag, wherein the degradation tag mediates degradation of the enzyme. In some embodiments, the polynucleotide is regulated by phosphate availability in the cell. In some embodiments, the production polynucleotide is regulated by phosphate availability in the cell. In some embodiments, the cell is an *E. coli* cell.

In some embodiments, a culture comprises the cell. In some embodiments, a rate of production of the alanine by the culture is at least 0.5 g/L/hour. In some embodiments, a rate of production of the alanine by the culture is at least 1.0 g/L/hour. In some embodiments, a rate of production of the alanine by the culture is at least 1.5 g/L/hour. In some embodiments, a rate of production of the alanine by the culture is at least 1.6 g/L/hour. In some embodiments, the culture produces at least 100 g/L of the alanine. In some embodiments, the culture produces at least 120 g/L of the alanine. In some embodiments, the culture produces at least 140 g/L of the alanine.

In some aspects, disclosed herein is a method of production of alanine comprising growing in a culture medium a cell comprising (i) a heterologous polynucleotide for controlled reduction of expression of a enzyme of a metabolic pathway, wherein the enzyme is selected from the group consisting of enoyl-ACP/CoA reductase, glucose-6-phosphate dehydrogenase, lipoamide dehydrogenase, citrate synthase, soluble transhydrogenase, and NADH-dependent glyceraldehyde-3-phosphate dehydrogenase; and (ii) an alanine exporter, wherein the alanine exporter is expressed at increased levels as compared to a wildtype cell.

In some embodiments, the controlled reduction of expression of the enzyme induces a stationary phase of the cell. In some embodiments, the method further comprises decreasing an oxygenation level or a sugar concentration of the culture medium during the stationary phase, wherein a rate of production of the cellular product is reduced less in response to the decreasing as compared to a cell lacking the heterologous polynucleotide. In some embodiments, the sugar is glucose. In some embodiments, the alanine exporter is encoded by an alaE gene. In some embodiments, the cell further comprises a heterologous production polynucleotide for controlled increase in expression of a production enzyme for generation of the alanine. In some embodiments, the production enzyme is selected from the group consisting of: NADPH-dependent alanine dehydrogenase and NADPH-dependent glyceraldehyde-3-phosphate dehydrogenase. In some embodiments, the heterologous polynucleotide is selected from the group consisting of: a silencing polynucleotide for mediating transcriptional repression of a gene encoding the enzyme; and a degradation polynucleotide for mediating cellular degradation of the enzyme. In some embodiments, the heterologous polynucleotide comprises a silencing polynucleotide, and the silencing polynucleotide comprises a guide RNA (gRNA) comprising a gRNA sequence that recognizes a promoter sequence of a gene encoding the enzyme. In some embodiments, the heterologous polynucleotide encodes a CRISPR enzyme, wherein the CRISPR enzyme specifically binds to the promoter sequence when bound to the gRNA. In some embodiments, the CRISPR enzyme is catalytically inactive. In some embodiments, the heterologous polynucleotide comprises a degradation polynucleotide, wherein the degradation polynucleotide comprises a sequence encoding a degradation tag, wherein the degradation tag mediates degradation of the enzyme.

In some embodiments, the expression of the heterologous polynucleotide is regulated by phosphate availability in the cell. In some embodiments, the production polynucleotide is regulated by phosphate availability in the cell. In some embodiments, the cell is an *E. coli* cell. In some embodiments, a rate of production of the alanine is at least 0.5 g/L/hour. In some embodiments, a rate of production of the alanine is at least 1.0 g/L/hour. In some embodiments, a rate of production of the alanine is at least 1.5 g/L/hour. In some embodiments, a rate of production of the alanine is at least 1.6 g/L/hour.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 3A-K depict an example of alanine production in *E. coli* utilizing 2-stage dynamic control.

FIGS. 4A-F depict example robustness comparison between 2-stage and growth associated approaches.

DETAILED DESCRIPTION OF THE INVENTION

Definitions

Figure 1A:
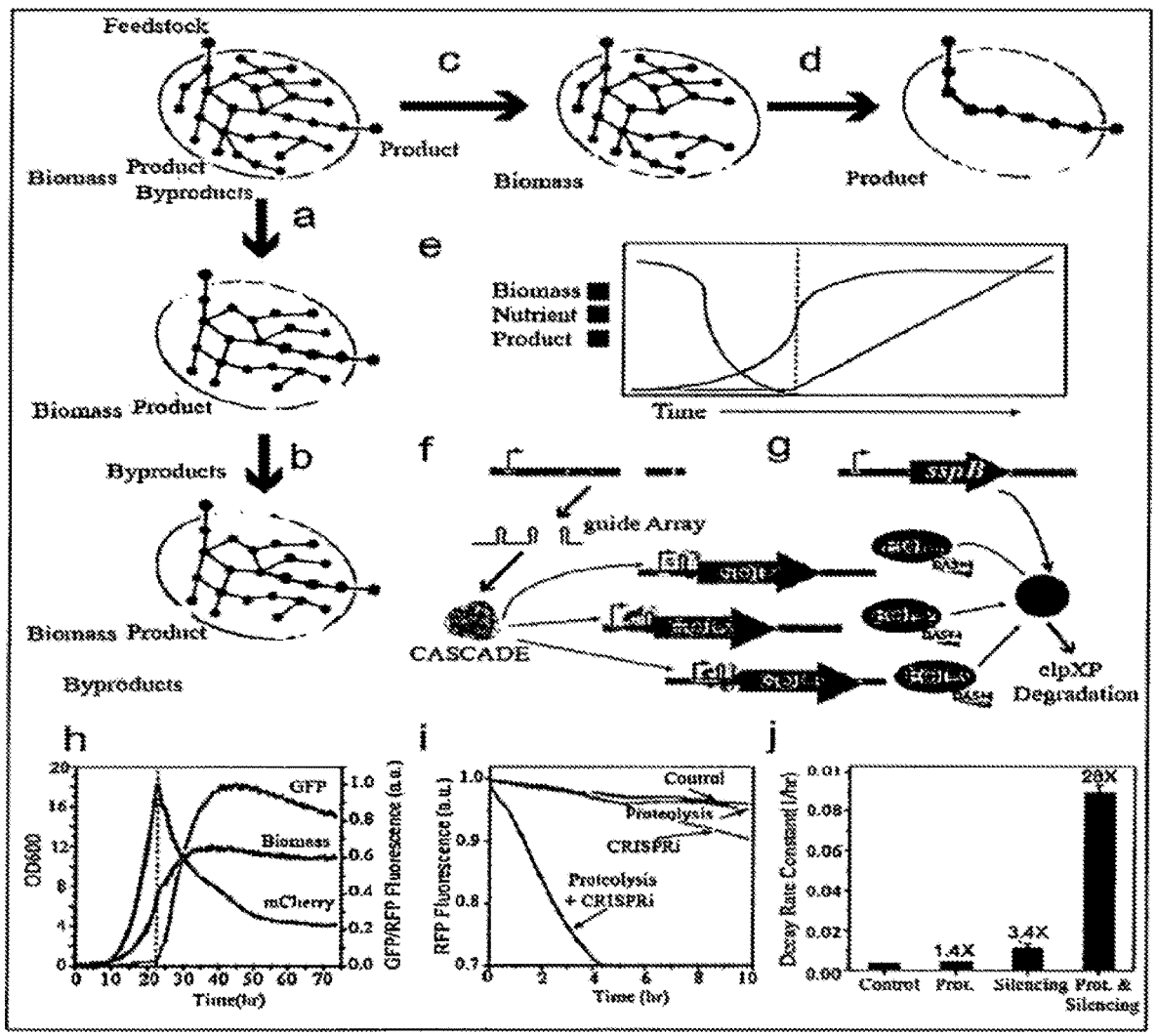
FIG. 1A depicts an overview of dynamic metabolic control in 2-stage fermentations.

As used in the specification and the claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "microorganism" includes a single microorganism as well as a plurality of microorganisms; and the like.

As used herein, "reduced enzymatic activity," "reducing enzymatic activity," and the like is meant to indicate that a microorganism cell's, or an isolated enzyme, exhibits a lower level of activity than that measured in a comparable cell of the same species or its native enzyme. That is, enzymatic conversion of the indicated substrate(s) to indicated product(s) under known standard conditions for that enzyme is at least 10, at least 20, at least 30, at least 40, at least 50, at least 60, at least 70, at least 80, or at least 90 percent less than the enzymatic activity for the same biochemical conversion by a native (non-modified) enzyme under a standard specified condition. This term also can include elimination of that enzymatic activity. A cell having reduced enzymatic activity of an enzyme can be identified using any method known in the art. For example, enzyme activity assays can be used to identify cells having reduced enzyme activity. See, for example, *Enzyme Nomenclature*, Academic Press, Inc., New York 2007.

The term "heterologous DNA," "heterologous nucleic acid sequence," and the like as used herein refers to a nucleic acid sequence wherein at least one of the following is true: (a) the sequence of nucleic acids foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid, such as a nonnative promoter driving gene expression.

The term "synthetic metabolic valve," and the like as used herein refers to either the use of controlled proteolysis, gene silencing or the combination of both proteolysis and gene silencing to alter metabolic fluxes.

The term "heterologous" is intended to include the term "exogenous" as the latter term is generally used in the art. With reference to the host microorganism's genome prior to the introduction of a heterologous nucleic acid sequence, the nucleic acid sequence that codes for the enzyme is heterologous (whether or not the heterologous nucleic acid sequence is introduced into that genome).

As used herein, the term "gene disruption," or grammatical equivalents thereof (and including "to disrupt enzymatic function," "disruption of enzymatic function," and the like), is intended to mean a genetic modification to a microorganism that renders the encoded gene product as having a reduced polypeptide activity compared with polypeptide activity in or from a microorganism cell not so modified. The genetic modification can be, for example, deletion of the entire gene, deletion or other modification of a regulatory sequence required for transcription or translation, deletion of a portion of the gene which results in a truncated gene product (e.g., enzyme) or by any of various mutation strategies that reduces activity (including reducing activities to no detectable activity level) the encoded gene product. A disruption may broadly include a deletion of all or part of the nucleic acid sequence encoding the enzyme, and also includes, but is not limited to other types of genetic modifications, e.g., introduction of stop codons, frame shift mutations, introduction or removal of portions of the gene, and introduction of a degradation signal, those genetic modifications affecting mRNA transcription levels and/or stability, and altering the promoter or repressor upstream of the gene encoding the enzyme.

Bio-production or fermentation, as used herein, may be aerobic, microaerobic, or anaerobic.

When the genetic modification of a gene product, e.g., an enzyme, is referred to herein, including the claims, it is understood that the genetic modification is of a nucleic acid sequence, such as or including the gene, that normally encodes the stated gene product, e.g., the enzyme.

As used herein, the term "metabolic flux" and the like refers to changes in metabolism that lead to changes in product and/or byproduct formation, including production rates, production titers and production yields from a given substrate.

Species and other phylogenic identifications are according to the classification known to a person skilled in the art of microbiology.

Enzymes are listed here within, with reference to a Universal Protein Resource (Uniprot) identification number, which would be well known to one skilled in the art (Uniprot is maintained by and available through the UniProt Consortium).

Where methods and steps described herein indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

The meaning of abbreviations is as follows: "C" means Celsius or degrees Celsius, as is clear from its usage, DCW means dry cell weight, "s" means second(s), "min" means minute(s), "h," "hr," or "hrs" means hour(s), "psi" means pounds per square inch, "nm" means nanometers, "d" means day(s), "µL" or "uL" or "ul" means microliter(s), "mL" means milliliter(s), "L" means liter(s), "mm" means millimeter(s), "nm" means nanometers, "mM" means millimolar, "µM" or "uM" means micromolar, "M" means molar, "mmol" means millimole(s), "µmol" or "uMol" means micromole(s), "g" means gram(s), "µg" or "ug" means microgram(s) and "ng" means nanogram(s), "PCR" means polymerase chain reaction, "OD" means optical density, "OD600" means the optical density measured at a photon wavelength of 600 nm, "kDa" means kilodaltons, "g" means the gravitation constant, "bp" means base pair(s), "kbp" means kilobase pair(s), "w/v" means weight/volume percent, "% v/v" means volume/volume percent, "IPTG" means isopropyl-µ-D-thiogalactopyranoiside, "aTc" means anhydrotetracycline, "RBS" means ribosome binding site, "rpm" means revolutions per minute, "HPLC" means high performance liquid chromatography, and "GC" means gas chromatography.

Overview

Provided herein is a high-throughput metabolic engineering platform enabling the rapid optimization of microbial production strains. The platform, which bridges a gap between current in vivo and in vitro bio-production approaches, relies on dynamic minimization of the active metabolic network. Dynamic metabolic network minimization can be accomplished using combinations of CRISPR interference and controlled proteolysis to reduce the activity of multiple enzymes in essential central metabolism. Minimization can be implemented in the context of standardized 2-stage bio-processes. This approach not only can result in a design space with greatly reduced complexity, but also in increased metabolic fluxes and production rates as well as in strains which are robust to environmental conditions. Robustness can lead to predictable scalability from high-throughput small-scale screens, or "micro-fermentations", to fully instrumented bioreactors. Predictive high-throughput approaches may be critical for metabolic engineering programs to truly take advantage of the rapidly increasing throughput and decreasing costs of synthetic biology. The examples provided herein have not only demonstrated proof of principle for this approach in the common industrial microbe: E. coli, and has validated this approach with the rapid optimization of E. coli strains producing two important industrial chemicals: alanine and mevalonic acid, at commercially meaningful rates, titers (147 g/L and 97 g/L, respectively), and yields.

Also provided herein are systems and methods to rapidly optimize a microorganism for chemical productions in a high-throughput fashion.

Also provided herein are microorganisms that can be used with the disclosed platform and/or methods for chemical productions.

Synthetic Metabolic Valves (SMVs)

The current disclosure describes the construction of synthetic metabolic valves (SMVs) comprising one or more or a combination of the following: controlled gene silencing and controlled proteolysis. It is appreciated that one well skilled in the art is aware of several methodologies for gene silencing and controlled proteolysis.

The development of platform microbial strains that utilize SMVs can decouple growth from product formation. These strains enable the dynamic control of metabolic pathways, including those that when altered have negative effects on microorganism growth. Dynamic control over metabolism is accomplished via a combination of methodologies including but not limited to transcriptional silencing and controlled enzyme proteolysis. These microbial strains are utilized in a multi-stage bioprocess encompassing as least two stages, the first stage in which microorganisms are grown and metabolism can be optimized for microbial growth and at least one other stage in which growth can be slowed or stopped, and dynamic changes can be made to metabolism to improve production of desired product, such as a chemical or fuel. The transition of growing cultures between stages and the manipulation of metabolic fluxes can be controlled by artificial chemical inducers or preferably by controlling the level of key limiting nutrients. In addition, genetic modifications may be made to provide metabolic pathways for the biosynthesis of one or more chemical or fuel products. Also, genetic modifications may be made to enable the utilization of a variety of carbon feedstocks including but not limited sugars such as glucose, sucrose, xylose, arabinose, mannose, and lactose, oils, carbon dioxide, carbon monoxide, methane, methanol and formaldehyde.

This approach allows for simpler models of metabolic fluxes and physiological demands during a production phase, turning a growing cell into a stationary phase biocatalyst. These synthetic metabolic valves can be used to turn off essential genes and redirect carbon, electrons and energy flux to product formation in a multi-stage fermentation process. One or more of the following enables these synthetic valves: 1) transcriptional gene silencing or repression technologies in combination with 2) inducible enzyme degradation and 3) nutrient limitation to induce a stationary or non-dividing cellular state. SMVs are generalizable to any pathway and microbial host. These synthetic metabolic valves allow for novel rapid metabolic engineering strategies useful for the production of renewable chemicals and fuels and any product that can be produced via whole cell catalysis.

In various cases, one SMV can refer to the manipulation of one gene (or its protein product). The manipulation can be controlled silencing of the gene and/or controlled degradation of its protein product. In certain cases, combination of SMVs can lead to improved production in yields, rate and/or robustness, which includes manipulation of two genes (or their protein products). In some cases, an engineered microorganism comprises at least one SMV. In some cases, an engineered microorganism comprises more than one SMV. In some cases, an engineered microorganism comprises two, three, four, five, six, seven, eight, nine, or ten, or more SMVs.

Method and Systems for Bio-Production

Provided herein are methods or systems for robust large scale production of molecules from biologics and small molecule therapeutics to specialty, bulk and commodity chemicals, and biofuels. The methods or systems provided herein comprise using engineered microorganism which comprises a limited set of metabolic enzymes. In some embodiments, the engineered microorganism comprises at least one metabolic enzyme that has reduced level or activity. In some embodiments, the engineered microorganism comprises two, three, four, five, six, seven, eight, nine, or ten, or more metabolic enzymes that have reduced level or activity. The methods and systems provided herein can reduce metabolic responses to environmental conditions and can be easily transferred from small scale (e.g. mgs) production to large scale (e.g. kgs) production. The methods and systems provided herein can reduce the time and costs associated with transitioning from small scale (e.g. mgs) to large scale (e.g. kgs) production.

Within the scope of the current disclosure are genetically modified microorganism, wherein the microorganism is capable of producing a product derived from any key metabolic intermediate including but not limited to malonyl-CoA, pyruvate, oxaloacetate, erthyrose-4-phosphate, xylulose-5-phosphate, alpha-ketoglutarate and citrate at a specific rate selected from the rates of greater than 0.05 g/gDCW-hr, 0.08 g/gDCW-hr, greater than 0.1 g/gDCW-hr, greater than 0.13 g/gDCW-hr, greater than 0.15 g/gDCW-hr, greater than 0.175 g/gDCW-hr, greater than 0.2 g/gDCW-hr, greater than 0.25 g/gDCW-hr, greater than 0.3 g/gDCW-hr, greater than 0.35 g/gDCW-hr, greater than 0.4 g/gDCW-hr, greater than 0.45 g/gDCW-hr, or greater than 0.5 g/gDCW-hr.

In various embodiments, the invention includes a culture system comprising a carbon source in an aqueous medium and a genetically modified microorganism, wherein said genetically modified organism is present in an amount selected from greater than 0.05 gDCW/L, 0.1 gDCW/L, greater than 1 gDCW/L, greater than 5 gDCW/L, greater than 10 gDCW/L, greater than 15 gDCW/L or greater than 20 gDCW/L, such as when the volume of the aqueous medium is selected from greater than 5 mL, greater than 100 mL, greater than 0.5 L, greater than 1 L, greater than 2 L, greater than 10 L, greater than 250 L, greater than 1000 L, greater than 10,000 L, greater than 50,000 L, greater than 100,000 L or greater than 200,000 L, and such as when the volume of the aqueous medium is greater than 250 L and contained within a steel vessel.

Carbon Sources

Bio-production media, which is used in the present invention with recombinant microorganisms must contain suitable carbon sources or substrates for both growth and production stages. Suitable substrates may include, but are not limited to glucose, sucrose, xylose, mannose, arabinose, oils, carbon dioxide, carbon monoxide, methane, methanol, formaldehyde and glycerol. It is contemplated that all of the above mentioned carbon substrates and mixtures thereof are suitable in the present invention as a carbon source(s).

Microorganisms

Features as described and claimed herein may be provided in a microorganism selected from the listing herein, or another suitable microorganism, that also comprises one or more natural, introduced, or enhanced product bio-production pathways. Thus, in some embodiments the microorganism(s) comprise an endogenous product production pathway (which may, in some such embodiments, be enhanced), whereas in other embodiments the microorganism does not comprise an endogenous product production pathway.

The examples describe specific modifications and evaluations to certain bacterial and fungal microorganisms. The scope of the invention is not meant to be limited to such species, but to be generally applicable to a wide range of suitable microorganisms.

Suitable host cells or host microorganisms for bio-production can be either prokaryotic or eukaryotic. Suitable host cells or host microorganisms can be bacteria such as *Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces,* and *Pseudomonas*. In some embodiments, a host cell or an engineered cell is *E. coli*. In some embodiments, a host cell or an engineered cell is *S. cerevisiae*.

In certain aspects, provided herein is a microorganism genetically modified to comprise: a production pathway comprising at least one enzyme for the biosynthesis of a product, and a combination of multiple synthetic metabolic valves to controllably reduce or eliminate flux through multiple metabolic pathways. In some embodiments, each of the multiple synthetic metabolic valves comprises one or more genes for (i) controlled silencing of gene expression of at least one gene or (ii) the controlled proteolytic inactivation of at least one protein. In some embodiments, a rate of the biosynthesis of the product is increased in a productive stationary phase upon a depletion of a nutrient, wherein the depletion of the nutrient induces the multiple synthetic metabolic valves. In some cases, the controlled silencing of gene expression is accomplished by RNA interference, CRISPR interference or transcriptional repression. In some cases, the controlled proteolytic inactivation is accomplished by protein cleavage by a specific protease or targeted degradation by specific peptide tags. In some cases, the nutrient is phosphate, nitrogen, sulfur, magnesium, or a combination thereof.

In certain aspects, provided herein is a genetically modified microorganism comprising: a production pathway comprising at least one enzyme for the biosynthesis of a product from one of the following metabolites: pyruvate, acetolactate, acetyl-CoA, acetoacetyl-CoA or malonyl-CoA; and a combination of multiple synthetic metabolic valves, wherein each of the multiple synthetic metabolic valves comprises one of a fabI, gltA, lpd, zwf or udhA gene for (i) controlled silencing of gene expression of a corresponding one of said fabI, gltA, lpd, zwf or udhA genes or (ii) controlled proteolytic inactivation of a protein encoded by a corresponding one of said fabI, gltA, lpd, zwf or udhA genes. In some embodiments, a rate of the biosynthesis of the product is increased in a productive stationary phase upon a depletion of a nutrient, wherein the depletion of the nutrient induces the multiple synthetic metabolic valves. In some embodiments, the product is alanine or a derivative thereof. In some embodiments, the product is mevalonate or a derivative thereof. In some embodiments, the product is malonic acid or a derivative thereof. In some embodiments, the nutrient is phosphate, nitrogen, sulfur, magnesium, or a combination thereof.

In certain aspects, provided herein is a genetically modified microorganism comprising: a production pathway to produce alanine from pyruvate; and a combination of multiple synthetic metabolic valves, wherein each of the multiple synthetic metabolic valves comprises one of a fabI, gltA, lpd, zwf or udhA gene for (i) controlled silencing of gene expression of a corresponding one of said fabI, gltA, lpd, zwf or udhA genes or (ii) controlled proteolytic inactivation of a protein encoded by one of said fabI, gltA, lpd, zwf or udhA genes. In some embodiments, a rate of the biosynthesis of alanine is increased in a productive stationary phase upon a depletion of a nutrient, wherein the depletion of the nutrient induces the multiple synthetic metabolic valves. In some embodiments, the nutrient is phosphate, nitrogen, sulfur, magnesium, or a combination thereof.

In some cases, a genetically modified microorganism is a heterologous cell. In some cases, provided herein is a heterologous cell for generating a product. In some cases, a heterologous cell comprises an engineered valve polynucleotide for mediating controlled reduction of expression of a valve enzyme acting in a metabolic pathway. In certain cases, a controlled reduction of expression of a valve enzyme reduces flux through a metabolic pathway, wherein the controlled reduction of expression of the valve enzyme induces a stationary phase of the heterologous cell. In some cases, a heterologous cell further comprises an engineered production polynucleotide for mediating controlled increase in expression of a production enzyme for generation of the product. In some situations, a heterologous cell comprises an engineered valve polynucleotide for mediating controlled reduction of expression of a valve enzyme acting in a metabolic pathway, wherein a rate of production of a product during a stationary phase is reduced less in response to a change of an environmental condition as compared to a cell lacking the controlled reduction of expression of the valve enzyme.

In some cases, provided herein is a heterologous cell for generating a product, wherein said cell comprises: an engineered valve polynucleotide for mediating controlled reduction of expression of a valve enzyme acting in a metabolic pathway, wherein said controlled reduction of expression of said valve enzyme reduces flux through said metabolic pathway, wherein said controlled reduction of expression of said valve enzyme induces a stationary phase of said cell; and an engineered production polynucleotide for mediating controlled increase in expression of a production enzyme for generation of said product; wherein a rate of production of said product during said stationary phase is reduced less in response to a change of an environmental condition as compared to a cell lacking said controlled reduction of expression of said valve enzyme.

In some cases, provided herein is a cell comprising a reduced expression or activity of a valve enzyme, wherein the valve enzyme comprises an enzyme selected from the group consisting of enoyl-ACP/CoA reductase (fabI), glucose-6-phosphate dehydrogenase (zwf), lipoamide dehydrogenase (lpd), citrate synthase (gltA), soluble transhydrogenase (udhA), NADH-dependent glyceraldehyde-3-phosphate dehydrogenase (gapA), and a combination thereof.

In some cases, provided herein is a cell comprising a production enzyme, wherein the production enzyme comprises an enzyme selected from the group consisting of NADPH-dependent alanine dehydrogenase (ald), alanine exporter (alaE), NADPH-dependent glyceraldehyde-3-phosphate dehydrogenase (gapN), and a combination thereof.

Environmental Conditions

Environmental conditions can comprise medium and culture conditions. Environmental factors that may influence production can be temperature, pH, acidity, ethanol, sulfite, and availability of nutrients.

In addition to an appropriate carbon source, such as selected from one of the herein disclosed types, bio-production media may contain suitable minerals, salts, cofactors, buffers and other components, known to those skilled in the art, suitable for the growth of the cultures and promotion of the enzymatic pathway necessary for chemical product bio-production under the present disclosure. Another aspect of the invention regards media and culture conditions that comprise genetically modified microorganisms of the invention and optionally supplements.

Typically cells are grown at a temperature in the range of about 25° C. to about 40° C. in an appropriate medium, as well as up to 70° C. for thermophilic microorganisms. Suitable growth media are well characterized and known in the art.

Suitable pH ranges for the bio-production are between pH 2.0 to pH 10.0, where pH 6.0 to pH 8.0 is atypical pH range for the initial condition. However, the actual culture conditions for a particular embodiment are not meant to be limited by these pH ranges.

Bio-productions may be performed under aerobic, microaerobic or anaerobic conditions with or without agitation.

In some cases, a change of an environmental condition comprises a change in sugar concentration of a culture medium contacting a cell. In some cases, a change in sugar concentration of a culture medium is an increase of sugar concentration. In some other cases, a change in sugar concentration is a decrease of sugar concentration. In some situations, an increase of sugar concentration is from 1% to 2%, from 2% to 3%, from 3% to 4%, from 4% to 5%, from 5% to 10%, from 10% to 15%, from 15% to 20%, from 20% to 30%, from 30% to 40%, from 40% to 50%, from 50% to 60%, from 60% to 70%, from 70% to 80%, from 80% to 90%, or from 90% to 100% more sugar compared with the original sugar concentration in the culture medium. In some situations, a decrease of sugar concentration is from 1% to 2%, from 2% to 3%, from 3% to 4%, from 4% to 5%, from 5% to 10%, from 10% to 15%, from 15% to 20%, from 20% to 30%, from 30% to 40%, from 40% to 50%, from 50% to 60%, from 60% to 70%, from 70% to 80%, from 80% to 90%, or from 90% to 100% less sugar compared with the original sugar concentration in the culture medium.

In some cases, a change of an environmental condition comprises a change in oxygenation of a culture medium contacting a cell. In some cases, a change in oxygenation of a culture medium is an increase of oxygenation. In some other cases, a change in oxygenation of a culture medium is a decrease of oxygenation. In some situations, an increase of oxygenation is the addition of oxygen from 1% to 2%, from 2% to 3%, from 3% to 4%, from 4% to 5%, from 5% to 10%, from 10% to 15%, from 15% to 20%, from 20% to 30%, from 30% to 40%, from 40% to 50%, from 50% to 60%, from 60% to 70%, from 70% to 80%, from 80% to 90%, or from 90% to 100% more than the original amount of oxygen added in a culture medium. In some situations, a decrease of oxygenation is the addition of oxygen from 1% to 2%, from 2% to 3%, from 3% to 4%, from 4% to 5%, from 5% to 10%, from 10% to 15%, from 15% to 20%, from 20% to 30%, from 30% to 40%, from 40% to 50%, from 50% to 60%, from 60% to 70%, from 70% to 80%, from 80% to 90%, or from 90% to 100% less than the original amount of oxygen added in a culture medium.

Bio-Production Reactors and Systems

Fermentation systems utilizing methods and/or compositions according to the invention are also within the scope of the invention.

Any of the recombinant microorganisms as described and/or referred to herein may be introduced into an industrial bio-production system where the microorganisms convert a carbon source into a product in a commercially viable operation. The bio-production system includes the introduction of such a recombinant microorganism into a bioreactor vessel, with a carbon source substrate and bio-production media suitable for growing the recombinant microorganism, and maintaining the bio-production system within a suitable temperature range (and dissolved oxygen concentration range if the reaction is aerobic or microaerobic) for a suitable time to obtain a desired conversion of a portion of the substrate molecules to a selected chemical product. Bio-productions may be performed under aerobic, microaerobic, or anaerobic conditions, with or without agitation. Industrial bio-production systems and their operation are well-known to those skilled in the arts of chemical engineering and bioprocess engineering. The amount of a product produced in a bio-production media generally can be determined using a number of methods known in the art, for example, high performance liquid chromatography (HPLC), gas chromatography (GC), or GC/Mass Spectroscopy (MS).

Genetic Modifications, Nucleotide Sequences, and Amino Acid Sequences

Embodiments of the present disclosure may result from introduction of an expression vector into a host microorganism, wherein the expression vector contains a nucleic acid sequence coding for an enzyme that is, or is not, normally found in a host microorganism.

The ability to genetically modify a host cell is essential for the production of any genetically modified (recombinant) microorganism. The mode of gene transfer technology may be by electroporation, conjugation, transduction, or natural transformation. A broad range of host conjugative plasmids and drug resistance markers are available. The cloning vectors are tailored to the host organisms based on the nature of antibiotic resistance markers that can function in that host. Also, as disclosed herein, a genetically modified (recombinant) microorganism may comprise modifications other than via plasmid introduction, including modifications to its genomic DNA.

More generally, nucleic acid constructs can be prepared comprising an isolated polynucleotide encoding a polypeptide having enzyme activity operably linked to one or more (several) control sequences that direct the expression of the coding sequence in a microorganism, such as *E. coli*, under conditions compatible with the control sequences. The isolated polynucleotide may be manipulated to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well established in the art.

The control sequence may be an appropriate promoter sequence, a nucleotide sequence that is recognized by a host cell for expression of a polynucleotide encoding a polypeptide of the present disclosure. The promoter sequence may contain transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell. The techniques for modifying and utilizing recombinant DNA promoter sequences are well established in the art.

For various embodiments of the invention the genetic manipulations may be described to include various genetic manipulations, including those directed to change regulation of, and therefore ultimate activity of, an enzyme or enzymatic activity of an enzyme identified in any of the respective pathways. Such genetic modifications may be directed to transcriptional, translational, and post-translational modifications that result in a change of enzyme activity and/or selectivity under selected and/or identified culture conditions and/or to provision of additional nucleic acid sequences such as to increase copy number and/or mutants of an enzyme related to product production. Specific methodologies and approaches to achieve such genetic modification are well known to one skilled in the art.

In various embodiments, to function more efficiently, a microorganism may comprise one or more gene deletions. For example, in *E. coli*, the genes encoding the lactate dehydrogenase (ldhA), phosphate acetyltransferase (pta), pyruvate oxidase (poxB), pyruvateformate lyase (pflB), methylglyoxal synthase (mgsA), acetate kinase (ackA), alcohol dehydrogenase (adhE), the clpXP protease specificity enhancing factor (sspB), the ATPdependent Lon protease (lon), the outer membrane protease (ompT), the arcA transcriptional dual regulator (arcA), and the iclR transcriptional regulator (iclR) may be disrupted, including deleted. Such gene disruptions, including deletions, are not meant to be limiting, and may be implemented in various combinations in various embodiments. Gene deletions may be accomplished by numerous strategies well known in the art, as are methods to incorporate foreign DNA into a host chromosome.

In various embodiments, to function more efficiently, a microorganism may comprise one or more synthetic metabolic valves, composed of enzymes targeted for controlled proteolysis, expression silencing or a combination of both controlled proteolysis and expression silencing. In some embodiments, a microorganism may comprise two, three, four, five, six, seven, eight, nine, or ten, or more synthetic metabolic valves. For example, one enzyme encoded by one gene or a combination of numerous enzymes encoded by numerous genes in $E.\ coli$ may be designed as synthetic metabolic valves to alter metabolism and improve product formation. Representative genes in $E.\ coli$ may include but are not limited to the following: fabI, zwf gltA, ppc, udhA, lpd, sucD, aceA, pfkA, lon, rpoS, tktA or tktB. It is appreciated that it is well known to one skilled in the art how to identify homologues of these genes and or other genes in additional microbial species.

For all nucleic acid and amino acid sequences provided herein, it is appreciated that conservatively modified variants of these sequences are included, and are within the scope of the invention in its various embodiments. Functionally equivalent nucleic acid and amino acid sequences (functional variants), which may include conservatively modified variants as well as more extensively varied sequences, which are well within the skill of the person of ordinary skill in the art, and microorganisms comprising these, also are within the scope of various embodiments of the invention, as are methods and systems comprising such sequences and/or microorganisms.

Accordingly, as described in various sections above, some compositions, methods and systems of the present disclosure comprise providing a genetically modified microorganism that comprises a production pathway to make a desired product from a central intermediate in combination with synthetic metabolic valves to redistribute flux.

Aspects of the invention also regard provision of multiple genetic modifications to improve microorganism overall effectiveness in converting a selected carbon source into a selected product. Particular combinations are shown, such as in the Examples, to increase specific productivity, volumetric productivity, titer and yield substantially over more basic combinations of genetic modifications. In addition to the above-described genetic modifications, in various embodiments genetic modifications, including synthetic metabolic valves also are provided to increase the pool and availability of the cofactor NADPH and/or NADH which may be consumed in the production of a product.

More generally, and depending on the particular metabolic pathways of a microorganism selected for genetic modification, any subgroup of genetic modifications may be made to decrease cellular production of fermentation product(s) other than the desired fermentation product, selected from the group consisting of acetate, acetoin, acetone, acrylic, malate, fatty acid ethyl esters, isoprenoids, glycerol, ethylene glycol, ethylene, propylene. butylene, isobutylene, ethyl acetate, vinyl acetate, other acetates, 1,4-butanediol, 2,3-butanediol, butanol, isobutanol, sec-butanol, butyrate, isobutyrate, 2-OH-isobutryate, 3-OHbutyrate, ethanol, isopropanol, D-lactate, L-lactate, pyruvate, itaconate, levulinate, glucarate, glutarate, caprolactam, adipic acid, propanol, isopropanol, fusel alcohols, and 1,2-propanediol, 1,3-propanediol, formate, fumaric acid, propionic acid, succinic acid, valeric acid, maleic acid and poly-hydroxybutyrate. Gene deletions may be made as disclosed generally herein, and other approaches may also be used to achieve a desired decreased cellular production of selected fermentation products other than the desired products.

VI.a Gene Silencing

In particular the invention describes the use of controlled gene silencing to help enable the control over metabolic fluxes in controlled multi-stage fermentation processes. There are several methodologies known in the art for controlled gene silencing, including but not limited to mRNA silencing or RNA interference, silencing via transcriptional repressors and CRISPR interference.

In some cases, a valve polynucleotide comprises a polynucleotide selected from the group consisting of: a silencing polynucleotide for repressing transcription of a gene encoding said valve enzyme; a degradation polynucleotide for mediating cellular degradation of said valve enzyme; and a combination thereof.

In some cases, a valve polynucleotide comprises a silencing polynucleotide, and said silencing polynucleotide comprises a guide RNA (gRNA) comprising a gRNA sequence that recognizes a promoter of a gene encoding said valve enzyme.

In some cases, a valve polynucleotide further encodes a CRISPR enzyme, wherein said CRISPR enzyme specifically binds to said promoter sequence when bound to said gRNA. In some cases, a CRISPR enzyme is catalytically inactive.

In some cases, a valve polynucleotide comprises a degradation polynucleotide, wherein said degradation polynucleotide comprises a sequence encoding a degradation tag, wherein said degradation tag mediates degradation of said valve enzyme. In some cases, the expression of a valve polynucleotide is regulated by phosphate availability in a cell. In some cases, the expression of a production polynucleotide is regulated by phosphate availability in a cell. In certain cases, the cell is an $E.\ coli$ cell.

Controlled Proteolysis

In particular the current disclosure describes the use of controlled protein degradation or proteolysis to help enable the control over metabolic fluxes in controlled multi-stage fermentation processes. There are several methodologies known in the art for controlled protein degradation, including but not limited to targeted protein cleavage by a specific protease and controlled targeting of proteins for degradation by specific peptide tags. Systems for the use of the $E.\ coli$ clpXP protease for controlled protein degradation can be used. This methodology relies upon adding a specific C-terminal peptide tag such as a DAS4 (or DAS+4) tag. Proteins with this tag are not degraded by the clpXP protease until the specificity enhancing chaperone sspB is expressed. sspB induces degradation of DAS4 tagged proteins by the clpXP protease. In additional numerous site specific protease systems are well known in the art. Proteins can be engineered to contain a specific target site of a given protease and then cleaved after the controlled expression of the protease. In some embodiments the cleavage can be expected lead to protein inactivation or degradation. For example, an N-terminal sequence can be added to a protein of interest to enable clpS dependent clpAP degradation. In addition, this sequence can further be masked by an additional N-terminal sequence, which can be controllable cleaved such as by a ULP hydrolase. This allows for controlled N-rule degradation dependent on hydrolase expression. It is therefore possible to tag proteins for controlled proteolysis either at the N-terminus or C-terminus.

The preference of using an N-terminal vs. C-terminal tag will largely depend on whether either tag affects protein function prior to the controlled onset of degradation. The invention describes the use of controlled protein degradation or proteolysis to help enable the control over metabolic fluxes in controlled multi-stage fermentation processes, in *E. coli*. There are several methodologies known in the art for controlled protein degradation in other microbial hosts, including a wide range of gram-negative as well as gram-positive bacteria, yeast and even archaea. In particular, systems for controlled proteolysis can be transferred from a native microbial host and used in a non-native host.

Synthetic Metabolic Valve Control

In particular the current disclosure describes the use of synthetic metabolic valves to control metabolic fluxes in multi-stage fermentation processes. There are numerous methodologies known in the art to induce expression that can be used at the transition between stages in multistage fermentations. These include but are not limited to artificial chemical inducers including: tetracycline, anhydrotetracycline, lactose, IPTG (isopropyl-beta-D-l-thiogalactopyranoside), arabinose, raffinose, tryptophan and numerous others. Systems linking the use of these well known inducers to the control of gene expression silencing and/or controlled proteolysis can be integrated into genetically modified microbial systems to control the transition between growth and production phases in multi-stage fermentation processes.

In addition, it may be desirable to control the transition between growth and production in multi-stage fermentations by the depletion of one or more limiting nutrients that are consumed during growth. Limiting nutrients can include but are not limited to: phosphate, nitrogen, sulfur and magnesium. Natural gene expression systems that respond to these nutrient limitations can be used to operably link the control of gene expression silencing and/or controlled proteolysis to the transition between growth and production phases in multi-stage fermentation processes.

Products

In some embodiments, provided herein is a microorganism or a cell for producing a product. In some cases, the product comprises 3-hydroxypropionic acid. In some cases, the product comprises an amino acid. In some cases, the amino acid comprises alanine. In some cases, the alanine is L-alanine. In some cases, the alanine is D-alanine. In some cases, a rate of production of alanine is at least 0.1 g/L/hr, 0.2 g/L/hr, 0.3 g/L/hr, 0.4 g/L/hr, 0.5 g/L/hr, 0.6 g/L/hr, 0.7 g/L/hr, 0.8 g/L/hr, 0.9 g/L/hr, 1.0 g/L/hr, 1.1 g/L/hr, 1.2 g/L/hr, 1.3 g/L/hr, 1.4 g/L/hr, 1.5 g/L/hr, 1.6 g/L/hr, 1.7 g/L/hr, 1.8 g/L/hr, 1.9 g/L/hr, 2.0 g/L/hr, 2.5 g/L/hr, 3.0 g/L/hr, 3.5 g/L/hr, 4.0 g/L/hr, 4.5 g/L/hr, 5.0 g/L/hr, 5.5 g/L/hr, 6.0 g/L/hr, 7.0 g/L/hr, 8.0 g/L/hr, 9.0 g/L/hr, or at least 10 g/L/hr.

In some cases, the alanine titers after 24 hours can be from 0 to 0.5 g/L, 0.5 g/L to 1 g/L, 1 g/L to 1.5 g/L, 1.5 g/L to 2 g/L, 2 g/L to 2.5 g/L, 2.5 g/L to 3 g/L, 3 g/L to 3.5 g/L, 3.5 g/L to 4 g/L, 4 g/L to 4.5 g/L, 4.5 g/L to 5 g/L, or from 5 g/L to 10 g/L. The dynamic range of alanine production offered by SMVs can be up to a 4-fold increase compared to that offered by solely altering the expression level of the production pathway enzymes (by changing the promoter). In some cases, the dynamic range of alanine production offered by SMVs can be up to a 2-fold, 3-fold, 4-fold, 5-fold, 6-fold, 7-fold, 8-fold, 9-fold, or 10-fold increase compared to that offered by solely altering the expression level of the production pathway enzymes.

In some cases, a production polynucleotide in the microorganism encodes an alanine exporter. In some cases, the alanine exporter is alaE.

In some cases, the product comprises mevalonic acid. In some cases, a rate of production of mevalonic acid is at least 0.1 g/L/hr, 0.2 g/L/hr, 0.3 g/L/hr, 0.4 g/L/hr, 0.5 g/L/hr, 0.6 g/L/hr, 0.7 g/L/hr, 0.8 g/L/hr, 0.9 g/L/hr, 1.0 g/L/hr, 1.1 g/L/hr, 1.2 g/L/hr, 1.3 g/L/hr, 1.4 g/L/hr, 1.5 g/L/hr, 1.6 g/L/hr, 1.7 g/L/hr, 1.8 g/L/hr, 1.9 g/L/hr, 2.0 g/L/hr, 2.5 g/L/hr, 3.0 g/L/hr, 3.5 g/L/hr, 4.0 g/L/hr, 4.5 g/L/hr, 5.0 g/L/hr, 5.5 g/L/hr, 6.0 g/L/hr, 7.0 g/L/hr, 8.0 g/L/hr, 9.0 g/L/hr, or at least 10 g/L/hr.

Methods

Provided herein are methods for producing a product in an engineered microorganism in a large scale. Also provided herein are methods for engineering microorganisms for large-scale production of a product in a high-throughput fashion.

In some cases, provided herein is a method, comprising: culturing a plurality of strains of a cell, wherein each strain of said plurality of strains comprises (i) an engineered valve polynucleotide for mediating controlled reduction of expression of a valve enzyme acting in a metabolic pathway, wherein said controlled reduction of expression of said valve enzyme reduces flux through said metabolic pathway; and (ii) an engineered production polynucleotide for mediating controlled increase in expression of a production enzyme for generation of said product; wherein each strain of said plurality of strains differs from another strain in a sequence of at least one of said engineered valve polynucleotide or said engineered production polynucleotide; measuring a level of said product generated by each of said plurality of strains; and selecting a strain based on said level of said product. In some embodiments, the method further comprises growing said selected strain in a bioreactor. In some embodiments, a culture medium comprising said selected strain has a volume of at least 100 ml, 200 ml, 300 ml, 400 ml, 500 ml, 600 ml, 700 ml, 800 ml, 900 ml, or at least 1000 ml. In some embodiments, a culture medium has a volume of at least 1 L.

In some embodiments, a valve polynucleotide comprises a polynucleotide selected from the group consisting of: a silencing polynucleotide for repressing transcription of a gene encoding said valve enzyme; a degradation polynucleotide for mediating cellular degradation of said valve enzyme; and a combination thereof. In some embodiments, a first and a second strain of said plurality of strains comprise a silencing polynucleotide. In some embodiments, a silencing polynucleotide comprises a guide RNA (gRNA) comprising a gRNA sequence that recognizes a promoter of a gene encoding said valve enzyme. In some embodiments, a gRNA sequence differs between said first and second strains. In some embodiments, a promoter recognized by said gRNA differs between said first and second strains. In some embodiments, a first strain comprises said silencing polynucleotide and said degradation polynucleotide, and a second strain comprises said silencing polynucleotide but does not comprise said degradation polynucleotide. In some embodiments, a level of product is greater in said second strain than said first strain. In some embodiments, a level of product is greater in said first strain than said second strain. In some embodiments, a valve enzyme comprises an enzyme selected from the group consisting of enoyl-ACP/

CoA reductase (fabI), glucose-6-phosphate dehydrogenase (zwf), lipoamide dehydrogenase (lpd), citrate synthase (gltA), soluble transhydrogenase (udhA), NADH-dependent glyceraldehyde-3-phosphate dehydrogenase (gapA), and a combination thereof. In some embodiments, a production enzyme comprises an enzyme selected from the group consisting of NADPH-dependent alanine dehydrogenase (ald), alanine exporter (alaE), NADPH-dependent glyceraldehyde-3-phosphate dehydrogenase (gapN), and a combination thereof.

In some embodiments, a product is selected from the group consisting of mevalonic acid, 3-hydroxypropionic acid, an amino acid, and a combination thereof. In some embodiments, the amino acid is alanine. In some embodiments, the alanine is L-alanine. In some embodiments, the alanine is D-alanine.

In some embodiments, a rate of production of the product during said stationary phase is reduced less in response to a change of an environmental condition as compared to a cell lacking said controlled reduction of expression of said valve enzyme.

In some embodiments, a change of an environmental condition comprises a change in a sugar concentration of a culture medium contacting said cell.

In some embodiments, a change of an environmental condition comprises a change in oxygenation of a culture medium contacting said cell.

In some cases, provided herein is a method of generating a cellular product comprising: culturing a heterologous cell in a culture medium, wherein said heterologous cell comprises: (i) an engineered valve polynucleotide for mediating controlled reduction of expression of a valve enzyme acting in a metabolic pathway, wherein said controlled reduction of expression of said valve enzyme reduces flux through said metabolic pathway, wherein said controlled reduction of expression of said valve enzyme induces a stationary phase of said cell; and (ii) an engineered production polynucleotide for mediating controlled increase in expression of a production enzyme for generation of said product; wherein a rate of production of said product during said stationary phase is reduced less in response to a change of an environmental condition as compared to a cell lacking said controlled reduction of expression of said valve enzyme. In some embodiments, the method further comprises changing said environmental condition. In some embodiments, the environmental condition comprises a sugar concentration of said culture medium, and changing said environmental condition comprises increasing or decreasing said sugar concentration. In some cases, said sugar is glucose, sucrose, lactose, maltose, xylose, mannitol, or a combination thereof. In some cases, said sugar is glucose. In some cases, the environmental condition comprises an oxygen concentration of said culture medium, and changing said environmental condition comprises increasing or decreasing said oxygen concentration. In some cases, said culturing is performed in a bioreactor.

In some cases, said culture medium has a volume of at least 100 ml, 200 ml, 300 ml, 400 ml, 500 ml, 600 ml, 700 ml, 800 ml, 900 ml, or at least 1000. In some cases, said culture medium has a volume of at least 1 L. In some case, said product comprises 3-hydroxypropionic acid. In some cases, said product comprises an amino acid. In some cases, said amino acid comprises alanine.

In some cases, a rate of production of said alanine is at least 0.1 g/L/hr, 0.2 g/L/hr, 0.3 g/L/hr, 0.4 g/L/hr, 0.5 g/L/hr, 0.6 g/L/hr, 0.7 g/L/hr, 0.8 g/L/hr, 0.9 g/L/hr, 1.0 g/L/hr, 1.1 g/L/hr, 1.2 g/L/hr, 1.3 g/L/hr, 1.4 g/L/hr, 1.5 g/L/hr, 1.6 g/L/hr, 1.7 g/L/hr, 1.8 g/L/hr, 1.9 g/L/hr, 2.0 g/L/hr, 2.5 g/L/hr, 3.0 g/L/hr, 3.5 g/L/hr, 4.0 g/L/hr, 4.5 g/L/hr, 5.0 g/L/hr, 5.5 g/L/hr, 6.0 g/L/hr, 7.0 g/L/hr, 8.0 g/L/hr, 9.0 g/L/hr, or at least 10 g/L/hr. In some cases, said production polynucleotide encodes an alanine exporter. In some cases, said alanine exporter is alaE. In some cases, said culturing occurs for less than 20 hours, 30 hours, 40 hours, 50 hours, 60 hours, 70 hours, 80 hours, 90 hours, or less than 100 hours. In some cases, said culturing occurs for less than 10 hours, 15 hours, 20 hours, 25 hours, 30 hours, 35 hours, 40 hours, or less than 45 hours.

In some cases, said culturing occurs for less than 30 hours.

In some cases, said product comprises mevalonic acid. In some cases, a rate of production of said mevalonic acid is at least 0.1 g/L/hr, 0.2 g/L/hr, 0.3 g/L/hr, 0.4 g/L/hr, 0.5 g/L/hr, 0.6 g/L/hr, 0.7 g/L/hr, 0.8 g/L/hr, 0.9 g/L/hr, 1.0 g/L/hr, 1.1 g/L/hr, 1.2 g/L/hr, 1.3 g/L/hr, 1.4 g/L/hr, 1.5 g/L/hr, 1.6 g/L/hr, 1.7 g/L/hr, 1.8 g/L/hr, 1.9 g/L/hr, 2.0 g/L/hr, 2.5 g/L/hr, 3.0 g/L/hr, 3.5 g/L/hr, 4.0 g/L/hr, 4.5 g/L/hr, 5.0 g/L/hr, 5.5 g/L/hr, 6.0 g/L/hr, 7.0 g/L/hr, 8.0 g/L/hr, 9.0 g/L/hr, or at least 10 g/L/hr. In some cases, said culturing occurs for less than 20 hours, 30 hours, 40 hours, 50 hours, 60 hours, 70 hours, 80 hours, 90 hours, or less than 100 hours. In some cases, said culturing occurs for less than 80 hours.

In some embodiments, a valve polynucleotide comprises a polynucleotide selected from the group consisting of: a silencing polynucleotide for repressing transcription of a gene encoding said valve enzyme; a degradation polynucleotide for mediating cellular degradation of said valve enzyme; and a combination thereof. In some cases, a valve polynucleotide comprises a silencing polynucleotide, and said silencing polynucleotide comprises a guide RNA (gRNA) comprising a gRNA sequence that recognizes a promoter of a gene encoding said valve enzyme. In some cases, a valve polynucleotide further encodes a CRISPR enzyme, wherein said CRISPR enzyme specifically binds to said promoter sequence when bound to said gRNA. In some cases, a CRISPR enzyme is catalytically inactive. In some case, a valve polynucleotide comprises a degradation polynucleotide, wherein said degradation polynucleotide comprises a sequence encoding a degradation tag, wherein said degradation tag mediates degradation of said valve enzyme. In some cases, an expression of said valve polynucleotide is regulated by phosphate. In some cases, an expression of said production polynucleotide is regulated by phosphate. In some cases, said cell is an *E. coli* cell.

Optimization of Bio-Production

Biotechnology based fermentation processes have been successfully developed to produce everything from biologics and small molecule therapeutics to specialty, bulk and commodity chemicals, and even next generation biofuels[1-3]. These processes have made rapid advancements in recent years due to numerous technology developments[4, 5]. It has never been easier to produce new molecules using synthetic biology. Despite these advances, a major challenge remains in taking molecules from proof of concept (POC) to commercially meaningful levels. Strain optimization, or overcoming the "mg" to "kg" hurdle has remained a key barrier to the successful commercialization of bio-processes. After the demonstration of POC, successful bio-process development routinely requires lengthy iterations of both microbial strain and fermentation optimization[6-8] (FIG. 1B). These optimization efforts are often specific to the product or host strain of interest. The throughput of synthetic biology has outpaced that of metabolic engineering, partly due to a lack of broadly useful tools to perform meaningful and standardized optimization of engineered microbial strains in a high-throughput manner[9].

There are numerous challenges in strain optimization and moving past POC levels, not the least of which are the size and complexity of the potential design space. In contrast to simpler gene circuits, amenable to electrical circuit models[10-12], metabolic networks are highly interconnected. Each metabolite and/or enzyme can interact with endless others. This combinatorial complexity results in a huge potential design space, which is intractable to the kinds of systematic experimentation required for the development of standardized design principles (Supplemental Materials, Table 1). The challenges in addressing such a large design space have persisted despite the dramatic advances in, and decreased costs of, reading and writing DNA that have led to new high-throughput DNA assembly and microbial strain construction methods[13-16]. It is not surprising that new synthetic biology technologies involving strain engineering are often demonstrated with easily screened or selected phenotypes[13, 17-19] Most of these are limited to a focus on optimizing a limited set of pathway specific enzymes.

One approach to overcome the complexity of this challenge is the use of in vitro systems for bio-production, which comprise a limited set of metabolic enzymes. However, these approaches have challenges in replicating key advantages of in vivo systems, including cofactor recycling and energy generation[20, 21]. Another approach to deal with this complexity is to develop faster screening methods for strain evaluation[22]. However, increased throughput alone can never evaluate the full complexity of the potential design space. In addition, results obtained from high-throughput studies often do not translate, even in the same microbe, to a different environment[20, 23, 24]. Small scale screens do not readily translate to larger scale production processes, leading to iterations of process optimization on top of strain optimization (FIG. 1B). This is because metabolism is highly regulated and can respond, sometimes dramatically, to changes in environmental conditions[25, 20, 26-28]. A lack of environmental robustness is traditionally one factor making the scale up of fermentation based processes difficult. This issue has led to the development of specialized complex micro-reactor systems for scale down offering only modest improvements in throughput[20, 29-31].

There remains a significant need for broadly applicable, rapid and robust approaches to greatly reduce the time and costs transitioning from "mgs" to "kgs". Ideally, approaches should be amenable to multiple products and production hosts. Provided herein is the development of a generalizable, high-throughput strain optimization approach that enables the use of truly scalable, standardized fermentation processes. This approach, as outlined in FIG. 1B, panel b, involves the dynamic minimization of the active metabolic network[32], which combines the benefits of a smaller design space common to in vitro approaches while maintaining the benefits of in vivo biosynthesis[20]. We can isolate and focus on the minimal metabolic networks required for production. Utilizing combinations of synthetic metabolic valves (SMVs)[32, 33] (FIG. 2AD) we can dynamically minimize the metabolic network and redirect metabolic flux in the context of a standardized 2-stage fermentation process[20].

This approach can reduce the complexity of the problem and the size of the relevant design space, greatly speeding up optimization. In various embodiments, it is demonstrated herein that dynamic metabolic network minimization can improve pathway fluxes beyond those achievable with production pathway modifications alone (FIGS. 3A-K and 6A-H). Simultaneously, we demonstrate that dynamic network minimization reduces metabolic responses to environmental conditions, which increases the robustness and scalability of engineered strains (FIGS. 3A-K and 5A-J).

EXAMPLES

2-Stage Synthetic Metabolic Valves in *E. coli*

We first developed improved synthetic metabolic valves (SMVs) in *E. coli* that are capable of the dynamic reduction of protein levels in a 2-stage process. These SMVs can be used to reduce levels of key metabolic enzymes (or reduce enzymatic activities of key metabolic enzymes) and rely on controlled proteolysis or CRISPR-based gene silencing or both proteolysis and silencing in combination (FIGS. 2A-D)[32-35]. Cell growth and dynamic metabolic control can be implemented using phosphate depletion as an environmental trigger. Phosphate can be an ideal candidate as a trigger, as one of the costliest components of minimal media. In addition, stationary phases induced in *E. coli* by phosphate depletion have retained glycolytic uptake as well as increased protein expression[31, 36] Numerous promoter systems responding to phosphate are well characterized in *E. coli* as well as other microbes including *S. cerevisiae*[37]. Phosphate responsive promoter variants were evaluated (Supplemental Materials, Section 1) and subsequently used for 2-stage control.

Figure 2A:
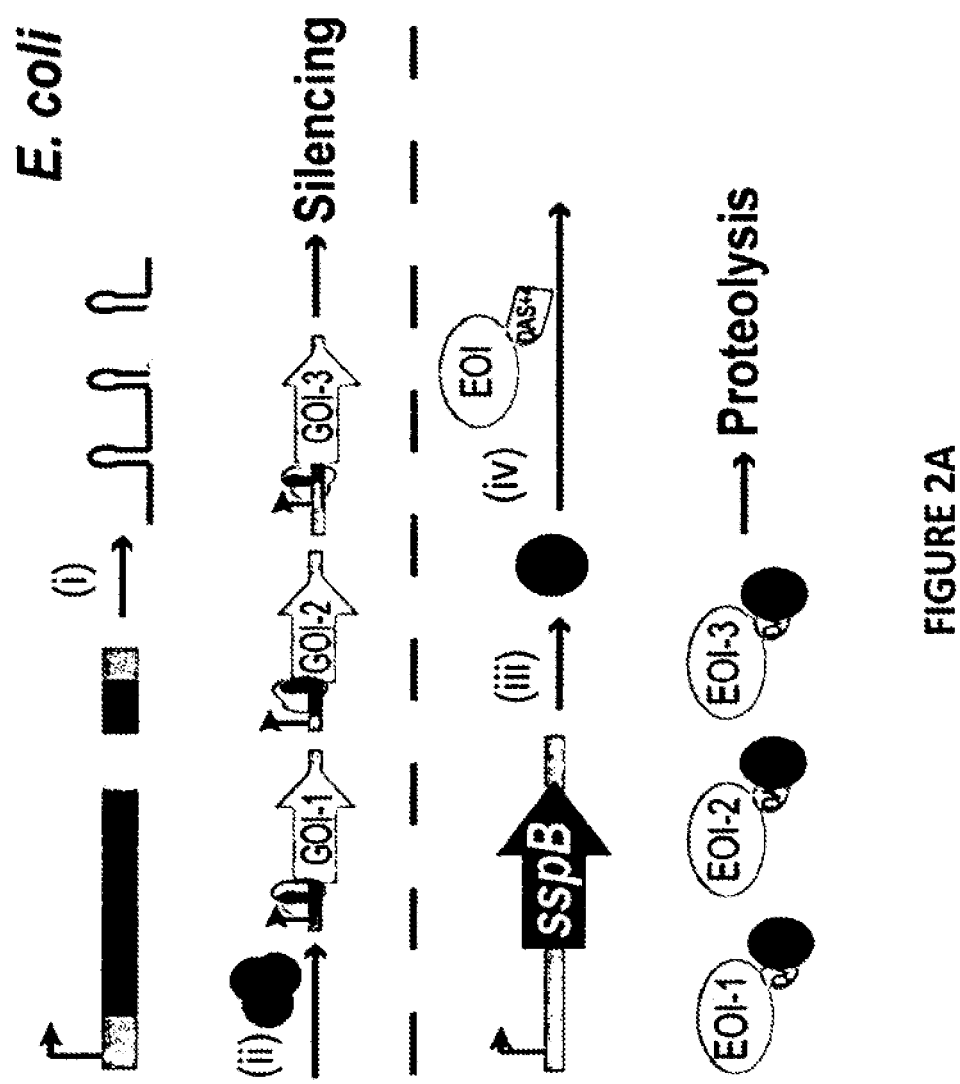
FIGS. 2A-D depict an example of implementation of 2-stage Synthetic Metabolic Valves (SMVs) in *E. coli*.

SMVs were implemented in *E. coli* using the native Type I-E Cascade CRISPR system for induced gene silencing[34, 38], while controlled proteolysis was induced by incorporating C-terminal degron tags on target proteins, both as previously demonstrated[63,33] (FIG. 2A). These systems were introduced into a host strain initially engineered for minimal byproduct formation and high biomass yields and growth rates (*E. coli* strain DLF_0025, Supplemental Materials, Section 3)[24, 27, 28, 39]. Using this approach, as FIGS. 2A-D demonstrate, protein levels can be controlled in 2-stage processes, as exemplified by turning "ON" GFPuv and "OFF" mCherry fluorescent proteins with phosphate depletion in minimal medium. The combination of gene silencing with proteolysis results in the largest rates of protein degradation (FIGS. 2C-D). The specific impact of gene silencing and proteolysis on decay rates will likely vary depending on the host, target gene/enzyme, and its specific natural turnover rates and expression levels[40, 41].

Metabolic Network Minimization Leads to Improved Fluxes

Figure 3A:
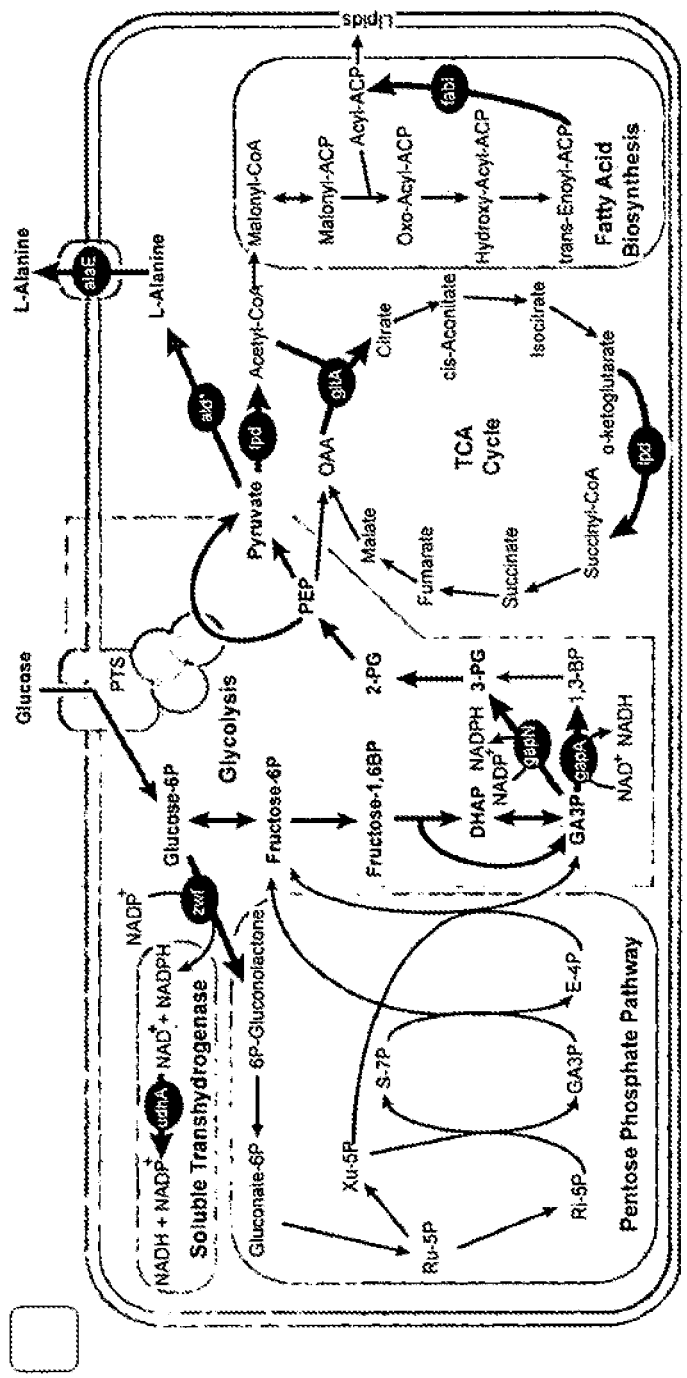
Figure 3B:
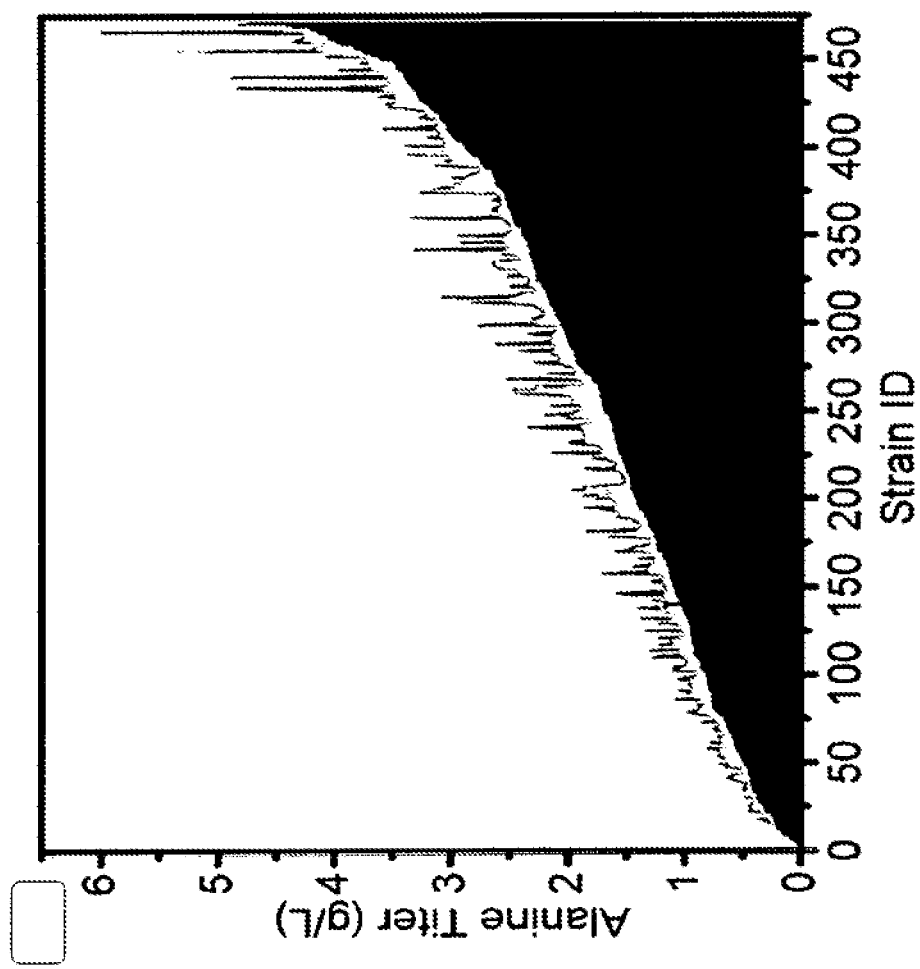
Figure 3C:
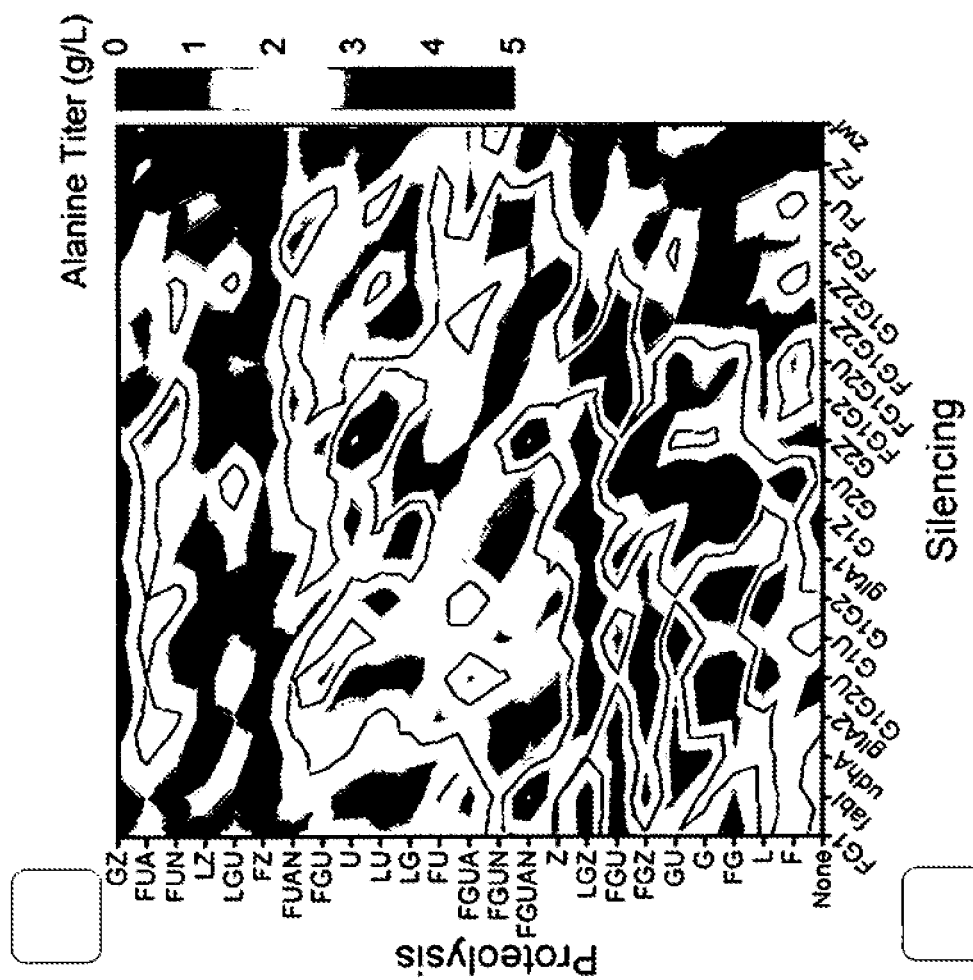
Figure 3D:
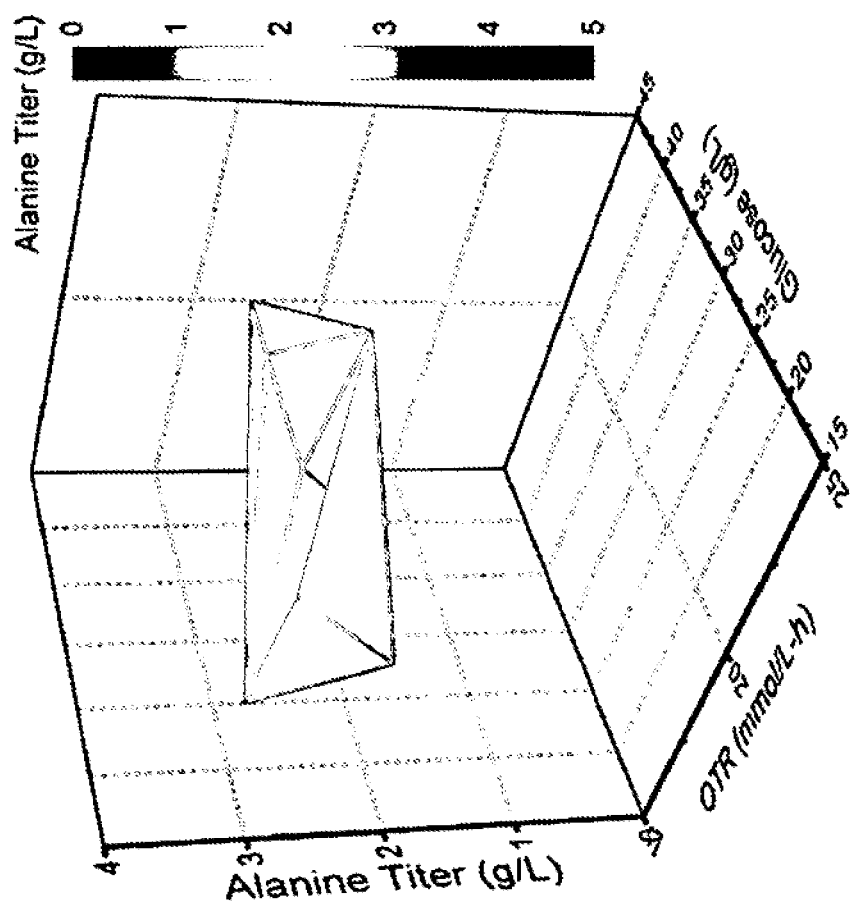

With the successful demonstration of dynamic control of protein levels in a 2-stage process, we turned to investigate the dynamic control of metabolic fluxes in *E. coli* through controlled reduction of key central metabolic enzymes alone and in combination. Reducing fluxes through thermodynamically favored "committed" reactions in the network is expected to lead to increases in network metabolite pools (Supplemental Materials Section 5), and as a result, changes in pathway fluxes. Enzymes in key committed steps in central metabolic pathways were identified and chosen as initial SMV targets and alanine was chosen as an initial test product (FIGS. 3A-K). A set of strains were constructed for alanine production (FIG. 3A), comprising an NADPH-dependent alanine dehydrogenase (ald*)[42]. Variants with multiple combinations of SMVs in central metabolic enzymes were made, with either modifications to induce proteolysis or gene silencing or both in combination. (Supplemental Materials, Section 3). Together the set of strains having SMVs evaluated in 2-stage processes are identified as "Valve" strains. A panel of alanine "Valve" strains (~500 strains in total) were evaluated for alanine production in standardized, 2-stage, 96-well plate based micro-fermentations (Supplemental Materials, Section 7). Alanine titers after 24 hours of production are given in FIGS. 3B-C. Briefly, alanine titers after 24 hours ranged from ~ 0 g/L to ~ 4.7 g/L, and as expected, varied significantly with respect to the number and combination of SMVs; most SMV combinations lead to improved performance when compared to the control with no SMVs and the alanine pathway alone. In some cases, the alanine titers after 24 hours can be from 0 to 0.5 g/L, 0.5 g/L to 1 g/L, 1 g/L to 1.5 g/L, 1.5 g/L to 2 g/L, 2 g/L to 2.5 g/L, 2.5 g/L to 3 g/L, 3 g/L to 3.5 g/L, 3.5 g/L to 4 g/L, 4 g/L to 4.5 g/L, 4.5 g/L to 5 g/L, or from 5 g/L to 10 g/L. The dynamic range of alanine production offered by SMVs can be up to a 4-fold increase compared to that offered by solely altering the expression level of the production pathway enzymes (by changing the promoter) (Supplemental Materials, Section 7). In some cases, the dynamic range of alanine production offered by SMVs can be up to a 2-fold, 3-fold, 4-fold, 5-fold, 6-fold, 7-fold, 8-fold, 9-fold, or 10-fold increase compared to that offered by solely altering the expression level of the production pathway enzymes. Importantly, the use of proteolysis or silencing alone and/or in combination had significant impacts on production, indicating that for each enzyme the fine tuning of activity using SMVs is critical. One of the best performing strains from the micro-fermentations was then evaluated in a minimal medium, 2-stage, 1 L fermentation with 10 gdcw/L of biomass (FIG. 3F), which resulted in 80 g/L 100% L-alanine after 48 hours of production with a yield of 0.8 g/g. Further engineering of this strain by overexpressing an alanine exporter (encoded by the E. coli alaE gene[43]) resulted in 147 g/L 100% L-alanine after 27 hours of production with a yield within error of theoretical yield ~1 g/g, (FIG. 3G).

Micro-Fermentation Robustness

A central hypothesis was that by restricting metabolism in the production stage, strain performance could not only be improved, but would be more robust to environmental (process) conditions. Simply put, carbon flow is restricted through a minimized metabolic network, which can no longer adapt via cellular responses to the environment. To test this hypothesis, strains were evaluated under different "micro-fermentation" process conditions. Glucose concentration and oxygen transfer rate (key process variables impacting strain performance in traditional fermentations[26]) were varied (FIG. 3D, Supplemental Materials, Section 8), and alanine production measured. A robustness score (RS) was developed to quantify environmental robustness. Larger RS scores indicate more robust strains. Whereas relative standard deviation (RSD) is one metric for robustness, we wanted to incorporate a stricter measure of robustness which also incorporates the maximal deviation (Max Dev) a strain has under all process conditions (RS, Equation (1)).

$$RS = 100 - \frac{\text{average}(RSD) + \max(Dev)}{2} * 100 \qquad \text{Equation (1)}$$

Figure 3E:
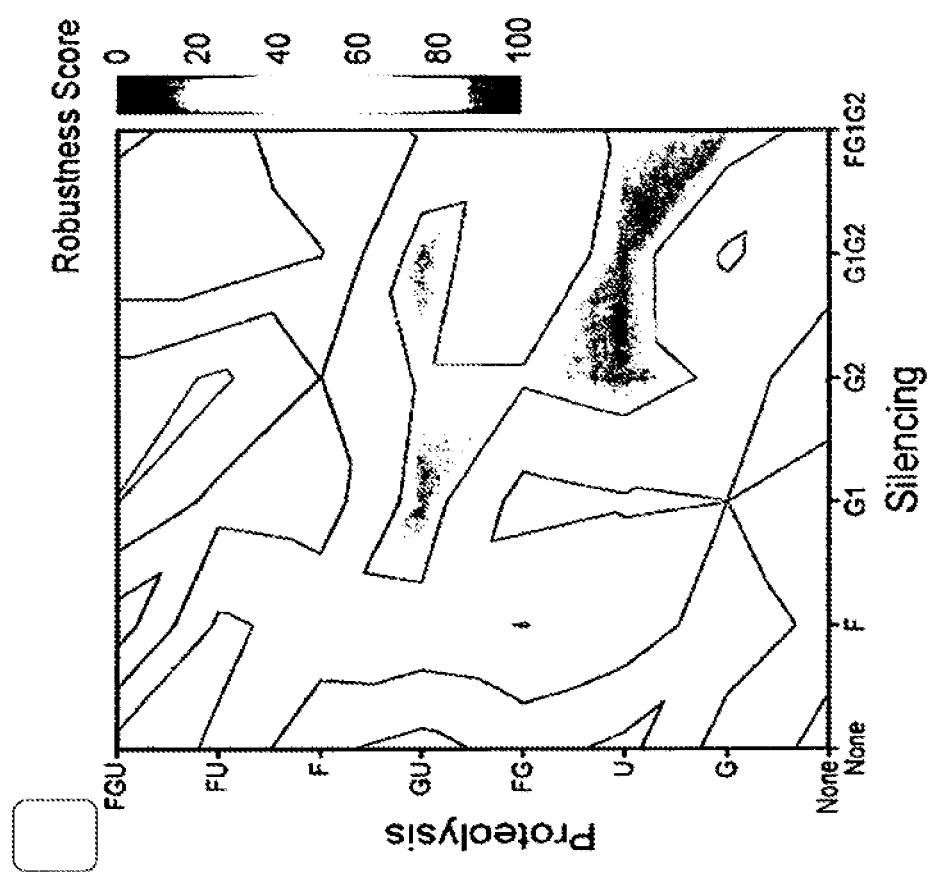
Figure 3G:
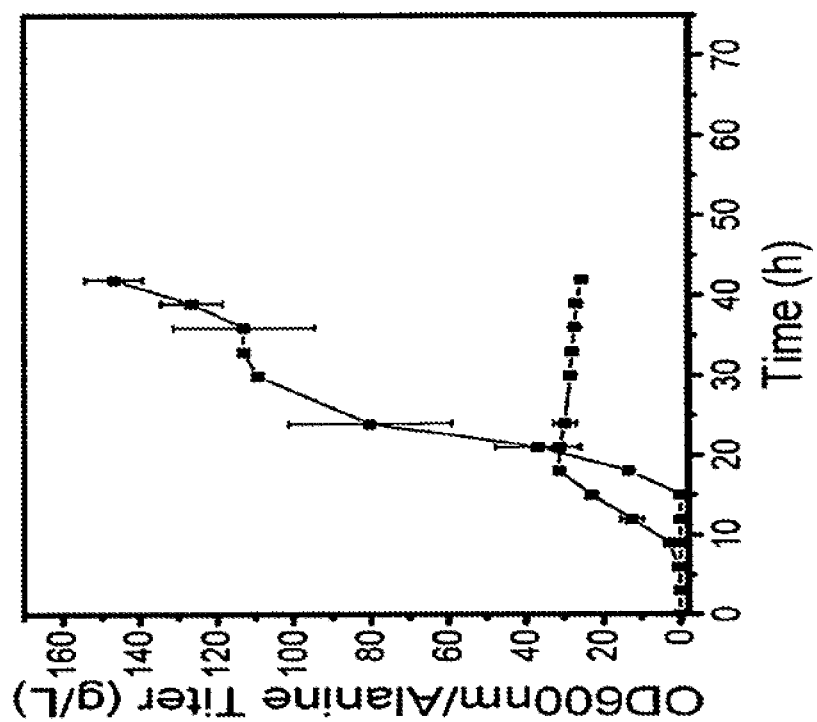

Robustness scores for a subset of 48 alanine "Valve" strains are given in FIG. 3E. Results from these experiments studies are tabulated in Supplemental Materials, Section 8. A Chi$^2$ analysis using a cutoff of RS>0.6 for robustness was used to identify key SMVs which statistically contribute to process robustness. The proteolytic degradation of fabI was a primary contributor to robustness (Chi$^2$=13.85, P$_{value}$<0.001) and as a result, "Valve" strains with proteolytic degradation of fabI were used in further studies. In addition, the "Valve" strains with proteolytic degradation of gltA and/or the combination of the proteolytic degradation of fabI and gltA were found to also be significant contributers of robustness, albeit with a large P$_{value}$.

2-Stage "Valve" Strains Compared to Traditional Growth Associated Strains

To compare the 2-stage approach enabled by SMVs to more traditional growth associated processes, we constructed 5 strains, with constitutively expressed alanine dehydrogenase (ald*), capable of the growth associated production of alanine. These growth associated strains varied in the strength of the promoter used to drive ald* expression[44] (Supplemental Materials, Section 2), yet utilized the same common no-valve control host strain. FIG. 5 illustrates the results of a direct comparison of "Valve" strains in a 2-stage process compared to "Growth Associated (GA)" strains in a traditional fermentation at the microtiter (FIGS. 5A-D) and 1 L (FIGS. 5E-J) scales. In micro-fermentations, 2-stage "Valve" strains outperformed GA strains with respect to titer and process robustness. The most robust GA strain from the micro-fermentation analysis (also with the highest production level) was compared to a robust "Valve" strain in 1 L fermentations with varied process conditions. The "Valve" strains showed consistent performance in all process conditions evaluated (FIG. 5E), consistent with results from micro-fermentations, where the GA strain had significant performance variability dependent on process. We hypothesized that the increased environmental robustness observed in both "micro-" and 1 L scale fermentations for "Valve" strains would lead to predictable scale up, where strains with improved performance in high-throughput micro-fermentations would reliably have improved performance in controlled bioreactors. To evaluate the scalability of the system, "Valve" alanine strains with statistically differentiated performance in micro-fermentations (P-value<0.001) were evaluated in standardized 2-stage 1 L fermentations and compared to all GA strains. Statistically different performances observed in "micro-fermentations" have scaled predictably to 1 L fermentations for 2-stage "Valve" strains. This contrasts with results obtained with GA strains where no correlation between micro-fermentation and 1 L performance was observed (FIGS. 5G-H).

Product Flexibility

Figure 6A:
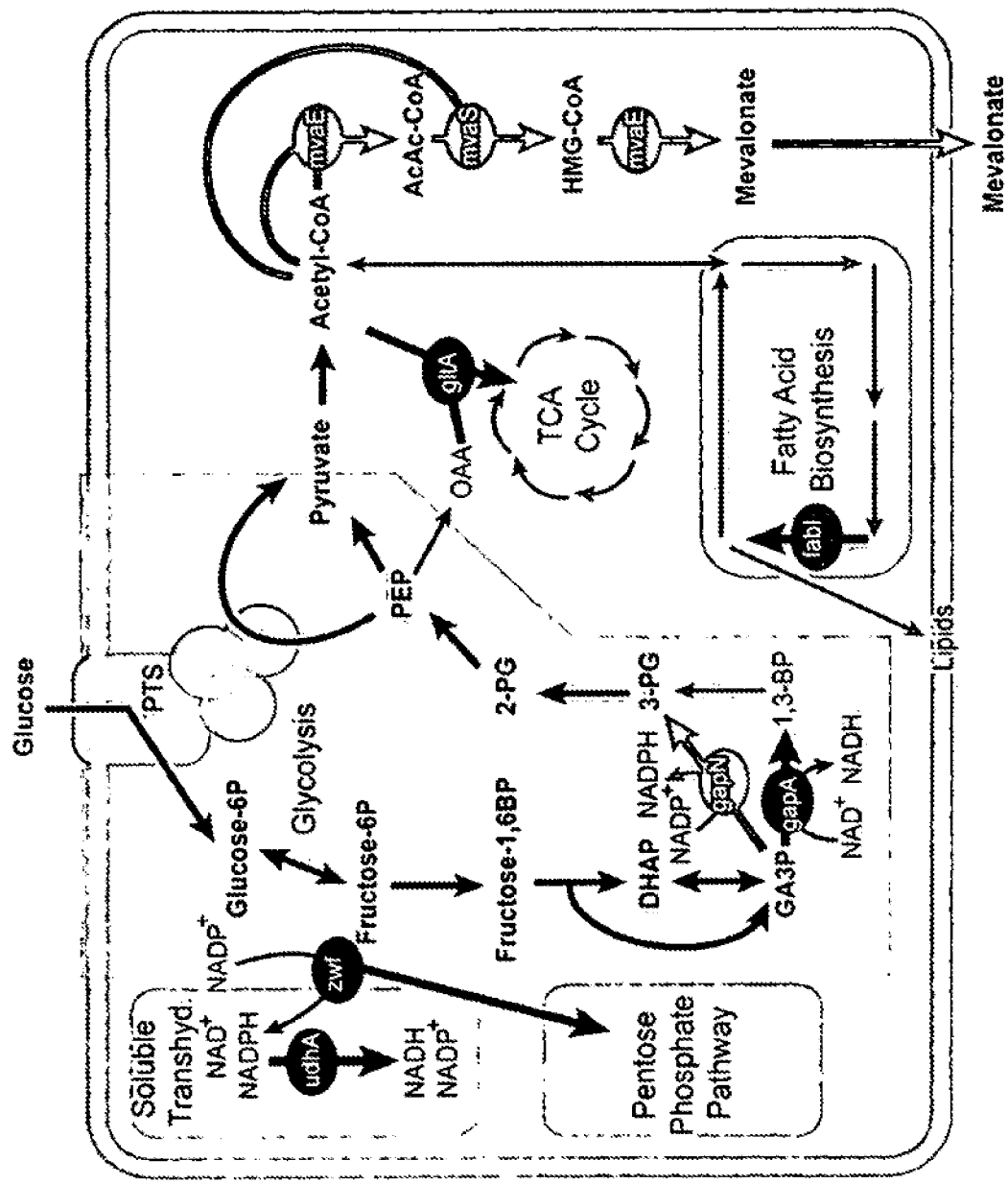
FIG. 6A-H depict an example of mevalonate production in *E. coli* utilizing 2-stage dynamic control.
Figure 6B:
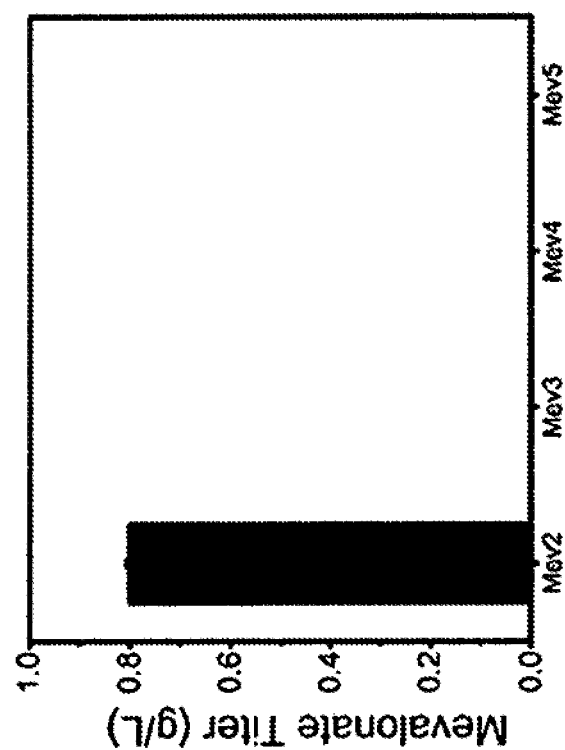
Figure 6C:
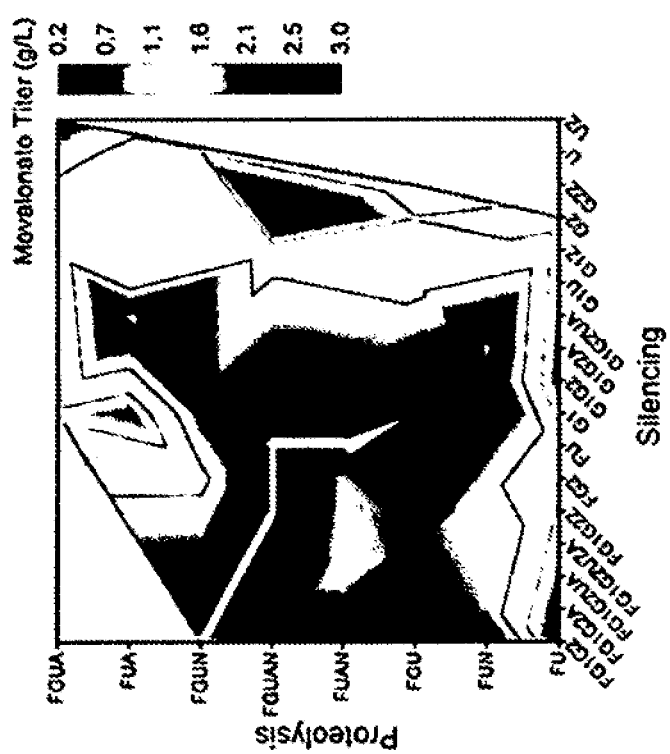

With the successful and predictable scale-up of alanine strains into 1 L fully instrumented fermentations, we moved to validate the technology platform for an additional product: mevalonic acid. To this end, additional dynamic production pathways were constructed for mevalonic acid biosynthesis (FIG. 6A). A set of two-gene production pathway plasmids encoding three enzymatic functions was constructed for mevalonic acid production, consisting of the E. faecalis mvaE and mvaS genes encoding a bifunctional acetyl-CoA acetyltransferase, NADPH dependent HMG-CoA reductase, and HMG-CoA synthase respectively. A mutant mvaS gene, mvaS(A110G) with higher activity was used[45, 46]. Production plasmids were initially evaluated for mevalonate production in the control strain (FIG. 6B). The best producing plasmid was then introduced into a variety of engineered "Valve" strains and evaluated in micro-fermentations (FIG. 6C). A subset of statistically differentiated strains were then evaluated in 1 L fermentations to assess scalability (FIG. 6D), which, as in the case of alanine, was predictive. In some cases, a performing strain produced meaningful titers and yields, 97 g/L in 78 hrs of production with a yield of 0.46 g/g (84% of theoretical yield) (FIG. 6E).

Specific productivity for this mevalonate strain is over 4-fold higher than the best previously reported results 4 (Supplemental Materials, Section 9).

Discussion

Historically some of the most successful efforts to metabolically engineer the production of small molecules have leveraged the power of anaerobic metabolism to couple product formation with growth. This has allowed for the classical design and selection of industrial strains to produce many products including ethanol, succinic acid, lactate and isobutanol, which have leveraged the power of evolution and selection to reach optimal metabolic fluxes in engineered networks[48, 49] ENREF_2. While growth associated production is not strictly linked to anaerobic metabolism, growth association greatly limits the number and variety of different molecules that can be made using synthetic biology. A generic, robust and accessible non-growth associated platform would greatly simplify the optimization and scale up of a diverse number of products.

In contrast to most existing 2-stage processes, which have relied on natural metabolic responses to environmental triggers for production improvement, we have taken the next step in actively minimizing the essential metabolic network and redirecting metabolites to products of interest. Many of the targeted essential central metabolic pathways in this work have traditionally been off limits to engineering strategies, as deleting essential enzymes is incompatible with growth and growth associated production in traditional fermentation. The dynamically minimized metabolic network also results in enhanced robustness to environmental variables enabling the faithful translation of high-throughput small-scale studies to larger instrumented fermentations. A current paradigm in the field is to improve the throughput of relevant strain evaluations by developing small-scale, custom-designed micro-reactors for enhanced process control. In contrast, our approach is a move in a new direction involving engineering microbial metabolism to be less sensitive to process changes, simplifying high-throughput experimentation.

Beyond robustness, we have demonstrated that combinatorial modifications to essential enzymes in minimal metabolic networks can lead to significant improvements in production, particularly when compared to altering production pathway expression levels alone. These large variations in performance are due to changes in a limited subset of key central metabolic nodes, likely resulting in altered metabolite levels. Compared to previous approaches to dynamically control enzyme levels, we demonstrate improved potential for fine tuning of protein levels with a combination of gene silencing and proteolysis[50]. As stationary phase cells cannot dilute existing proteins with cell division, this dual approach makes sense. The specific control of the level of any given enzyme will of course also depend on natural turnover mechanisms. At first glance, it may still be surprising that the combination of both gene silencing and proteolysis together does not always result in improved performance, i.e. "more is not always better". Future efforts may be needed to explain these results, which could either be due to a requirement of maintaining minimal fluxes in the larger network or a consequence of changes in the levels of key regulatory metabolites that are not part of the minimal network, yet influence network activity.

While the approach as demonstrated can address many issues common to most bio-production processes, many product specific challenges remain. The toxicity of a product or pathway metabolite may limit titers or production rates. A minimal network that may be optimal at a low titer, may not be optimal at elevated titers. In addition, the engineering of improved enzymes is often a challenge in many "mg" to "kg" projects.

Feasibility of adapting this approach to other microbial hosts is expected. Key requirements for new hosts include a rapid and robust growth phase, the ability to engineer dynamic control over protein levels, and a metabolically active stationary phase. Numerous microbes have well characterized nutrient triggers for productive stationary phase metabolism[36], for example nitrogen limitation in *Ralstonia* species, *Yarrowia* species and others[51, 52] Even when these requirements are not naturally met, they can be engineered into the host such as *S. cerevisiae* or other microbes, with each potential host presenting unique challenges and corresponding solutions.

Future efforts can be aimed at applying this platform for molecules with more complex production pathways. This approach can offer a tractable route for rapid optimization to metabolic engineers and synthetic biologists, who wish to move past POC levels and begin to tackle problems at more industrially relevant rates, titers and yields.

Methods

Reagents and Media

Unless otherwise stated, all materials and reagents were of the highest grade possible and purchased from Sigma (St. Louis, Mo.). C13 labeled Alanine (2,3-13C2, 99%) (Item #CLM-2734-PK) was purchased from Cambridge Isotope Laboratories, Inc. (Tewksbury, Mass.). Luria Broth was used for routine strain and plasmid propagation and construction. Working antibiotic concentrations were as follows: ampicillin (100 µg/mL), kanamycin (35 µg/mL), chloramphenicol (35 µg/mL), spectinomycin (100 µg/mL), zeocin (50 µg/mL), gentamicin (10 µg/mL), blasticidin (100 µg/mL), puromycin (150 µg/mL), tetracycline (5 µg/mL). Luria broth with low salt (Lennox formulation) was used to select for zeocin, blasticidin and puromycin resistant clones. In addition, for puromycin selection, phosphate buffer (pH=8.0) was added to LB Lennox to a final concentration of 50 mM. Media formulations including stock solutions are described in Supplemental Materials, Section 7.

*E. coli* Strain Construction

Oligonucleotides and synthetic linear DNA (Gblocks™) used for strain construction and confirmation are all given in Supplemental Materials, Section 3, and they were obtained from Integrated DNA Technologies (IDT, Coralville, Iowa). Strain BW25113 was obtained from the Yale Genetic Stock Center (CGSC http://cgsc.biology.yale.edu/). Strain BWapldf was a kind gift from George Chen (Tsinghua University)[62]. Chromosomal modifications were made using standard recombineering methodologies[63] either with direct antibiotic cassette integration in the case of C-terminal DAS+4 tags carrying antibiotic resistance cassettes, or through scarless tet-sacB selection and counterselection, strictly following the protocols of Li et al[64]. The recombineering plasmid pSIM5 and the tet-sacB selection/counterselection marker cassette were kind gifts from Donald Court (NCI, https://redrecombineering.ncifcrf.gov/courtlab.html). Briefly, the tet-sacB selection/counterselection cassette was amplified using the appropriate oligos supplying ~50 bp flanking homology sequences using Econotaq (Lucigen Middleton, Wis.) according to manufacturer's instructions, with an initial 10 minutes denaturation at 94° C., followed by 35 cycles of 94° C., for 15 seconds, 52° C. for 15 seconds, and 72° C. for 5 minutes. Cassettes used for "curing" of the tet-sacB cassette or direct integration (when an antibiotic marker is present) were obtained as gBlocks from IDT. In the case of the sspB gene deletion, the open reading frame deletion replaced with a kanamycin resistance was amplified from the Keio Collection strain, JW3197-1[65], and moved to the appropriate background strain using standard methodologies. The kanamycin resistance cassette was cured using the pCP20 plasmid, leaving an frt scar[63, 65]. Chromosomal modifications were confirmed by PCR amplification and sequencing (Eton Biosciences) using paired oligonucleotides, either flanking the entire region, or in the case of DAS+4 tag insertions an oligo 5' of the insertion and one internal to the resistance cassette.

E. coli Plasmid Construction

Primers used for the design and construction of CASCADE guides arrays were listed in Supplemental Materials, Section 6. Gene silencing guide arrays were expressed from a series of pCASCADE plasmids. The pCASCADE-control plasmid was prepared by swapping the pTet promoter in pcrRNA.Tet[73] with an insulated low phosphate induced ugpB promoter[74]. Promoter sequences for all genes were obtained from EcoCyc database (https://ecocyc.org/). In order to design CASCADE guide array, CASCADE PAM sites near the −35 or −10 box of the promoter of interest were identified, 30 bp at the 3' end of PAM site was selected as the guide sequence and cloned into pCASCADE plasmid using Q5 site-directed mutagenesis (NEB, MA) following manufacturer's protocol, with the modification that 5% v/v DMSO was added to the Q5 PCR reaction. PCR cycles were as follows: amplification involved an initial denaturation step at 98° C. for 30 second followed by cycling at 98° C. for 10 second, 72° C. for 30 second, and 72° C. for 1.5 min (the extension rate was 30 second/kb) for 25 cycles, then a final extension for 2 min at 72° C. 2 µL of PCR mixture was used for 10 µL KLD reaction, which proceeded under room temperature for 1 hour, after which, 1 µL KLD mixture was used for electroporation.

The pCASCADE guide array plasmids were prepared by sequentially amplifying complementary halves of each smaller guide plasmid by PCR, followed by subsequent DNA assembly. The pCASCADE-control vector was used as template. pCASCADE plasmids with arrays of two or more guides were prepared using Q5 High-Fidelity 2× Master Mix (NEB, MA). PCR cycles were as follows: amplification involved an initial denaturation step at 98° C. for 30 second followed by cycling at 98° C. for 10 second, 66° C. for 30 second, and 72° C. for 45 second (the extension rate was 30 second/kb) for 35 cycles, then a final extension for 2 min at 72° C. PCR product was purified by gel-extraction, 20 µL ultrapure water was used to elute 50 µL PCR reaction purification. 1 µL of each eluted PCR product was used for 10 µL of Gibson Assembly (NEB, MA), which was completed by incubation at 50° C. for 15 min. 1 µL Gibson Assembly mix was used for electroporation.

Production pathways enzymes were expressed from high copy plasmids via low phosphate inducible promoters. Production pathway gene sequences were codon optimized using the Codon Optimization Tool from the IDT website, phosphorylated G-blocks™ were designed and purchased from IDT for each pathway. Plasmids were assembled using NEBuilder® HiFi DNA Assembly Master Mix following manufacturer's protocol (NEB, MA). pSMART-HC-Kan (Lucigen, WI) was used as backbone for all pathway plasmids. All plasmid sequences were confirmed by DNA sequencing (Eton Bioscience, NC) and deposited with Addgene.

E. coli BioLector

Single colonies of each strain were inoculated into 5 mL LB with appropriate antibiotics and cultured at 37° C., 220 rpm for 9 hours or until OD600 reached >2. 500 µL of the culture was inoculated into 10 mL SM10 medium with appropriate antibiotics, and cultured in a square shake flask (CAT #: 25-212, Genesee Scientific, Inc. San Diego, Calif.) at 37° C., 220 rpm for 16 hours. Cells were pelleted by centrifugation and the culture density was normalized to OD600=5 using FGM3 media. Growth and fluorescence measurements were obtained in a Biolector (m2p labs, Baesweiler, Germany) using a high mass transfer Flower-Plate (CAT #: MTP-48-B, m2p-labs, Germany). 40 µL of the OD normalized culture was inoculated into 760 µL of FGM3 medium with appropriate antibiotics. Biolector settings were as follows: RFP gain=100, GFP gain=20, Biomass gain=20, shaking speed=1300 rpm, temperature=37° C., humidity=85%. Every strain was analyzed in triplicate.

E. coli Micro-Fermentations

Plasmids were transformed into host strains by electroporation using ECM 630 High Throughput Electroporation System (Harvard Apparatus, Inc. Holliston, Mass.) following manufacturer's protocol or using individual electroporation cuvettes. Glycerol stocks were prepared for each transformation plate by adding equal volume of sterile 20% glycerol, and 3 µL were used to inoculate overnight culture in 150 µL SM10++ medium with appropriate antibiotics. Plates were covered with sandwich covers (Model #CR1596 obtained from EnzyScreen, Haarlam, The Netherlands). These covers ensured minimal evaporative loss during incubation. Unless otherwise stated, 96 well plates were cultured at 37° C., 400 rpm for 16 hours, shaker orbit is 25 mm. This combination of orbit and minimal shaking speed is required to obtain needed mass transfer coefficient and enable adequate culture oxygenation.

After 16 hours of growth, cells were pelleted by centrifugation, excess media was removed and cells were resuspended in 150 µL of FGM3 Wash solution. Subsequently cells were once again pelleted and again excess media was removed, pellet was resuspended in 50 µL FGM3 No Phosphate media containing appropriate antibiotics. 5 µL of the resuspended culture was added to 195 µL of water for OD600 measurement using standard flat bottom 96 well plate. OD600 for production was normalized to OD600=1, using FGM3 No Phosphate media containing appropriate antibiotics, in a total volume of 150 µL using standard 96 well plate. Plates were covered with sandwich covers (Model #CR1596 obtained from EnzyScreen, Haarlam, The Netherlands) and 96 well plate cultures were incubated at 37° C., 400 rpm for 24 hours. After 24 hours of production, all samples from each well were pelleted by centrifugation and the supernatant collected for subsequent analytical measurement. Triplicate micro-fermentations were performed for each strain.

For growth associated alanine micro-fermentations, glycerol stock preparation and 16 hour overnight culture in SM10++ proceeded as described above. After 16 hours of growth in SM10++ medium, 5 µL of overnight culture was inoculated into 150 µL FGM3 with 40 mM phosphate containing appropriate antibiotic. Plates were covered with sandwich covers (Model #CR1596 obtained from Enzy-Screen, Haarlam, The Netherlands) and 96 well plate cultures were incubated at 37° C., 400 rpm for 24 hours. After 24 hours of production, OD600 was recorded, all samples from each well were then pelleted by centrifugation and the supernatant collected for subsequent analytical measurement. Triplicate micro-fermentations were performed for each strain.

Micro-fermentation robustness evaluations were conducted as described in Supplemental Materials, Section 8.

1 L Fermentation Seeds

Single colony from transformation plate was inoculated into 5 mL LB with appropriate antibiotics and cultured at 37° C., 220 rpm for 16 hours. 500 µL of the LB culture was inoculated into 50 mL SM10 media with appropriate antibiotics in square shake flask (CAT #: 25-214, Genesee Scientific, Inc. San Diego, Calif.), the culture was incubated at 37° C. with a shaking speed of 220 rpm for 24 hours, at which time OD600 is usually between 3 and 10, the culture was harvested by centrifugation at 4000 rpm for 15 min, supernatant was discarded and cell culture was normalized to OD600=10 using SM10 media. For 1 L fermentation seed, 6 mL of normalized OD600=10 culture was added to 1.5 mL of 50% glycerol in cryovials, and stored at −80° C.

1 L Fermentations

An Infors-HT Multifors (Laurel, Md., USA) parallel bioreactor system was used to perform 1 L fermentations, including three gas connection mass flow controllers configured for air, oxygen and nitrogen gases. Vessels used had a total volume of 1400 mL and a working volume of up to 1 L. Online pH and pO2 monitoring and control were accomplished with Hamilton probes. Offgas analysis was accomplished with a multiplexed Blue-in-One BlueSens gas analyzer (BlueSens. Northbrook, Ill., USA). Culture densities were continually monitored using Optek 225 mm OD probes, (Optek, Germantown, Wis., USA). The system used was running IrisV6.0 command and control software and integrated with a Seg-flow automated sampling system (Flownamics, Rodeo, Calif., USA), including FISP cell free sampling probes, a Segmod 4800 and FlowFraction 96 well plate fraction collector.

For the standardized 2-stage process with ~ 10 gcdw/L biomass, tanks were filled with 800 mL of FGM10 medium, with enough phosphate to target a final E. coli biomass concentration ~ 10 gcdw/L. Antibiotics were added as appropriate. Frozen seed vials were thawed on ice and 7.5 mL of seed culture was used to inoculate the tanks. After inoculation, tanks were controlled at 37° C. and pH 6.8 using 5 M ammonium hydroxide and 1 M hydrochloric acid as titrants. 10 M ammonium hydroxide was used for FIG. 3G fermentation run. The following oxygen control scheme was used to maintain the desired dissolved oxygen set point. First gas flow rate was increased from a minimum of 0.3 L/min of air to 0.8 L/min of air, subsequently, if more aeration was needed, agitation was increased from a minimum of 300 rpm to a maximum of 1000 rpm. Finally, if more oxygen was required to achieve the set point, oxygen supplementation was included using the integrated mass flow controllers. Starting glucose concentration was 25 g/L. A constant concentrated sterile filtered glucose feed (500 g/L) was added to the tanks at specified rate, i.e. 2 g/h, once agitation reached 800 rpm. In cases where feed rate or dissolved oxygen content needed to be varied for robustness study, changes were made after cells entered stationary phase. Fermentation runs were extended for up to ~50 hours after entry into stationary phase and samples automatically withdrawn every 3 hours. Samples were saved for subsequent analytical measurement.

In the case of growth associated fermentation processes, tanks were filled with 800 mL of FGM10 medium with 40 mM phosphate, which was in great excess and ensured phosphate depletion doesn't happen for growth associated fermentation processes. Antibiotics were added as appropriate. Frozen seed vials were thawed on ice and 7.5 mL of seed culture was used to inoculate the tanks. After inoculation, tanks were controlled at 37° C. and pH 6.8 using 5 M ammonium hydroxide and 1 M hydrochloric acid as titrants.

The following oxygen control scheme was used to maintain the desired dissolved oxygen set point. First gas flow rate was increased from a minimum of 0.3 L/min of air to 0.8 L/min of air, subsequently, if more aeration was needed, agitation was increased from a minimum of 300 rpm to a maximum of 1000 rpm. Finally, if more oxygen was required to achieve the set point, oxygen supplementation was included using the integrated mass flow controllers. Starting glucose concentration was 25 g/L. A constant concentrated sterile filtered glucose feed (500 g/L) was added to the tanks at specified rate, i.e. 2 g/h, once agitation reached 800 rpm. Feed rate and dissolved oxygen concentration was set to desired values in the beginning, and maintained throughout the fermentation process. Fermentation runs were continued for up to ~50 hours and samples automatically withdrawn every 3 hours. Samples were saved for subsequent analytical analysis.

Analytical Methods

Sample standard curves for all compounds quantified are shown in Supplemental Materials, Section 10.

Glucose and Ethanol Quantification: A UPLC-RI method was developed for the simultaneous quantification of glucose and ethanol concentrations, using an Acquity H-Class UPLC integrated with a Waters 2414 Refractive Index (RI) detector (Waters Corp., Milford, Mass. USA). Chromatographic separation was performed using a Bio-Rad Fast Acid Analysis HPLC Column (100×7.8 mm, 9 µm particle size; CAT #: #1250100, Bio-Rad Laboratories, Inc., Hercules, Calif.) at 65° C. 5 mM sulfuric acid was used as the eluent. The isocratic elution was as follows: 0-0.1 min, flow rate increased from 0.4 mL/min to 0.42 mL/min, 0.1-12 min flow rate at 0.48 mL/min. Sample injection volume was 10 µL. UPLC method development was carried out using standard aqueous stock solutions of analytes. Peak integration and further analysis was performed using MassLynx v4.1 software. The linear range used for glucose was 1-10 g/L, for ethanol was 1-20 g/L. Samples were diluted as needed to be within the accurate linear range.

Dilution was Performed Using Ultrapure Water.

Alanine Quantification: A reverse phase UPLC-MS/MS method was developed for alanine. Chromatographic separation was performed using a Restek Ultra AQ C18 column (150 mm×2.1 i.d., 3 µm; CAT #: 9178362, Restek Corporation, Bellefonte, Pa.) at 70° C. The following eluents were used: solvent A: $H_2O$, 0.2% formic acid and 0.05% ammonium (v/v); solvent B: MeOH, 0.2% formic acid and 0.05% ammonium (v/v). The gradient elution was as follows: 0-0.1 min isocratic 5% B, flow rate increased from 0.65 mL/min to 0.75 mL/min; 0.1-0.3 min, linear from 5% to 95% B at 0.75 mL/min; 0.3-0.9 min isocratic 95% B at 0.75 mL/min; and 0.9-1.2 min linear from 95% to 5% B at 0.75 mL/min; 1.2-1.3 min isocratic 5% B at 0.75 mL/min. Sample injection volume was 5 µL. UPLC method development was carried out using standard aqueous stock solutions of analyte. Separations were performed using an Acquity H-Class UPLC integrated with a Xevo™ TQD Mass spectrometer (Waters Corp., Milford, Mass. USA). MS/MS parameters including MRM transitions were tuned for each analyte and are listed in Table 22. Alanine (2,3-13C2, 99%) was used as internal standard for alanine at a concentration of 5 mg/L. Peak integration and further analysis was performed using MassLynx v4.1 software. The linear range for alanine was 1-100 mg/L. Samples were diluted as needed to be within the accurate linear range. Dilution was performed using ultrapure water, and the final 10-fold dilution was performed using solvent A, with 5 mg/L of C13 alanine (2,3-13C2, 99%).

Mevalonic Acid Quantification: A reverse phase UPLC-TUV method was developed for the simultaneous quantification of mevalonic acid and mevalonolactone. Chromatographic separation was performed using a Restek Ultra AQ C18 column (150 mm×2.1 i.d., 3 µm; CAT #: 9178362, Restek Corporation, Bellefonte, Pa.) at 30° C. 20 mM phosphoric acid was used as the eluent. The isocratic elution was as follows: 0-3 min isocratic at 1 mL/min. Sample injection volume was 10 µL. Absorbance was monitored at 210 nm. UPLC method development was carried out using standard aqueous stock solutions of analytes. Separations were performed using an Acquity H-Class UPLC (Waters Corp., Milford, Mass. USA). Peak integration and further analysis was performed using MassLynx v4.1 software. The linear range for mevalonic acid and mevalonolactone were 0.01-0.1 g/L. Samples were diluted as needed to be within the accurate linear range. Mevalonic acid diluted in 20 mM phosphoric acid would spontaneously convert to mevalonolactone 80, thus, quantification of both mevalonic acid and mevalonolactone was necessary for fermentation samples. Mevalonic acid and mevalonolactone standards were prepared fresh each time, and ran immediately on UPLC. Dilution was performed using ultrapure water, and the final 10-fold dilution was performed using 20 mM phosphoric acid.

Alanine Stereoisomer Quantification: A reverse phase UPLC-TUV method was developed for the simultaneous quantification and differentiation of L-/D-alanine. Chromatographic separation was performed using a Chirex 3126 (D)-penicillamine column (150×4.6 mm, 5 µm; Phenomenex Inc., Torrance, Calif.) at 50° C. 2 mM Copper Sulfate was used as the eluent. The isocratic elution was as follows: 0-10 min at 0.75 mL/min. Sample injection volume was 10 µL. Absorbance was monitored at 254 nm. UPLC method development was carried out using standard aqueous stock solutions of analytes. Separations were performed using an Acquity H-Class UPLC (Waters Corp., Milford, Mass. USA). Peak integration and further analysis was performed using MassLynx v4.1 software. The linear range for L-/D-alanine was 0.1-1 g/L. Samples were diluted as needed to be within the accurate linear range. Dilution was performed using ultrapure water.

Supplemental Materials

TABLE 1

Combinatorial complexity of metabolic networks.

| Combination # | Entire E. coli Gene Network | Reduced Central Metabolism Network Number of Experiments |
|---|---|---|
| 1 | 4500 | ~45 (Glycolysis, TCA, PPP and ETC genes only) |
| 2 | $1.0 \times 10^6$ | 990 |
| 3 | $1.5 \times 10^{10}$ | 14,190 |
| 4 | $1.7 \times 10^{13}$ | 148,995 |
| 5 | $1.5 \times 10^{16}$ | $1.2 \times 10^6$ |

Section 1: Phosphate Promoters

Figure 7:
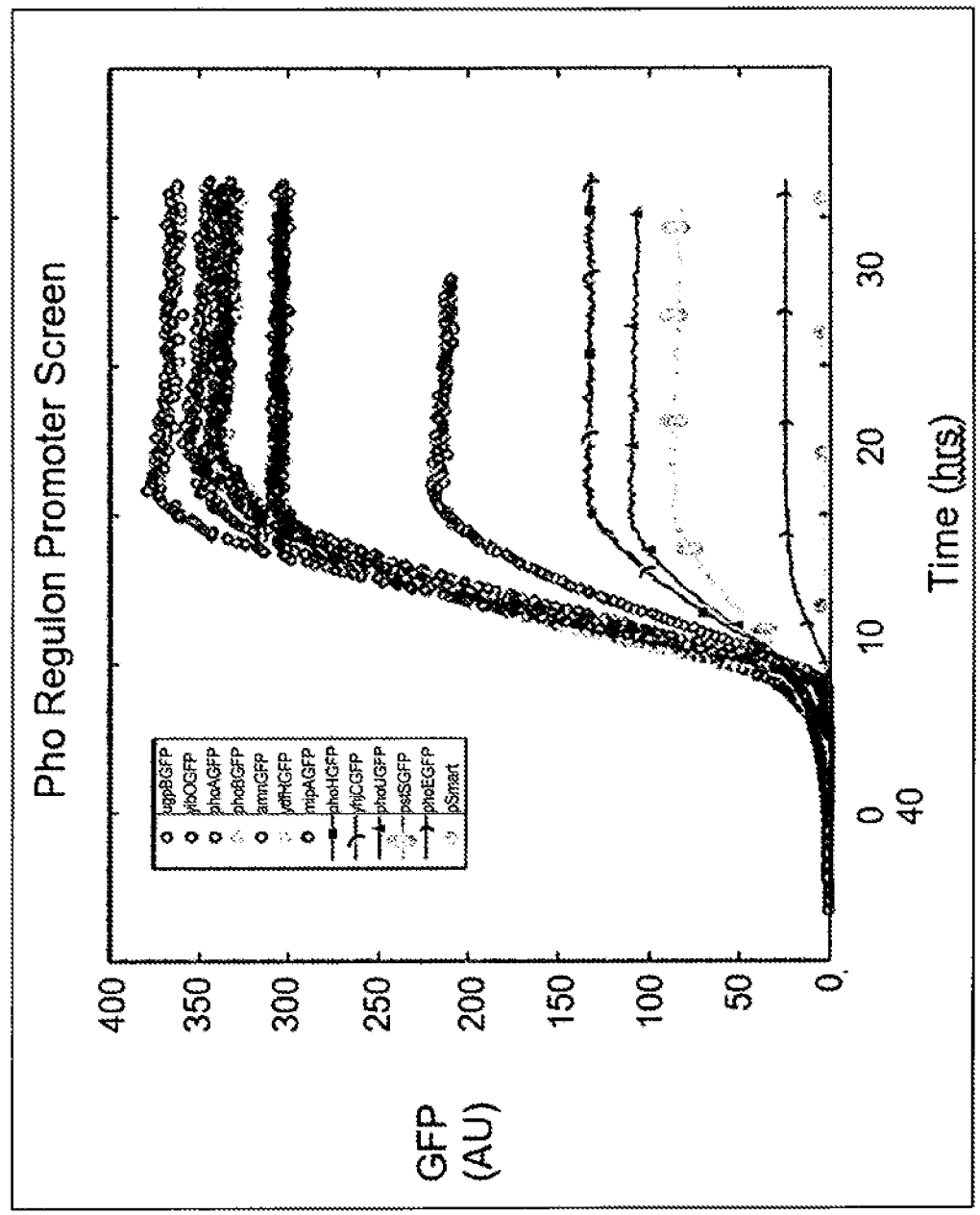
FIG. 7 depicts an example of phosphate depletion promoter characterization.

Phosphate promoter sequences were obtained from the EcoCyc database 81 for PhoB regulated promoters (https://ecocyc.org/, Table 2). We sought to evaluate not only the relative strength of promoters previously characterized to respond to phosphate depletion, but in addition the relative leakiness in phosphate rich conditions. To this aim we constructed a set of fluorescent reporter plasmids. We cloned the ultraviolet excitable GFPuv gene behind a set of 12 phosphate dependent promoters, in the pSMART-HC-Kan (Lucigen, WI) backbone. These reporter strains were evaluated in a 2-stage micro-fermentation protocol in an m2p-labs Biolector™. Results are illustrated in FIG. 7. The ugpB gene promoter was often chosen for high level tightly controlled expression when expression cassettes were chromosomally integrated or for the inducible expression of guide arrays.

Figure 8:
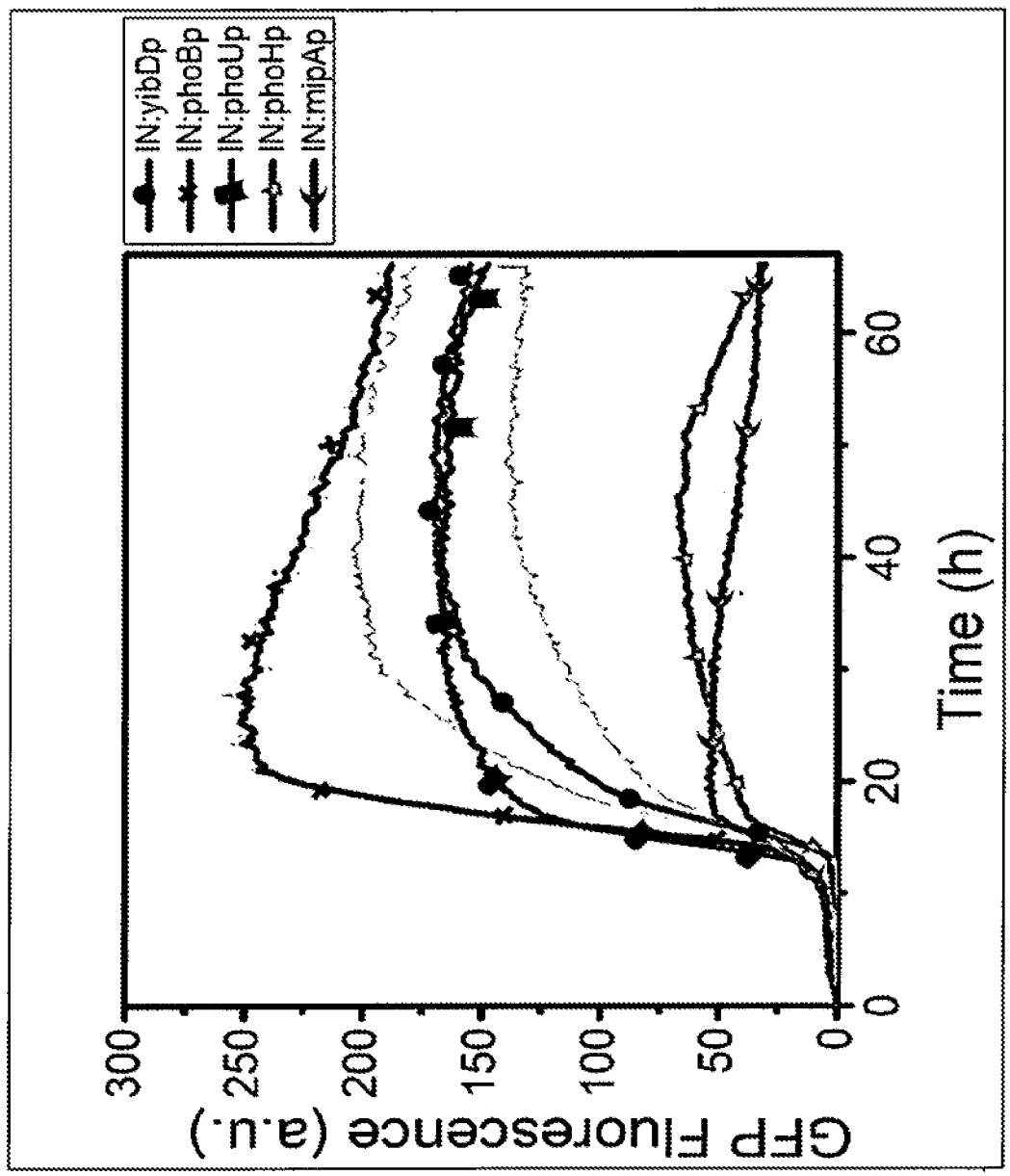
FIG. 8 depicts an example of insulated phosphate depletion promoter characterization.

Insulators[82] were added to both 5' and 3' end of a subset of phosphate promoters (Table 3) to help with consistent performance in different sequence contexts. To reduce read-through transcription, a unique terminator was added to the 5' end of each insulated promoter. Terminator sequences were from http://parts.igem.org/Terminators/Catalog. Insulated phosphate promoters were similarly characterized using GFPuv expression in a m2p-labs Biolector™ (FIG. 8).

TABLE 2

Phosphate inducible promoter sequences evaluated, the ribosomal binding site is underlined, and the start codon of the gene (GFPuv) is shown in green.

| Promoter Name | Sequence | SEQ ID NO |
|---|---|---|
| ugpBp | TCCTTTCTGACACCTTACTATCTTACAAATGTAACAAAAAAGTTATTTTTCTGTAATTCGA GCATGTCATGTTACCCCGCGAGCATAAAACGCGTGTGT<u>AGGAGGA</u>TAATCTATG | 1 |
| yibDp | GTGCGTAATTGTGCTGATCTCTTATATAGCTGCTCTCATTATCTCTCTACCCTGAAGTGAC TCTCTCACCTGTAAAATAATATCTCACAGGCTTAATAGTTTCTTAATACAAAGCCTGTA AAACGTCAGGATAACTTCTGTGT<u>AGGAGGA</u>TAATCTATG | 2 |
| phoAp | CGATTACGTAAAGAAGTTATTGAAGCATCCTCGTCAGTAAAAAGTTAATCTTTTCAACA GCTGTCATAAAGTTGTCACGGCCGAGACTTATAGTCGCTTTGTTTTTATTTTTTAATGTAT TTGTAGTGTAGGAGGATAATCTATGGCTAGCAAAGG<u>AGAAGAA</u>CTTTTCACATG | 3 |
| phoBp | GCCACGGAAATCAATAACCTGAAGATATGTGCGACGAGCTTTTCATAAATCTGTCATAA ATCTGACGCATAATGACGTCGCATTAATGATCGCAACCTATTTATTGTGTAGGAGGATA ATCTATGGCTAGCAAAGG<u>AGAAGAA</u>CTTTTCACATG | 4 |
| amnp | AGACAGTCAACGCGCTTGATAGCCTGGCGAAGATCATCCGATCTTCGCCTTACACTTTG TTTCACATTTCTGTGACATACTATCGGATGTGCGGTAATTGTAT<u>AGGAGGA</u>TAATCTATG | 5 |
| ydfHp | GCTATGCCGGACTGAATGTCCACCGTCAGTAATTTTTATACCCGGCGTAACTGCCGGTT ATTGCTTGTCACAAAAAAGTGGTAGACTCATGCAGTTAACTCACTGTGT<u>AGGAGGA</u>TAA TCTATG | 6 |

TABLE 2-continued

Phosphate inducible promoter sequences evaluated, the ribosomal binding site is underlined, and the start codon of the gene (GFPuv) is shown in green.

| Promoter Name | Sequence | SEQ ID NO |
|---|---|---|
| mipAp | CATCCATAAATTTTGCATAATTAATGTAAAGACCAGGCTCGCCAGTAACGCTAAATTCA TTTGGCTGTAAGCGCGGTGTCATCCGCGTCAGGAAAATTAAACAGTTACTTTAAAAAAT GAAAACGTAAAAAGGTTGGGTTTCGATGTATTGACGGGTAAACTTTGTCGCCCGCTAAA CATTTGTTTGTGT<u>AGGAGGA</u>TAATCTATG | 7 |
| phoHp | AATCCTGCTGAAAGCACACAGCTTTTTTCATCACTGTCATCACTCTGTCATCTTTCCAGT AGAAACTAATGTCACTGAAATGGTGTTTTATAGTTAAATATAAGTAAATATATTGTTGCA ATAAATGCGAGATCTGTTGTACTTATTAAGTAGCAGCGGAAGTTCGTGT<u>AGGAGGA</u>TAA TCTATG | 8 |
| yhjCp | CTACAGAGATGACGTGTAGAAAATAGTTACCGATATAAATAGTTACAGCTAAACGCCTG AAATTACATGTCGAGGGCACTATTTAAAACAATTTTGAGGATTTCCTTATATTGGTGGTT AGTACGCATGCAATTAAAAATGAAATTCCGCGACCACAAGCCAAAATAACAAACGGCA AGGAGACAAAATAAGCACAAATAGCCAACACGTCCTCTGTTCACTTTAAAGGGAATCG CTGAAAAATACGCTCTGTTTAAGGGGATTCACCTTTCTCAGAAAGCTATTCCGCCCTTTT CCTGCTGAGAAATCGCCACATTCGGCATGACAACATTGTGAAAGTGT<u>AGGAGGA</u>TAATC TATG | 9 |
| phoUp | ACCGAACTGAAGCAGGATTACACCGTGGTGATCGTCACCCACAACATGCAGCAGGCTGC GCGTTGTTCCGACCACACGGCGTTTATGTACCTGGGCGAATTGATTGAGTTCAGCAACA CGGACGATCTGTTCACCAGTGT<u>AGGAGGA</u>TAATCTATG | 10 |
| pstSp | AAGACTTTATCTCTCTGTCATAAAACTGTCATATTCCTTACATATAACTGTCACCTGTTTG TCCTATTTTGCTTCTCGTAGCCAACAAACAATGCTTTATGAGTGTAGGAGGATAATCTAT GGCTAGCAAAGG<u>AGAAGAA</u>CTTTTCACATG | 11 |
| phoEp | AGCATGGCGTTTTGTTGCGCGGGATCAGCAAGCCTAGCGGCAGTTGTTTACGCTTTTATT ACAGATTTAATAAATTACCACATTTTAAGAATATTATTAATCTGTAATATATCTTTAACA ATCTCAGGTTAAAAACTTTCCTGTTTTCAACGGGACTCTCCCGCTGGTGT<u>AGGAGGA</u>TAA TCTATG | 12 |

TABLE 3

Insulated promoter sequences. Insulator sequences are italicized. -35 and -10 boxes are highlighted in bold and underlined.

| Insulated Promoter | Sequence | SEQ ID NO |
|---|---|---|
| BBa_B0015_IN_yibDp | CCAGGCATCAAATAAAACGAAAGGCTCAGTCGAAAGACTGGGCCTTTCGTT TTATCTGTTGTTTGTCGGTGAACGCTCTCTACTAGAGTCACACTGGCTCACCT TCGGGTGGGCCTTTCTGCGTTTATA*CACAGCTAACACCACGTCGTCCCTATCTG CTGCCCTAGGTCTATGAGTGGTTGCTGGATAACGTGCGTAATTGTGCTGATCTC* TTATATAGCTGCTCTCATTATCTCTCTACCCTGAAGTGACTCTCTCACCTGTA AAATAATATCTCACAGGCTTAATAGTTTCTTAATACAAAGCCTGTAAAACG TCAGGATAACTTCT*ATATTCAGGGAGACCACAACGGTTTCCCTCTCAAATAATTT TGTTTAACTTT* | 13 |
| BBa_B1002_IN_phoBp | CGCAAAAAACCCCGCTTCGGCGGGTTTTTTCGCACGTCTCCATCGCTTGCC CAAGTTGTGAAG*CACAGCTAACACCACGTCGTCCCTATCTGCTGCCCTAGGTCT ATGAGTGGTTGCTGGATAACGCCACGGAAATCAATAACCTGAAGATATGTGCG* ACGAGCTTTTCATAAATCTGTCATAAATCTGACGCATAATGACGTCGCATTA ATGATCGCAACCTATTTATTATATTCAGGGAGACCACAACGGTTTCCCTCTACAA *ATAATTTTGTTTAACTTT* | 14 |
| BBa_B1004_IN_mipAp | CGCCGAAAACCCCGCTTCGGCGGGTTTTGCCGCACGTCTCCATCGCTTGCC CAAGTTGTGAAG*CACAGCTAACACCACGTCGTCCCTATCTGCTGCCCTAGGTCT ATGAGTGGTTGCTGGATAACCATCCATAAATTTTGCATAATTAATGTAAAGAC CAGGCTCGCCAGTAACGCTAAATTCATTTGGCTGTAAGCGCGGTGTCATCCG CGTCAGGAAAATTAAACAGTTACTTTAAAAAATGAAAACGTAAA*AAGGTTG GGTTTCGATGTATTGACGGGTAAACTTTGTCGCCCGCTAAACATTTGTTTATA *TTCAGGGAGACCACAACGGTTTCCCTCTACAAATAATTTTGTTTAACTTT* | 15 |
| BBa_B1006_IN_phoUp | AAAAAAAACCCCGCCCCTGACAGGGCGGGGTTTTTTTACGTCTCCATCGC TTGCCCAAGTTGTGAAG*CACAGCTAACACCACGTCGTCCCTATCTGCCTA GGTCTATGAGTGGTTGCTGGATAACACCGAACTGAAGCAGGATTACACCGTG* TGATCGTCACCCACAACATGCAGCAGGCTGCGCGTTGTTCCGACCACACGG CGTTTATGTACCTGGGCGAATTGATTGAGTTCAGCAACACGGACGATCTGTT CACCAATATTCAGGGAGACCACAACGGTTTCCCTCTACAAATAATTTTGTTTAACTT *T* | 16 |

TABLE 3-continued

Insulated promoter sequences. Insulator sequences are italicized. -35 and -10 boxes are highlighted in bold and underlined.

| Insulated Promoter | Sequence | SEQ ID NO |
|---|---|---|
| BBa_B1010_IN_phoHp | CGCCGCAAACCCCGCCCCTGACAGGGCGGGGTTTCGCCGCACGTCTCCATCG CTTGCCCAAGTTGTGAAG*CACAGCTAACACCACGTCGTCCCTATCTGCTGCCCT AGGTCTATGAGTGGTTGCTGGATAA*CAATCCTGCTGAAAGCACACAGCTTTTTT CATCACTGTCATCACTCTGTCATCTTTCCAGTAGAAACTAATGTCACTGAAA TGGTGTTTTATAGTTAAATATAAGTAAATATATTGTTGCAATAAATGCGAGA TCTGTTGTACTTATTAAGTAGCAGCGGAAGTTC*ATATTCAGGGAGACCACAAC GGTTTCCCTCTACAAATAATTTTGTTTAACTTT* | 17 |

Section 2: Constitutive Promoters

Figure 9:
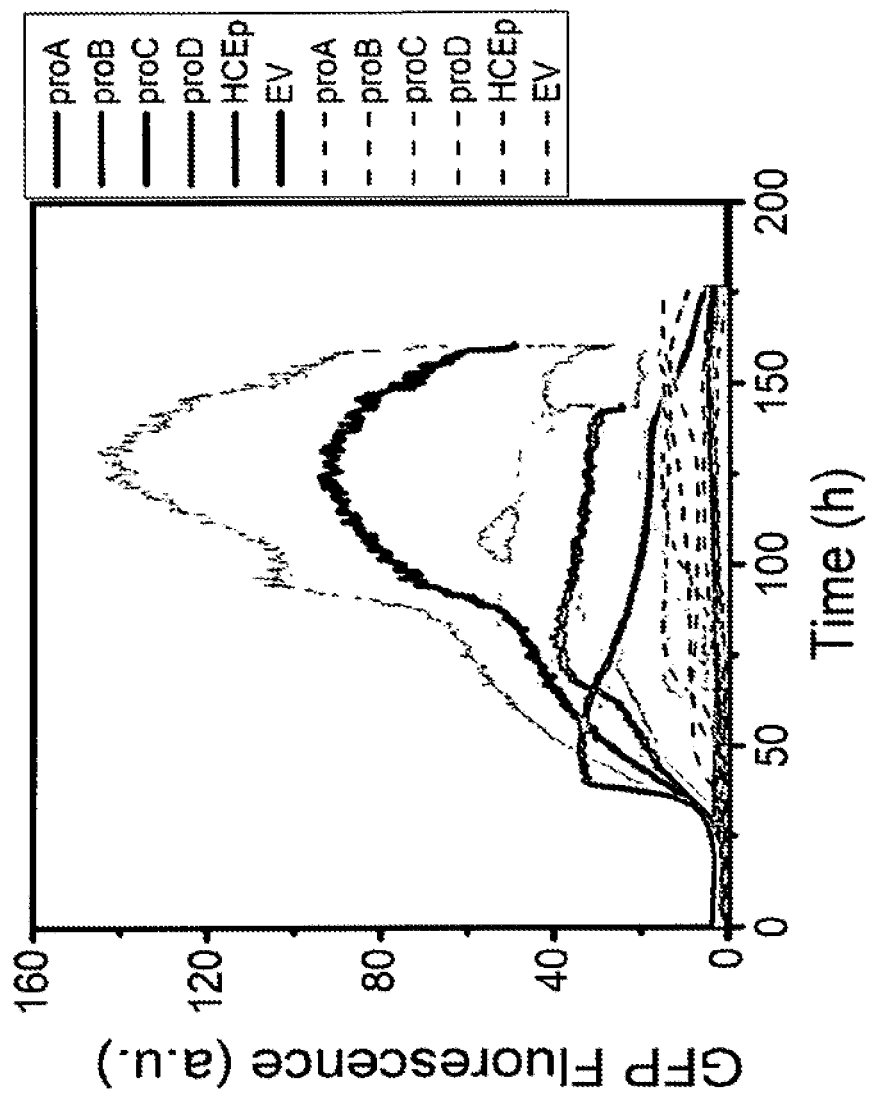
FIG. 9 depicts an example of insulated constitutive promoter characterization.

A set of constitutive insulated promoters of varying strength were used for constitutive expression and taken directly from Davis et al., including the proA, proB, proC, proD promoters[82] and HCEp promoter[83]. Insulator was added to 5' and 3' of HCEp promoter. Similar to insulated phosphate promoters, a unique terminator was added to the 5' end of constitutive promoters. These were used to drive constitutive pathway expression in growth associated production strains as well as to make strain modifications where constitutive heterologous gene expression was appropriate. These promoter sequences are given in Table 4 below and promoter characterized using GFPuv expression (FIG. 9).

TABLE 4

Constitutive promoter sequences.

| Promoter | Sequence | SEQ ID NO |
|---|---|---|
| BBa_B1004_proA | CGCCGAAAACCCCGCTTCGGCGGGGTTTTGCCGCACGTC TCCATCGCTTGCCCAAGTTGTGAAGCACAGCTAACACCA CGTCGTCCCTATCTGCTGCCCTAGGTCTATGAGTGGTTG CTGGATAACTTTACGGGCATGCATAAGGCTCGTAGGCTA TATTCAGGGAGACCACAACGGTTTCCCTCTACAAATAAT TTTGTTTAACTTT | 18 |
| BBa_B1006_proB | AAAAAAAAACCCCGCCCCTGACAGGGCGGGGTTTTTTT ACGTCTCCATCGCTTGCCCAAGTTGTGAAGCACAGCTAA CACCACGTCGTCCCTATCTGCTGCCCTAGGTCTATGAGT GGTTGCTGGATAACTTTACGGGCATGCATAAGGCTCGTA ATATATATTCAGGGAGACCACAACGGTTTCCCTCTACAA ATAATTTTGTTTAACTTT | 19 |
| BBa_B1010_proC | CGCCGCAAACCCCGCCCCTGACAGGGCGGGGTTTCGCC GCACGTCTCCATCGCTTGCCCAAGTTGTGAAGCACAGCT AACACCACGTCGTCCCTATCTGCTGCCCTAGGTCTATGA GTGGTTGCTGGATAACTTTACGGGCATGCATAAGGCTCG TATGATATATTCAGGGAGACCACAACGGTTTCCCTCTAC AAATAATTTTGTTTAACTTT | 20 |
| BBa_B1002_proD | CGCAAAAAACCCCGCTTCGGCGGGGTTTTTTCGCACGTC TCCATCGCTTGCCCAAGTTGIGAAGCACAGCTAACACCA CGTCGTCCCTATCTGCTGCCCTAGGTCTATGAGTCGTTG CTGGATAACTTTACGGGCATGCATAAGGCTCGTATAATA TATTCAGGGAGACCACAACGGTTTCCCTCTACAAATAAT TTTGTTTAACTTT | 21 |
| BBa_B0015_IN_HCEp | CCAGGCATCAAATAAAACGAAAGGCTCAGTCGAAAGAC TGGGCCTTTCGTTTTATCTGTTGTTTGTCGGTGAACGCTC TCTACTAGAGTCACACTGGCTCACCTTCGGGTGGGCCTT TCTGCGTTTATACACAGCTAACACCACGTCGTCCCTATC TGCTGCCCTAGGTCTATGAGTGGTTGCTGGATAACCTCC TTCACAGATTCCCAATCTCTTGTTAAATAACGAAAAGC ATCAATTAAAACCCATGTCTTTCTATATTCCAGCAATGT TTTATAGGGACATATTGATGAAGATGGGTATCACCTTA GTGAATTGCTATAAGCTGCTCTTTTTTGTTCGTGATATAC TGATAAATTGAATTTTCACACTTCATATTCAGGGAGACC ACAACGGTTTCCCTCTACAAATAATTTTGTTTAACTTT | 22 |

Section 3: Chromosomally Modified Host Strains

Figure 11:
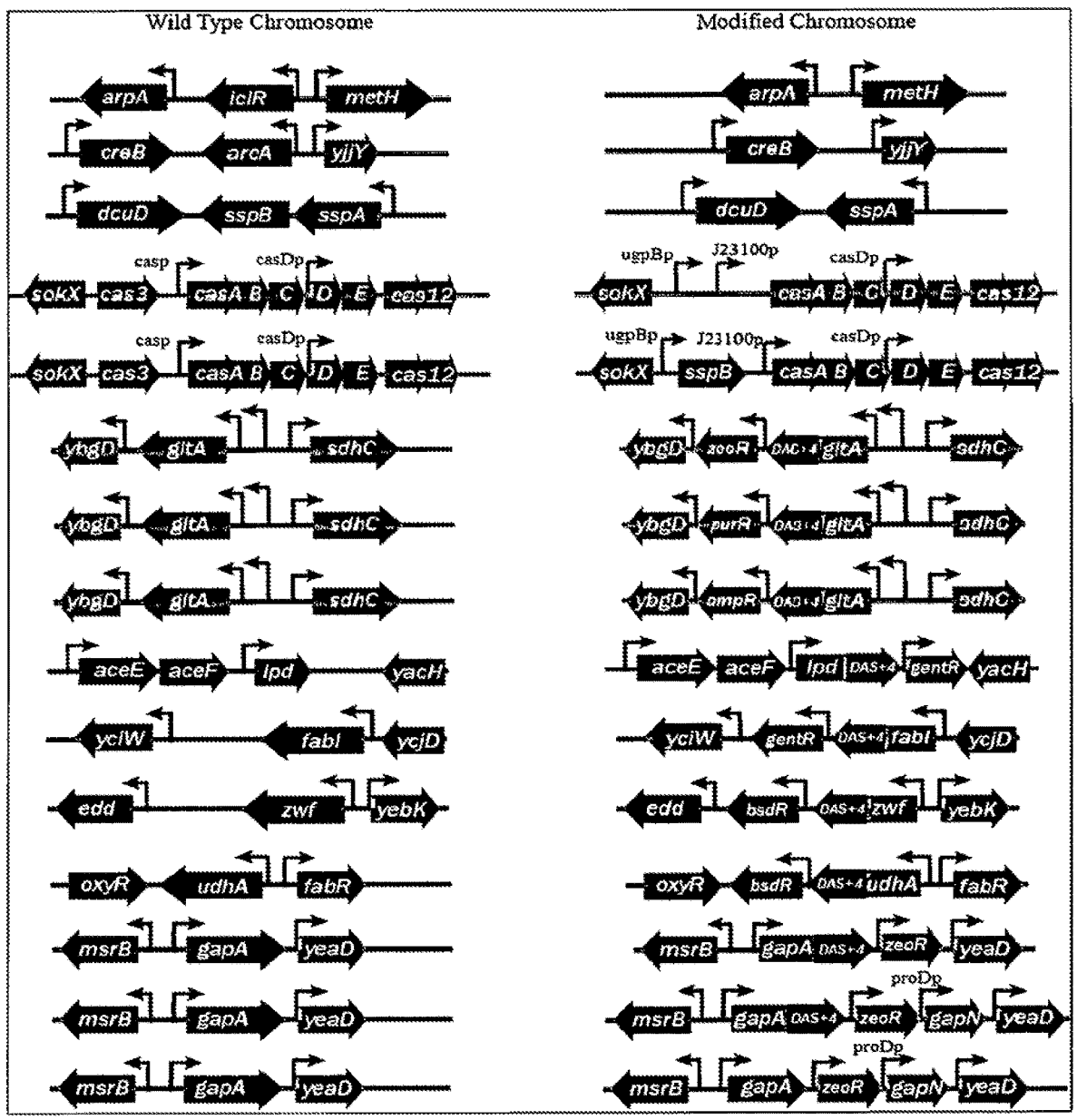
FIG. 11 depicts examples of chromosomal modifications.

FIG. 11 depicts each chromosomal modification. Strains utilized and/or constructed for this study are listed in Table 5. Tables 6 and 7 lists oligonucleotides and synthetic DNA sequences used for strain construction and/or confirmation. FIG. 12 and FIG. 13A-E show growth rates and glucose distribution during growth for control strains in 1 L fermentation.

TABLE 5

List of chromosomally modified strains.

| Strain | Genotype | Source |
|---|---|---|
| BW25113 (wt) | F-, λ-, Δ(araD-araB)567, lacZ4787(del)(::rrnB-3), rph-1, Δ(rhaD-rhaB)568, hsdR514 | CGSC |
| JW3197-1 | BW25113, sspB756(del)::kan | 53 |
| Bwapldf | BW25113, ΔackA-pta, ΔpoxB, ΔpflB, ΔldhA, ΔadhE | 39 |
| DLF_0001 | Bwapldf, ΔiclR, ΔarcA | this study |
| DLF_0002 | Bwapldf, ΔiclR, ΔarcA, ΔsspB::frt | this study |
| DLF_0025 | DLF_0002, Δcas3::tm-ugpb-sspB-pro-casA(N2S) | this study |
| DLF_0028 | DLF_0025, fabI-DAS + 4-gentR | this study |
| DLF_0031 | DLF_0025, lpd-DAS + 4-gentR | this study |
| DLF_0038 | DLF_0025, fabI-DAS + 4-gentR, udhA-DAS + 4-bsdR | this study |
| DLF_0039 | DLF_0025, fabI-DAS + 4-gentR, gltA-DAS + 4-zeoR | this study |
| DLF_0040 | DLF_0025, fabI-DAS + 4-gentR, zwf-DAS + 4-bsdR | this study |
| DLF_0041 | DLF_0025, lpd-DAS + 4-gentR, gltA-DAS + 4-zeoR | this study |
| DLF_0042 | DLF_0025, lpd-DAS + 4-gentR, udhA-DAS + 4-bsdR | this study |
| DLF_0043 | DLF_0025, gltA-DAS + 4-zeoR | this study |
| DLF_0044 | DLF_0025, gltA-DAS + 4-zeoR, zwf-DAS + 4-bsdR | this study |
| DLF_0045 | DLF_0025, gltA-DAS + 4-zeoR, udhA-DAS + 4-bsdR | this study |
| DLF_0046 | DLF_0025, fabI-DAS + 4-gentR, gltA-DAS + 4-zeoR, zwf-DAS + 4-bsdR | this study |
| DLF_0047 | DLF_0025, fabI-DAS + 4-gentR, gltA-DAS + 4::zeoR, udhA-DAS + 4-bsdR | this study |
| DLF_0048 | DLF_0025, lpd-DAS + 4-gentR, gltA-DAS + 4-zeoR, zwf-DAS + 4-bsdR | this study |
| DLF_0049 | DLF_0025, lpd-DAS + 4-gentR, gltA-DAS + 4-zeoR, udhA-DAS + 4-bsdR | this study |
| DLF_0165 | DLF_0025, lpd-DAS + 4-gentR, zwf-DAS + 4-bsdR | this study |
| DLF_0763 | DLF_0025, udhA-DAS + 4-bsdR | this study |
| DLF_01002 | DLF_0025, zwf-DAS + 4-bsdR | this study |
| DLF_01517 | DLF_0012, Δcas3::pro-casA(N2S) | this study |
| DLF_01530 | DLF_0025, fabI-DAS + 4-gentR, udhA-DAS + 4-bsdR, zeoR-proDp-gapN-zeoR | this study |
| DLF_01531 | DLF_0025, fabI-DAS + 4-gentR, udhA-DAS + 4-bsdR, gltA-DAS + 4-purR | this study |
| DLF_01532 | DLF_0025, fabI-DAS + 4-gentR, udhA-DAS + 4-bsdR, gapA-DAS + 4-zeoR-proDp-gapN | this study |
| DLF_01533 | DLF_0025, fabI-DAS + 4-gentR, udhA-DAS + 4-bsdR, gapA-DAS + 4-zeoR-proDp-gapN, gltA-DAS + 4-purR | this study |
| DLF_01536 | DLF_0025, fabI-DAS + 4-gentR, udhA-DAS + 4-bsdR, zeoR-proDp-gapN, gltA-DAS + 4-purR | this study |
| DLF_01537 | DLF_0025, fabI-DAS + 4-gentR, udhA-DAS + 4-bsdR, gapA-DAS + 4-zeoR | this study |
| DLF_01538 | DLF_0025, fabI-DAS + 4-gentR, gltA-DAS + 4-zeoR, udhA-DAS + 4-bsdR, gapA-DAS + 4-zeoR | this study |

TABLE 6

Oligonucleotides utilized for strain construction

| Oligo | Sequence | SEQ ID NO |
|---|---|---|
| ilcR_tetA_f | TAACAATAAAAATGAAAATGATTTCCACGATACAGAAA AAAGAGACTGTCATCCTAATTTTTGTTGACACTCTATC | 23 |
| ilcR_sacB_R | TGCCACTCAGGTATGATGGGCAGAATATTGCCTCTGCCC GCCAGAAAAACATCAAAGGGAAAACTGTCCATATGC | 24 |
| iclR_500up | CCGACAGGGATTCCATCTG | 25 |
| iclR_500dn | TTGACGACCATTTTGTCTACAGTTC | 26 |
| arcA_tetA_F | GGACTTTTGTACTTCCTGTTTCGATTTAGTTGGCAATTTA GGTAGCAAACTCCTAATTTTTGTTGACACTCTATC | 27 |
| arcA_sacB_R | ATAAAAACGGCGCTAAAAAGCGCCGTTTTTTTTGACGGT GGTAAAGCCGAATCAAAGGGAAAACTGTCCATATGC | 28 |
| arcA_500up | CCTGACTGTACTAACGGTTGAG | 29 |
| arcA_500dn | TGACTTTTATGGCGTTCTTTGTTTTTG | 30 |
| sspB_kan_F | CTGGTACACGCTGATGAACACC | 31 |
| sspB_kan_R | CTGGTCATTGCCATTTGTGCC | 32 |
| sspB_conf_F | GAATCAGAGCGTTCCGACCC | 33 |

TABLE 6-continued

Oligonucleotides utilized for strain construction

| Oligo | Sequence | SEQ ID NO |
|---|---|---|
| sspB_conf_R | GTACGCAGTTTGCCAACGTG | 34 |
| cas3_tetA_F | AATAGCCCGCTGATATCATCGATAATACTAAAAAAACAG GGAGGCTATTATCCTAATTTTTGTTGACACTCTATC | 35 |
| cas3_sacB_R | TACAGGGATCCAGTTATCAATAAGCAAATTCATTTGTTCT CCTTCATATGATCAAAGGGAAAACTGTCCATATGC | 36 |
| cas3_conf_F | CAAGACATGTGTATATCACTGTAATTC | 37 |
| cas3_500dn | GCGATTGCAGATTTATGATTTGG | 38 |
| fabI_conf_F | GCAAAATGCTGGCTCATTG | 39 |
| gapA_conf_F | GAACTGAATGGCAAACTGACTG | 40 |
| gapA_500dn | TGGGGATGATCGACCACA | 41 |
| gltA_conf_F | TATCATCCTGAAAGCGATGG | 42 |
| lpd_conf_F | ATCTCACCGTGTGATCGG | 43 |
| udhA_conf_F | CAAAAGAGATTCTGGGTATTCACT | 44 |
| zwf_conf_F | CTGCTGGAAACCATGCG | 45 |
| zwf_500dn | AGAGCATGTCTTATAGGAGGTGAT | 46 |
| ampR_intR | AGTACTCAACCAAGTCATTCTG | 47 |
| bsdR_intR | GAGCATGGTGATCTTCTCAGT | 48 |
| gentR_intR | GCGATGAATGTCTTACTACGGA | 49 |
| purR_intR | GTCGCTGGGTAATCTGCAA | 50 |
| tetA_intR | ATCAACGCATATAGCGCTAGCAG | 51 |
| zeoR_intR | ACTGAAGCCCAGACGATC | 52 |

TABLE 7

Synthetic DNA utilized for strain construction.

| | SEQ ID NO |
|---|---|
| tetA-sacB Cassette<br>TCCTAATTTTTGTTGACACTCTATCATTGATAGAGTTATTTTACCACTCCCTA TCAGTGATAGAGAAAAGTGAAATGAATAGTTCGACAAAGATCGCATTGGTA ATTACGTTACTCGATGCCATGGGGATTGGCCTTATCATGCCAGTCTTGCCAA CGTTATTACGTGAATTTATTGCTTCGGAAGATATCGCTAACCACTTTGGCGT TTGCTTGCACTTTATGCGTTAATGCAGGTTATCTTTGCTCCTTGGCTTGGAA AAATGTCTGACCGATTTGGTCGGCGCCCAGTGCTGTTGTTGTCATTAATAGG CGCATCGCTGGATTACTTATTGCTGGCTTTTTCAAGTGCGCTTTGGATGCTGT ATTTAGGCCGTTTGCTTTCAGGGATCACAGGAGCTACTGGGGCTGTCGCGGC ATCGGTCATTGCCGATACCACCTCAGCTTCTCAACGCGTGAAGTGGTTCGGT TGGTTAGGGGCAAGTTTTGGCTTGGTTTAATAGCGGGGCCTATTATTGGTG GTTTTGCAGGAGAGATTTCACCGCATAGTCCCTTTTTTATCGCTGCGTTGCTA AATATTGTCACTTTCCTTGTGGTTATGTTTTGGTTCCGTGAAACCAAAAATAC ACGTGATAATACAGATACCGAAGTAGGGGTTGAGACGCAATCGAATTCGGT ATACATCACTTTATTTAAAACGATGCCCATTTTGTTGATTATTTATTTTTCAG CGCAATTGATAGGCCAAATTCCCGCAACGGTGTGGGTGCTATTTACCGAAA ATCGTTTTGGATGGAATAGCATGATGGTTGGCTTTTCATTAGCGGGTCTTGG TCTTTTACACTCAGTATTCCAAGCCTTTGTGGCAGGAAGAATAGCCACTAAA TGGGGCGAAAAAACGGCAGTACTGCTCGGATTATTGCAGATAGTAGTGCA TTTGCCTTTTTAGCGTTTATATCTGAAGGTTGGTTAGTTTTCCCTGTTTTAATT TTATTGGCTGGTGGTGGGATCGCTTTACCTGCATTACAGGGAGTGATGCTA TCCAACAAAGAGTCATCAGCAAGGTGCTTTACAGGGATTATTGGTGAGCC TTACCAATGCAACCGGTGTTATTGCCCATTACTGTTTGCTGTTATTTTATAAT CATTCACTACCAATTTGGGATGGCTGGATTTGGATTATTGGTTTAGCGTTTTA CTGTATTATTATCCTGCTATCGATGACCTTCATGTTAACCCCTCAAGCTCAGG | 53 |

TABLE 7-continued

Synthetic DNA utilized for strain construction.

| | SEQ ID NO |
|---|---|
| GGAGTAAACAGGAGACAAGTGCTTAGTTATTTCGTCACCAAATGATGTTATT CCGCGAAATATAATGACCCTCTTGATAACCCAAGAGCATCACATATACCTGC CGTTCACTATTATTTAGTGAAATGAGATATTATGATATTTTCTGAATTGTGAT TAAAAAGGCAACTTTATGCCCATGCAACAGAAACTATAAAAAATACAGAGA ATGAAAAGAAACAGATAGATTTTTAGTTCTTTAGGCCCGTAGTCTGCAAAT CCTTTATGATTTTCTATCAAACAAAAGAGGAAAATAGACCAGTTGCAATCC AAACGAGAGTCTAATAGAATGAGGTCGAAAAGTAAATCGCGCCTGGTTTGTT ACTGATAAAGCAGGCAAGACCTAAAATGTGTAAAGGGCAAAGTGTATACTT TGGCCTCACCCCTTACATATTTTAGGTCTTTTTTTATTGTGCGTAACTAACTT GCCATCTTCAAACAGGAGGGCTGGAAGAAGCAGACCGCTAACACAGTACAT AAAAAAGGAGACATGAACGATGAACATCAAAAAGTTTGCAAAACAAGCAA CAGTATTAACCTTTACTACCGCACTGCTGGCAGGAGGCGCAACTCAAGCCTTT TGCGAAAGAAACGAACCAAAAGCCATATAAGGAAACATACGGCATTTCCCA TATTACACGCCATGATATGCTGCAAATCCCTGAACAGCAAAAAAATGAAAA ATATCAAGTTCCTGAGTTCGATTCGTCCACAATTAAAAATATCTCTTCTGCA AAAGGCCTGGACGTTTGGGACAGCTGGCCATTACAAAACGCTGACGGCACT GTCGCAAACTATCACGGCTACCACATCGTCTTTGCATTAGCCGGAGATCCTA AAAATGCGGATGACACATCGATTTACATGTTCTATCAAAAAGTCGGCGAAA CTTCTATTGACAGCTGGAAAAACGCTGGCCGCGTCTTTAAAGACAGCGACA AATTCGATGCAAATGATTCTATCCTAAAAGACCAAACACAAGAATGGTCAG GTTCAGCCACATTTACATCTGACGGAAAAATCCGTTTATTCTACACTGATTT CTCCGGTAAACATTACGGCAAACAAACACTGACAACTGCACAAGTTAACGT ATCAGCATCAGACAGCTCTTTGAACATCAACGGTGTAGAGGATTATAAATC AATCTTTGACGGTGACGGAAAAACGTATCAAAATGTACAGCAGTTCATCGA TGAAGGCAACTACAGCTCAGGCGACAACCATACGCTGAGAGATCCTCACTA CGTACAAGATAAAGGCCACAAATACTTAGTATTTGAAGCAAACACTGGAAC TGAAGATGGCTACCAAGGCGAAGAATCTTTATTTAACAAAGCATACTATGG CAAAAGCACATCATTCTTCCGTCAAGAAAGTCAAAAACTTCTGCAAAGCGA TAAAAAACGCTCACGGCTGAGTTAGCAAACGGCGCTCTCGGTATGATTGAGCT AAACGATGATTACACACTGAAAAAAGTGATGAAACCGCTGATTGCATCTAA CACAGTAACAGATGAAATTGAACGCGCGAACGTCTTTAAAATGAACGGCAA ATGGTACCTGTTCACTGACTCCCGCGGATCAAAAATGACGATTCATGGCATT ACGTCTAACGATATTTACATCTCTTGGTTATGTTTCTAATTCTTTAACTGGCCC ATACAAGTCCGCTGAACAAACTGGCCTTGTGTTAAAAATGGATCTTGATCCT AACGATGTAACCTTTACTTACTCACACTTCGCTGTACCTCAAGCGAAAGGAA ACAATGTCGTGATTACAAGCTATATGACAAACAGAGGATTCTACGCAGACA AACAATCAACGTTTGCGCCAAGCTTCCTGCTGAACATCAAAGGCAAGAAAA CATCTGTTGTCAAAGACAGCATCCTTGAACAAGGACAATTAACAGTTAACA AATAAAAACGCAAAAGAAATGCCGATATTTTGACTACCGGAAGCAGTGTGAC CGTGTGCTTCTCAAATGCCTGATTCAGGCTGTCTATGTGTGACTGTTGAGCT GTAACAAGTTGTCTCAGGTGTTTCAATTTCATGTTCTAGTTGCTTTGTTTTACT GGTTTCACCTGTTTCTATTAGGTGTTACATGCTGTTCATCTGTTACATTGTCGA TCTGTTCATGGTGAACAGCTTTAAATGCACCAAAAACTCGTAAAAGCTCTGA TGTATCTATCTTTTTTACACCGTTTTCATCTGTGCATATGGACAGTTTTCCCTT TGAT | |
| ΔiclR-cure AAATGATTTCCACGATACAGAAAAAAGAGACTGTCATGGGCAGAATATTGC CTCTGCCCGCCAGAAAAG | 54 |
| ΔarcA-cure CTGTTTCGATTTAGTTGGCAATTTAGGTAGCAAACTCGGCTTTACCACCGTC AAAAAAAACGGCGCTTTT | 55 |
| Δcas3-pro-casA CAAGACATGTGTATATCACTGTAATTCGATATTTATGAGCAGCATCGAAAAA TAGCCCGCTGATATCATCGATAATACTAAAAAAACAGGGAGGCTATTACCA GGCATCAAATAAAACGAAAGGCTCAGTCGAAAGACTGGGCCTTTCGTTTTA TCTGTTGTTTGTCGGTGAACGTCTCTCTACTAGAGTCACACTGGCTCACCTTCG GGTGGGCCTTTCTGCGTTTATATCTTTCTGACACCTTACTATCTTACAAATGT AACAAAAAGTTATTTTACTGTAATTCGAGCATGTCATGTTACCCCGCGAGC ATAAAACGCTGTGTAGGAGGATAATCTTTGACGGCTAGCTCAGTCCTAGGT ACAGTGCTAGCCATATGAAGGAGAACAAATGAATTTGCTTATTGATAACTG GATCCCTGTACGCCCGCGAAACGGGGGGAAAGTCCAAATCATAAATCTGCA ATCGCTATAC | 56 |
| Δcas3::ugBp-sspB-pro-casA CAAGACATGTGTATATCACTGTAATTCGATATTTATGAGCAGCATCGAAAAA TAGCCCGCTGATATCATCGATAATACTAAAAAAACAGGGAGGCTATTACCA GGCATCAAATAAAACGAAAGGCTCAGTCGAAAGACTGGGCCTTTCGTTTTA TCTGTTGTTTGTCGGTGAACGCTCTCTACTAGAGTCACACTGGCTCACCTTCG GGTGGTGCCTTTCTGCGTTTATATCTTTCTGACACCTTACTATCTTACAAATGT AACAAAAAGTTATTTTTCTGTAATTCGAGCATGTCATGTTACCCCGCGAGC ATAAAACCTCGTGTGTAGGAGGATAATCTATGGATTTGTCACAGCTAACACC ACGTCGTCCCTATCTGCTGCGTGCATTCTATGAGTGGTTGCTGGATAACCAG | 57 |

TABLE 7-continued

Synthetic DNA utilized for strain construction.

| | SEQ ID NO |
|---|---|
| CTCACGCCGCACCTGGTGGTGGATGTGACGCTCCCTGGCGTGCAGGTTCCTA<br>TGGAATATGCGCGTGACGGGCAAATCGTACTCAACATTGCGCCGCGTGCTGT<br>CGGCAATCTGGAACTGGCGAATGATGAGGTGCGCTTTAACGCGCGCTTTGGT<br>GGCATTCCGCGTCAGGTTTCTGTGCCGCTGGCTGCCGTGCTGGCTATCTACG<br>CCCGTGAAAATGGCGCAGGCACGATGTTTGAGCCTGAAGCTGCCTACGATG<br>AAGATACCAGCATCATGAATGATGAAGAGGCATCGGCAGACAACGAAACC<br>GTTATGTCGGTTATGATGGCGACAAGCCAGATCACGATGATGACACTCATC<br>CTGACGATGAACCTCCGCAGCCACCACGCGGTGGTCGACCGGCATTACGCG<br>TTGTGAAGTAATTGACGGCTAGCTCAGTCCTAGGTACAGTGCTAGCCATATG<br>AAGGAGAACAAATGAATTTGCTTATTGATAACTGGATCCCTGTACGCCCGCG<br>AAACGGGGGAAAGTCCAAATCATAAATCTGCAATCGCTATAC | |
| fabI-DAS + 4-gentR<br>CTATTGAAGATGTGGGTAACTCTGCGGCATTCCTGTGCTCCGATCTCTCTGC<br>CGGTATTCTCCGGTGAAGTGGTCCACGTTGACGGCGGTTTCAGCATTGCTGCA<br>ATGAACGAACTCGAACTGAAAGCGGCCAACGATGAAAACTATTCTGAAAAC<br>TATGCGGATGCGTCTTAATAGGAAGTTCCTATTCTCTAGAAAGTATAGGAAC<br>TTCCGAATCCATGTGGGAGTTTATTCTTGACACAGATATTTATGATATAATA<br>ACTGAGTAAGCTTAACATAAGGAGGAAAAACATATGTTACGCAGCAGCAAC<br>GATGTTACGCAGCAGGGCAGTCGCCCTAAAACAAAGTTAGGTGGCTCAAGT<br>ATGGGCATCACGCACATGTAGGCTCGGCCCTGACCAAGTCAAATCCATGC<br>GGGCTGCTCTTGATCTTTTCGGTCGTGAGTTCGGAGACGTAGCCACCTACTC<br>CCAACATCAGCCGGACTCCGATTACCTCGGGAACTTGCTCCGTAGTAAGACA<br>TTCATCGCGCTTGCTGCCTTCGACCAAGAAGCGGTTGTTGGCGCTCTCGCGG<br>CTTACGTTCTGCCCAAGTTTGAGCAGCCGCGTAGTGAGATCTATATCTATGA<br>TCTCGCAGTCTCCGGCGAGCACCGGAGGCAGGGCATTGCCACCGCGCTCAT<br>CAATCTCCTCAAGCATGAGGCCAACGCGCTTGGTGCTTATGTGATCTACGTG<br>CAAGCAGATTACGGTGACGATCCCGCAGTGGCTCTCTATACAAAGTTGGGC<br>ATACGGGAAGAAGTGATGCACTTTGATATCGACCCAAGTACCGCCACCTAA<br>GAAGTTCCTATTCTCTAGAAAGTATAGGAACTTCCGTTCTGTTGGTAAAGAT<br>GGGCGGCGTTCTGCCGCCCGTTATCTCTGTTATACCTTTCTGATATTTGTTAT<br>CGCCGATCCGTCTTTCTCCCCTTCCCGCCTTGCGTCAGG | 58 |
| gapA-DAS + 4-zeoR-proDp-gapN<br>TCTCCAAAGCGGCCAACGATGAAAACTATTCTGAAAACTATGCGGATGCGT<br>CTTGATTGACAGCTAGCTCAGTCCTAGGTATAATGCTAGCAACTTTAAAATT<br>AAAGAGGTATATATTAATGACTAAGCAATATAAGAATTACGTAAATGGGGA<br>GTGGAAGCTTTCGGAGAATGAAATTAAGATCTATGAACCAGCCAGTGGGGC<br>GGAATTGGGGTCAGTCCCGGCAATGTCCACTGAAGAAGTTGACTATGTCTAC<br>GCCTCGGCCAAAAAGCGCAGCCAGCATGGCGCTCGCTTTCCTATATTGAGC<br>GTGCGGCTTATTTGCACAAAGTCGCAGACATCCTGATGCGTGACAAGGAGA<br>AAATTGGAGCGGTATTGTCCAAGGAAGTAGCGAAAGGCTACAAATCCGCAG<br>TATCGGAGGTCGTCCGCACCGCCGAGATTATTAATTATGCGGCCGAAGAAG<br>GGCTTCGCATGGAGGGTGAGGTTCTTGGAGGGCGGCAGTTTTGAGGCGGCAT<br>CCAAGAAAAAAATCGCTGTCGTCCGTCGCGAGCCGGTGGGACTTGTGCTTG<br>CTATTAGTCCGTTCAATTACCCCGTGAATCTGGCCGGCTCCAAGATTGCCCC<br>TGCACTGATCGCGGGCAATGTAATCGCTTTTAAACCACCGACCCAAGGATCG<br>ATTAGTGGACTTCTTTTAGCGGAGGCGTTTGCGGAGGCAGGTCTTCCAGCCG<br>GCGTATTCAATACCATCACGGGGCGTGGAAGTGAAATCGGGGATTACATCG<br>TGGAGCACCAGGCAGTAAATTTCATCAACTTCACGGGTTCCACGGGGATCG<br>GGGAGCGTATCGGTAAGATGGCTGGGATGCGTCCGATCATGTTGGAACTTC<br>GCGGCAAGGATAGTGCGATTGTGCTGGAAGACGCAGACTTGGAATTGACAG<br>CTAAAAACATTATCGCTGGAGCCTTCGGGTATAGTGGTCAACGTTGCACGGC<br>AGTTAAGCGCGTTCTTGTTATGGAAAGTGTCGCGGATGAATTGGTCGAGAA<br>GATTCGCGAGAAAGTGTTAGCTCTTACGATTGGAAATCCAGAGGACGATGC<br>TGACATCACTCCATTGATCGACACGAAATCCGCGGATTACGTCGAGGGGCT<br>GATCAACGACGCGAACGATAAGGGAGCAGCGGCTTTGACCGAGATCAAACG<br>CGAGGGGAACCTGATCTGCCCGATTCTTTTTGACAAAGTCACAACTGACATG<br>CGCTTGGCATGGGAAGAACCCTTCGGCCCAGTCTTGCCTATTATCCGCGTTA<br>CTAGCGTAGAGGAAGCAATTGAAATTTCCAATAAATCCGAATATGGGTTGC<br>AAGCGAGTATCTTTACTAACGATTTTCCACGTGCCTTTGGTATTGCGGAACA<br>GTTAGAAGTCGGACAGTTCACATCAACAACAAGACGCAGCGCGGGACAGA<br>TAACTTCCCCTTTTTGGGAGCAAAGAAGTCTGGGGCTGGAATCCAAGGGGT<br>GAAATACTCCATCGAAGCCATGACGACGGTGAAGAGCGTTGTTTTTGACATC<br>AAGTAAAACATAAGGAGGAAAAACAGATGGCGAAACTGACCTCGGCGGTT<br>CCGGTTCTGACGGCACGTGATGTGGCGGGCGCGGTTGAATTTTGGACGGATC<br>GTCTGGGCTTCAGTCGTGATTTTGTGGAAGATGACTTCGCAGGCGTGGTTCG<br>CGATGACGTCACCCTGTTTATTTCCGCAGTTCAGGATCAAGTCGTGCCGGAC<br>AACACGCTGGCTTGGGTGTGGGTTCGTGGCCTGGATGAACTGTATGCGAAT<br>GGAGCGAAGTTGTCTCTACCAATTTCCGTGACGCGAGCGGTCCGGCCATGAC<br>GGAAATCGGCGAACAGCCGTGGGGTCGCGAATTTGCTCTGCGTGACCCGGC<br>TGGCAACTGTGTCCATTTCGTGGCTGAAGAACAAGATTGAGTTGAGATGAC<br>ACTCTTGATCTAAAAAGAGCGACTTCGGTCGCTCTTTTTTTTACCTGA | 59 |

TABLE 7-continued

Synthetic DNA utilized for strain construction.

| | SEQ ID NO |
|---|---|
| gapA-zeaR-proDp-gapN<br>ACGAAACCGGTTACTCCAACAAAGTTCTGGACCTGATCGCTCACATCTCCAA<br>ATGATTGACAGCTAGCTCAGTCCTAGGTATAATGCTAGCAACTTTAAAATTA<br>AAGAGGTATATATTAATGACTAAGCAATATAAGAATTACGTAAATGGGGAG<br>TGGAAGCTTTCGGAGAATGAAATTAAGATCTATGAACCAGCCAGTGGGGCG<br>GAATTGGGGTCAGTCCCGGCAATGTCCACTGAAGAAGTTGACTATGTCTACG<br>CCTCGGCCAAAAAAGCGCAGCCAGCATGGCGCTCGCTTTCCTATATTGAGCG<br>TGCGGCTTATTTGCACAAAGTCGCAGACATCCTGATGCGTGACAAGGAGAA<br>AATTGGAGCGGTATTGTCCAAGGAACTTAGCGAAAGGCTACAAATCCGCAGT<br>ATCGGAGGTCGTCCGCACCGCCGAGATTATTAATTATGCGGCCGAAGAAGG<br>GCTTCGCATGGAGGGTGAGGTCTTGGAGGGCGGCAGTTTTGAGGCGGCATC<br>CAAGAAAAAAATCGCTGTCCTCCGTCGCGAGCCCTGTGGGACTTGTGCTTGCT<br>ATTAGTCCGTTCAATTACCCCGTGAATCTGGCCGGCTCCAAGATTGCCCCTG<br>CACTGATCGCGGGCAATGTAATCGCTTTTAAACCACCGACCCAAGGATCGAT<br>TAGTGGACTTCTTTTAGCGGAGGCGTTTGCGGAGGCAGGTCTTCCAGCCGGC<br>GTATTCAATACCATCACGGGGCGTGGAAGTGAAATCGGGGATTACATCGTG<br>GAGCACCAGGCAGTAAATTTCATCAACTTCACGGGTTCCACGGGGATCGGG<br>GAGCGTATCGGTAAGATGGCTGGGATGCGTCCGATCATGTTGGAACTTGGC<br>GGCAAGGATAGTGCGATTGTGCTGGAAGACGCAGACTTGGAATTGACAGCT<br>AAAAACATTATCGCTGGAGCCTTCGGGTATAGTGGTCAACGTTGCACGGCA<br>GTTAAGCGCGTTCTTGTTTATGGAAAGTGTCGCGGATGAATTTGGTCGAGAAG<br>ATTCGCGAGAAAGTMTAGCTCTTACGATTGGAAATCCAGAGGACGATGCT<br>GACATCACTCCATTGATCGACACGAAATCCGCGGATTACGTCGAGGGGCTG<br>ATCAACGACGCGAACGATAAGGGAGCAGCGGCTTTGACCGAGATCAAACGC<br>GAGGGGAACCTGATCTGCCCGATTCTTTTTGACAAAGTCACAACTCTACATGC<br>GCTTGGCATGGGAAGAACCCTTCGGCCCAGTCTTGCCTATTATCCGCGTTAC<br>TAGCGTAGAGGAAGCAATTGAAATTTCCAATAAATCCGAATATGGGTTGCA<br>AGCGAGTATCTTTACTAACGATTTTCCACGTGCCTTTGGTATTGCGGAACAG<br>TTAGAAGTCGGGACAGTTCACATCAACAACAAGACGCACTCGCGGGACAGAT<br>AACTTCCCCTTTTTGGGAGCAAAGAAGTCTGGGGCTGGAATCCAAGGGGTG<br>AAATACTCCATCGAAGCCATGACGACGGTGAAGAGCGTTGTTTTTGACATCA<br>AGTAAAACATAAGGAGGAAAAACAGATGGCGAAACTGACCTCGGCGGTTCC<br>GGTTCTGACGGCACGTGATGTGGCGGGCGCGGTTGAATTTTGGACGGATCCTT<br>CTGGGCTTCAGTCGTGATTTTGTGGAAGATGACTTCGCAGGCGTGGTTCGCG<br>ATGACGTCACCCTGTTTATTTCCGCAGTTCAGGATCAAGTCGTGCCGGACAA<br>CACGCTGGCTTGGGTGTGGGTTCGTGGCCTGGATGAACTGTATGCGGAATGG<br>AGCGAAGTTGTCTCTACCAATTTCCGTGACGCGAGCGGTCCGGCCATGACGG<br>AAATCGGCGAACAGCCGTGGGGTCGCGAATTTGCTCTGCGTGACCCGGCTG<br>GCAACTGTGTCCATTTCGTGGCTGAAGAACAAGATTGAGTTGAGATGACACT<br>GTGATCTAAAAAGAGCGACTTCGGTCGCTCTTTTTTTTACCTGA | 60 |
| gapA-DAS + 4-zeoR<br>TCTACCGATTTCAACGGCGAAGTTTGCACTTCCGTGTTCGATGCTAAAGCTG<br>GTATCGCTCTGAACCACAACTTCGTGAAACTGGTATCCTGGTACGACAACGA<br>AACCGGTTACTCCAACAAAGTTCTGGACCTGATCGCTCACATCTCCAAAGCG<br>GCCAACGATGAAAACTATTCTGAAAACTATGCGGATGCGTCTTGATCCTGAC<br>GGATGGCCTTTTTGCGTTTCTACAAACTCTTTTTGTTTATTTTTCTAAATACAT<br>TCAAATATGTATCCGCTCATGAGACAATAACCCTGATAAATGCTTCAATAAT<br>ATTGAAAAAGGAAGAGTAATGGCGAAACTGACCTCGGCGCGGTTCCGGTTCTG<br>ACGGCACGTGATGTGGCGGGCGCGGTTGAATTTTGGACGGATCGTCTGGGC<br>TTCAGTCGTGATTTTGTGGAAGATGACTTCGCAGGCGTGGTTCGCGATGACG<br>TCACCCTGTTTATTTCCGCAGTTCAGGATCAAGTCGTGCCGGACAACACGCT<br>GGCTTGGGTGTGGGTTCGTGGCCTGGATGAACTGTATGCGGAATGGAGCGA<br>AGTTGTCTCTACCAATTTCCGTGACGCGAGCGGTCCGGCCATGACGGAAATC<br>GGCGAACAGCCGTGGGGTCGCGAATTTGCTCTGCGTGACCCGGCTGGCAAC<br>TGTGTCCATTTCGTGGCTGAAGAACAAGATTGAGTTGAGATGACACTGTGAT<br>CTAAAAAGAGCGACTTCGGTCGCTCTTTTTTTTACCTGATAAATGAAGTTA<br>AAGGACTGCGTCATGATTAAGAAAATTTTTGCCCTTCCGGTCATCGAACAAA<br>TCTCCCCTGTCCTCTCCCGTCGTAAACTGGATGAACTGGACCTCATTGTGGTC<br>GATCATCCCCAGGTAAAAGCCTCT | 61 |
| gltA-DAS + 4-ampR?<br>GTATTCCGTCTTCCATGTTCACCGTCATTTCGCAATGGCACGTACCGTTGGC<br>TGGATCGCCCACTGGAGCGAAATGCACAGTGACGGTATGAAGATTGCCCGT<br>CCGCGTCAGCTGTATACAGGATATGAAAAACGCGACTTTAAAAGCGATATC<br>AAGCGTGCGGCCAACGATGAAAACTATTCTGAAAACTATGCCTGATGCGTCT<br>TAATAGTCCTGACGGATGGCCTTTTTGCGTTTCTACAAACTCTTTTTGTTTAT<br>TTTTCTAAATACATTCAAATATGTATCCGCTCATGAGACAATAACCCTGATA<br>AATGCTTCAATAATATTGAAAAGGAAGAGTATGAGTATTCAACATTTCCGT<br>GTCGCCCTTATTCCCTTTTTTGCGGCATTTTGCCTTCCTGTTTTTGCTCACCCA<br>GAAACGCTGGTGAAAGTAAAACTATGCTGAAGATCAGTTTGGGTGCACGAGTG<br>GGTTACATCGAACTGGATCTCAACAGCGGTAAGATCCTTGAGAGTTTTCGCC<br>CCGAAGAACGTTTTCCAATGATGAGCACTTTTAAAGTTCTGCTATGTGGCGC<br>GGTATTATCCCCTTGTTGACGCGGGGCAAGAGCAACTCGGTCGCCGCATACA<br>CTATTCTCAGAATGACTTGGTTGAGTACTCACCAGTCACAGAAAAGCATCTT | 62 |

TABLE 7-continued

Synthetic DNA utilized for strain construction.

| | SEQ ID NO |
|---|---|
| ACGGATGGCATGACAGTAAGAGAATTATGCAGTGCTGCCATAACCATGAGT GATAACACTGCGGCCAACTTACTTCTGACAACGATCGGAGGACCGAAGGAG CTAACCGCTTTTTTGCACAACATGGGGGATCATGTAACTCGCCTTGATCGTT GGGAACCGGAGCTGAATGAAGCCATACCAAACGACGAGCGTGACACCACG ATGCCTACAGCAATGGCAACAACGTTGCGCAAACTATTAACTGGCGAACTA CTTACTCTAGCTTCCCGGCAACAATTAATAGACTGGATGGAGGCGGATAAA GTTGCAGGACCACTTCTGCGCTCGGCCCTTCCGGCTGGCTGGTTTATTGCTG ATAAATCTGGAGCCGGTGAGCGTGGGTCTCGCCTGTATCATTGCAGCACTGG GGCCAGATGGTAAGCCCTCCCGTATCGTAGTTATCTACACGACGGGGAGTC AGGCAACTATGGATGAACGAAATAGACAGATCGCTGAGATAGGTGCCTCAC TGATTAAGCATTGGTAACTGTCAGACTAATGGTTTGATTGCTAAGTTGTAAAT ATTTTAACCCGCCGTTCATATGGCGGGTTGATTTTTATATGCCTAAACACAA AAAATTGTAAAAATAAAATCCATTAACAGACCTATATAGATATTTAAAAAG AATAGAACAGCTCAAATTATCAGCAACCCAATACTTTCAATTAAAAACTTCA TGGTAGTCGCATTTATAACCCTATGAAA | |
| gltA-DAS + 4-purR ACCGTCATITTCGCAATGGCACGTACCGTTGGCTGGATCGCCCACTGGAGCG AAATGCACAGTGACGGTATGAAGATTGCCCGTCCGCGTCAGCTGTATACAG GATATGAAAAACGCGACTTTAAAAGCGATATCAAGCGTGCGGCCAACGATG AAAACTATTCTGAAAACTATGCGGATGCGTCTTAATCCTGACGGATGGCCTT TTTGCGTTTCTACAAACTCTTTTTGTTTATTTTTCTAAATACATTCAAATATGT ATCCGCTCATGAGACAATAACCCTGATAAATGCTTCAATAATATTGAAAAA GGAAGAGTATGACTGAATACAAGCCCACGGTACGCTTGGCGACGCGCGACG ATGTTCCCCGCGCTGTTCGTACATTAGCTGCGGCCTTTGCAGATTACCCAGC GACGCGCCATACCGGTCGATCCGGACCGCCATATCGAGCGTGTCACAGAATT GCAGGAACTTTTCTTAACTCGCGTGGGCCTTGACATCGGAAAGGTCTGGGTG GCTGACGATGGCGCTGCAGTGGCTGTTTGGACCACTCCGGAGAGTGTAGAG GCTGGCTGCAGTGTTCGCCGAAATTGGTCCTCGTATGGCCGAATTAAGTGGAA GTCGTCTGGCAGCCCAACAACAAATGGAAGGGTTGCTTGCGCCCCACCGTC CGAAAGAACCCGCGTGGTTCCTTGCCACCGTTGGAGTAAGCCCAGATCACC AGGGGAAGGGTTTAGGATCTGCCGTAGTTTTACCAGGTGTGGAGGCAGCAG AACGTGCGGGAGTTCCGGCCTTCCTTGAGACGTCGGCGCCGCGCAATTTACC GTTTTACGAACGTCTTGGATTCACCGTTACGGCGGACGTGGAGGTGCCGGAG GGACCCCGTACTTGGTGTATGACTCGTAAACCGGGAGCCTGATAATGGTTGA TTGCTAAGTTGTAAATATTTTAACCCGCCGTTCATATGGCGGGTTGATTTTTA TATGCCTAAACACAAAAAATTGTAAAAATAAAATCCATTAACAGACCTATA TAGATATTTAAAAAGAATAGAACAGCTCAAATTATCAGCAACCCA | 63 |
| gltA-DAS + 4-zeoR GTATTCCGTCTTCCATGTTCATTTTCGCAATGGCACGTACCGTTGGC TGGATCGCCCACTGGAGCGAAATGCACAGTGACGGTATGAAGATTGCCCGT CCGCGTCAGCTGTATACAGGATATGAAAAACGCGACTTTAAAAGCGATATC AAGCGTGCGGCCAACGATGAAAACTATTCTGAAAACTATGCGGATGCGTCT TAATAGTTGACAATTAATCATCGGCATAGTATATCGGCATAGTATAATACGA CTCACTATAGGAGGGCCATCATGGCCAAGTTGACCAGTGCCCGTTCCGGTGCT CACCGCGCGCGACGTCGCCGGAGCGGTCGAGTTCTGGACCGACCGGCTCGG GTTCTCCCGGGACTTCGTGGAGGACGACTTCGCCGGTGTGGTCCGGGACGAC GTGACCCTGTTCATCAGCGCGGTCCAGGACCAGGTGGTGCCGGACAACACC CTGGCCTGGGTGTGGGTGCGCGGCCTGGACGAGCTGTACGCCGAGTGGTCG GAGGTCGTGTCCACGAACTTCCGGGACGCCTCCGGGCCGGCCATGACCGAG ATCGGCGAGCAGCCGTGGGGCGGGAGTTCGCCCTGCGCGACCCGGCCGGC AACTGCGTGCACTTTGTGGCAGAGGAGCAGGACTGAGGATAAGTAATGGTT GATTGCTAAGTTGTAAATATTTTAACCCGCCGTTCATATGGCGGGTTGATTTT TATATGCCTAAACACAAAAAATTGTAAAAATAAAATCCATTAACAGACCTA TATAGATATTTAAAAAGAATAGAACAGCTCAAATTATCAGCAACCCAATAC TTTCAATTAAAAACTTCATGGTAGTCGCATTTATAACCCTTATGAAA | 64 |
| lpd-DAS + 4-gentR GCGGCGAGCTGCTGGGTGAAATCGGCCTGGCAATCGAAATGCGTTGTGATG CTGAAGACATCGCACTGACCATCCACGCGCACCCGACTCTGCACGAGTCTGT GGGCCTGGCGGCAGAAGTGTTCGAAGGTAGCATTACCGACCTGCCGAACCC GAAAGCGAAGAAGAAGGCGGCCAACGATGAAAACTATTCTGAAAACTATG CGGATGCGTCTTAATAGCGAATCCATGTGGGAGTTTATTCTTGACACAGATA TTTATGATATAATAACTGAGTAAGCTTAACATAAGGAGGAAAACATATGT TACGCAGCAGCAACGATGTTACGCAGCAGGGCAGTCGCCCTAAAACAAAGT TAGGTGGCTCAAGTATGGGCATCATTCGCACATGTAGGCTCGGCCCTGACCA AGTCAAATCCATGCGGGCTGCTCTTGATCTTTTCGGTCGTGAGTTCGGAGA GTAGCCACCTACTCCCAACATCAGCCGGACTCCGATTACCTCGGGAACTTGC TCCGTAGTAAGACATTCATCGCGCTTGCTGCCTTCGACCAAGAAGCGGTTGT TGGCGCTCTCGCGCGCTTACGTTCTGCCCAAGTTTGAGCAGCCGCGTAGTGAG ATCTATATCTATGGATCTCGCAGTCTCCGGCGAGCACCGGAGGCAGGGCATTG CCACCGCGCTCATCAATCICCTCAAGCATGAGGCCAACGCGCTTGGTGCTTA TGTGATCTACGTGCAAGCGAGATTACGGTGACGATCCCGCAGTGGCTCTCTAT ACAAAGTTGGGCATACGGGAAGAAGTGATGCACTTTGATATCGACCCAAGT | 65 C |

TABLE 7-continued

Synthetic DNA utilized for strain construction.

| | SEQ ID NO |
|---|---|
| ACCGCCACCTAATTTTTCGTTTHCCGGAACATCCGGCAATTAAAAAAGCGGC<br>TAACCACGCCGCTTTTTTTACGTCTGCAATTTACCTTTCCAGTCTTCTTGCTC<br>CACGTTCAGAGAGACGTTCGCATACTGCTGACCGTTGCTCGTTATTCAGCCT<br>GACAGTATGGTTACTGTC | |
| udhA-DAS + 4-bsdR<br>TCTGGGTATTCACTGCTTTGGCGAGCGCGCTGCCGAAATTATTCATATCGGT<br>CAGGCGATTATGGAACAGAAAGGTGGCGGCAACACTATTGAGTACTTCGTC<br>AACACCACCTTTAACTACCCGACGATGGCGGAAGCCTATCGGGTAGCTGCG<br>TTAAACGGTTTAAACCGCCTGTTTGCGGCCAACGATGAAAACTATTCTGAAA<br>ACTATGCGGATGCGTCTTAATAGTTGACAATTAATCATCGGCATAGTATATC<br>GGCATAGTATAATACGACTCACTATAGGAGGGCCATCATGAAGACCTTCAA<br>CATCTCTCAGCAGGATCTGGAGCTGGTGGAGGTCGCCACTGAGAAGATCAC<br>CATGCTCTATGAGGACAACAAGCACCATGTCGGGGCGGCCATCAGGACCAA<br>GACTGGGGAGATCATCTCTGCTGTCCACATTGAGGCCTACATTGGCAGGGTC<br>ACTGTCTGTCCTGAAGCCATTGCCATTGGGTCTGCTGTGAGCAACGGGCAGA<br>AGGACTTTGACACCATTGTGGCTGTCAGGCACCCCTACTCTGATGAGGTGGA<br>CAGATCCATCAGGGTGGTCAGCCCTGTGGCATGTGCAGAGAGCTCATCTCT<br>GACTATGCTCCTGACTGCTTTGTGCTCATTGAGATGAATGGCAAGCTGGTCA<br>AAACCACCATTGAGGAACTCATCCCCCTCAAGTACACCAGGAACTAAAGTA<br>AAACTTTATCGAAATGGCCATCCATTCTTGCGCGGATGGCCTCTGCCAGCTG<br>CTCATAGCGGCTGCGCAGCGGTGAGCCAGGACGATAAACCAGGCCAATAGT<br>GCGGCGTGGTTCCGGCTTAATGCACGG | 66 |
| zwf-DAS + 4-bsdR<br>GAAGTGGAAGAAGCCTGGAAATGGGTAGACTCCATTACTGAGGCGTGGGCG<br>ATGGACAATGATGCGCCGAAACCGTATCAGGCCGGAACCTGGGGACCCGTT<br>GCCTCGGTGGCGATGATTACCCGTGATGGTCGTTCCTGGAATGAGTTTGAGG<br>CGGCCAACGATGAAAACTATTCTGAAAACTATGCGGATGCGTCTTAATAGTT<br>GACAATTAATCATCGGCATAGTATATCGGCATAGTATAATACGACTCACTAT<br>AGGAGGGCCATCATGAAGACCTTCAACATCTCTCAGCAGGATCTGGAGCTG<br>GTGGAGGTCGCCACTGACAAGATCACCATGCTCTATGAGGACAACAAGCAC<br>CATGTCGGGGCGGCCATCAGGACCAAGACTGGGGAGATCATCTCTGCTGTC<br>CACATTGAGGCCTACATTGGCAGGGTCACTGTCTGTGCTGAAGCCATTGCCA<br>TTGGGTCTGCTGTGAGCAACGGGCAGAAGGACTTTGACACCATTGTGGCTGT<br>CAGGCACCCCTACTCTGATGAGGTGGACAGATCCATCAGGGTGGTCAGCCC<br>CTGTGGCATGTGCAGAGAGCTCATCTCTGACTATGCTCCTGACTGCTTTGTG<br>CTCATTGAGATGAATGGCAAGCTGGTCAAAACCACCATTGAGGAACTCATC<br>CCCCTCAAGTACACCAGGAACTAAAGTAATATCTGCGCTTATCCTTTATGGT<br>TATTTTACCGGTAACATGATCTTGCGCAGATTGTAGAACAATTTTTACACTTT<br>CAGGCCTCGTGCGGATTCACCCACGAGGCTTTTTTATTACACTGACTGAAA<br>CGTTTTTGCCCTATGAGCTCCGGTTACAGGCGTTTCAGTCATAAATCCTCTGA<br>ATGAAACGCGTTGTGAATC | 67 |
| dadX-DAS + 4-purR<br>GCGTGCGCACCATGACGGTGGGGACCGTCTCGATGGATATGCTAGCGGTCG<br>ATTAACGCCTTGCCCGCAGGCGGGTATTGGTACGCCGGTTGAGCTGTGGGG<br>CAAGGAGATCAAAATTGATGATGTCGCCGCCGCTGCCGGAACGGTGGGCTA<br>TGAGTTGATGTGCGCGCTGGCGCTACGCGTCCCGGTTGTGACGGTGGCGGCC<br>AACGATCAAAACTATTCTGAAAACTATGCGGATGCGTCTTAATCCTGACGG<br>ATGGCCTTTTTGCGTTTCTACAAACTCTTTTTGTTTATTTTTCTAAATACATTC<br>AAATATGTATCCGCTCATGAGAGACATAACCCTGATAAATGCTTCAATAATAT<br>TGAAAAAGGAAGAGTATGACTGAATACAAGCCCACGGTACGCTTGGCGACG<br>CGCGACGATGTTCCCCGCGCTGTTCGTACATTAGCTGCGGCCTTTGCAGATT<br>ACCCAGCGACGCGCCATACGGTCGATCCCGACCGCCATATCGAGCGTGTCA<br>CAGAATTGCAGGAACTTTTCTTAACTCGCGTGGGCCTTGACATCGGAAAGGT<br>CTGGGTGGCTGACGATGGCGCTGCAGTGGCTGTTTGGACCACTCCGGAGAG<br>TGTAGAGGCTGGTGCAGTGTTCGCCGAAATTGGTCCTCGTATGGCCGAATTA<br>AGTGGAAGTCGTCTGGCAGCCCAACAACAAATGGAAGGGTTGCTTGCGCCC<br>CACCGTCCGAAAGAACCCGCGTGGTTCCTTGCCACCGTTGGAGTAAGCCCA<br>GATCACCAGGGGAAGGGTTTAGGATCTGCCGTAGTTTTACCAGGTGTGGAG<br>GCAGCGAACGTGCGGGAGTTCCGGCCTTCCTTGAGACGTCGGCGCCGCGC<br>AATTTACCGTTTTACGAACGTCTTGGATTCACCGTTACGGCGGACGTGGAGG<br>TGCCGGAGGGACCCCGTACTTGGTGTATGACTCGTAAACCGGGAGCCTGAT<br>AACTTGTTGTAAGCCGGATCGGAGGCAACGTCTTCTGGGTGCAAAAAAATC<br>ATCCATCCGGCTGGTCAGCAACTGTAGTTGTTAATGTGACAGAGCCATTGCC<br>CATGATAGTGTCCATTAAAAGGATGGACACTATTTCCCCGGAACCTGAACTC<br>ACCGCACAGGCGTTCTACATAAAACGCTTACGCTTCATTGTTGACTC | 68 |

Section 4: Dynamic Control Over Protein Levels.

Plasmids expressing fluorescent proteins and silencing guides were transformed into the corresponding hosts strain listed in Table 8. Strains were evaluated in triplicate in an m2p-labs Biolector™, which simultaneously measures fluorescence including GFPuv and mCherry levels, as well as biomass levels.

TABLE 8

Strains used for Dynamic Control over protein levels

| Microbe | Synthetic Metabolic Valves | Plasmid | Host Strain |
|---|---|---|---|
| E. coli | RFP-control | pCDF-mcherry1 + pSMART-IN:yibDp-GFPuv | DLF_0002 |
| | Proteolysis | pCDF-mcherry2 + pSMART-IN:yibDp-GFPuv | DLF_0025 |
| | Silencing | pCDF-mcherry1 + pCASCADE-proD + pSMART-IN:yibDp-GFPuv | DLF_01517 |
| | Proteolysis + Silencing | pCDF-mcherry2 + pCASCADE-proD + pSMART-IN:yibDp-GFPuv | DLF_0025 |

OD600 readings were corrected using the formula below, where OD600 refers to an offline measurement, OD600* refers to Biolector biomass reading, t0 indicates the start point, and tf indicates the final point.

$$OD600_t = (OD600_t^* - OD600_{t0}^*) * \frac{(OD600_{tf} - OD600_{t0})}{(OD600_{tf}^* - OD600_{t0}^*)} + 0.25 \qquad \text{Equation S1}$$

Section 5: Metabolic Control

Near Equilibrium Reactions

The impact of Valves on metabolite pools for near equilibrium reactions is illustrated using the G6P node as an example. Abbreviations: Gluc, glucose; G6P, glucose-6-phosphate; F6P, fructose-6-phosphate; 6PGl, 6-phosphate-gluconolactone.

G6P Node without Valves

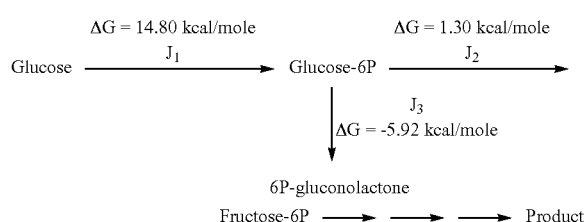

$$\text{Steady State Mass balance } J_1 = J_2 + J_3 \qquad \text{Equation S2}$$

$$\text{Net Flux} = J_i = e^{\frac{-dG}{RT}} - 1 \qquad \text{Equation S3}$$

$$e^{\frac{-dG1}{RT}} - 1 = e^{\frac{-dG2}{RT}} - 1 + e^{\frac{-dG3}{RT}} - 1 \qquad \text{Equation S4}$$

$$e^{\frac{-dG1}{RT}} = e^{\frac{-dG2}{RT}} + e^{\frac{-dG3}{RT}} - 1 \qquad \text{Equation S5}$$

$$Keq1 = Keq2 + Keq3 - 1 \qquad \text{Equation S6}$$

$$Keq1 + 1 = Keq2 + Keq3 \qquad \text{Equation S7}$$

$$\frac{[G6P]}{[Gluc]} + 1 = \frac{[F6P]}{[G6P]} + \frac{[6PGl]}{[G6P]} \qquad \text{Equation S8}$$

$$\frac{[G6P]}{[Gluc]} + 1 = \frac{[F6P] + [6PGl]}{[G6P]} \qquad \text{Equation S9}$$

$$\frac{[G6P]^2}{[Gluc]} + [G6P] = [F6P] + [6PGl] \qquad \text{Equation S10}$$

$$[F6P] = \frac{[G6P]^2}{[Gluc]} + [G6P] - [6PGl] \qquad \text{Equation S11}$$

G6P Node with Valves

When zwf valve is in effect, $J_3 \approx 0$.

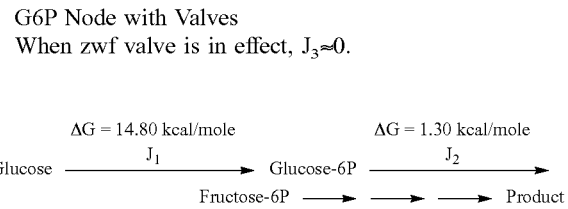

$$\text{Steady State Mass balance } J_1 = J_2 \qquad \text{Equation S12}$$

$$\text{Net Flux} = J_i = e^{\frac{-dG}{RT}} - 1 \qquad \text{Equation S13}$$

$$e^{\frac{-dG1}{RT}} - 1 = e^{\frac{-dG2}{RT}} - 1 \qquad \text{Equation S14}$$

$$Keq1 = Keq2 \qquad \text{Equation S15}$$

$$\frac{[G6P]}{[Gluc]} = \frac{[F6P]}{[G6P]} \qquad \text{Equation S16}$$

$$[F6P] = \frac{[G6P]^2}{[Gluc]} \qquad \text{Equation S17}$$

Impact of Valves $$[F6P] \text{ network} = \frac{[G6P]^2}{[Gluc]} + [G6P] - [6PGl] \qquad \text{Equation S11}$$

$$[F6P] \text{ valve} = \frac{[G6P]^2}{[Gluc]} \qquad \text{Equation S17}$$

Since close to equilibrium $[6PGl] > [G6P]$ $[F6P]$ valve >= $[F6P]$ network

The removal of thermodynamically favored reactions near equilibrium from the network will result in increased metabolite pools.

Section 6: Gene Silencing Arrays & Pathway Expression Constructs

The design and construction of CASCADE guides and guide arrays is illustrated below in FIG. 14 and FIG. 15A-B. The pCASCADE-control plasmid was prepared by swapping the pTet promoter in pcrRNA.Tet 88 with an insulated low phosphate induced ugpB promoter[82]. Two promoters were responsible for regulating gltA gene, and sgRNA was designed for both promoters, resulting in guide gltA1 (G1) and gltA2 (G2).[89] Four promoters were responsible for regulating gapA gene, and sgRNA was designed for the first promoter, since during exponential phase of growth, gapA mRNAs were mainly initiated at the highly efficient gapA P1 promoter and remained high during stationary phase compared to the other three gapA promoters.[90] Multiple promoters upstream of lpd gene were involved in lpd regulation (https://ecocyc.org/gene?orgid=ECOLI&id=EG10543#tab=showAll), thus design of unique and effective sgRNA for lpd only was not possible. Promoter sequences for fabI, udhA and zwf were obtained from EcoCyc database (https://ecocyc.org/). To design CASCADE guide array, CASCADE PAM sites near the −35 or −10 box of the promoter of interest were identified, 30 bp at the 3' end of PAM site was selected as the guide sequence and cloned into pCASCADE plasmid using Q5 site-directed mutagenesis (NEB, MA) following manufacturer's protocol, with the modification that 5% v/v DMSO was added to the Q5 PCR reaction. The pCASCADE-control vector was used as template. pCASCADE plasmids with arrays of two or more guides were prepared as illustrated in FIG. 15A-B. The pCASCADE guide array plasmid was prepared by sequentially amplifying complementary halves of each smaller guide plasmid by PCR, followed by subsequent DNA assembly. Table 9 lists sgRNA guide sequences and primers used to construct them. All pCASCADE silencing plasmids are listed in Table 10 below and are available at Addgene.

TABLE 9

List of sgRNA guide sequences and primers used to construct them. Spacers are italicized.

| sgRNA/Primer Name | Sequence | SEQ ID NO | Template |
|---|---|---|---|
| fabI | TCGAGTTCCCCGCGCCAGCGGG GATAAACCGTTGATTATAATAA CCGTTTATCTGTTCGTATCGAG TTCCCCGCGCCAGCGGGGATAA ACCG | 69 | |
| fabI-FOR | GTTTATCTGTTCGTATCGAGTT CCCCGCGCCAGCGGGGATAAAC CGAAAAAAAAACCCC | 70 | pCASCADE control |
| fabI-REV | GGTTATTATAATCAACCTGTTTA TCCCCGCTGGCCTCGGGGAACT CGAGGTGGTACCAGATC | 71 | |
| gapAP1 | TCGAGTTCCCCGCGCCAGCGGG GATAAACCGGTTTTTGTAATTTT ACAGGCAACCTTTTATTCGAGT TCCCCGCGCCAGCGGGGATAAA CCG | 77 | |
| gapAP1-FOR | CAGGCAACCTTTTATTCGAGTT CCCCGCGCCAGCGGGGATAAAC CGAAAAAAAAACCCC | 73 | pCASCADE control |
| gapAP1-REV | TAAAATTACAAAAACCGGTTT ATCCCCGCTGGCGCGGGGAAC TCGAGGTGGTACCAGATC | 74 | |
| gltA1 | TCGAGTTCCCCGCGCCAGCGGG GATAAACCGAAAAGCATATAAT GCGTAAAAGTTATGAAGTTCG AGTTCCCCGCGCCAGCGGGGAT AAACCG | 75 | |
| gltA1-FOR | GCGTAAAAGTTATGAAGTTCG AGTTCCCCGCGCCAGCGGGGAT AAACCGAAAAAAAAACCCC | 76 | pCASCADE control |
| gltA1-REV | ATTATATGCTTTTCGGTTTATC CCCGCTGGCGCGCTGCTAACTCG AGGTGGTACCAGATCT | 77 | |
| gltA2 | TCGAGTTCCCCGCGCCAGCGGG GATAAACCGTATTGACCAATTC ATTCGGGACAGTTATTAGTTCG AGTTCCCCGCGCCAGCGGGGAT AAACCG | 78 | |
| gltA2-FOR | GGGACAGTTATTAGTTCGAGTT CCCCGCGCCAGCGGGGATAAAC CGAAAAAAAAACCCC | 79 | pCASCADE control |
| gltA2-REV | GAATGAATTGGTCAATACGGT TTATCCCCGCTGGCGCGGGGA ACTCGAGGTGGTACCAGATCT | 80 | |
| proD | TCGAGTTCCCCGCGCCAGCGGG GATAAACCGAGTGGTTGCTGGA TAACTTTACGGGCATGCTCGAG TTCCCCGCGCCAGCGGGGATAA ACCG | 81 | |

TABLE 9-continued

List of sgRNA guide sequences and primers used to construct them. Spacers are italicized.

| sgRNA/Primer Name | Sequence | SEQ ID NO | Template |
|---|---|---|---|
| proD-FOR | AACTTTACGGGCATGC*TCGAGT TCCCCGCGCCAGCGGGGATAAA CCGAAAAAAAAAACCCC* | 82 | pCASCADE control |
| proD-REV | ATCCAGCAACCACTCGGTTTAT CCCCGCTGGCGCGGGGAACTC GAGGTGGTACCAGATCT | 83 | |
| udhA | *TCGAGTTCCCCGCGCCAGCGGG GATAAACCGTTACCATTCTGTT GCTTTTATGTATAAGAATCGAG TTCCCCGCGCCAGCGGGGATAA ACCG* | 84 | |
| udhA-FOR | TTTTATGTATAAGAATCGAGTT *CCCCGCGCCAGCGGGGATAAAC CGAAAAAAAAACCCC* | 85 | pCASCADE control |
| udhA-REV | GCAACAGAATGGTAACGGTTT ATCCCCGCTGGCGCGGGGAAC TCGAGGTGGTACCAGATC | 86 | |
| zwf | *TCGAGTTCCCCGCGCCAGCGGG GATAAACCGCTCGTAAAAGCAG TACAGTGCACCGTAAGATCGA GTTCCCCGCGCCAGCGGGGATA AACCG* | 87 | |
| zwf-FOR | CAGTGCACCGTAAGATCGAGTT *CCCCGCGCCAGCGGGGATAAAC CGAAAAAAAAACCCC* | 88 | pCASCADE control |
| zwf-REV | TACTGCTTTTACGAGCGGTTTA TCCCCGCTGGCGCGGGAACT CGAGGTGGTACCAGATC | 89 | |
| FG1 | *TCGAGTTCCCCGCGCCAGCGGG GATAAACCGTTGATTATAATAA CCGTTTATCTGTTCGTATCGAG TTCCCCGCGCCAGCGGGGATAA ACCGAAAAGCATATAATGCGT AAAAGTTATGAAGTTCGAGTTC CCCGCGCCAGCGGGGATAAACC G* | 90 | |
| gltA1-FOR | GCGCCAGCGGGGATAAACCGA *AAAGCATATAAATGCG* | 91 | pCASCADE-gltA1 |
| pCASCADE-REV | CTTGCCCGCCTGATGAATGCTC ATCCGG | 92 | |
| pCASCADE-FOR | CCGGATGAGCATTCATCAGGC GGGCAAG | 93 | pCASCADE-fabI |
| fabI-REV | CGGTTTATCCCCGCTGGCGCG GGGAACTCGATACGAACAGAT AAACGGTTATTATAATC | 94 | |
| FG2 | *TCGAGTTCCCCGCGCCAGCGGG GATAAACCGTTGATTATAATAA CCGTTTATCTGTTCGTATCGAG TTCCCCGCGCCAGCGGGGATAA ACCGTATTGACCAATTCATTCG GACAGTTATTAGTTCGAGTTC CCCGCGCCAGCGGGGATAAACC G* | 95 | |
| gltA2-FOR | GCGCCAGCGGGGATAAACCGT *ATTGACCAATTCATTC* | 96 | pCASCADE-AtA2 |
| pCASCADE-REV | CTTGCCCGCCTGATGAATGCTC ATCCGG | 97 | |
| pCASCADE-FOR | CCGGATGAGCATTCATCAGGC CTGGCAAG | 98 | pCASCADE-fabI |
| fabI-REV | CGGTTTATCCCCGCTGGCGCG GGGAACTCGATACGAACAGAT AAACGGTTATTATAATC | 99 | |

TABLE 9-continued

List of sgRNA guide sequences and primers used to construct them. Spacers are italicized.

| sgRNA/Primer Name | Sequence | SEQ ID NO | Template |
|---|---|---|---|
| FU | *TCGAGTTCCCCGCGCCAGCGGG GATAAACCGTTGATTATAATAA CCGTTTATCTGTTCGTATCGAG TTCCCCGCGCCAGCGGGGATAA ACCGTTACCATTCTGTTGCTTT TATGTATAAGAATCGAGTTCCC CGCGCCAGCGGGGATAAACCG* | 100 | |
| adhA-FOR | GCGCCAGCGGGGATAAACCGT TACCATTCTGTTG | 101 | pCASCADE-udhA |
| pCASCADE-REV | CTTGCCCGCCTGATGAATGCTC ATCCGG | 102 | |
| pCASCADE-FOR | CCGGATGAGCATTCATCAGGC CTGGCAAG | 103 | pCASCADE-fabI |
| fabI-REV | CGGTTTATCCCCGCTGGCGCG GGGAACTCGATACGAACAGAT AAACGGTTATTATAATC | 104 | |
| FZ | *TCGAGTTCCCCGCGCCAGCGGG GATAAACCGTTGATTATAATAA CCGTTTATCTGTTCGTATCGAG TTCCCCGCGCCAGCGGGGATAA ACCGCTCGTAAAAGCAGTACA GTGCACCGTAAGATCGAGTTCC CCGCGCCAGCGGGGATAAACCG* | 105 | |
| zwf-FOR | GCGCCAGCGGGGATAAACCGC TCGTAAAAG | 106 | pCASCADE-zwf |
| pCASCADE-REV | CTTGCCCGCCTGATGAATGCTC ATCCGG | 107 | |
| pCASCADE-FOR | CCGGATGAGCATTCATCAGGC CTGGCAAG | 108 | pCASCADE-fabI |
| fabI-REV | CGGTTTATCCCCGCTGGCGCG GGGAACTCGATACGAACAGAT AAACGGTTATTATAATC | 109 | |
| G1G2 | *TCGAGTTCCCCGCGCCAGCGGG GATAAACCGAAAAGCATATAAT GCGTAAAAGTTATGAAGTTCG AGTTCCCCGCGCCAGCGGGGAT AAACCGTATTGACCAATTCATT CGGGACAGTTATTAGTTCGAGT TCCCCGCGCCAGCGGGGATAAA CCG* | 110 | |
| gltA2-FOR | GCGCCAGCGGGGATAAACCGT ATTGACCAATTCATTC | 111 | pCASCADE-gltA2 |
| pCASCADE-REV | CTTGCCCGCCTGATGAATGCTC ATCCGG | 112 | |
| pCASCADE-FOR | CCGGATGAGCATTCATCAGGC GGGCAAG | 113 | pCASCADE-gltA1 |
| gltA1-REV | CGGTTTATCCCCGCTGGCGCG GGGAACTCGAACTTCATAACT TTTAC | 114 | |
| G1U | *TCGAGTTCCCCGCGCCAGCGGG GATAAACCGAAAAGCATATAATG CGTAAAAGTTATGAAGTTCGA GTTCCCCGCGCCAGCGGGGATA AACCGTTACCATTCTGTTGCTT TTATGTATAAGAATCGAGTTCC CCGCGCCAGCGGCTGATAAACCG* | 115 | |
| udhA-FOR | GCGCCAGCGGGGATAAACCGT TACCATTCTGTTG | 116 | pCASCADE-udhA |
| pCASCADE-REV | CTTGCCCGCCTGATGAATGCTC ATCCGG | 117 | |
| pCASCADE-FOR | CCGGATGAGCATTCATCAGGC GGGCAAG | 118 | |

TABLE 9-continued

List of sgRNA guide sequences and primers used to construct them. Spacers are italicized.

| sgRNA/Primer Name | Sequence | SEQ ID NO | Template |
|---|---|---|---|
| gltA1-REV | CGGTTTATCCCCGCTGGCGCG GGGAACTCGAACTTCATAACT TTTAC | 119 | pCASCADE-gltA1 |
| G1Z | *TCGAGTTCCCCGCGCCAGCGGG GATAAACCGAAAAGCATATAAT GCGTAAAAGTTATGAAGTTCG AGTTCCCCGCGCCAGCGGGGAT AAACCGCTCGTAAAAGCAGTA CAGTGCACCGTAAGATCGAGTT CCCCGCGCCAGCGGGGATAAAC CG* | 120 | |
| zwf-FOR | GCGCCAGCGGGGATAAACCGC TCGTAAAAG | 121 | pCASCADE-zwf |
| pCASCADE-REV | CTTGCCCGCCTGATGAATGCTC ATCCGG | 122 | |
| pCASCADE-FOR | CCGGATGAGCATTCATCAGGC GGGCAAG | 123 | pCASCADE-gltA1 |
| gltA1-REV | CGGTTTATCCCCGCTGGCGCG GGGAACTCGAACTTCATAACT TTTAC | 124 | |
| G2U | *TCGAGTTCCCCGCGCCAGCGGG GATAAACCGTATTGACCAATTCA TTCGGGACAGTTATTAGTTCGA GTTCCCCGCGCCAGCGGGGATA AACCGTTACCATTCTGTTGCTT TTATGTATAAGAATCGAGTTCC CCGCGCCAGCGGGGATAAACCG* | 125 | |
| udhA-FOR | GCGCCAGCGGGGATAAACCGT TACCATTCTGTTG | 126 | pCASCADE-udhA |
| pCASCADE-REV | CTTGCCCGCCTGATGAATGCTC ATCCGG | 127 | |
| pCASCADE-FOR | CCGGATGAGCATTCATCAGGC GGGCAAG | 128 | pCASCADE-gltA2 |
| gltA2-REV | CGGTTTATCCCCGCTGGCGCG GGGAACTCGAACTAATAACTG TC | 129 | |
| G2Z | *TCGAGTTCCCCGCGCCAGCGGG GATAAACCGTATTGACCAATTCA TTCGGGACAGTTATTAGTTCGA GTTCCCCGCGCCAGCGGGGATA AACCGCTCGTAAAAGCAGTAC AGTGCACCGTAAGATCGAGTTC CCCGCGCCAGCGGGGATAAACC G* | 130 | |
| zwf-FOR | GCGCCAGCGGGGATAAACCGC TCGTAAAAG | 131 | pCASCADE-zwf |
| pCASCADE-REV | CTTGCCCGCCTGATGAATGCTC ATCCGG | 132 | |
| pCASCADE-FOR | CCGGATGAGCATTCATCAGGC GGGCAAG | 133 | pCASCADE-gltA2 |
| gltA2-REV | CCGGTTTATCCCCGCTGGCGCG GGGAACTCGAACTAATAACTG TC | 134 | |
| UZ | *TCGAGTTCCCCGCGCCAGCGGG GATAAACCGTTACCATTCTGTT GCTTTTATGTATAAGAATCGAG TTCCCCGCGCCAGCGGGGATAA ACCGCTCGTAAAAGCAGTACA GTGCACCGTAAGATCGAGTTCC CCGCGCCAGCGGGGATAAACCG* | 135 | |
| zwf-FOR | GCGCCAGCGGGGATAAACCGC TCGTAAAAG | 136 | pCASCADE-zwf |
| pCASCADE-REV | CTTGCCCGCCTGATGAATGCTC ATCCGG | 137 | |

TABLE 9-continued

List of sgRNA guide sequences and primers used to construct them. Spacers are italicized.

| sgRNA/Primer Name | Sequence | SEQ ID NO | Template |
|---|---|---|---|
| pCASCADE-FOR | CCGGATGAGCATTCATCAGGC GGGCAAG | 138 | pCASCADE-udhA |
| udhA-REV | CCGGTTTATCCCCGCTGGCGCG GGGAACTCGATTCTTATACAT AAAAGC | 139 | |
| FG1G2 | *TCGAGTTCCCCGCGCCAGCGGG GATAAACCGTTGATTATAATAA* CCGTTTATCTGTTCGTATCGAG *TTCCCCGCGCCAGCGGGGATTA ACCGAAAAGCATATAATGCGT AAAAGTTATGAAGT TCGAGTTC CCCGCGCCAGCGGGGATAAACC GTATTGACCAATTCATTCGGG ACAGTTATTAGT TCGAGTTCCC CGCGCCAGCGGGGATAAACCG* | 140 | |
| gltA2-FOR | GCGCCAGCGGGGATAAACCGT *ATTGACCAATTCATC* | 141 | pCASCADE-gltA2 |
| pCASCADE-REV | CTTGCCCGCCTGATGAATGCTC ATCCGG | 142 | |
| pCASCADE-FOR | CCGGATGAGCATTCATCAGGC GGGCAAG | 143 | pCASCADE-FG1 |
| gltA1-REV | CGGTTTATCCCCGCTGGCGCG GGGAACTCGAACTTCATAACT TTTAC | 144 | |
| G1G2A | *TCGAGTTCCCCGCGCCAGCGGG GATAAACCGAAAAGCATATAAT GCGTAAAAGTTATGAAGT TCG AGTTCCCCGCGCCAGCGGGGAT AAACCGTATTGACCAATTCATT CGGGACAGTTATTAGT TCGAGT TCCCCGCGCCAGCGGGGATAAA CCGGTTTTGTAATTT TACAGG CAACCTTTTATT CGAGTTCCCC GCGCCAGCGGGGATAAACCG* | 145 | |
| gapAP1-FOR | GCGCCAGCGGGGATAAACCGG *TTTTGTAATTT TACAGGC* | 146 | pCASCADE-gapAP1 |
| pCASCADE-REV | CTTGCCCGCCTGATGAATGCTC ATCCGG | 147 | |
| pCASCADE-FOR | CCGGATGAGCATTCATCAGGC GGGCAAG | 148 | pCASCADE-G1G2 |
| gltA2-REV | CGGTTTATCCCCGCTGGCGCG GGGAACTCGAACTAATAACTG TC | 149 | |
| G1G2U | *TCGAGTTCCCCGCGCCAGCGGG GATAAACCGAAAAGCATATAAT GCGTAAAAGTTATGAAGT TCG AGTTCCCCGCGCCAGCGGGGAT AAACCGTATTGACCAATTCATT CGGGACAGTTATTAGT TCGAGT TCCCCGCGCCAGCGGGGATAAA CCGTTACCATTCTGTTGCTTTT ATGTATAAGAATCGAGTTCCCC GCGCCAGCGGGGATAAACCG* | 150 | |
| udhA-FOR | GCGCCAGCGGGGATAAACCGT *TACCATTCTGTTG* | 151 | pCASCADE-udhA |
| pCASCADE-REV | CTTGCCCGCCTGATGAATGCTC ATCCGG | 152 | |
| pCASCADE-FOR | CCGGATGAGCATTCATCAGGC GGGCAAG | 153 | pCASCADE-G1G2 |
| gltA2-REV | CGGTTTATCCCCGCTGGCGCG GGGAACTCGAACTAATAACTG TC | 154 | |
| G1G2Z | *TCGAGTTCCCCGCGCCAGCGGG GATAAACCGAAAAGCATATAAT* | 155 | |

TABLE 9-continued

List of sgRNA guide sequences and primers used to construct them. Spacers are italicized.

| sgRNA/Primer Name | Sequence | SEQ ID NO | Template |
|---|---|---|---|
| | GCGTAAAAGTTATGAAGT*TCG AGTTCCCCGCGCCAGCGGGGAT AAACCGTATTGACCAATTCATT CGGGACAGTTATTAGTTCGAGT TCCCCGCGCCAGCGGGGATAAA CCGCTCGTAAAAGCAGTACAG* TGCACCGTAAGA*TCGAGTTCCC CGCGCCAGCGGGGATAAACCG* | | |
| zwf-FOR | GCGCCAGCGGGGATAAACCGC TCGTAAAAG | 156 | pCASCADE-zwf |
| pCASCADE-REV | CTTGCCCGCCTGATGAATGCTC ATCCGG | 157 | |
| pCASCADE-FOR | CCGGATGAGCATTCATCAGGC GGGCAAG | 158 | pCASCADE-G1G2 |
| gltA2-REV | CGGTTTATCCCCGCTGGCGCG GGGAACTCGAACTAATAACTG TC | 159 | |
| FG1G2A | *TCGAGTTCCCCGCGCCAGCGGG GATAAACCGTTGATTATAATAA CCGTTTATCTGTTCGTATCGAG TTCCCCGCGCCAGCGGGGATAA ACCGAAAAGCATATAATGCGT AAAAGTTATGAAGTTCGAGTTC CCCGCGCCAGCGGGGATAAACC GTATTGACCAATTCATTCGGG ACAGTTATTAGTTCGAGTTCCC CGCGCCAGCGGGGATAAACCGG TTTTTGTAATTT TACAGGCAAC CTTTTATTCGAGTTCCCCGCGC CAGCGGGGATAACCG* | 160 | |
| gapAP1-FOR | GCGCCACTCGGGGATAAACCGG TTTTTGTAATTT TACAGGC | 161 | pCASCADE-gapAP1 |
| pCASCADE-REV | CTTGCCCGCCTGATGAATGCTC ATCCGG | 162 | |
| pCASCADE-FOR | CCGGATGAGCATTCATCACTGC CTGGCAAG | 163 | pCASCADE-FG1G2 |
| gltA2-REV | CGGTTTATCCCCGCTGGCGCG GGGAACTCGAACTAATAACTG TC | 164 | |
| FG1G2U | *TCGAGTTCCCCGCGCCAGCGGG GATAAACCGTTGATTATAATAA CCGTTTATCTGTTCGTATCGAG TTCCCCGCGCCAGCGGGGATAA ACCGAAAAGCATATAATGCGT AAAAGTTATGAAGTTCGAGTTC CCCGCGCCAGCGGGGATAAACC GTATTGACCAATTCATTCGGG ACAGTTATTAGTTCGAGTTCCC CGCGCCAGCGGGGATAAACCGT TACCATTCTGTTGCTTTTATGT ATAAGAATCGAGTTCCCCGCGC CAGCGGGGATAAACCG* | 165 | |
| gltA2-FOR | GCGCCAGCGGGGATAAACCGT *ATTGACCAATTCATTC* | 166 | pCASCADE-udhA |
| pCASCADE-REV | CTTGCCCGCCTGATGAATGCTC ATCCGG | 167 | |
| pCASCADE-FOR | CCGGATGAGCATTCATCAGGC GGGCAAG | 168 | pCASCADE-FG1G2 |
| gltA1-REV | CCTGTTTATCCCCGCTGGCGCG GGAACTCGAACTTCATAACT TTTAC | 169 | |
| FG1G2Z | *TCGAGTTCCCCGCGCCAGCGGG GATAAACCGTTGATTATAATAA CCGTTTATCTGTTCGTATCGAG TTCCCCGCGCCAGCGGGGATAA ACCGAAAAGCATATAATGCGT* | 170 | |

TABLE 9-continued

List of sgRNA guide sequences and primers used to construct them. Spacers are italicized.

| sgRNA/Primer Name | Sequence | SEQ ID NO | Template |
|---|---|---|---|
| | *AAAAGTTATGAAGTTCGAGTTC* *CCCGCGCCAGCGGGGATAAACC* *GTATTGACCAATTCATTCGGG* *ACAGTTATTAGTTCGAGTTCCC* *CGCGCCAGCGGGGATAAACCGC* TCGTAAAAGCAGTACAGTGCA CCGTAAGA*TCGAGTTCCCCGCG* *CCAGCGGGGATAAACCG* | | |
| gltA2-FOR | GCGCCAGCGGGGATAAACCGT *ATTGACCAATTCATTC* | 171 | pCASCADE-zwf |
| pCASCADE-REV | CTTGCCCGCCTGATGAATGCTC ATCCGG | 172 | |
| pCASCADE-FOR | CCGGATGAGCATTCATCAGGC GGGCAAG | 173 | pCASCADE-FG1G2 |
| gltA1-REV | CGGTTTATCCCCGCTGGCGCG GGGAACTCGAACTTCATAACT TTTAC | 174 | |
| G1G2UA | *TCGAGTTCCCCGCGCCAGCGGG* *GATAAACCGAAAAGCATATAAT* *GCGTAAAAGTTATGAAGTTCG* *AGTTCCCCGCGCCAGCGGGGAT* *AAACCGTATTGACCAATTCATT* *CGGGACAGTTATTAGTTCGAGT* *TCCCCGCGCCAGCGGGGATAAA* *CCGTTACCATTCTGTTGCTTTT* *ATGTATAAGAATCGAGTTCCCC* *GCGCCAGCGGGGATAAACCGGT* *TTTTGTAATTT TACAGGCAAC* *CTTTTATTCGAGTTCCCCGCGC* *CAGCGGGGATAAACCG* | 175 | |
| gapAP1-FOR | GCGCCAGCGGGGATAAACCGG *TTTTGTAATTT TACAGGC* | 176 | pCASCADE-gapAP1 |
| pCASCADE-REV | CTTGCCCGCCTGATGAATGCTC ATCCGG | 177 | |
| pCASCADE-FOR | CCGGATGAGCATTCATCAGGC GGGCAAG | 178 | pCASCADE-G1G2U |
| udhA-REV | CGGTTTATCCCCGCTGGCGCG GGGAACTCGATTCTTATACAT AAAAGC | 179 | |
| G1G2UZ | *TCGAGTTCCCCGCGCCAGCGGG* *GATAAACCGAAAAGCATATAAT* *GCGTAAAAGTTATGAAGTTCG* *AGTTCCCCGCGCCAGCGGGGAT* *AAACCGTATTGACCAATTCATT* *CGGGACAGTTATTAGTTCGAGT* *TCCCCGCGCCAGCGGGGATAAA* *CCGTTACCATTCTGTTGCTTTT* *ATGTATAAGAATCGAGTTCCCC* *GCGCCAGCGGGGATAAACCGCT* CGTAAAAGCAGTACAGTGCAC CGTAAGA*TCGAGTTCCCCGCGC* *CAGCGGGGATAAACCG* | 180 | |
| zwf-FOR | GCGCCAGCGGGGATAAACCGC TCGTAAAAG | 181 | pCASCADE-zwf |
| pCASCADE-REV | CTTGCCCGCCTGATGAATGCTC ATCCGG | 182 | |
| pCASCADE-FOR | CCGGATGAGCATTCATCAGGC GGGCAAG | 183 | pCASCADE-G1G2U |
| udhA-REV | CGGTTTATCCCCGCTGGCGCG GGGAACTCGATTCTTATACAT AAAAGC | 184 | |
| FG1G2UA | *TCGAGTTCCCCGCGCCAGCGGG* *GATAAACCGTTGATTATAATAA* *CCGTTTATCTGTTCGTATCGAG* *TTCCCCGCGCCAGCGGGGATAA* *ACCGAAAAGCATATAATGCGT* | 185 | |

TABLE 9-continued

List of sgRNA guide sequences and primers used to construct them. Spacers are italicized.

| sgRNA/Primer Name | Sequence | SEQ ID NO | Template |
|---|---|---|---|
| | *AAAAGTTATGAAGTTCGAGTTC* *CCCGCGCCAGCGGGGATAAACC* *GTATTGACCAATTCATTCGGG* *ACAGTTATTAGTTCGAGTTCCC* *CGCGCCAGCGGGGATAAAACCGT* *TACCATTCTGTTGCTTTTATGT* *ATAAGAATCGAGTTCCCCGCGC* *CAGCGGGGATAAACCGGTTTTT* *GTAATTTTACAGGCAACCTTT* *TATTCGAGTTCCCCGCGCCAGC* *GGGGATAAACCG* | | |
| gapAP1-FOR | GCGCCAGCGGGGATAAACCGG TTTTTGTAATTT TACAGGC | 186 | pCASCADE-gapAP1 |
| pCASCADE-REV | CTTGCCCGCCTGATGAATGCTC ATCCGG | 187 | |
| pCASCADE-FOR | CCGGATGAGCATTCATCGGC GGGCAAG | 188 | pCASCADE-FG1G2U |
| udhA-REV | CGGTTTATCCCCGCTGGCGCG GGGAACTCGATTCTTATACAT AAAAGC | 189 | |
| FG1G2UZ | *TCGAGTTCCCCGCGCCAGCGGG* *GATAAACCGTTGATTATAATAA* *CCGTTTATCTGTTCGTATCGAG* *TTCCCCGCGCCAGCGGGGATAA* *ACCGAAAAGCATATAATGCGT* *AAAAGTTATGAAGTTCGAGTTC* *CCCGCGCCAGCGGGGATAAACC* *GTATTGACCAATTCATTCGGG* *ACAGTTATTAGTTCGAGTTCCC* *CGCGCCAGCGGGGATAAAACCGT* *TACCATTCTGTTGCTTTTATGT* *ATAAGAATCGAGTTCCCCGCGC* *CAGCGGGGATAAACCGCTCGTA* *AAAGCAGTACAGTGCACCGTA* *AGATCGAGTTCCCCGCGCCAGC* *GGGGATAAACCG* | 190 | |
| zwf-FOR | GCGCCAGCGGGGATAAACCGC TCGTAAAAG | 191 | pCASCADE-zwf |
| pCASCADE-REV | CTTGCCCGCCTGATGAATGCTC ATCCGG | 192 | |
| pCASCADE-FOR | CCGGATGAGCATTCATCAGGC GGGCAAG | 193 | pCASCADE-FG1G2U |
| udhA-REV | CGGTTTATCCCCGCTGGCGCG GGGAACTCGATTCTTATACAT AAAAGC | 194 | |
| FG1G2UZA | *TCGAGTTCCCCGCGCCAGCGGG* *GATAAACCGTTGATTATAATAA* *CCGTTTATCTGTTCGTATCGAG* *TTCCCCGCGCCAGCGGGGATAA* *ACCGAAAAGCATATAATGCGT* *AAAAGTTATGAAGTTCGAGTTC* *CCCGCGCCAGCGGGGATAAACC* *GTATTGACCAATTCATTCGGG* *ACAGTTATTAGTTCGAGTTCCC* *CGCGCCAGCGGGGATAAACCGT* *TACCATTCTGTTGCTTTTATGT* *ATAAGAATCGAGTTCCCCGCGC* *CAGCGGGGATAAACCGCTCGTA* *AAAGCAGTACAGTGCACCGTA* *AGATCGAGTTCCCCGCGCCAGC* *GGGGATAAACCGGTTTTTGTAA* *TTT TACAGGCAACCTTTTATTC* *GAGTTCCCCGCGCCAGCGGGGA* *TAAACCG* | 195 | |
| gapAP1-FOR | GCGCCAGCGGGGATAAACCGG TTTTTGTAATTT TACAGGC | 196 | pCASCADE-gapAP1 |
| pCASCADE-REV | CTTGCCCGCCTGATGAATGCTC ATCCGG | 197 | |

TABLE 9-continued

List of sgRNA guide sequences and primers used to construct them. Spacers are italicized.

| sgRNA/Primer Name | Sequence | SEQ ID NO | Template |
|---|---|---|---|
| pCASCADE-FOR | CCGGATGAGCATTCATCAGGC GGGCAAG | 198 | pCASCADE-FG1G2UZ |
| zwf-REV | CGGTTTATCCCCGCTGGCGCG GGGAACTCGATCTTACGGTGC ACTGTAC | 199 | |
| UZ | *TCGAGTTCCCCGCGCCAGCGGG GATAAACCGTTTACCATTCTGTT* GCTTTTATGTATAAGA*ATCGAG TTCCCCGCCTCCAGCGGGGATAA* ACCGCTCGTAAAGCAGTACA GTGCACCGTAAGATCGAGTTCC *CCGCGCCAGCGGGGATAAACCG* | 200 | |
| zwf-FOR | GCGCCAGCGGGGATAAACCGC TCGTAAAAG | 201 | pCASCADE-zwf |
| pCASCADE-REV | CTTGCCCGCCTGATGAATGCTC ATCCGG | 202 | |
| pCASCADE-FOR | CCGGATGAGCATTCATCAGGC GGGCAAG | 203 | pCASCADE-udhA |
| udhA-REV | CGGTTTATCCCCGCTGGCGCG GGGAACTCGATTCTTATACAT AAAAGC | 204 | |

TABLE 10

List of plasmids used in this study.

| Plasmid Utilized in this Study | | |
|---|---|---|
| Plasmid | Purpose | Source |
| pSIM5 | Recombineering and Strain Construction | Court Lab[54] |
| pCP20 | FRT kanamycin cassette curing | Court Lab[54] |
| pSMART-HC-Kan | Backbone Vector | Lucigen |
| pcrRNA.Tet | pCASCADE-control backbone | Beisel Lab[34] |

| Plasmid Constructed in this Study | | |
|---|---|---|
| Plasmid | Plasmid Name | Addgene ID |
| pSMART-Ala2 | pSMART-HCKan-IN:yibDp-ald* | 71326 |
| pSMART-Ala3 | pSMART-HCKan-IN:phoBp-ald* | 71327 |
| pSMART-Ala4 | pSMART-HCKan-IN:phoHp-ald* | 71328 |
| pSMART-Ala5 | pSMART-HCKan-IN:mipAp-ald* | 71329 |
| pSMART-Ala11 | pSMART-HCKan-proA-ald* | 87172 |
| pSMART-Ala12 | pSMART-HCKan-proC-ald* | 87173 |
| pSMART-Ala13 | pSMART-HCKan-proD-ald* | 87174 |
| pSMART-Ala14 | pSMART-HCKan-proB-ald* | 101079 |
| pSMART-Ala15 | pSMART-HCKan-HCEp-ald* | 101080 |
| pSMART-Mev2 | pSMART-IN:yibDp1-mvaE-IN:phoBp2-mvaS(A110G) | 66642 |
| pSMART-Mev3 | pSMART-IN:yibDp1-mvaE-IN:mipAp2-mvaS(A110G) | 102761 |
| pSMART-Mev4 | pSMART-IN:yibDp1-mvaE-IN:phoHp2-mvaS(A110G) | 102762 |
| pSMART-Mev5 | pSMART-IN:mipAp1-mvaE-IN:yibD2-mvaS(A110G) | 102763 |
| pSMART-3HP | pSMART-3HP-NADPH-rhtA | 87143 |
| pCDF-mcherry2 | pCDF-proD-mcherry-DAS4 | 87145 |
| pSMART-GFPuv | pSMART-IN:yibDp-GFPuv | 65822 |
| pSMART-GFPuv2 | pSMART-IN:phoBp-GFPuv | 71517 |
| pSMART-GFPuv3 | pSMART-IN:phoUp-GFPuv | 71518 |
| pSMART-GFPuv4 | pSMART-IN:phoHp-GFPuv | 71519 |
| pSMART-GFPuv5 | pSMART-IN:mipAp-GFPuv | 71520 |
| pCASCADE-control | pCASCADE | 65821 |
| pCASCADE-proD | pCASCADE-proD | 65820 |
| pCASCADE-gapAP1 | pCASCADE-gapAP1 | 87146 |
| pCASCADE-fabI | pCASCADE-fabI | 66635 |
| pCASCADE-FG1 | pCASCADE-fabI-gltA1 | 71340 |
| pCASCADE-FG1G2 | pCASCADE-fabI-gltA1-gltA2 | 71342 |
| pCASCADE-FG1G2A | pCASCADE-fabI-gltA1-gltA2-gapA | 87147 |
| pCASCADE-FG1G2U | pCASCADE-fabI-gltA1-gltA2-udhA | 66637 |
| pCASCADE-FG1G2UA | pCASCADE-fabI-gltA1-gltA2-udhA-gapA | 87154 |

TABLE 10-continued

List of plasmids used in this study.

| | | |
|---|---|---|
| pCASCADE-FG1G2UZ | pCASCADE-fabI-gltA1-gltA2-udhA-zwf | 87148 |
| pCASCADE-FG1G2UZA | pCASCADE-fabI-gltA1-gltA2-udhA-zwf-gapA | 87149 |
| pCASCADE-FG1G2Z | pCASCADE-fabI-gltA1-gltA2-zwf | 66638 |
| pCASCADE-FG2 | pCASCADE-fabI-gltA2 | 71341 |
| pCASCADE-FU | pCASCADE-fabI-udhA | 66636 |
| pCASCADE-FZ | pCASCADE-fabI-zwf | 71335 |
| pCASCADE-G1G2 | pCASCADE-gltA1-gltA2 | 71348 |
| pCASCADE-G1G2A | pCASCADE-gltA1-gltA2-gapA | 87150 |
| pCASCADE-G1G2U | pCASCADE-gltA1-gltA2-udhA | 71343 |
| pCASCADE-G1G2UA | pCASCADE-gltA1-gltA2-udhA-gapA | 87151 |
| pCASCADE-G1G2UZ | pCASCADE-gltA1-gltA2-udhA-zwf | 87152 |
| pCASCADE-GG2Z | pCASCADE-gltA1-gltA2-zwf | 71347 |
| pCASCADE-G1U | pCASCADE-gltA1-udhA | 71339 |
| pCASCADE-G1Z | pCASCADE-gltA1-zwf | 71337 |
| pCASCADE-G2U | pCASCADE-gltA2-udhA | 65819 |
| pCASCADE-G2Z | pCASCADE-gltA2-zwf | 71338 |
| pCASCADE-gltA1 | pCASCADE-gltA1 | 71334 |
| pCASCADE-gltA2 | pCASCADE-gltA2 | 65817 |
| pCASCADE-udhA | pCASCADE-udhA | 65818 |
| pCASCADE-UZ | pCASCADE-udhA-zwf | 87153 |
| pCASCADE-zwf | pCASCADE-zwf | 65825 |

Section 7: 2-Stage Micro-Fermentations

*E. coli* Media Stock Solutions

10× concentrated Ammonium-Citrate 30 salts (1 L), mix 30 g of $(NH_4)_2SO_4$ and 1.5 g citric acid in water with stirring, adjust pH to 7.5 with 10 M NaOH. Autoclave and store at room temperature (RT).

10× concentrated Ammonium-Citrate 90 salts (1 L), mix 90 g of $(NH_4)_2SO_4$ and 2.5 g citric acid in water with stirring, adjust pH to 7.5 with 10 M NaOH. Autoclave and store at RT.

1 M Potassium 3-(N-morpholino) propanesulfonic Acid (MOPS), adjust to pH 7.4 with 5000 KOH. Filter sterilize (0.2 m) and store at RT.

0.5 M potassium phosphate buffer, pH 6.8, mix 248.5 mL of 1.0 M $K_2HPO_4$ and 251.5 mL of 1.0 M $KH_2PO_4$ and adjust to a final volume of 1000 mL with ultrapure water. Filter sterilize (0.2 μm) and store at RT.

2 M $MgSO_4$ and 10 mM $CaSO_4$ solutions. Filter sterilize (0.2 μm) and store at RT.

50 g/L solution of thiamine-HCl. Filter sterilize (0.2 m) and store at 4° C.

500 g/L solution of glucose, dissolve by stirring with heat. Cool, filter sterilize (0.2 μm), and store at RT.

100 g/L yeast extract, autoclave, and store at RT.

100 g/L casamino acid, autoclave, and store at RT.

500× Trace Metal Stock: Prepare a solution of micronutrients in 1000 mL of water containing 10 mL of concentrated $H_2SO_4$. 0.6 g $CoSO_4$ $7H_2O$, 5.0 g $CuSO_4$ $5H_2O$, 0.6 g $ZnSO_4.7H_2O$, 0.2 g $Na_2MoO_4.2H_2O$, 0.1 g $H_3BO_3$, and 0.3 g $MnSO_4.H_2O$. Filter sterilize (0.2 μm) and store at RT in the dark.

Prepare a fresh solution of 40 mM ferric sulfate heptahydrate in water, filter sterilize (0.2 μm) before preparing media each time.

Media Components

Prepare the final working medium by aseptically mixing stock solutions based on the following tables in the order written to minimize precipitation, then filter sterilize (with a 0.2 μm filter).

TABLE 11

Seed Media, pH 6.8:

| Ingredient | Unit | SM10 | SM10++ |
|---|---|---|---|
| $(NH_4)_2SO_4$ | g/L | 9 | 9 |
| Citric Acid | g/L | 0.25 | 0.25 |
| Potassium Phosphate | mM | 5 | 5 |
| $CoSO_4·7H_2O$ | g/L | 0.0048 | 0.0048 |
| $CuSO_4·5H_2O$ | g/L | 0.04 | 0.04 |
| $ZnSO_4·7H_2O$ | g/L | 0.0048 | 0.0048 |
| $Na_2MoO_4·2H_2O$ | g/L | 0.0016 | 0.0016 |
| $H_3BO_3$ | g/L | 0.0008 | 0.0008 |
| $MnSO_4·H_2O$ | g/L | 0.0024 | 0.0024 |
| $FeSO_4·7H_2O$ | g/L | 0.044 | 0.044 |
| $MgSO_4$ | mM | 2.5 | 2.5 |
| $CaSO_4$ | mM | 0.06 | 0.06 |
| Glucose | g/L | 45 | 45 |
| MOPS | mM | 200 | 200 |
| Thiamine-HCl | g/L | 0.01 | 0.01 |
| Yeast Extract | g/L | 1 | 2.5 |
| Casamino Acids | g/L | 0 | 2.5 |

TABLE 12

Production/Wash Media, pH 6.8:

| Ingredient | Unit | FGM3 | FGM3 No Phosphate | FGM3 Wash | FGM3 + 40 mM phosphate | FGM10 |
|---|---|---|---|---|---|---|
| $(NH_4)_2SO_4$ | g/L | 3 | 3 | 3 | 3 | 9 |
| Citric Acid | g/L | 0.15 | 0.15 | 0.15 | 0.15 | 0.25 |
| Potassium Phosphate | mM | 1.8 | 0 | 0 | 40 | 5 |
| $CoSO_4·7H_2O$ | g/L | 0.0024 | 0.0024 | 0 | 0.0024 | 0.0048 |
| $CuSO_4·5H_2O$ | g/L | 0.02 | 0.02 | 0.00 | 0.02 | 0.04 |
| $ZnSO_4·7H_2O$ | g/L | 0.0024 | 0.0024 | 0 | 0.0024 | 0.0048 |

TABLE 12-continued

Production/Wash Media, pH 6.8:

| Ingredient | Unit | FGM3 | FGM3 No Phosphate | FGM3 Wash | FGM3 + 40 mM phosphate | FGM10 |
|---|---|---|---|---|---|---|
| $Na_2MoO_4 \cdot 2H_2O$ | g/L | 0.0008 | 0.0008 | 0 | 0.0008 | 0.0016 |
| $H_3BO_3$ | g/L | 0.0004 | 0.0004 | 0 | 0.0004 | 0.0008 |
| $MnSO_4 \cdot H_2O$ | g/L | 0.0012 | 0.0012 | 0 | 0.0012 | 0.0024 |
| $FeSO_4 \cdot 7H_2O$ | g/L | 0.022 | 0.022 | 0 | 0.022 | 0.044 |
| $MgSO_4$ | mM | 2 | 2 | 0 | 2 | 2.5 |
| $CaSO_4$ | mM | 0.05 | 0.05 | 0 | 0.05 | 0.06 |
| Glucose | g/L | 45 | 25 | 0 | 45 | 25 |
| MOPS | mM | 200 | 200 | 0 | 200 | 0 |
| Thiamine-HCl | g/L | 0.01 | 0.01 | 0 | 0.01 | 0.01 |

Micro-Fermentations

Figure 16A:
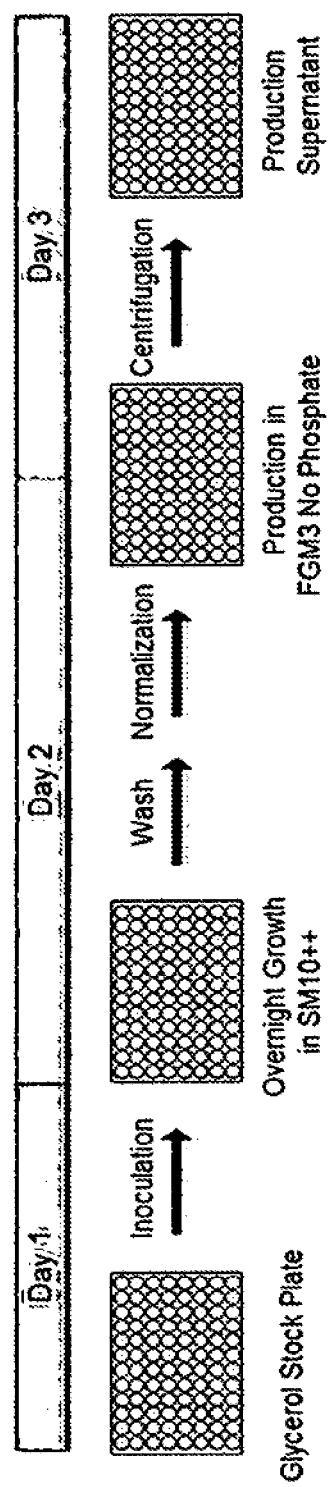
FIGS. 16A-C depict an overview of micro-fermentation process.
Figure 16B:
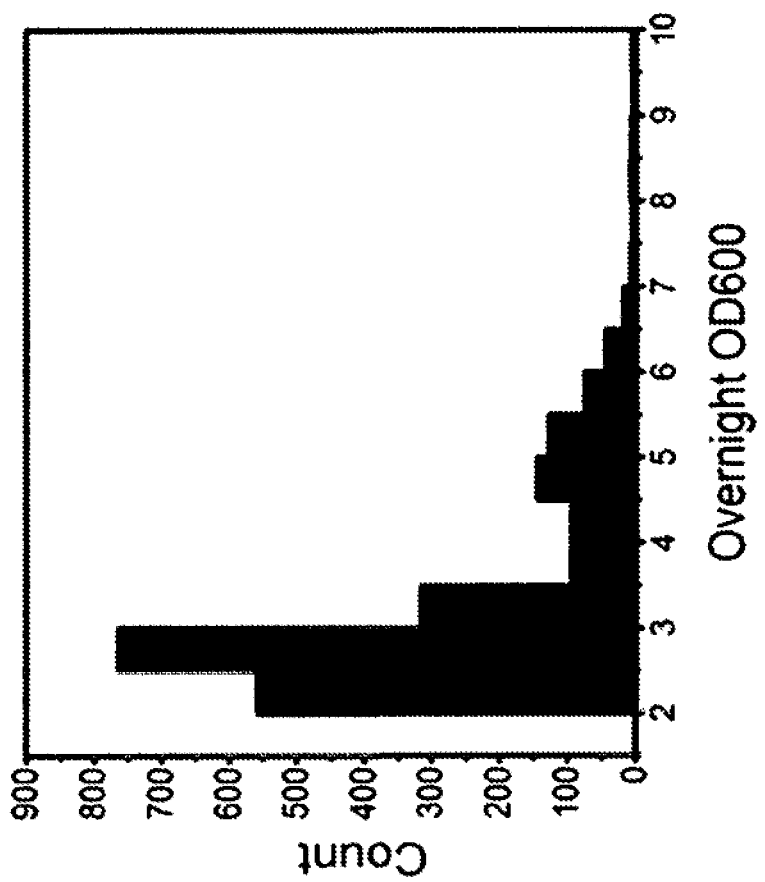
Figure 16C:
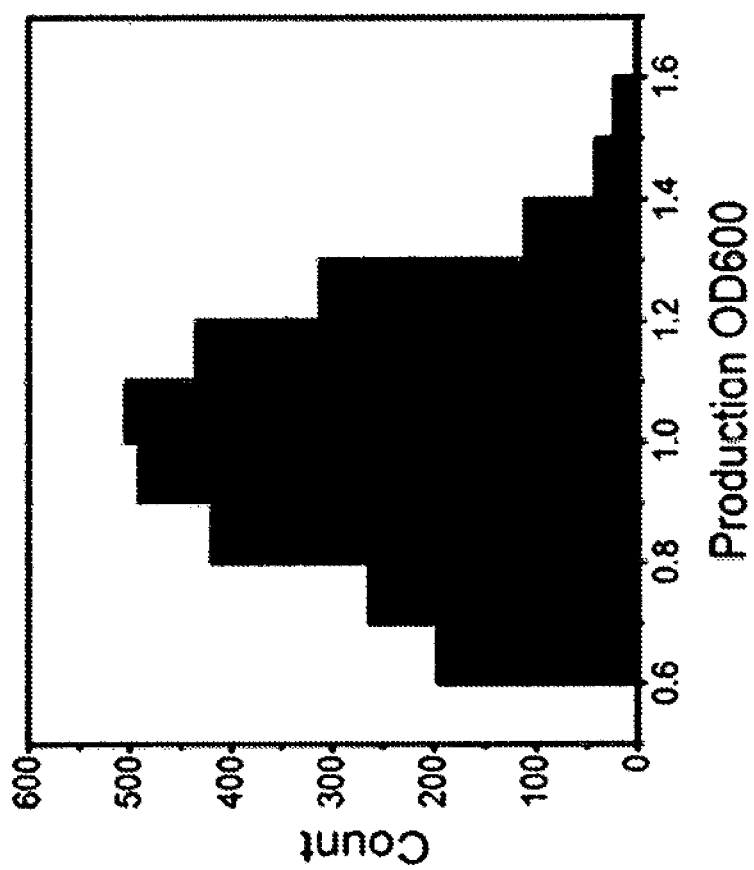
Figure 17:
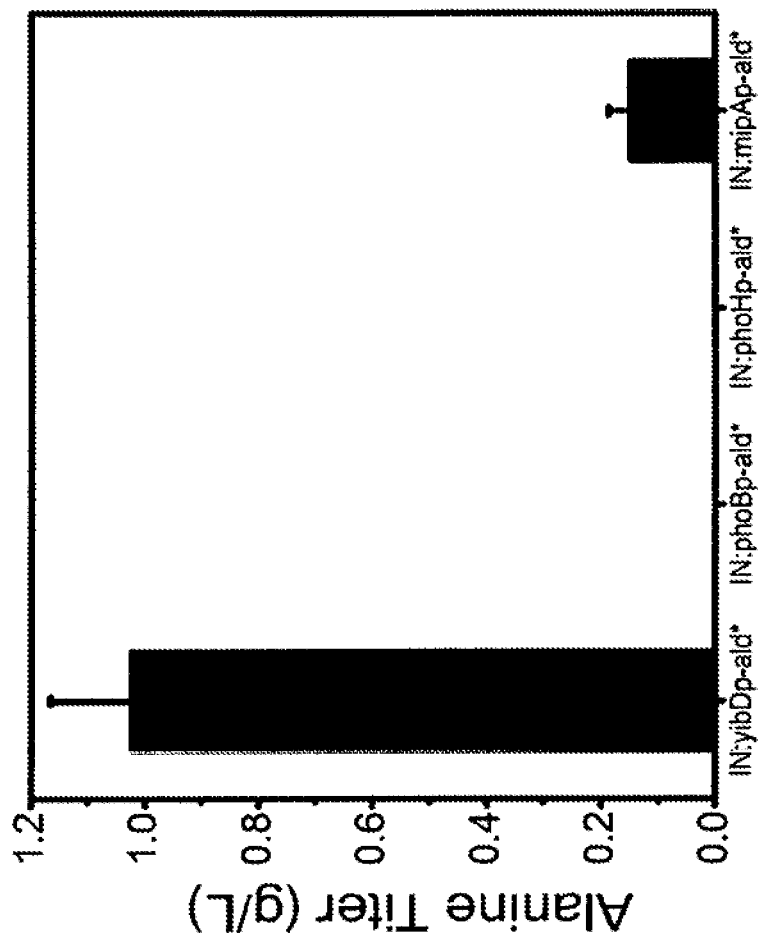
FIG. 17 depicts micro-fermentation for L-alanine production using different insulated phosphate promoters in DLF_0025 strain.

An overview of the micro-fermentation protocol is illustrated in FIG. 16A-C. Strains were evaluated for production in 96 well plate micro-fermentations, wherein cells were initially grown to mid-log phase, harvested, washed, resuspended and normalized in a phosphate free production medium to an OD600=1, for a 24 hour production stage. The success of the micro-fermentations required: (1) syncing strains up by harvesting all strains in exponential phase; (2) the use of low biomass levels, so that batch sugar could be kept low while enabling significant potential product accumulation; and (3) a method to supply adequate mixing and aeration, while minimizing evaporative losses. To address the final requirement, commercially available microplate sandwich covers and clamps from EnzyScreen™ was used, which greatly reduce evaporative losses while enabling high levels of mixing and aeration in standard 25 mm orbit shakers operating at 400 rpm[92-93]. Micro-fermentation results for alanine production with different insulated phosphate promoters are shown in FIG. 17. Micro-fermentation results for strains evaluated with gapA and gapN gene alterations are given in FIG. 18.

Section 8: Micro-Fermentations Robustness Evaluation

During micro-fermentation oxygen robustness studies, production culture volume was varied to achieve desired oxygen transfer rate (OTR) values as previously reported (http://www.enzyscreen.com/oxygen_transfer_rates.htm)[92-93], and as listed below in Table 14. Batch glucose levels during the production stage were altered to assess robustness to glucose. Strains utilized in the robustness experiments at the micro-fermentation scale are listed in Table 15. Results from the micro-fermentation robustness studies are given in FIGS. 19A-D, FIGS. 20A-D, FIGS. 21A-D, FIGS. 22A-D, FIGS. 23A-D, FIGS. 24A-D, FIGS. 25A-D, FIGS. 26A-D, FIGS. 27A-D, FIGS. 28A-D, FIGS. 29A-D, FIGS. 30A-D, FIG. 31AD, and FIG. 32.

TABLE 14

Culture conditions for different OTR values.
25 mm orbit shaker

| Max OTR (mmol/L-hr) | Shaking Speed (rpm) | Fill Volume (μL) |
|---|---|---|
| 25 | 400 | 100 |
| 20 | 400 | 150 |
| 15 | 400 | 200 |

TABLE 15

List of strains used for micro-fermentation robustness evaluations and their RS scores.

| Strain # | Silencing | Proteolysis | Plasmid | RS |
|---|---|---|---|---|
| 1 | gltA1 | FU | pSMART-Ala2 | 89.6 |
| 2 | gltA1 | F | pSMART-Ala2 | 89.5 |
| 3 | gltA1 | GU | pSMART-Ala2 | 89.4 |
| 4 | FG1G2 | None | pSMART-Ala2 | 89.3 |
| 5 | G1G2 | GU | pSMART-Ala2 | 88.8 |
| 6 | FG1G2 | G | pSMART-Ala2 | 88.2 |
| 7 | G1G2 | F | pSMART-Ala2 | 83.4 |
| 8 | gltA2 | FGU | pSMART-Ala2 | 83.4 |
| 9 | gltA1 | FGU | pSMART-Ala2 | 83.1 |
| 10 | G1G2 | FGU | pSMART-Ala2 | 82.3 |
| 11 | gltA2 | U | pSMART-Ala2 | 82.2 |
| 12 | gltA2 | F | pSMART-Ala2 | 80.6 |
| 13 | FG1G2 | FG | pSMART-Ala2 | 80.5 |
| 14 | None | G | pSMART-Ala2 | 79.9 |
| 15 | gltA2 | GU | pSMART-Ala2 | 77.9 |
| 16 | fabI | FGU | pSMART-Ala2 | 75.7 |
| 17 | None | FG | PSMART-Ala2 | 75.4 |
| 18 | G1G2 | FU | pSMART-Ala2 | 75.3 |
| 19 | None | FGU | pSMART-Ala2 | 73.4 |
| 20 | None | FU | pSMART-Ala2 | 73.3 |
| 21 | gltA1 | U | pSMART-Ala2 | 72.9 |
| 22 | fabI | FG | pSMART-Ala2 | 69.1 |
| 23 | FG1G2 | FU | pSMART-Ala2 | 67.6 |
| 24 | gltA2 | FU | pSMART-Ala2 | 67.5 |
| 25 | None | F | pSMART-Ala2 | 65.6 |
| 26 | gltA2 | FG | pSMART-Ala2 | 62.1 |
| 27 | FG1G2 | F | pSMART-Ala2 | 61.1 |
| 28 | fabI | GU | pSMART-Ala2 | 59.9 |
| 29 | fabI | F | pSMART-Ala2 | 59.6 |
| 30 | gltA1 | FG | pSMART-Ala2 | 58.1 |
| 31 | gltA1 | None | pSMART-Ala2 | 57.1 |
| 32 | None | None | pSMART-Ala2 | 55.5 |
| 33 | G1G2 | None | pSMART-Ala2 | 54.1 |
| 34 | fabI | U | pSMART-Ala2 | 53.9 |
| 35 | gltA2 | G | pSMART-Ala2 | 52.8 |
| 36 | fabI | None | pSMART-Ala2 | 50.3 |
| 37 | fabI | FU | pSMART-Ala2 | 48.4 |
| 38 | gltA2 | None | pSMART-Ala2 | 47.8 |
| 39 | FG1G2 | FGU | pSMART-Ala2 | 44.6 |
| 40 | None | GU | pSMART-Ala2 | 42.9 |
| 41 | None | U | pSMART-Ala2 | 39.3 |
| 42 | fabI | G | pSMART-Ala2 | 39.2 |
| 43 | gltA1 | G | pSMART-Ala2 | 34.7 |
| 44 | G1G2 | FG | pSMART-Ala2 | 32.8 |
| 45 | FG1G2 | U | pSMART-Ala2 | 29.4 |
| 46 | FG1G2 | GU | pSMART-Ala2 | 24.3 |
| 47 | G1G2 | G | pSMART-Ala2 | 24.1 |
| 48 | G1G2 | U | pSMART-Ala2 | −25.3 |
| 49 | None | None | pSMART-Ala13 | 55.7 |
| 50 | None | None | pSMART-Ala12 | −31.5 |
| 51 | None | None | pSMART-Ala15 | −103.2 |
| 52 | None | None | pSMART-Ala11 | −114.1 |
| 53 | None | None | pSMART-Ala14 | −441.5 |

Section 9: Standardized 2-Stage Fermentations

Figure 33A:
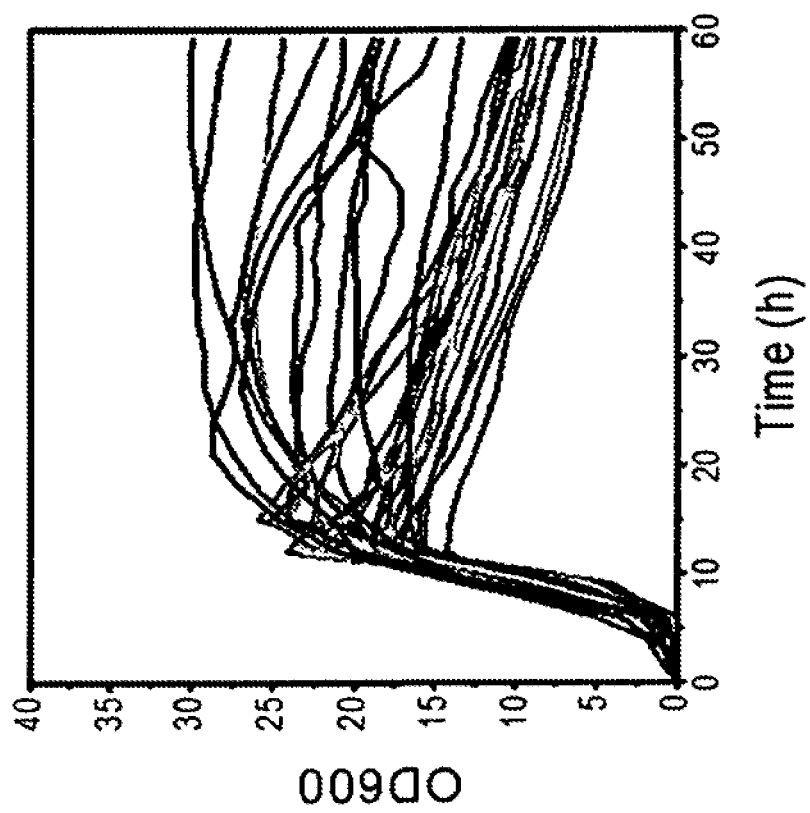
FIGS. 33A-B depict growth profile for all valve and growth associated strains at 1 L scale evaluated in this paper.

A standardized phosphate limited 2-stage fermentation protocol was utilized for evaluation of all valve strains. This protocol yields highly reproducible growth stage results, with minimal strain to strain variability even with strains making different products. More significant variability was observed during the production stage as a result of differing feed rates and base utilization by different strains. FIG. 33A gives the growth curves for all valve strains with a 10 g cdw/L biomass level in 1 L fermentations performed in this study. This consistency is contrasted to the more variable growth of growth associated production strains, given in FIG. 33B.

TABLE 16

Strains used for mevalonic acid scalability.

| Strain # | Silencing | Proteolysis | Plasmid |
|---|---|---|---|
| 1 | FG1G2 | FU | pSMART-Mev2 |
| 2 | G2Z | FGUA | pSMART-Mev2 |
| 3 | FG1G2A | FUN | pSMART-Mev2 |
| 4 | UZ | FGUA | pSMART-Mev2 |

Section 10: Analytical Methods

TABLE 17

UPLC-MS/MS parameters

| Analyte | Retention Time (min) | ESI Mode | MRM Transition(s) | Cone Voltage | Collision Energy |
|---|---|---|---|---|---|
| Alanine | 0.5 | + | 89.95→44.08 | 15 | 9 |
| C13-Alanine | 0.5 | + | 91.95→46.08 | 15 | 9 |

DETAILED DESCRIPTION OF FIGURES

Figure 1B:
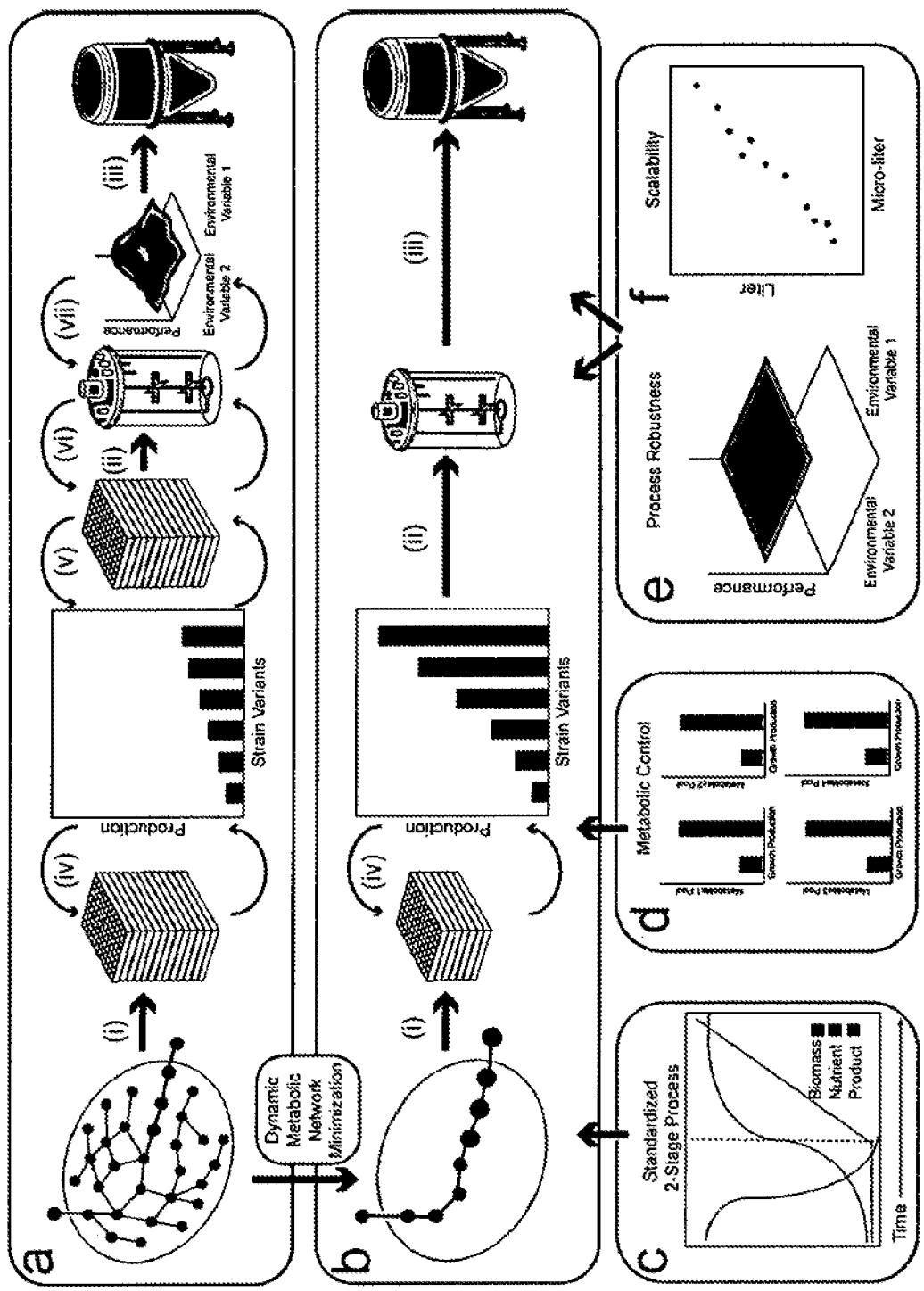
FIG. 1B depicts strain and bioprocess optimization.

FIG. 1A: An Overview of Dynamic Metabolic Control in 2-Stage Fermentations. Metabolic engineering involves optimizing a metabolic pathway to a desired product to the existing metabolic network of a host, converting feedstocks to a desired product. Filled circles indicate metabolites and lines indicate enzymatic reactions. Traditional optimization in metabolic engineering, often involves three key steps (a) the deletion of competing non-essential metabolic pathways including those leading to undesired byproducts and the overexpression of enzymes in the pathway converting feedstock molecules to the product (indicated by thicker lines) and potentially (b) attenuating enzymes in essential metabolism (indicated by orange lines) to further increase production. This process is iterated to optimize the yield to the desired product (pie charts). By contrast, dynamic metabolic network minimization can be used to fully unlock the potential of commonly used 2-stage fermentation processes (c-d). In the first stage of these processes (c) biomass growth and yield are optimized, while in the second stage (d) product formation is optimized, which is well suited for a 2-stage process (e) in which biomass levels accumulate and consume a limiting nutrient (in this case inorganic phosphate), which when depleted triggers entry into a productive stationary phase. Synthetic metabolic valves utilizing CRISPRi based gene silencing and/or controlled proteolysis can be used (f and g) to greatly reduce the pertinent metabolic network upon the transition to the production stage, (f) and array of silencing guides can be induced, processed by the CASCADE complex into individual guides and used to silencing target multiple genes of interest (GOI). (g) If C-terminal DAD+4 tags are added to enzymes of interest (EOI) through chromosomal modification, they can be inducibly degraded by the clpXP protease in the present of and inducible sspB chaperone. (h) Dynamic control over protein levels in E. coli using 2 stage dynamic control with inducible proteolysis and CRISPRi silencing. As cells grow phosphate is depleted, and cells "turn off mCherry and "turn on" GFPuv. Shaded areas represent one standard deviation from the mean, n=3. (i) Relative impact of proteolysis and gene silencing alone and in combination on mCherry degradation, with (j) decays rates.

FIG. 1B: Strain and Bioprocess Optimization. (a) Conventional approaches for strain and process optimization in metabolic engineering often involves deletion of competing non-essential metabolic pathways and overexpression of pathway enzymes (Filled circles: metabolites; lines: enzymatic reactions. green indicated a production pathway). (a-i) Strain variants are evaluated at screening scale (microtiter plates, shake flasks, etc), (a-ii) the best strains are assessed in larger scale instrumented bioreactors. Numerous design-build-test cycles (a-vi-vii) are used to iteratively optimize both the production strain and process, including the often-critical optimization of environmental (process) variables (a-vii). (a-iii) The best performing strains and associated optimized process conditions are scaled to industrially relevant levels. (b) Rapid strain and bioprocess optimization using 2-stage dynamic metabolic control. The metabolic network in the cell is dynamically minimized to only the steps essential for product formation. This is accomplished in a standardized 2-stage bioprocess (c), where a biomass accumulating growth stage is followed by a production stage, with only a minimal metabolic network. The limitation of a macronutrient can be used to "switch" cellular metabolism from growth to production. The approach results in a smaller subset of potential strain variants for screening (b-i). Metabolic network minimization helps increase relevant metabolite levels (d) and thus production levels, it also enhances process robustness (e), and as a result process and strain scalability (f). The best producers identified from screening are predictably and rapidly scaled to (b-ii) larger instrumented bioreactors, and (b-iii) subsequently to industrially relevant levels. If needed, limited design-build-test cycles (b-iv) are incorporated to guide improvements. Product independent, standardized protocols are followed for strain evaluation at all scales, eliminating the need for intensive process optimization.

Figure 2B:
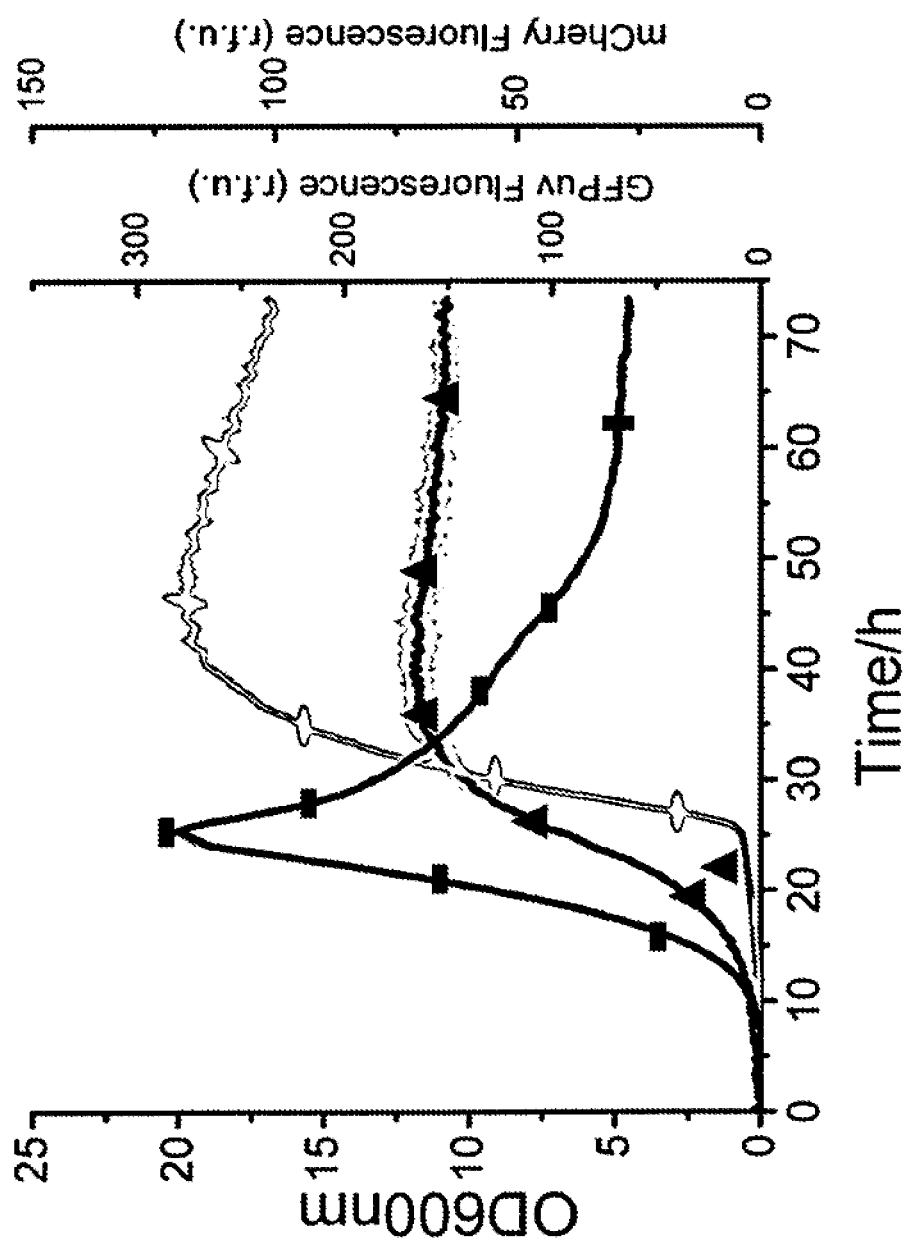
Figure 2C:
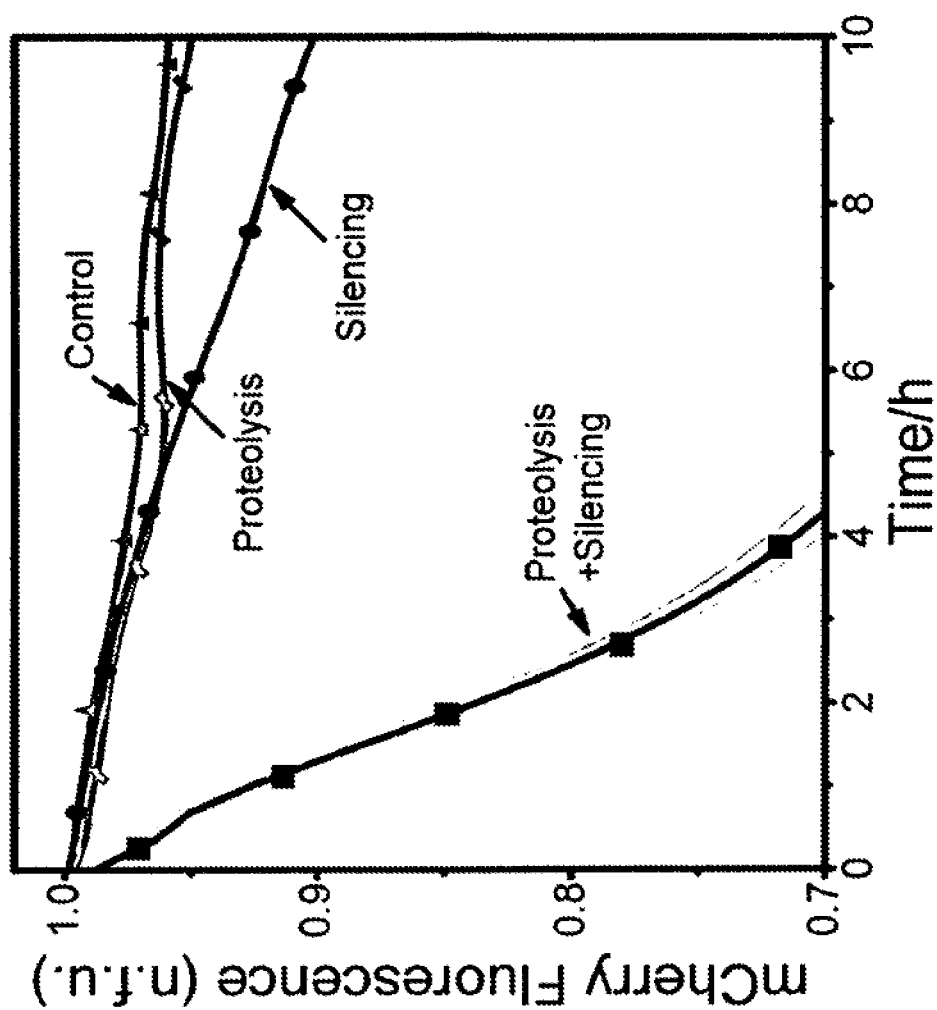
Figure 2D:
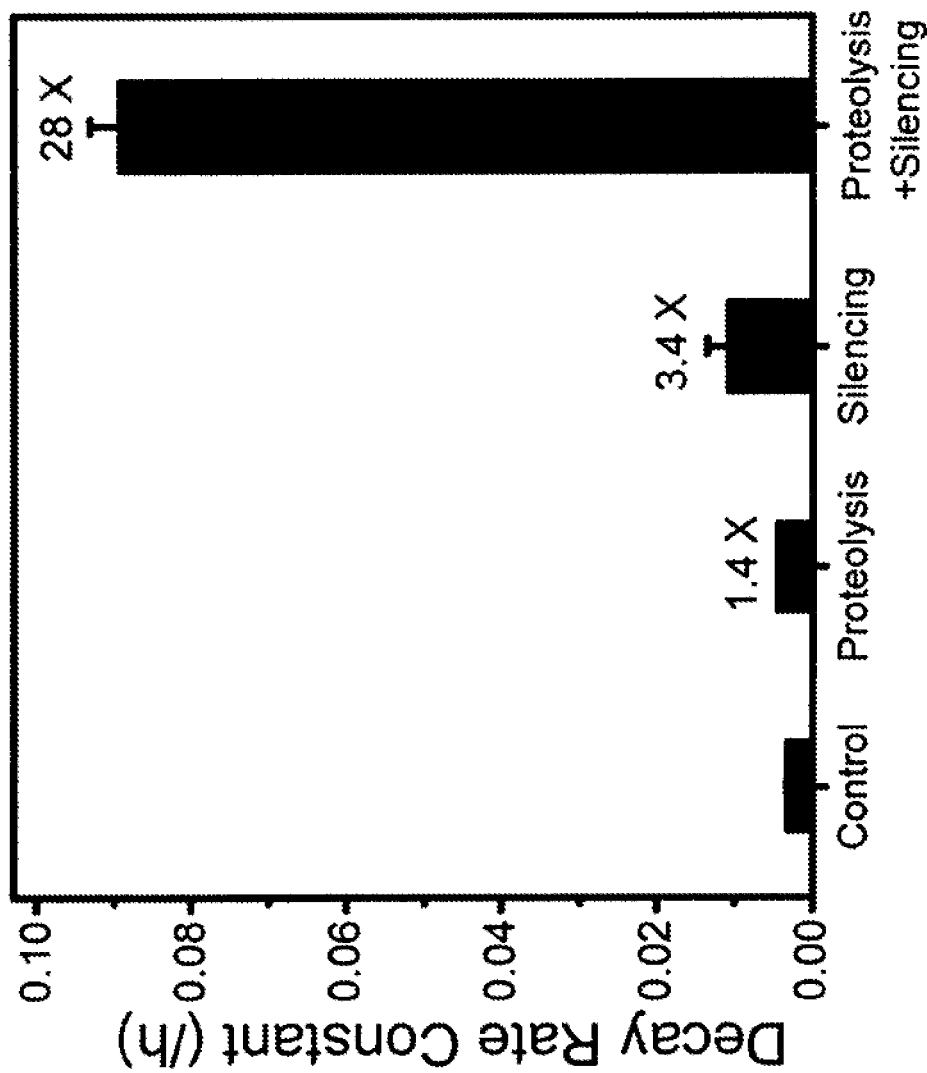

FIGS. 2A-D: Implementation of 2-stage Synthetic Metabolic Valves (SMVs) in E. coli. FIG. 2A depicts SMVs utilizing CRISPRi based gene silencing and/or controlled proteolysis were constructed. (Top) Silencing: An array of inducible silencing guide RNAs (i) can be used to silence expression of multiple genes of interest (GOI) when the native E. coli CRISPR/Cascade machinery is expressed, which can process guide arrays into individual guides (ii). (Bottom) Proteolysis: When C-terminal DAS+4 tags are added to enzymes of interest (EOI) (through chromosomal modification), they can be degraded by the clpXP protease (iv) upon the controlled induction of the sspB chaperone (iii). FIG. 2B depicts dynamic control over protein levels in E. coli using inducible proteolysis and CRISPRi silencing. As cells grow phosphate is depleted, cells "turn OFF" mCherry and "turn ON" GFPuv. Shaded areas represent one standard deviation from the mean, r.f.u, relative fluorescence units. FIG. 2C depicts relative impact of proteolysis and gene silencing alone and in combination on mCherry degradation, n.f.u. normalized fluorescence units (normalized to maximal fluorescence). FIG. 2D depicts relative impact of proteolysis and gene silencing alone and in combination on observed mCherry fluorescence decays rates (per hour).

Figure 3F:
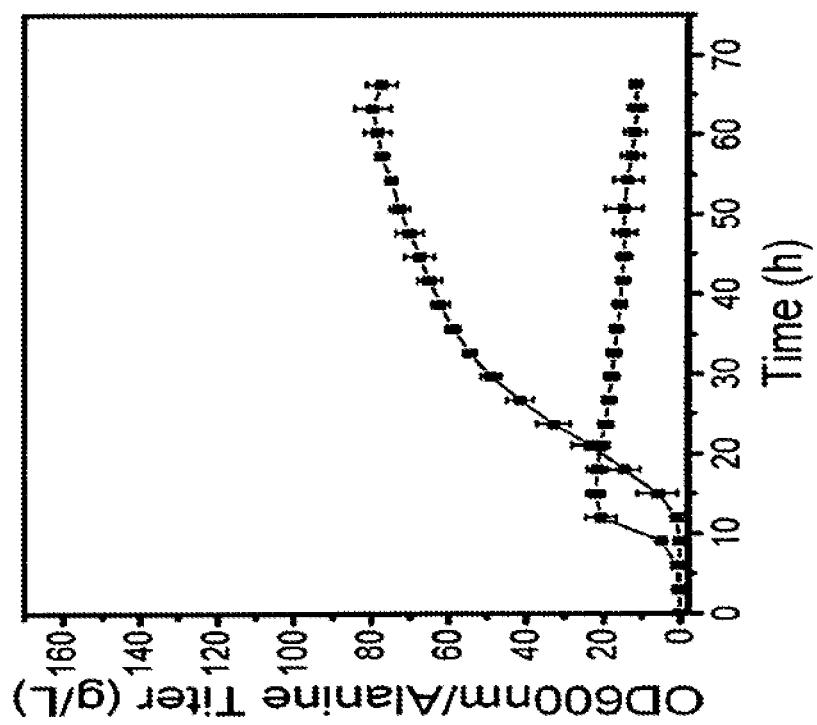
Figure 3H:
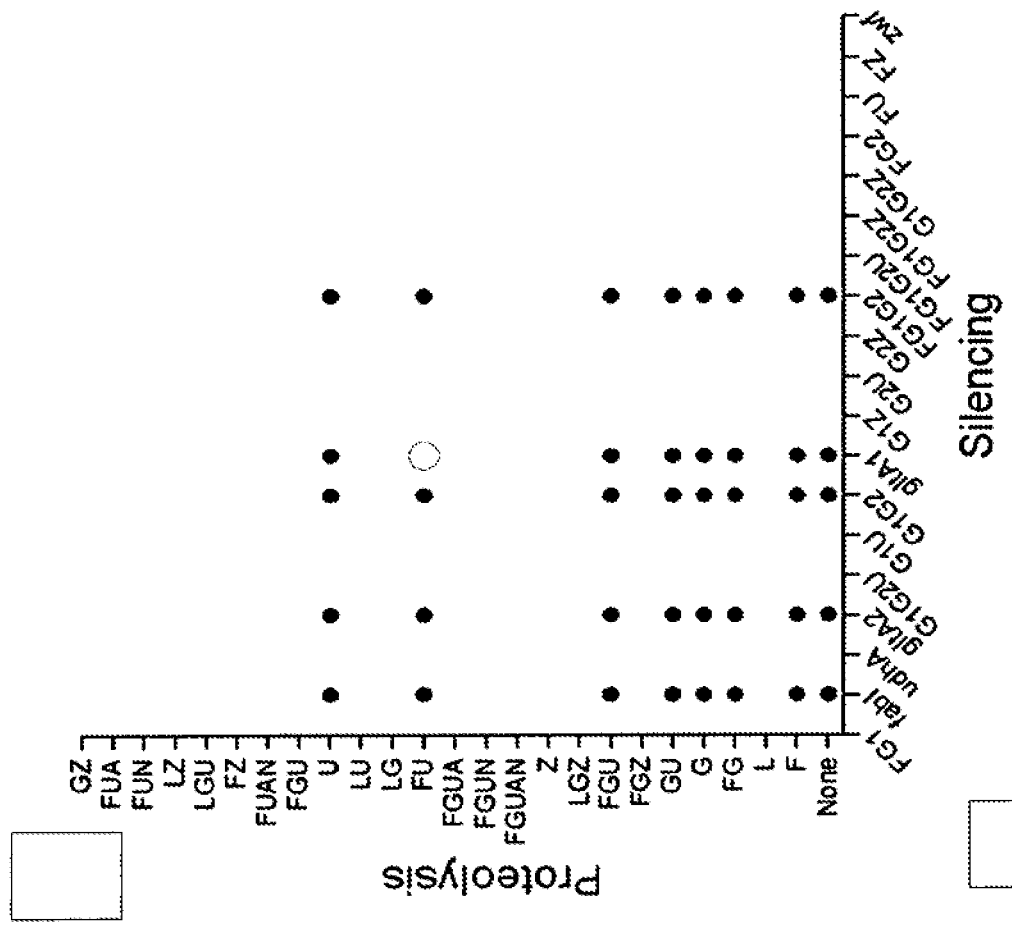
Figure 3I:
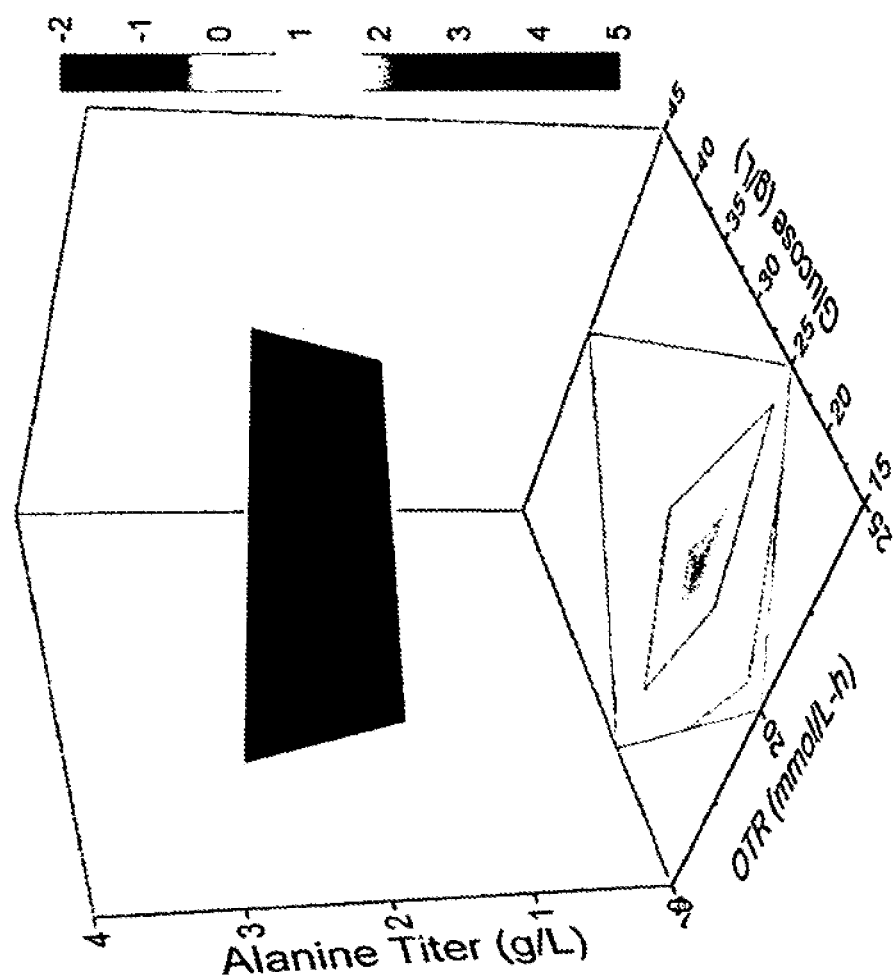

FIGS. 3A-K: Alanine Production in *E. coli* utilizing 2-stage Dynamic Control. FIG. 3A depicts strain variant design. Primary pathways in central metabolism are shown including: Glycolysis, the Pentose Phosphate Pathway, the Citric Acid Cycle (TCA), Fatty Acid Biosynthesis, and the Soluble Transhydrogenase. Key valve candidate enzymes/genes that are "turned OFF" to reduce flux through central metabolism can include: glucose-6-phosphate dehydrogenase (zwf-"Z"), lipoamide dehydrogenase (lpd-"L"), citrate synthase (gltA-"G"), enoyl-ACP reductase (fabI-"F"), and the soluble transhydrogenase (udhA-"U"). Importantly, dynamic elimination of fabI has been previously demonstrated to increase intracellular malonyl-CoA pools as well as malonyl-CoA flux[55]. Enzymes that are dynamically "turned ON" can include the metabolic pathways to produce the products of interest, in this case alanine. Specific pathway enzymes include an NADPH-dependent alanine dehydrogenase (ald*) and an alanine exporter (alaE). Additionally, as the alanine production pathway utilizes NADPH as a cofactor, the NADPH-dependent glyceraldehyde-3-phosphate dehydrogenase encoded by the gapN gene 6 from *S. mutans* was turned on alone and in combination with turning off the native gapA-"A" gene (NADH dependent glyceraldehyde dehydrogenase). Abbreviation: PTS—glucose phosphotransferase transport system, P—phosphate, BP—bisphosphate, OAA—oxaloacetate, DHAP—dihydroxyacetone phosphate, GA3P—glyceraldehyde-3-phosphate, 1,3-BPG—1,3 bisphosphoglycerate, 3-PG—3-phosphoglycerate, 2-PG—2-phosphoglycerate, PEP—phosphoenolpyruvate, MSA—malonate semialdehyde, ACP—acyl carrier protein, Ru—ribulose, Xu—xylulose, E—erthryose, Ri—ribose, S—sedoheptulose. Strains were engineered with SMVs for the dynamic control of all combinations of valve genes/enzymes, either through gene silencing alone, proteolysis alone, or the combination of both. These strains were evaluated for alanine production in standardized micro-fermentations. FIG. 3B depicts rank order plot for average alanine titer (black) of all valve strains examined in 2-stage micro-fermentation, grey area represents standard deviation. Alanine production in the control strain was colored in red. FIG. 3C depicts average alanine titer in 2-stage production in response to different proteolysis and silencing combinations, from 0 g/L (purple) to 5 g/L (red). FIG. 3D depicts average alanine titer in response to different oxygen transfer rates (OTR) and glucose concentrations evaluated for a single "Valve" alanine strain (Silencing of gltA1 ("G1"), Proteolysis of fabI and udhA ("FU")). The results of this surface were used to calculate a strain-specific robustness score (RS) (refer to text), this strain has the highest RS score. FIG. 3E depicts a heat map of the robustness score for a subset of 48 "Valve" strains evaluated across multiple process conditions. FIG. 3F depicts scale up of one of the best producing strain from micro-fermentations (Silencing of fabI-gltA1-gltA2 ("FG1G2"), Proteolysis of fabI, gltA and udhA ("FGU")) to 1 L bioreactors results in a titer of 80 g/L after 48 hrs of production, with a yield of 0.8 g/g. FIG. 3G depicts overexpression of the alaE alanine exporter in this strain (Panel f) results in significantly improved production, reaching 147 g/L in 27 hrs of production, with a yield of ~1 g/g. (Refer to Supplemental Materials, Section 3 for additional details). FIG. 3H depicts strains selected for robustness evaluation in micro-fermentations. FIG. 3I depicts robustness and titer for the most robust "Valve" alanine strain (Silencing_gltA1, Proteolysis_FU). Bottom surface shows heat map for the alanine titer normalized to the median of all process conditions assessed, upper surface shows alanine tiler under all process conditions, the same color scale (alanine titer in g/L) was used for both panels. FIG. 3J depicts RS3 scores for the selected strains. FIG. 3K depicts process reproducibility heat map for all conditions evaluated, the same grayscale was used for FIG. 3J and FIG. 3K.

Figure 4C:
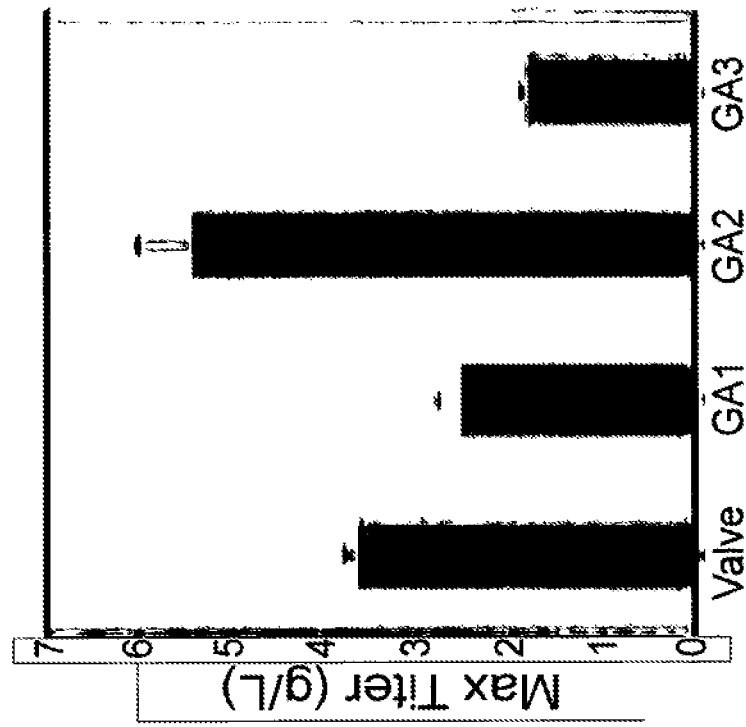
Figure 4B:
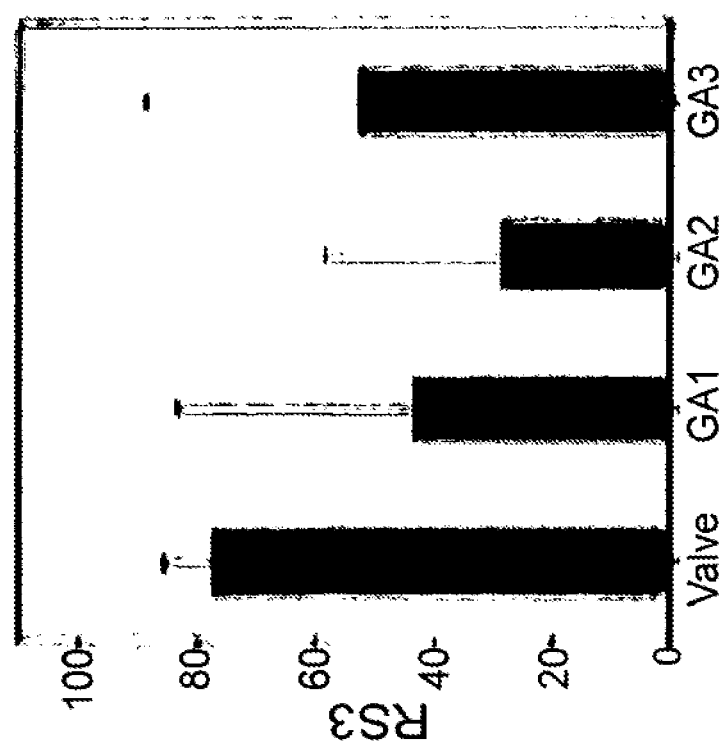
Figure 4D:
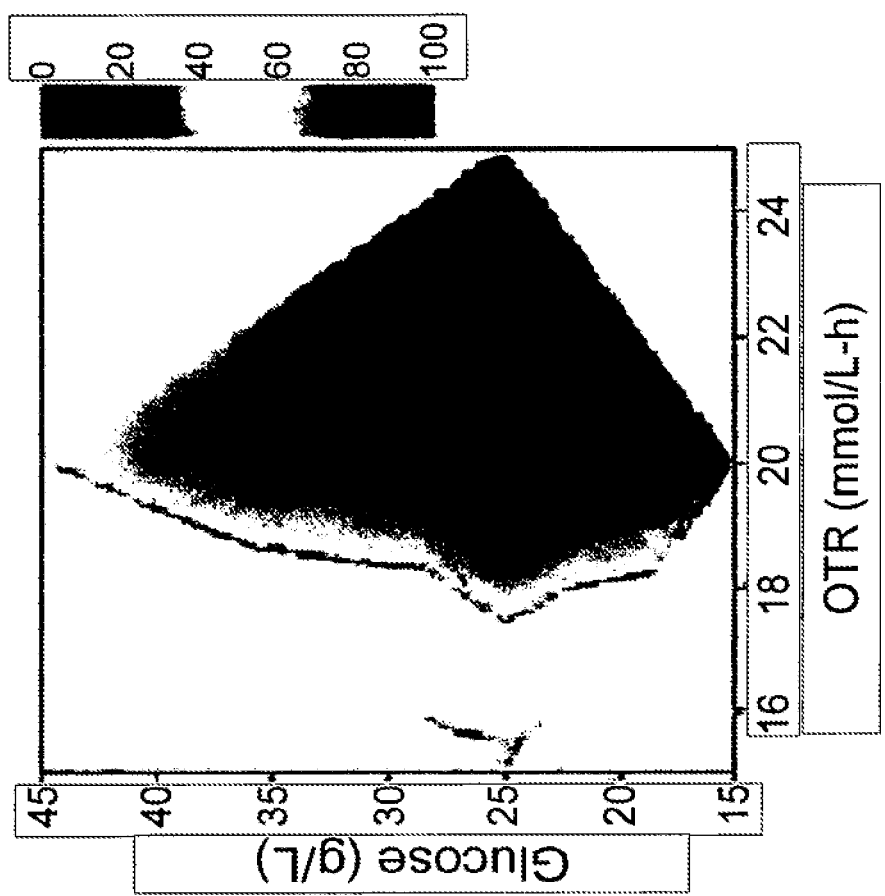
Figure 4E:
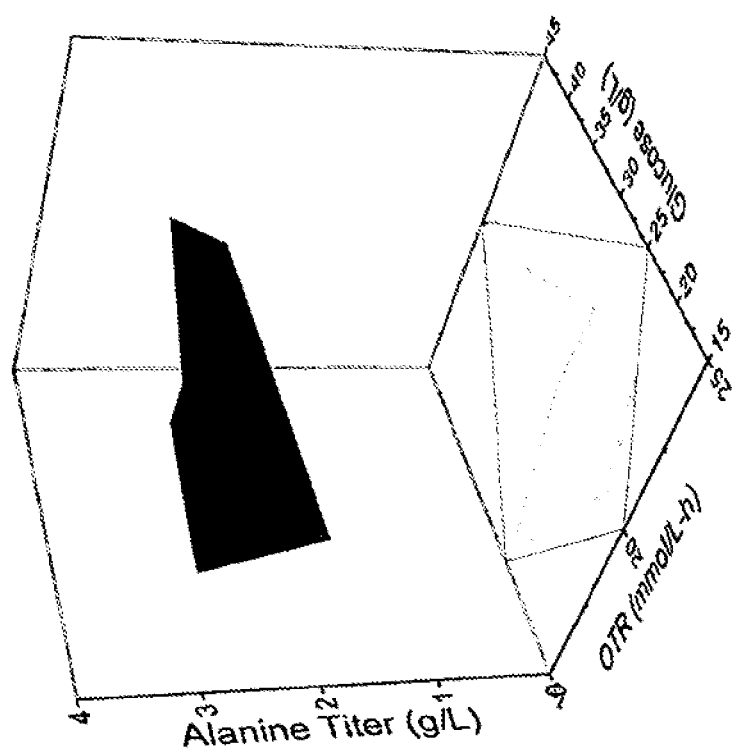
Figure 4F:
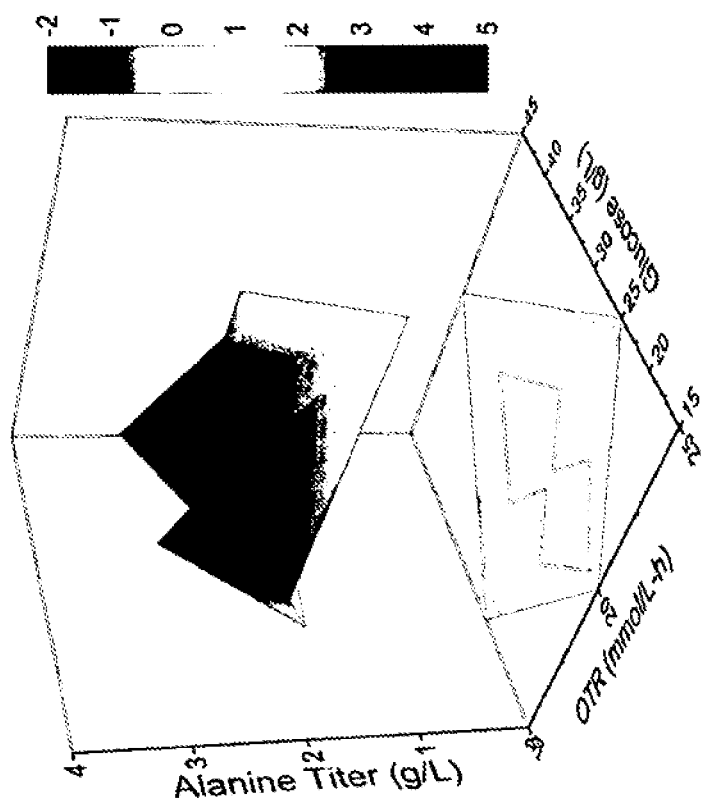

FIGS. 4A-F: Robustness Comparison Between 2-Stage and Growth Associated Approaches. FIG. 4A depicts rank order of the RS3 scores for all alanine strains evaluated, red bars indicate valve alanine strains, and blue bars indicate growth associated (GA) alanine strains. FIG. 4B depicts average RS3 score for "Valve" alanine strains with proteolysis "F" valve, and growth associated alanine strains. FIG. 4C depicts max titer plot for a representative "Valve" alanine (Proteolysis_FGU, Silencing_gltA1), and growth associated alanine strains in micro-fermentation of all conditions evaluated. FIG. 4D depicts process reproducibility for growth associated alanine strains under all conditions evaluated. FIG. 4E depicts robustness and titer for a representative robust "Valve" alanine (Proteolysis_FGU, Silencing_gltA1). FIG. 4F depicts robustness and titer for the GA2 strain. Bottom surface, heat map for the alanine titer normalized to the median of all process conditions assessed, upper surface, alanine titer under all process conditions, the same color scale (alanine titer in g/L) was used for both panels.

Figure 5A:
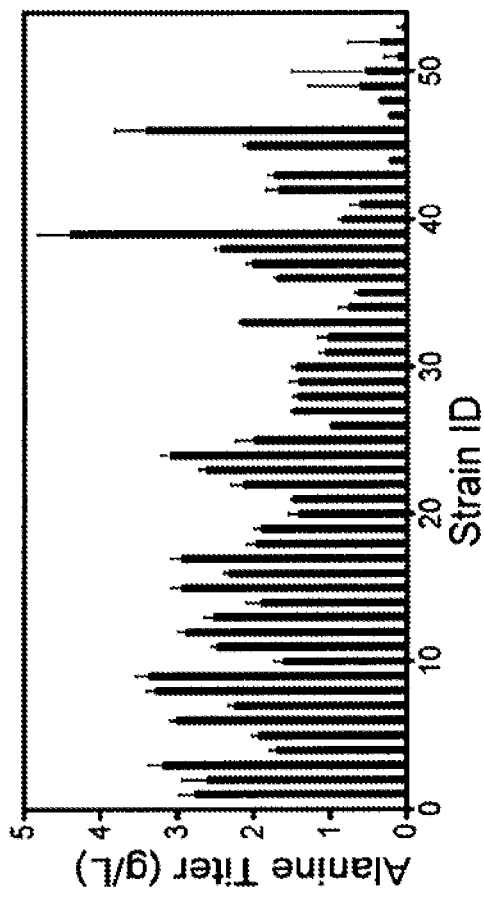
FIGS. 5A-J depict example comparisons of "Valve" and growth associated alanine production in micro-fermentations and 1 L fermentation.
Figure 5B:
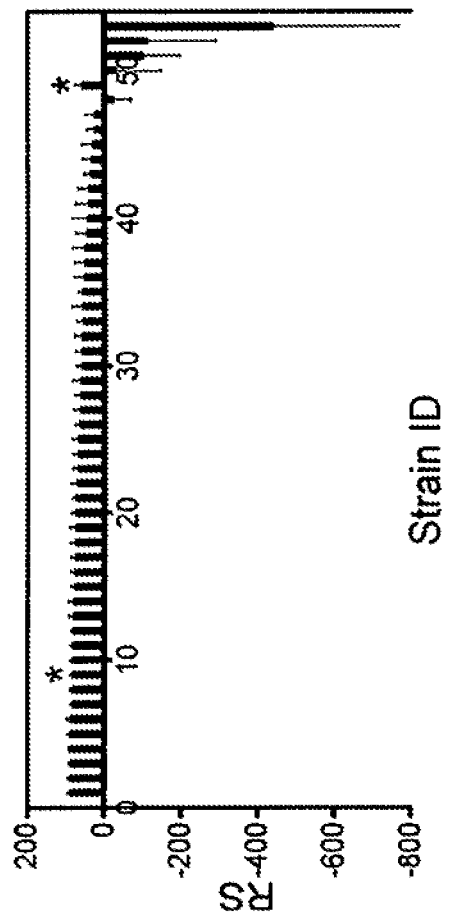
Figure 5C:
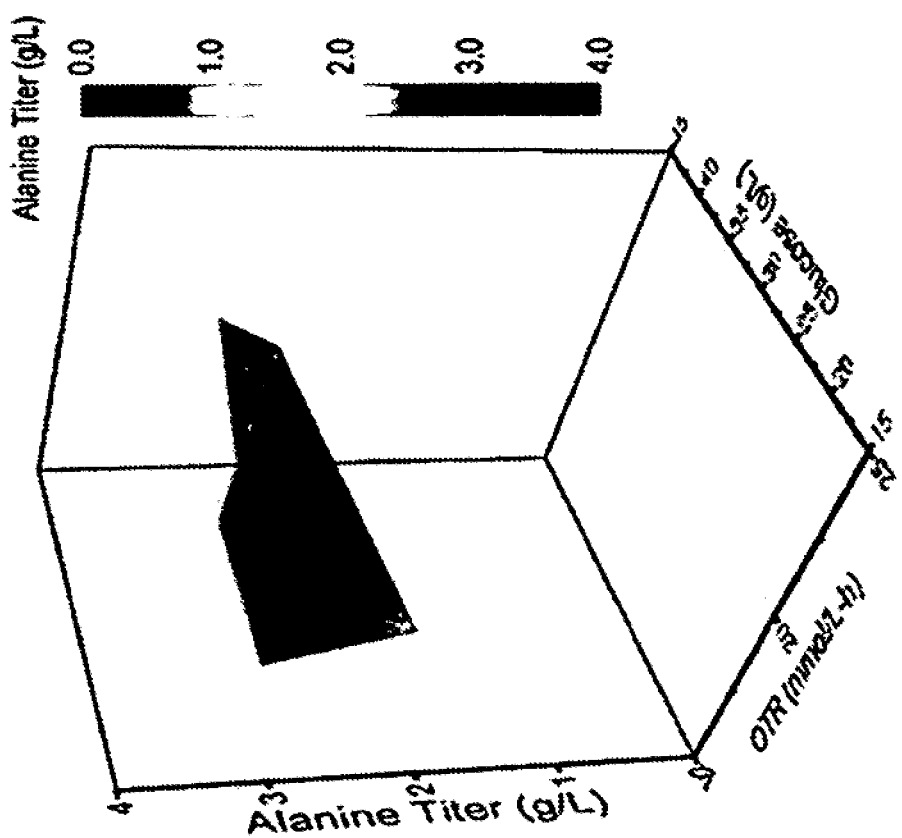
Figure 5D:
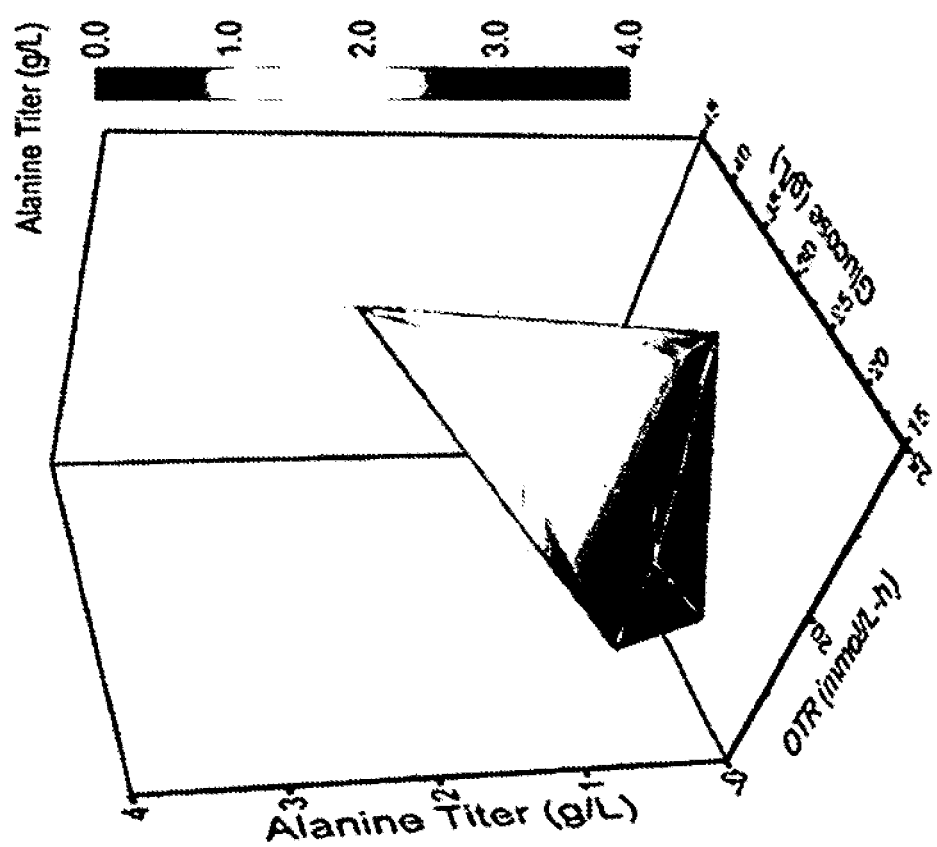
Figure 5E:
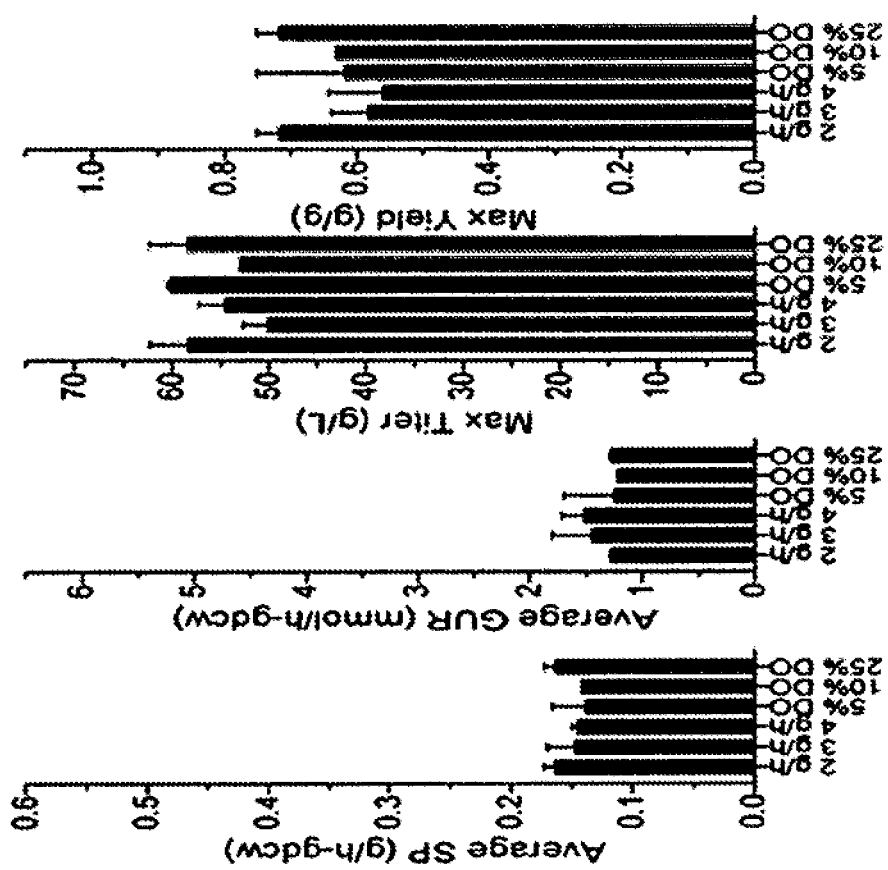
Figure 5F:
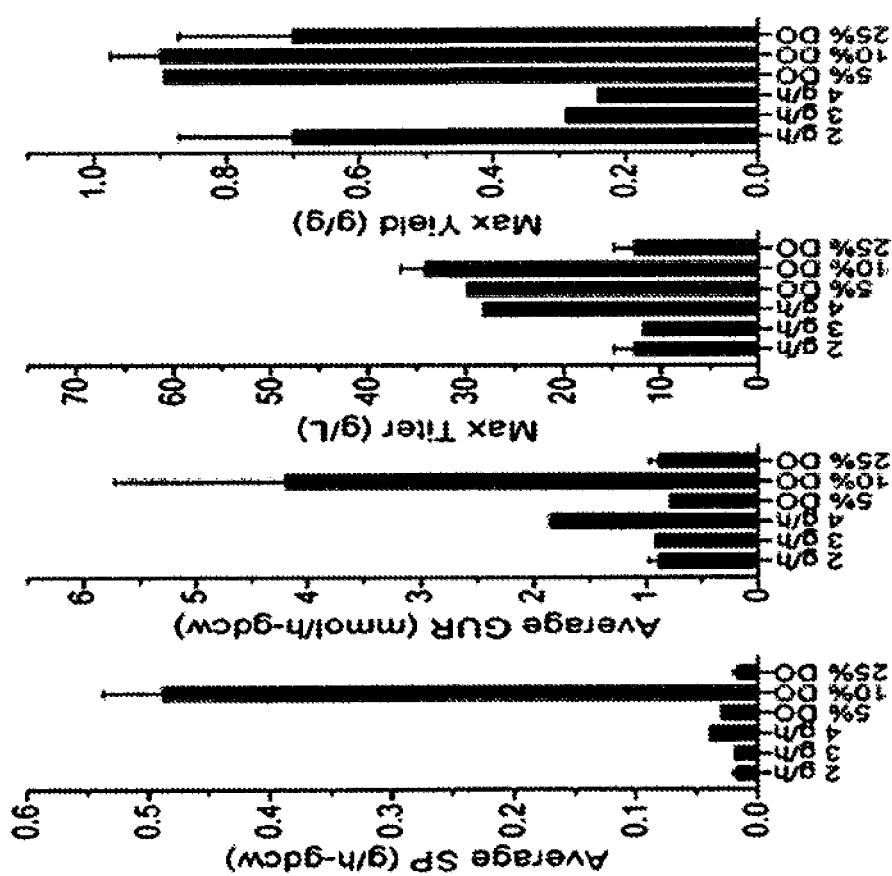
Figure 5G:
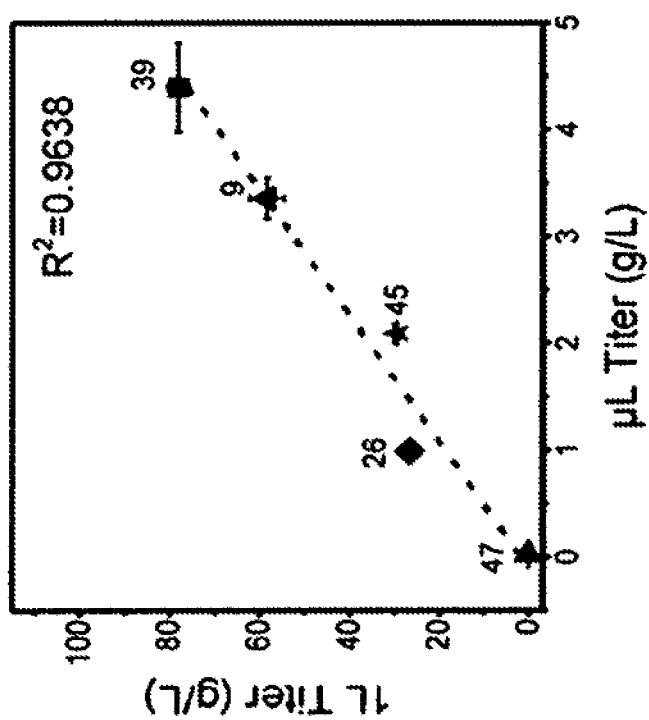
Figure 5H:
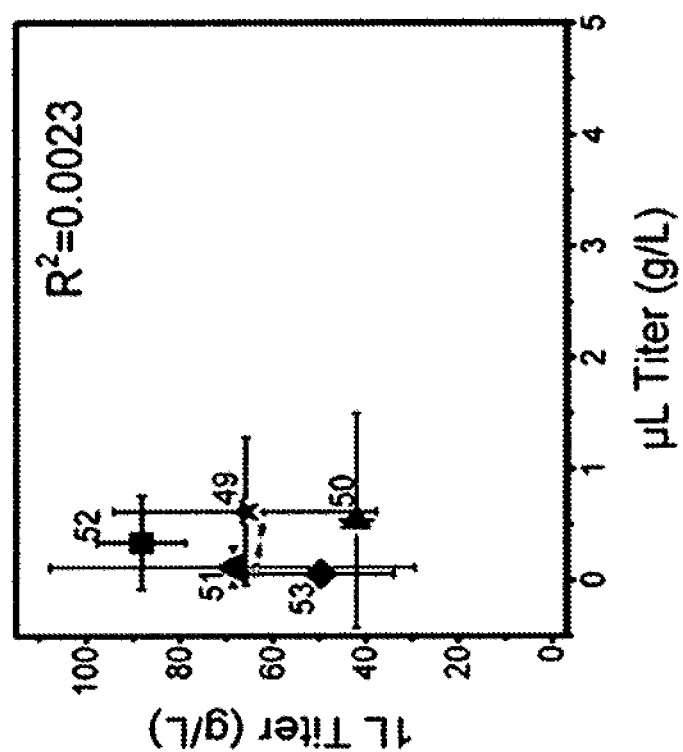
Figure 5I:
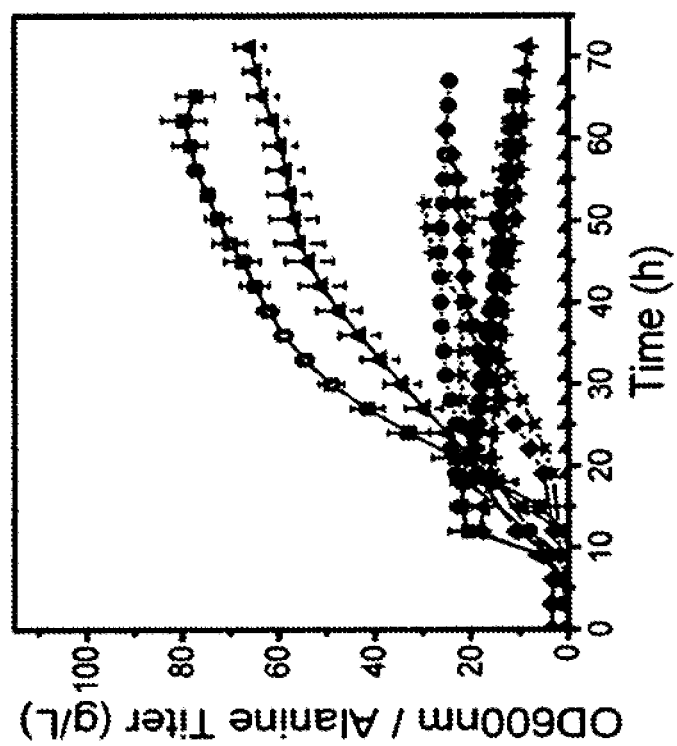
Figure 5J:
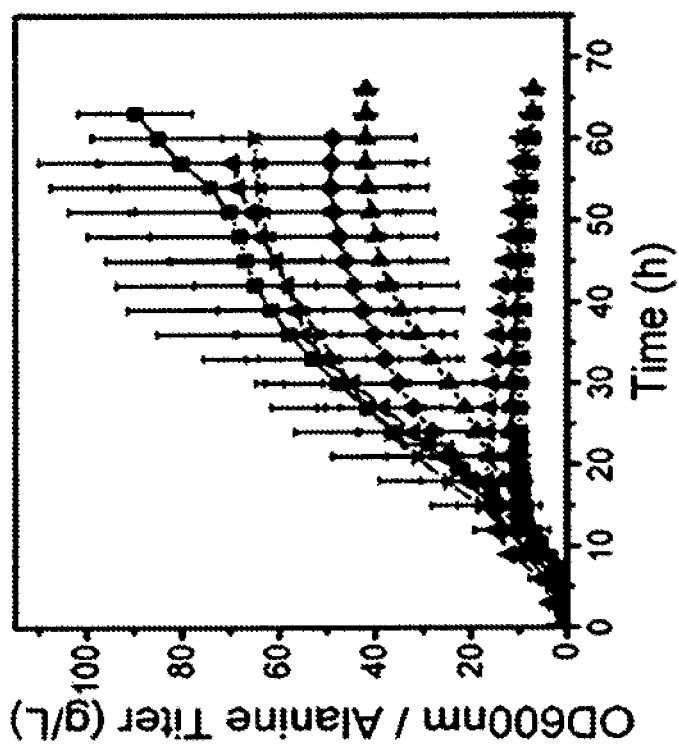

FIGS. 5A-J: Comparisons of "Valve" and growth associated alanine production in micro-fermentations (FIGS. 5A-D) and 1 L fermentation (FIGS. 5E-J). Average alanine titer (FIG. 5A) and robustness score (FIG. 5B) for all strains used for robustness analysis. Average alanine titer in response to different OTR and glucose concentrations for selected "Valve" (FIG. 5C) and growth associated (FIG. 5D) alanine strains. Strains marked by asterisk in (FIG. 5B) were used for this analysis. These two strains were selected for 1 L performance comparison. FIG. 5E and FIG. 5F depicts 1 L performance metrics evaluated, including average specific productivity (SP, g/gdcw-h), average glucose uptake rate (GUR, g/gcdw-h), max titer (g/L), and max yield (g/g). FIG. 5G and FIG. 5H depicts µL to 1 L scalability. 1 L data was standardized to the maximal titer within 50 hours of production. Adequate feed was used for growth associated strains to avoid glucose depletion. FIG. 5I and FIG. 5J depicts 1 L production profiles for all strains used in scalability plot FIG. 5G and FIG. 5H respectively, darker symbols represent growth curves, lighter symbols represent production curves, shape of symbols encode the same strains in FIG. 5G or FIG. 5H.

Figure 6D:
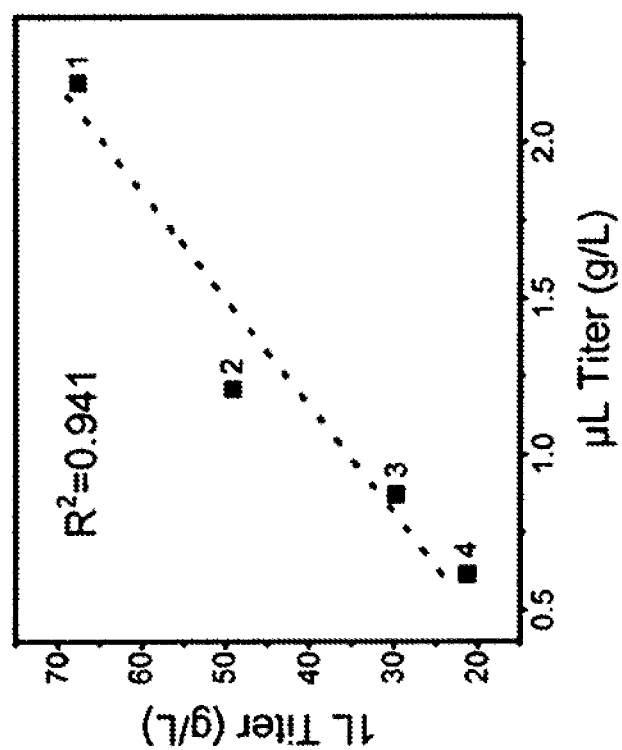
Figure 6E:
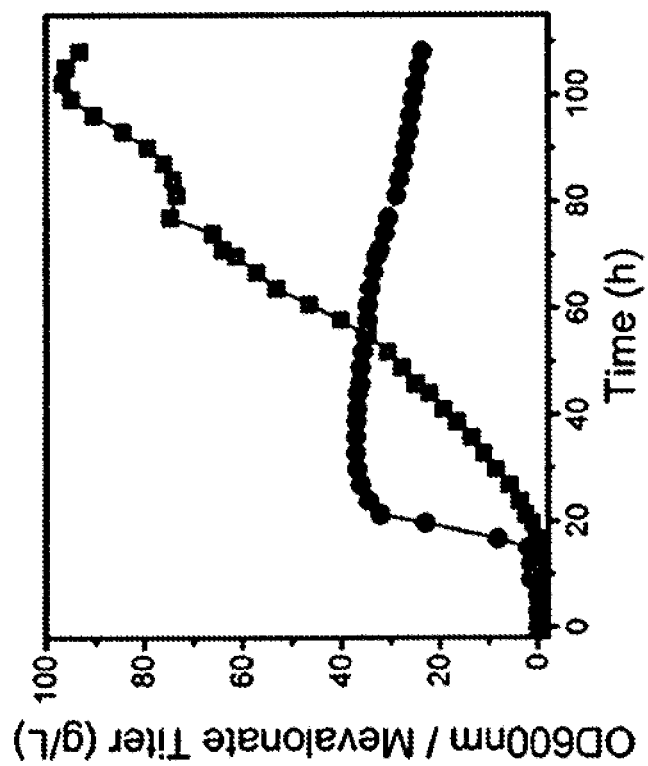
Figure 6F:
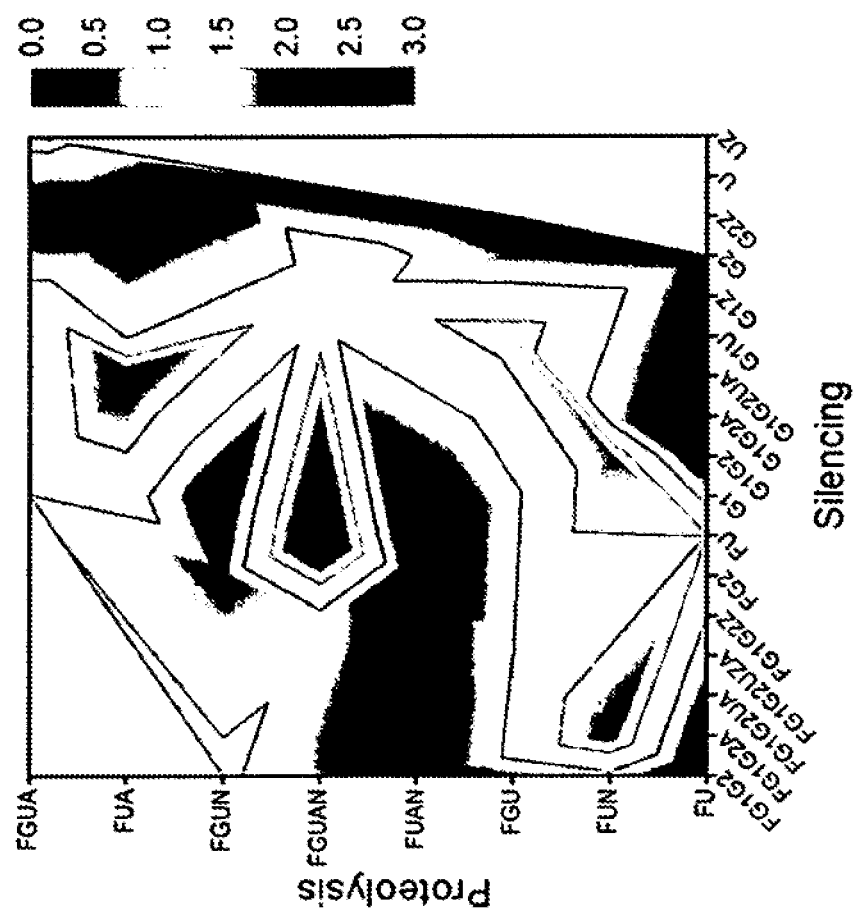
Figure 6G:
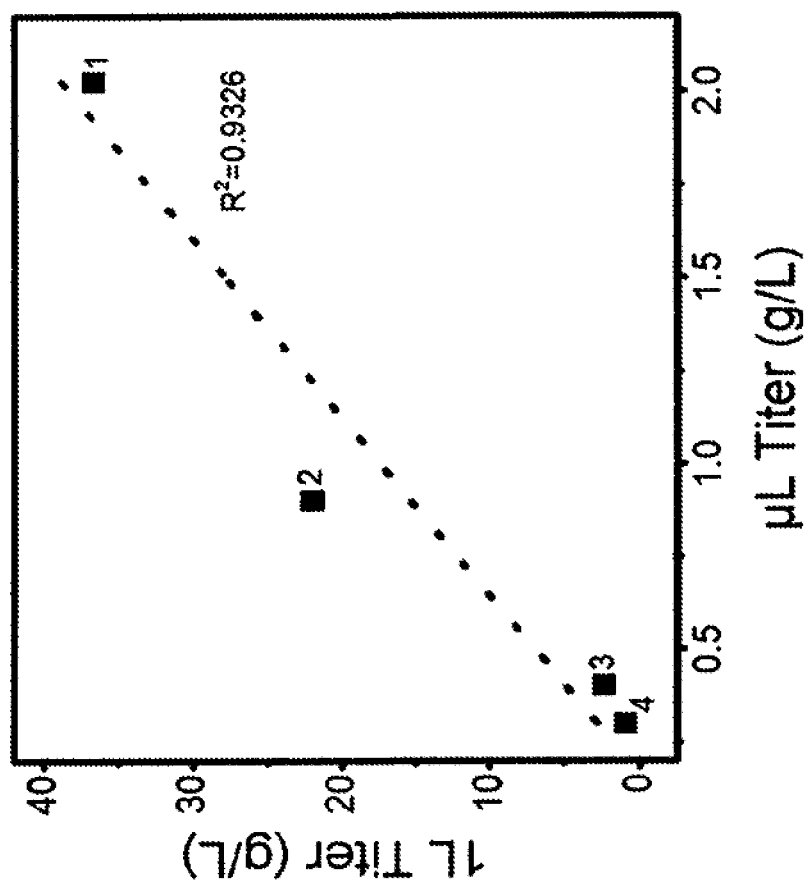
Figure 6H:
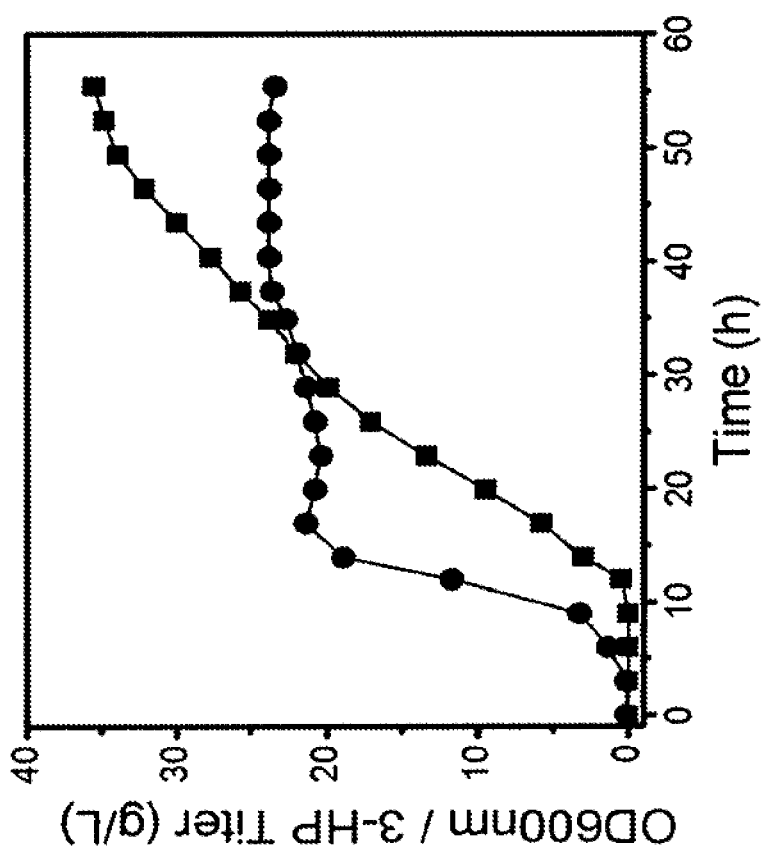

FIG. 6A-E: Mevalonate Production in *E. coli* utilizing 2-stage Dynamic Control. FIG. 6A depicts Metabolic Pathways and SMVs for mevalonate production. FIG. 6B depicts mevalonate production using several production pathway plasmid variants with varied promoter combinations in the control strain. FIG. 6C depicts micro-fermentation results for a subset of "Valve" strains producing mevalonate, using the best production pathway from FIG. 6B, along with combinations of proteolytic and silencing SMVs. FIG. 6D depicts µL to 1 L scalability for a subset of mevalonate strains evaluated at the 1 L scale. n=3 for µL data and n=1 for 1 L data. The maximal titer within 50 hours of production time was used for the correlation. FIG. 6E depicts production of the best mevalonate strain from FIG. 6D (Silencing of fabI-gltA1-gltA2 ("FG1G2"), Proteolysis of fabI and udhA ("FU")) in 1 L bioreactors. A titer of 97 g/L was observed in 78 hrs of production. Yields during the production stage reached 0.46 g/g (84% of theoretical yield). (Refer to Supplemental Materials, Section 9 for additional details). FIG. 6F depicts micro-fermentation results for a subset of strains producing 3-HP. FIG. 6G depicts μL to 1 L scalability for a subset of 3-HP strains evaluated at the 1 L scale (Supplemental Materials Tables S21 and S22). FIG. 6H depicts production performance for the best 3-HP strains in the 1 L systems, squares, 3-HP/mevalonic acid titer; circles, OD600. Yields during the production stage reached for the 0.46 g/g for mevalonic acid and 0.63 g/g for 3-HP in the highest producers.

FIG. 7: Phosphate depletion promoter characterization. A set of GFP reporter vectors were constructed to assess the expression level of 12 previously identified phosphate regulated promoters. Strains were evaluated continuously for GFP expression in the Biolector™ using a standardized protocol wherein in minimal medium limited for phosphate is used. After Biomass levels reach a peak (not shown for clarity), GFP expression begins. Importantly the current set of promoters enables a large range of expression levels.

FIG. 8: Insulated phosphate depletion promoter characterization. A set of GFP reporter vectors were constructed to assess the expression level of five insulated phosphate regulated promoters in FGM3 media. Strains were evaluated continuously for GFP expression in the Biolector™ using a standardized protocol wherein in minimal medium limited for phosphate is used. After Biomass levels reach a peak (not shown for clarity), GFP expression begins. Importantly the current set of promoters enables a large range of expression levels.

FIG. 9: Insulated constitutive promoter characterization. A set of GFP reporter vectors were constructed to assess the expression level of five insulated constitutive promoters in FGM3 with 40 mM phosphate media. Shaded area represents standard deviations, n=3. Strains were evaluated continuously for GFP expression in the Biolector™ GFP expression was observed only for promoters proA, proB and proD.

Figure 10:
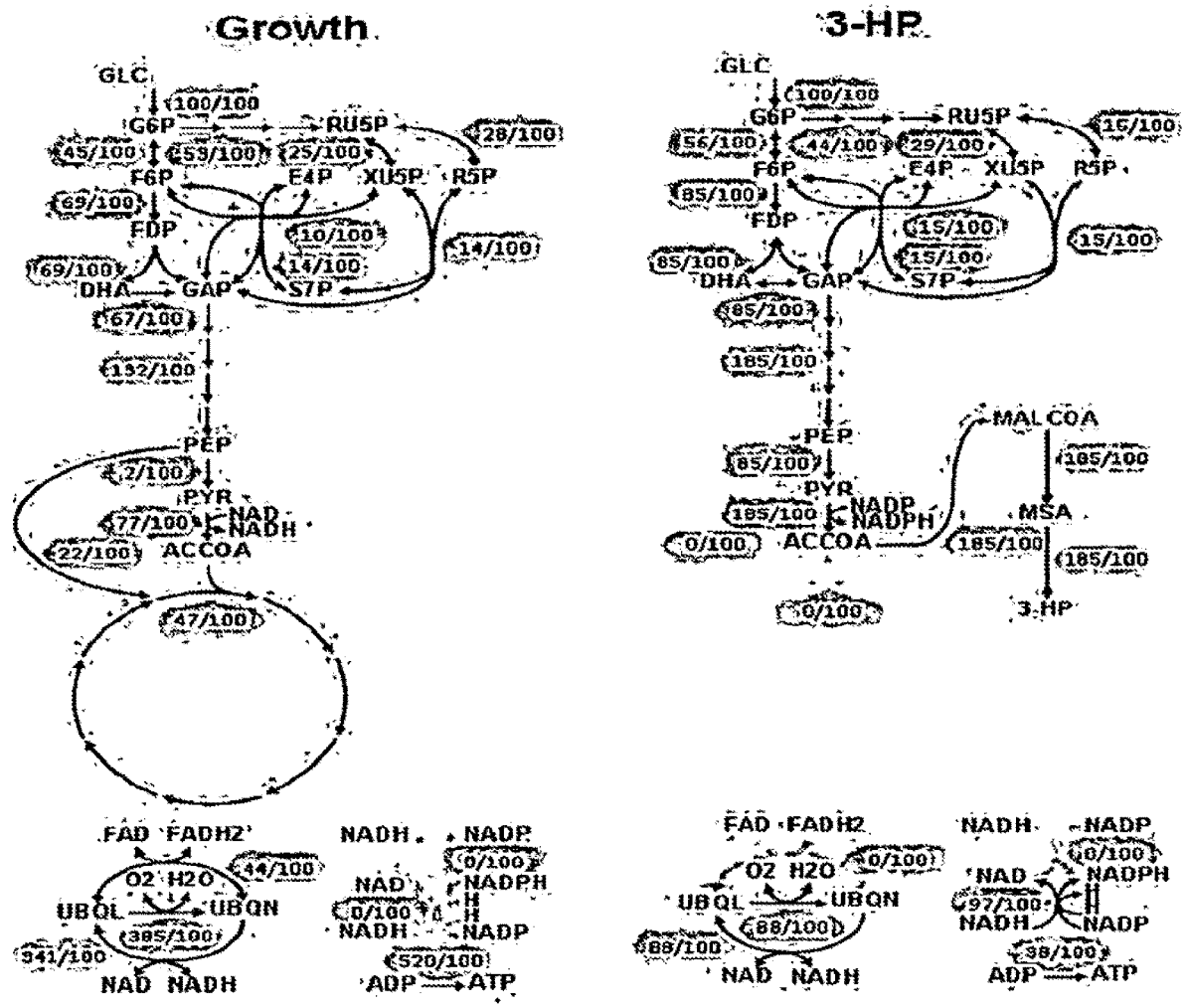
FIG. 10 depicts an example of metabolic modeling results for optimal 3-HP flux in two stage fermentations.

FIG. 10: Metabolic modeling results for optimal 3-HP flux in two stage fermentations. LEFT: Optimized fluxes during the growth stage where biomass production was used as the objective function. RIGHT: Optimized fluxes during the 3-HP production stage where 3-HP production was used as the objective function (biomass production was set to 0). Fluxes are listed as relative ratios or moles of flux through a given reaction per 100 moles of glucose utilized.

FIG. 11: Chromosomal modifications.

Figure 12:
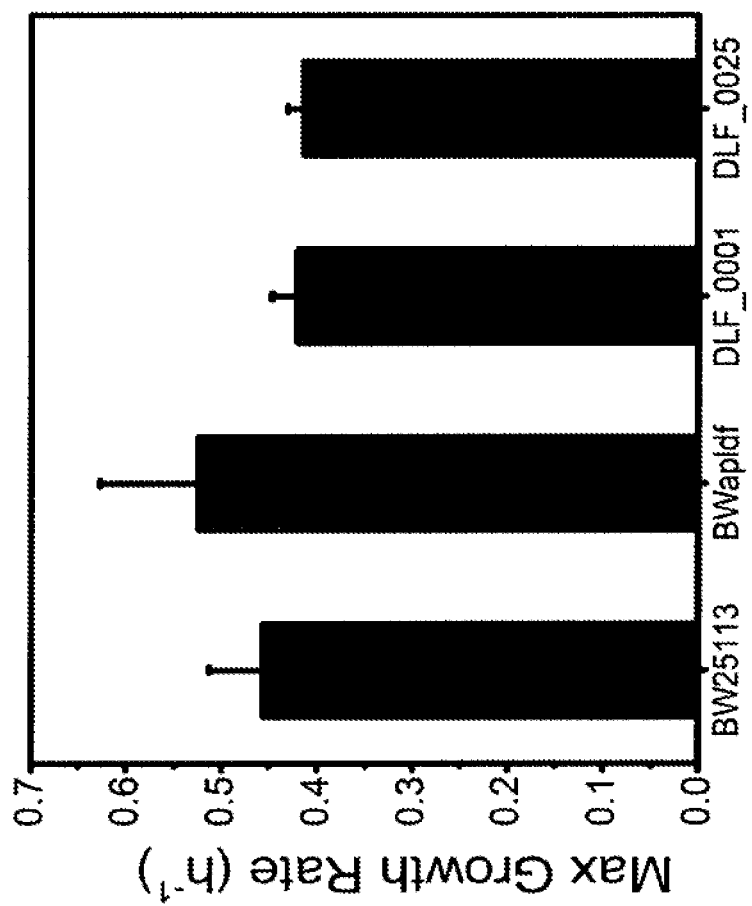
FIG. 12 depicts an example of average maximal growth rates of starting host strains in 1 L FGM10 minimal medium fermentations, n=2.

FIG. 12: Average maximal growth rates of starting host strains in 1 L FGM10 minimal medium fermentations, n=2.

Figure 13B:
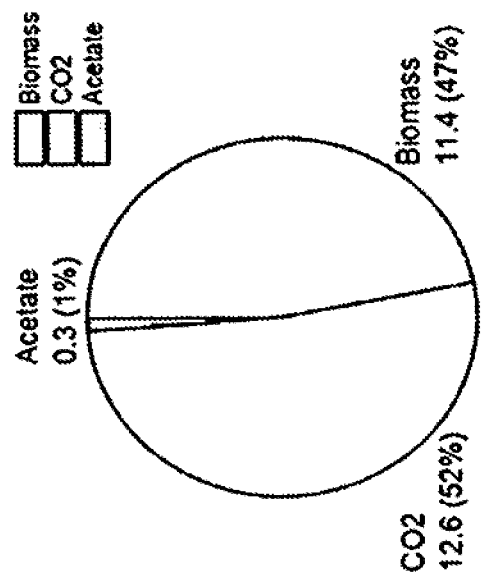
FIG. 13A-E depict examples of distribution of glucose utilized during the growth phase of starting host strains in 1 L standard minimal medium fermentations.
Figure 13A:
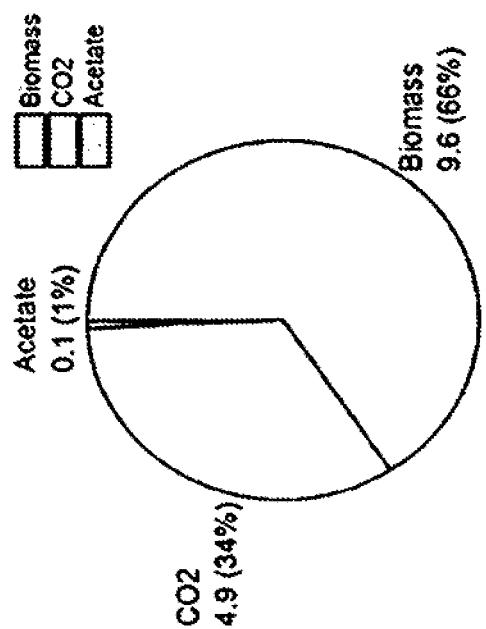
Figure 13C:
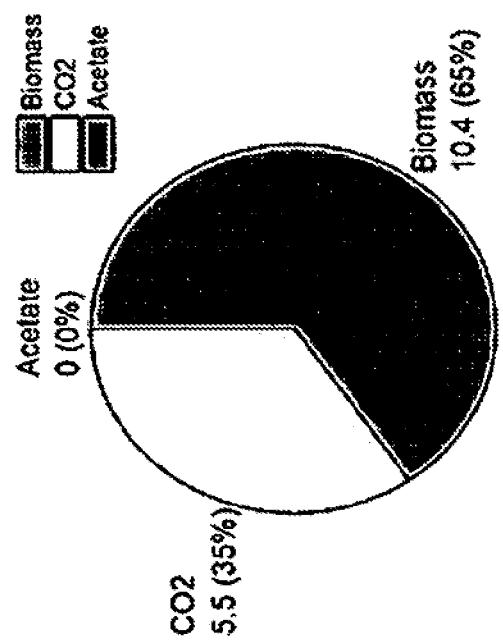
Figure 13D:
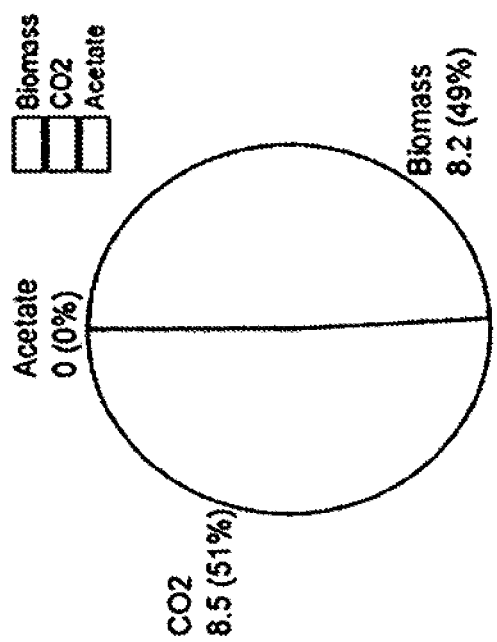
Figure 13E:
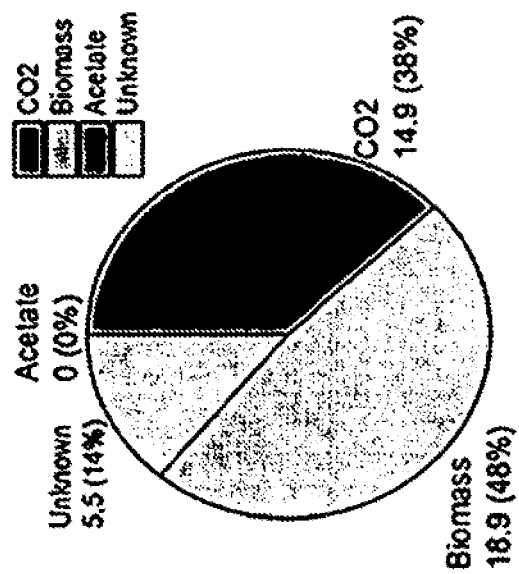

FIG. 13A-E: Distribution of glucose utilized during the growth phase of starting host strains in 1 L standard minimal medium fermentations. Mid exponential and final growth period results are given for DLF_0025 as "production" begins in mid-late exponential phase. Results are averages of duplicate fermentations. FIG. 13A, BW25113; FIG. 13B, BWapldf; FIG. 13C, DLF_0001; FIG. 13D, DLF_0025 at mid-exponential; FIG. 13E, DLF_0025 at end of growth phase. Unit was gram glucose.

Figure 14:
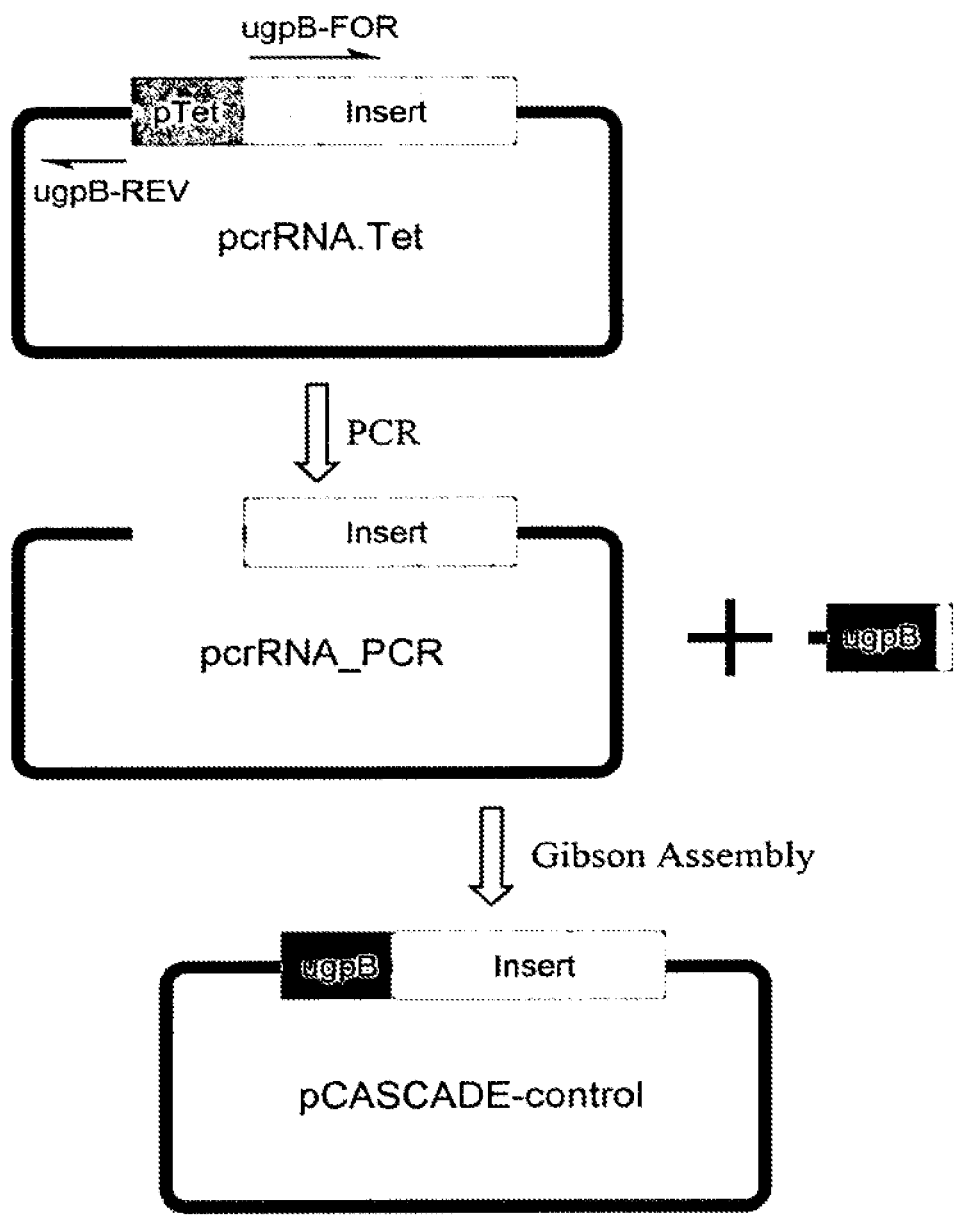
FIG. 14 depicts pCASCADE-control plasmid construction scheme.
Figure 15A:
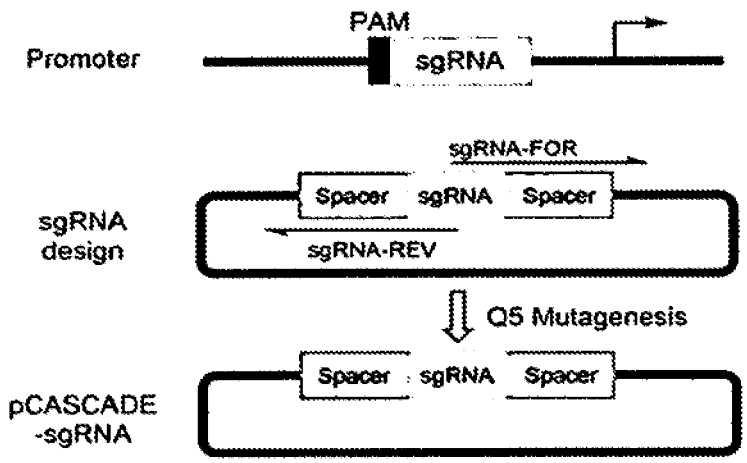
FIGS. 15A-B depict pCASCADE construction scheme.
Figure 15B:
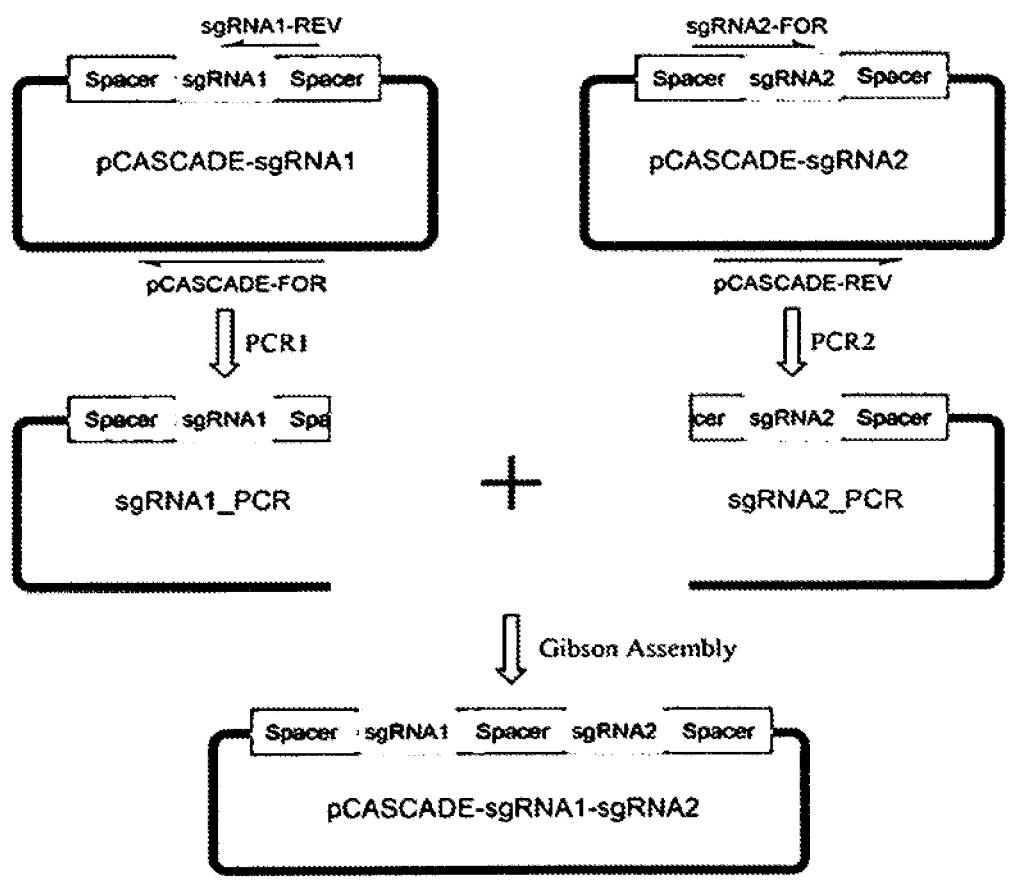

FIG. 14: pCASCADE-control plasmid construction scheme.

FIG. 15A-B: pCASCADE construction scheme. FIG. 15A, single sgRNA cloning;

FIG. 15B, double sgRNA.

FIG. 16A-C: Micro-fermentation process overview. (A) An overview of the high throughput micro-fermentation protocol. Freezer stocks (alternatively colonies may be used) are used to inoculate into SM10++ in 96 well plates. Cultures are grown overnight for 16 hours, harvested by centrifugation, washed with no-phosphate medium and resuspended in no-phosphate medium at target biomass levels. (OD600 nm=1.0). EnzyScreen™ covers and clamps are used to reduce evaporation and enable high oxygen transfer rates. The protocol is implemented with a Tecan Evo liquid handler. (B) Representative overnight growth in a 96 well plates culture, distribution of OD600 for overnight culture was plotted. (C) Representative OD600 distribution after normalization using Tecan Evo liquid handler.

FIG. 17: Micro-fermentation for L-alanine production using different insulated phosphate promoters in DLF_0025 strain.

Figure 18:
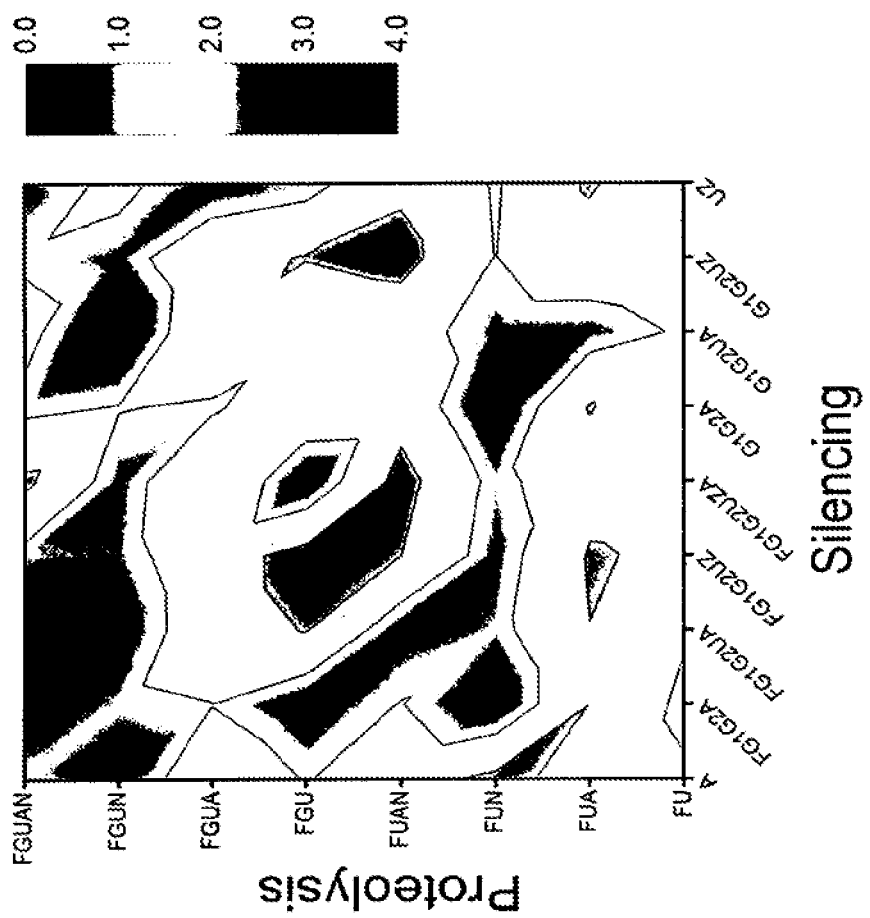
FIG. 18 depicts Heatmap for L-alanine production by gapN/gapA strains.
Figure 19A:
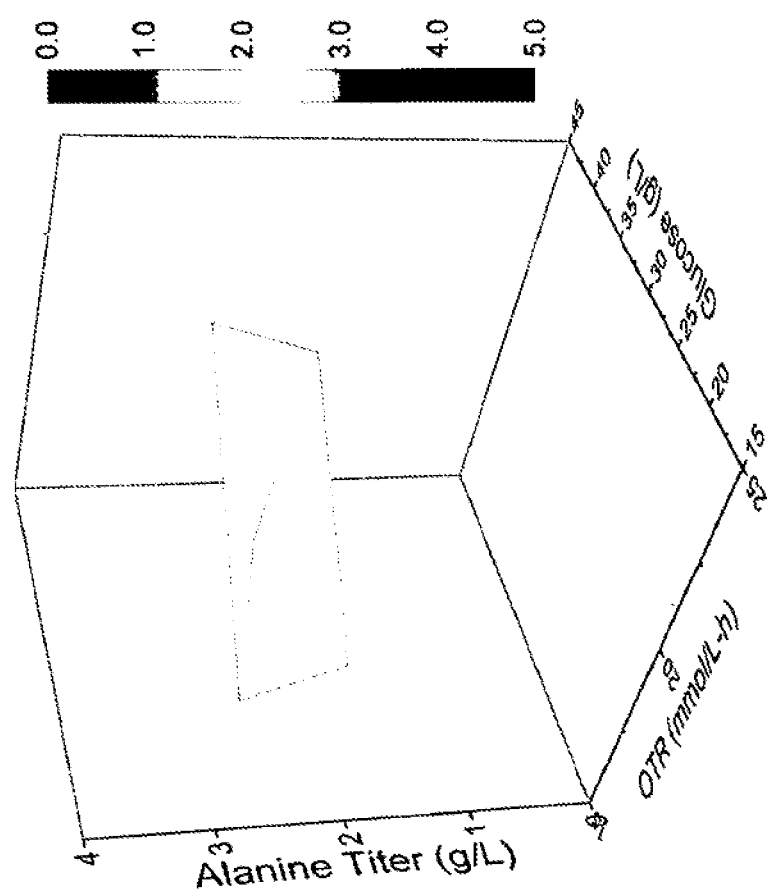
FIGS. 19A-D depict alanine production in response to different OTR and glucose concentration in micro-fermentation for 4 strains evaluated for robustness.
Figure 19B:
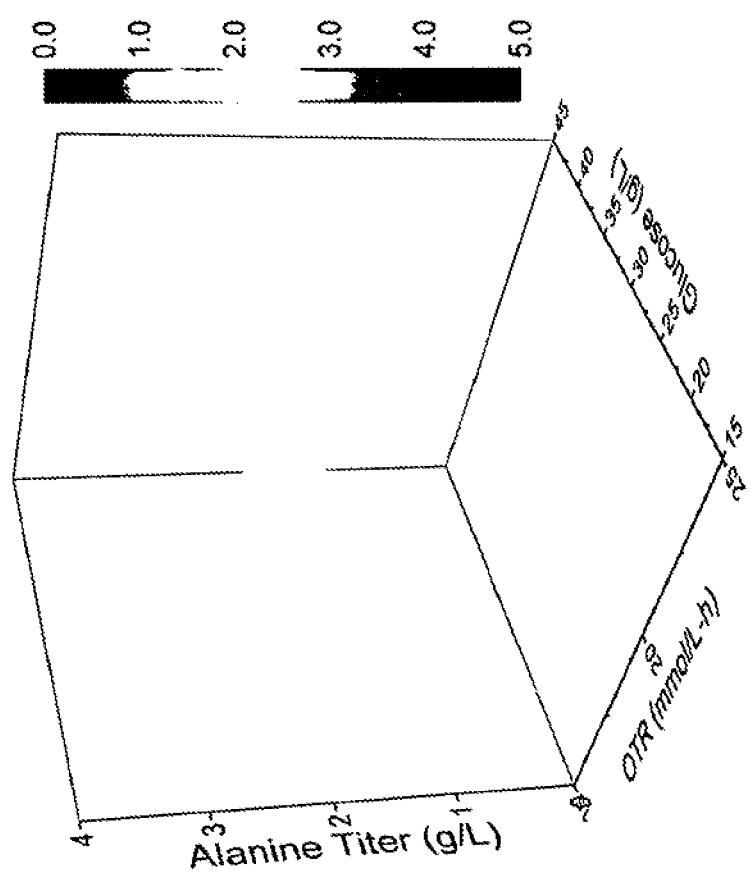
Figure 19C:
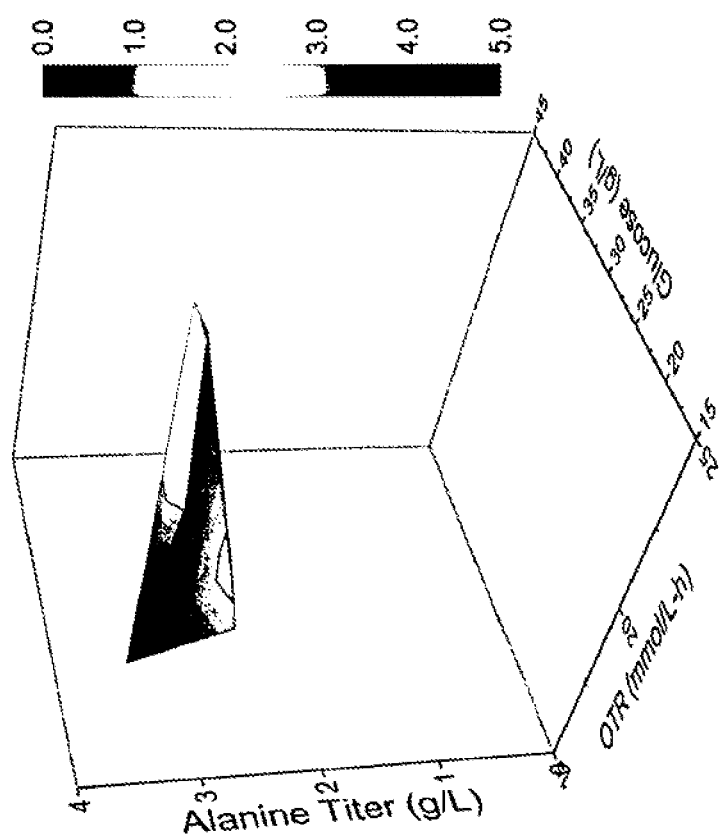
Figure 19D:
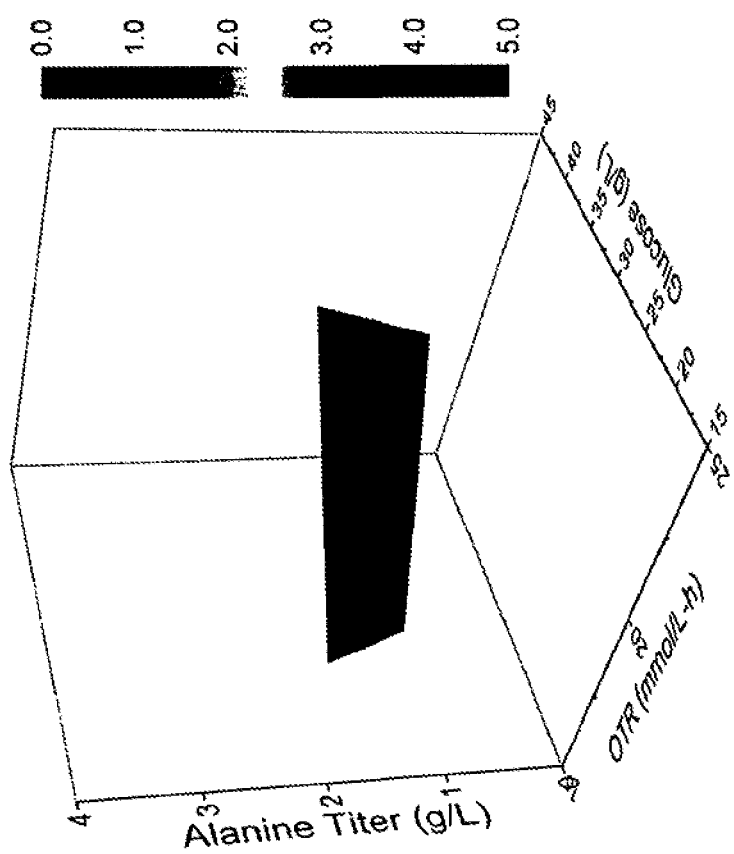
Figure 20A:
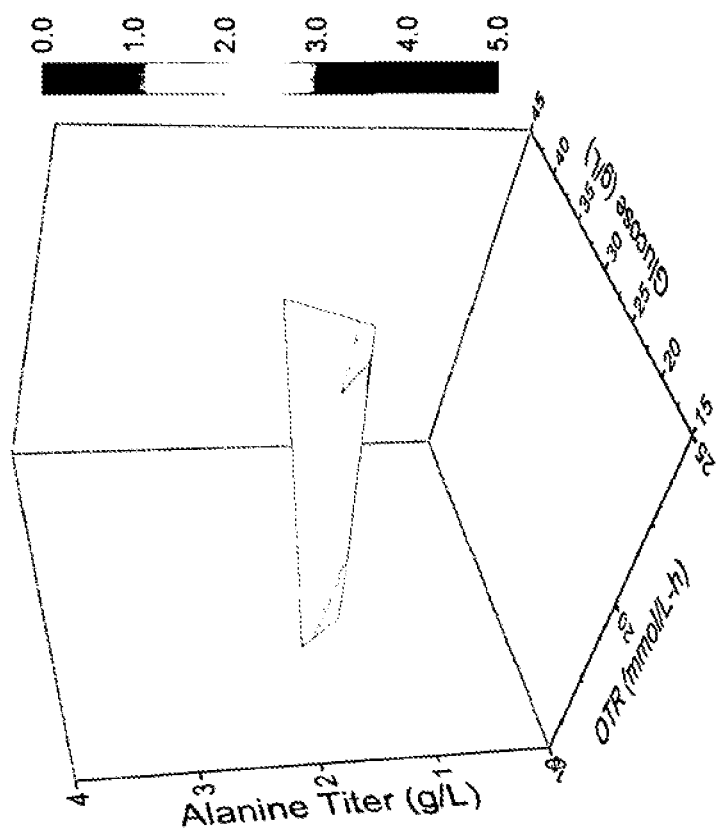
FIGS. 20A-D depict alanine production in response to different OTR and glucose concentration in micro-fermentation for 4 strains evaluated for robustness.
Figure 20B:
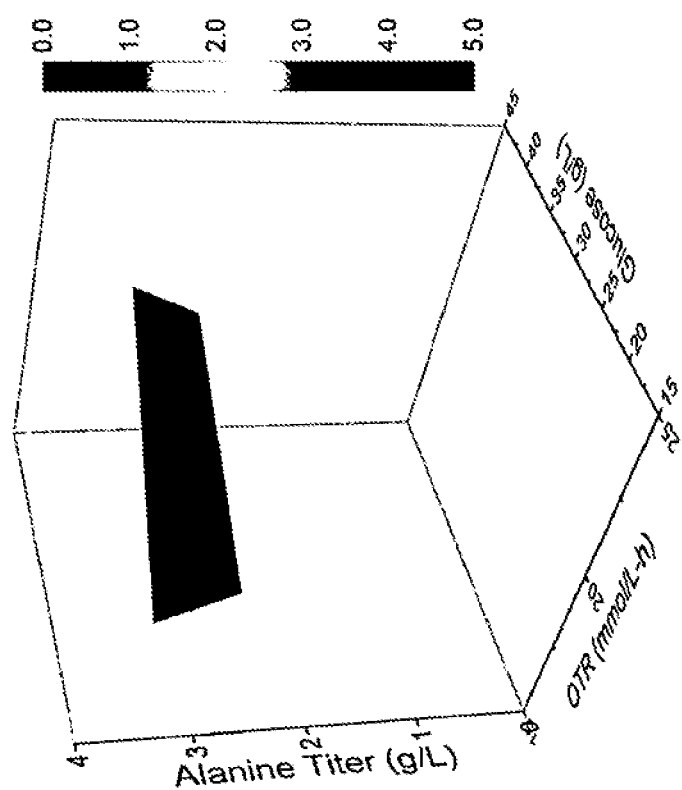
Figure 20C:
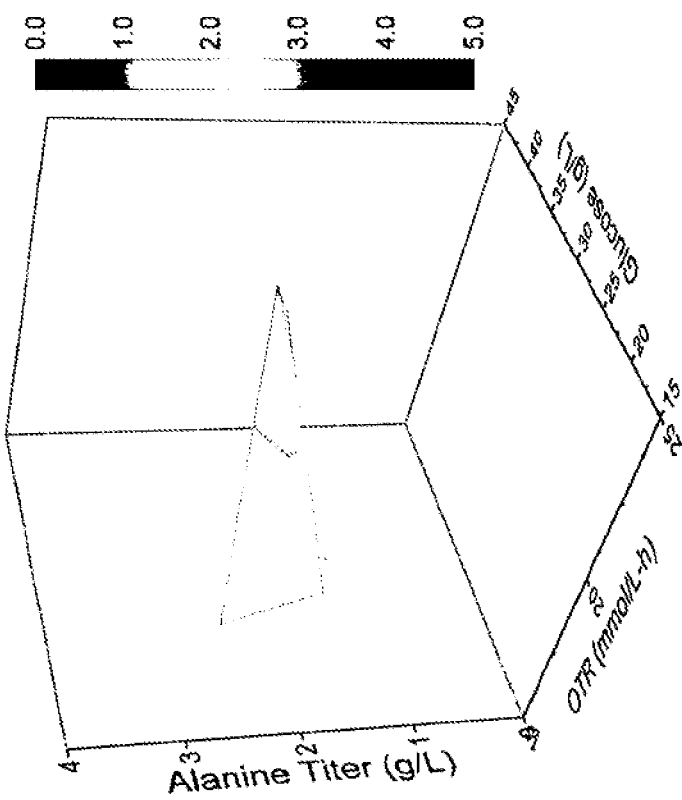
Figure 20D:
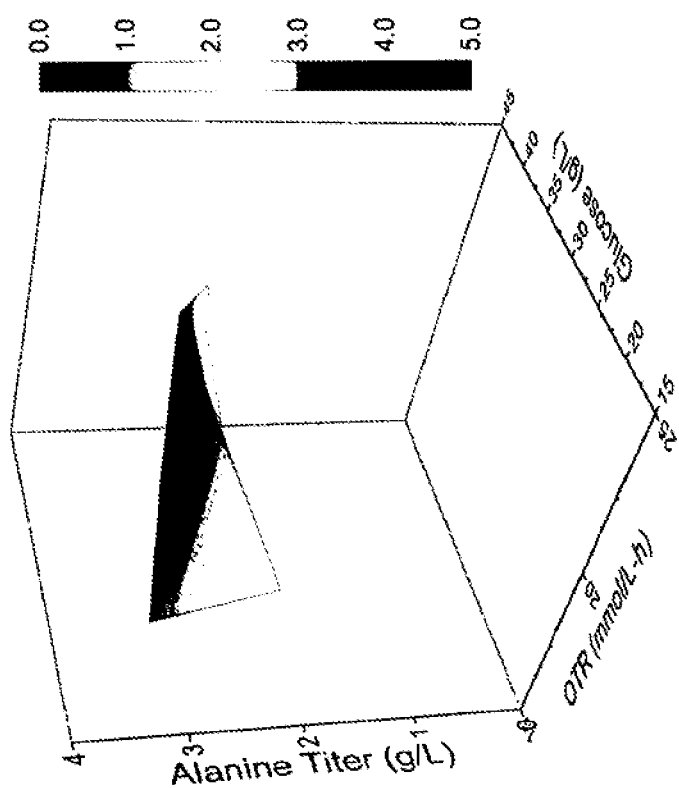
Figure 21A:
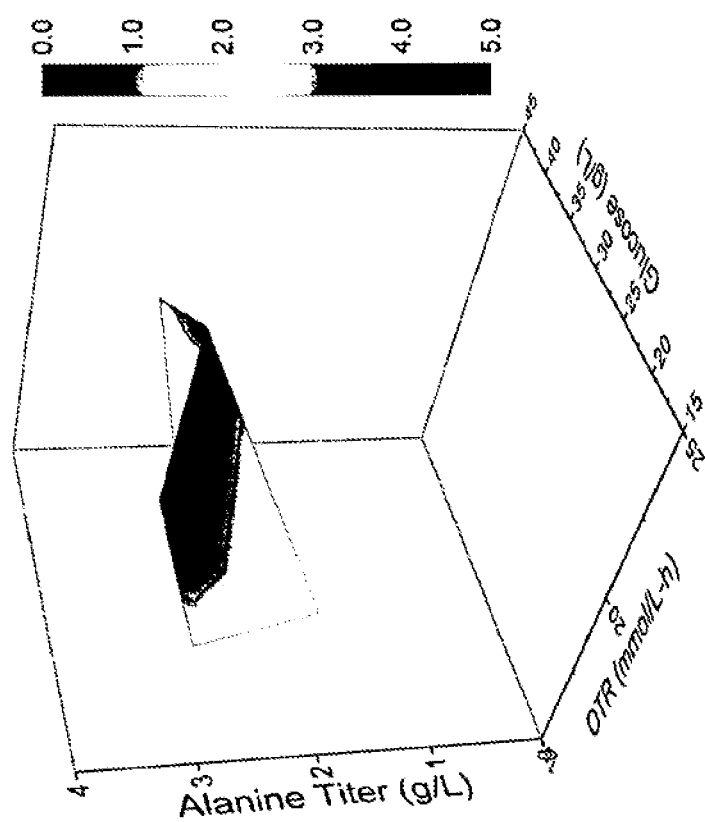
FIGS. 21A-D depict alanine production in response to different OTR and glucose concentration in micro-fermentation for 4 strains evaluated for robustness.
Figure 21B:
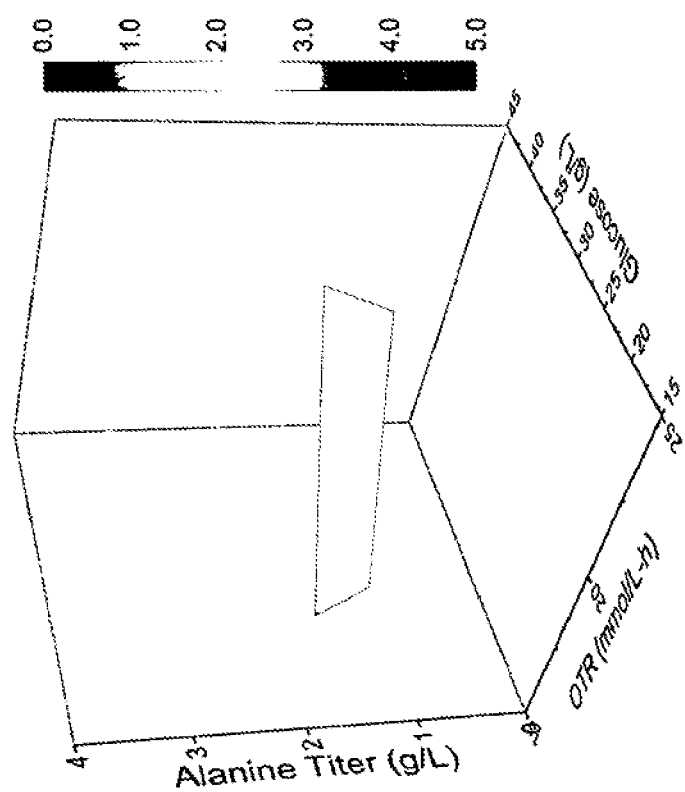
Figure 21C:
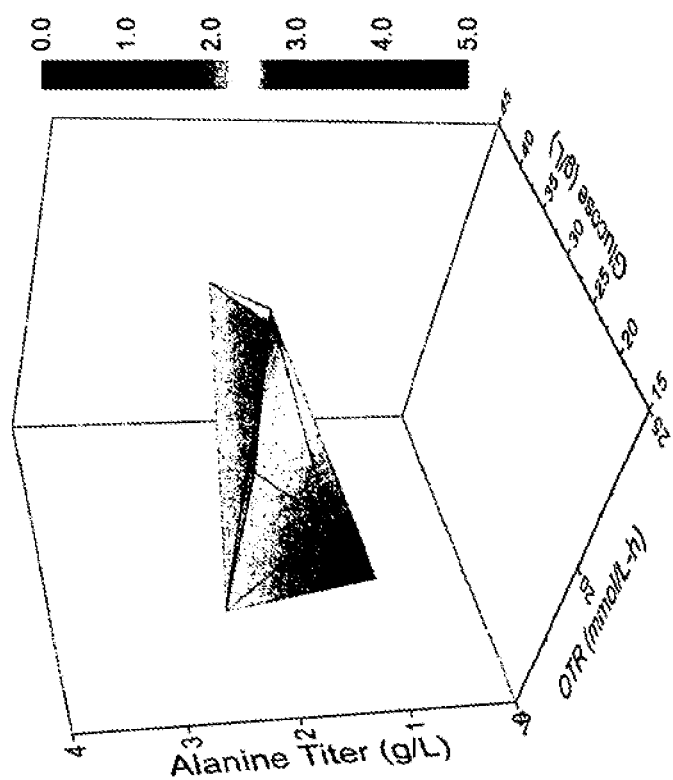
Figure 21D:
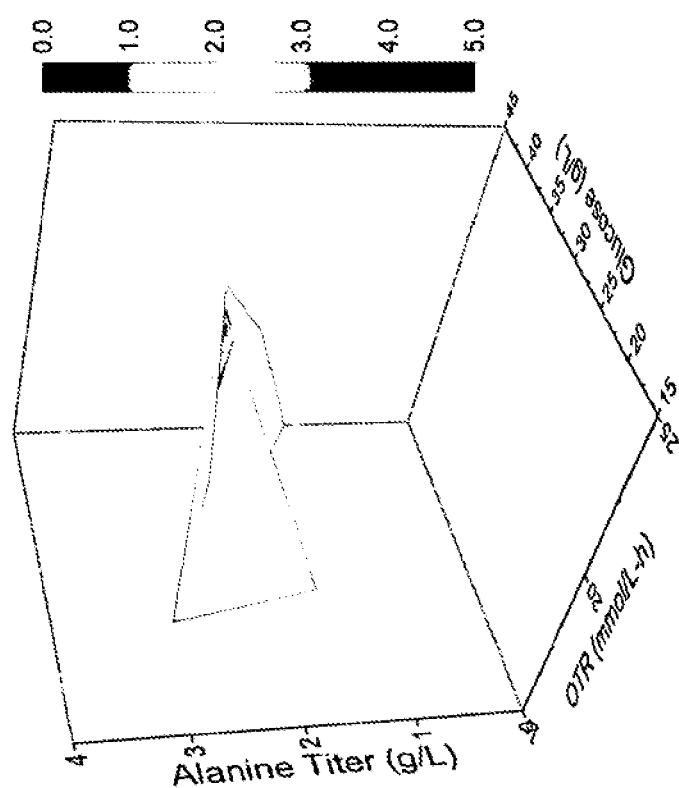
Figure 22A:
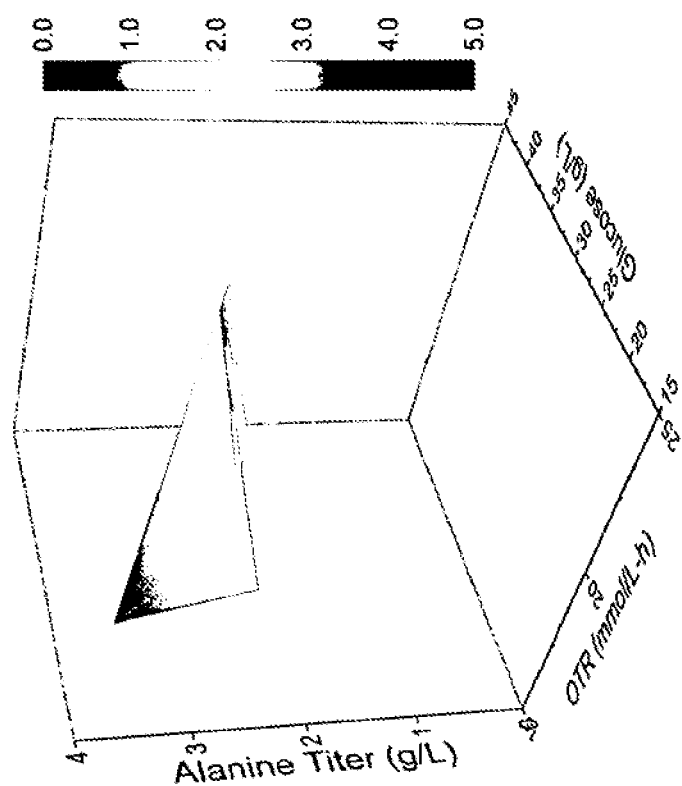
FIGS. 22A-D depict alanine production in response to different OTR and glucose concentration in micro-fermentation for 4 strains evaluated for robustness.
Figure 22B:
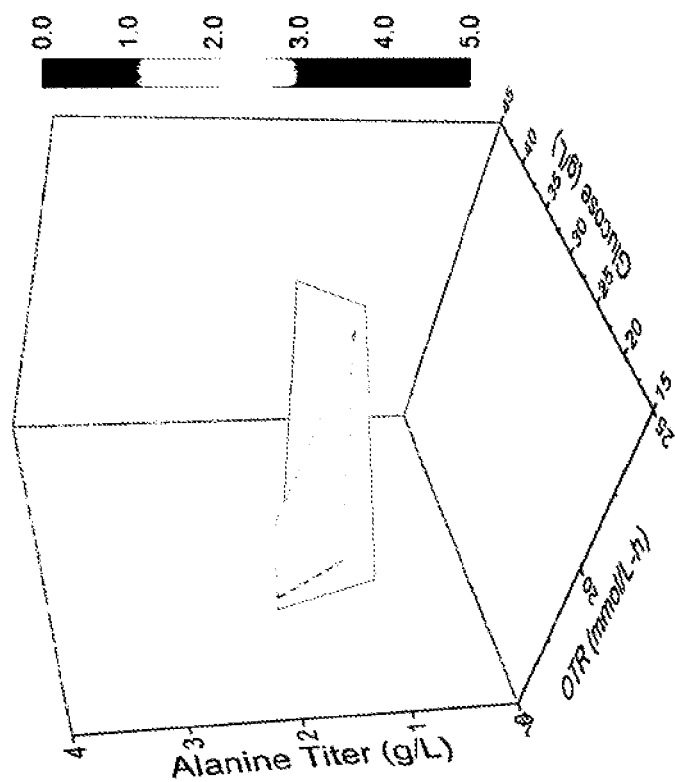
Figure 22C:
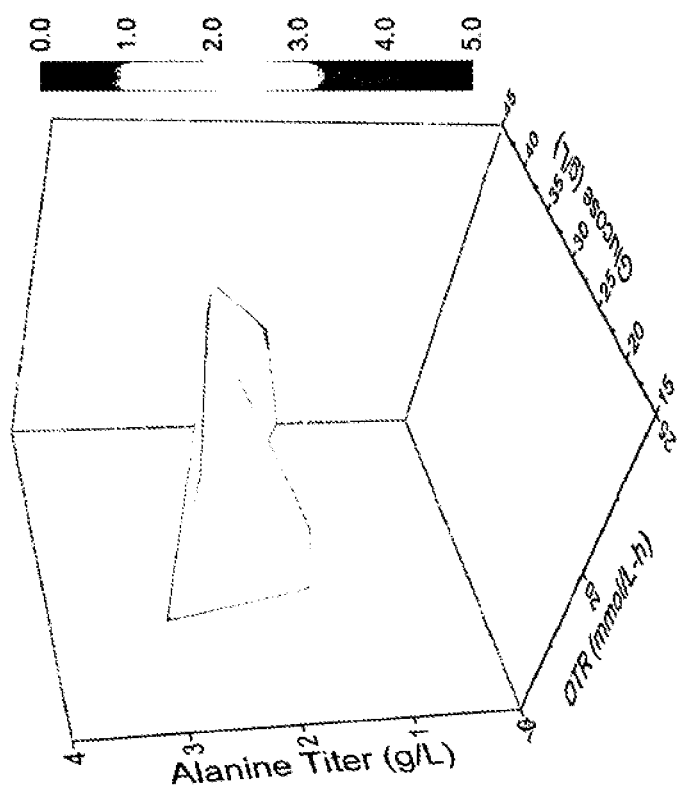
Figure 22D:
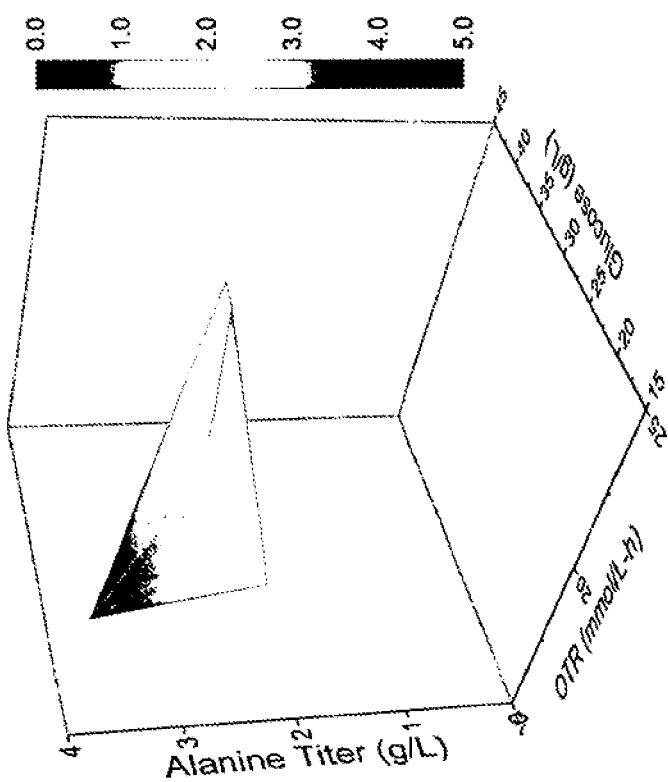
Figure 23A:
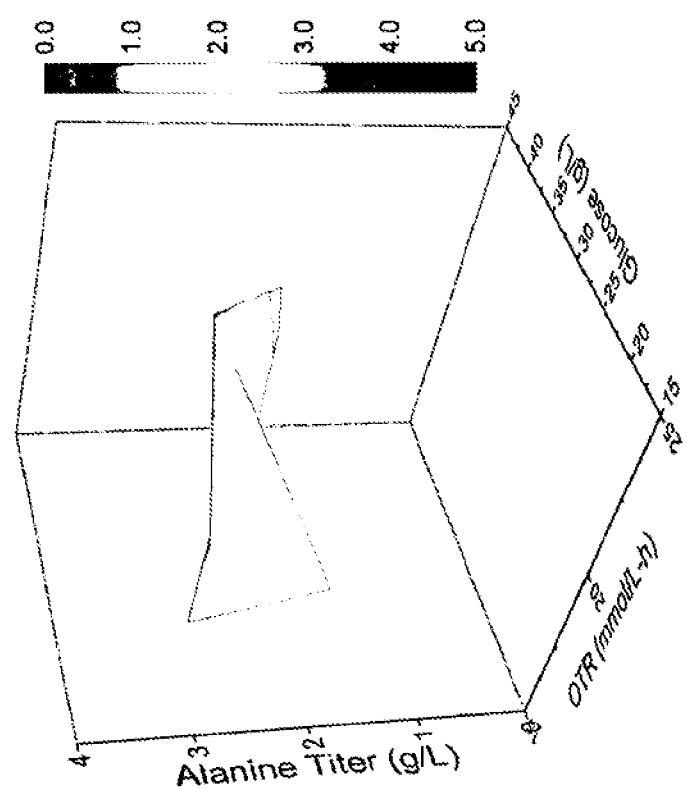
FIGS. 23A-D depict alanine production in response to different OTR and glucose concentration in micro-fermentation for 4 strains evaluated for robustness.
Figure 23B:
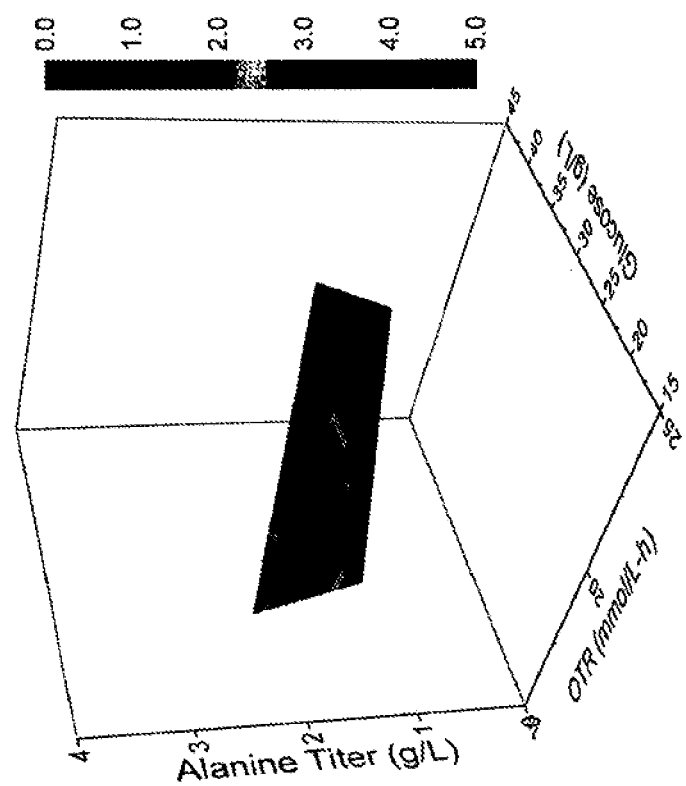
Figure 23C:
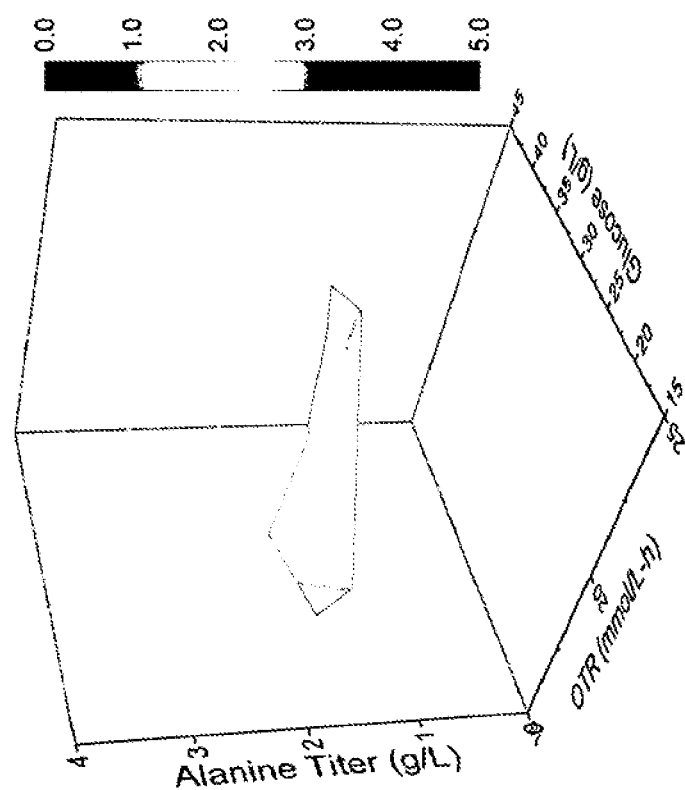
Figure 23D:
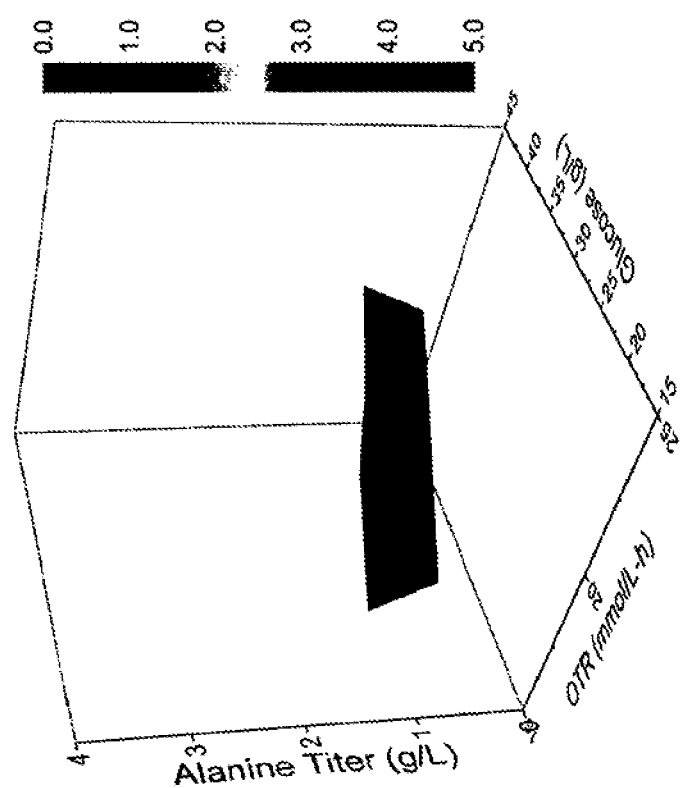
Figure 24A:
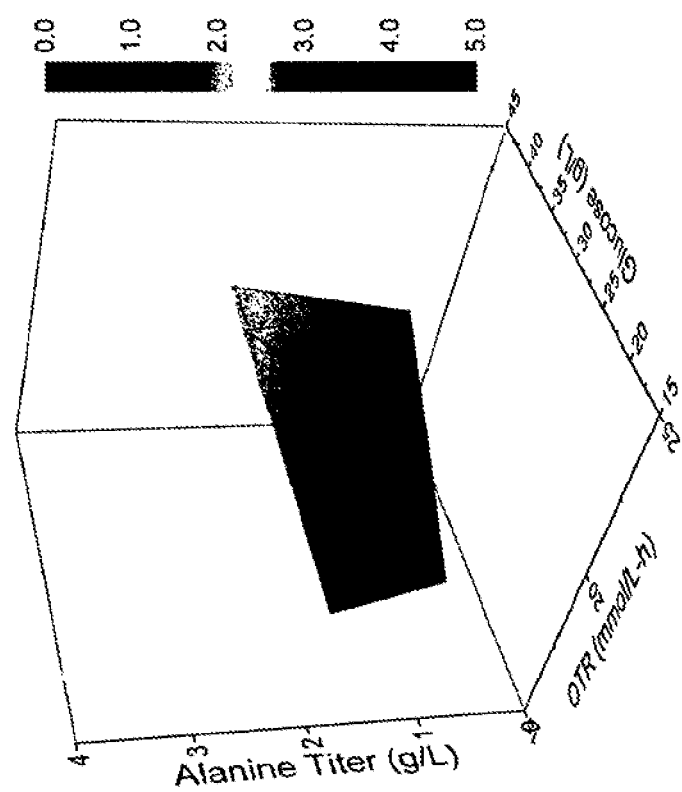
FIGS. 24A-D depict alanine production in response to different OTR and glucose concentration in micro-fermentation for 4 strains evaluated for robustness.
Figure 24B:
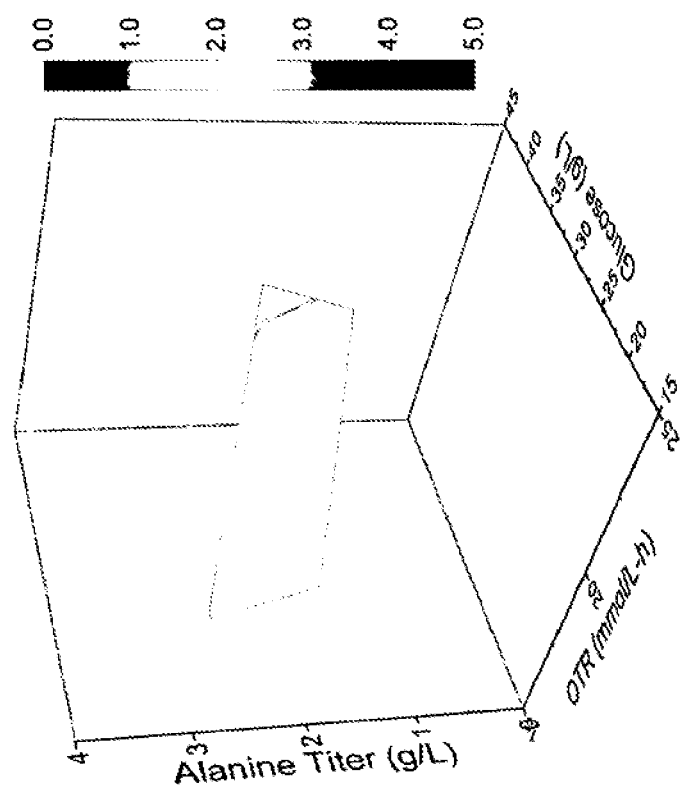
Figure 24C:
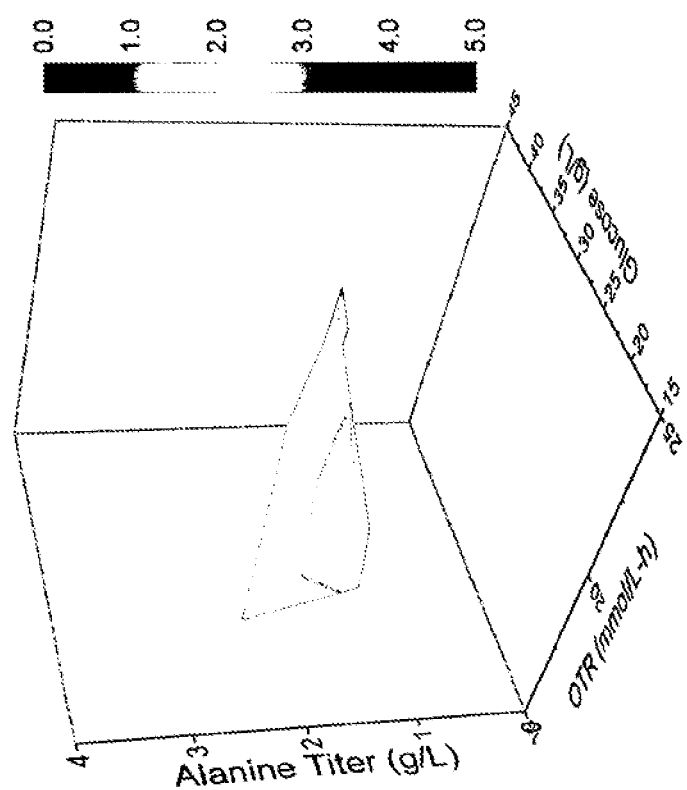
Figure 24D:
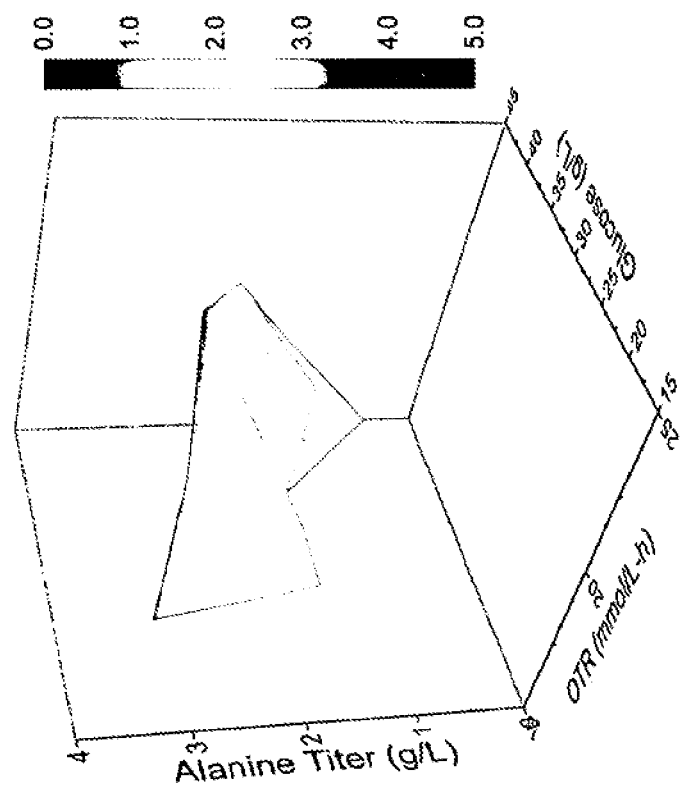
Figure 25A:
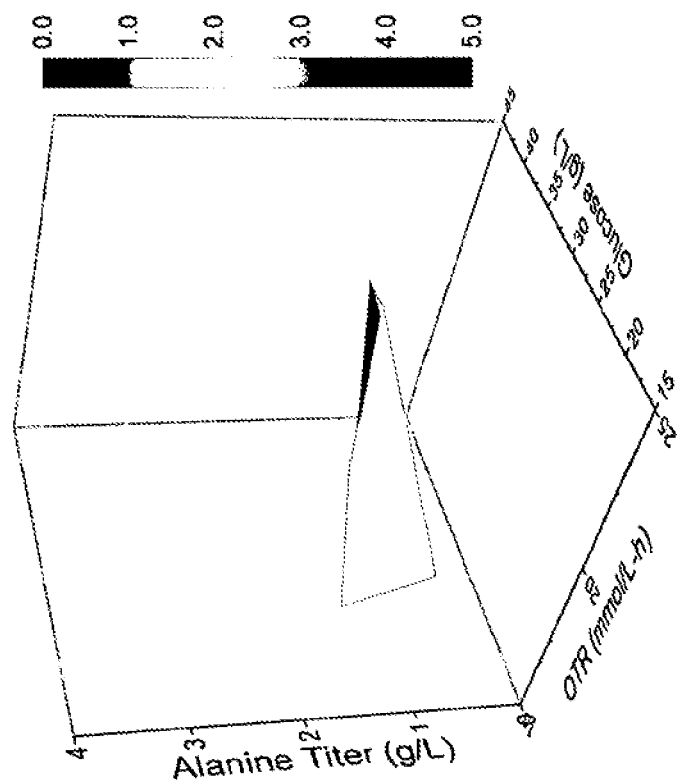
FIGS. 25A-D depict alanine production in response to different OTR and glucose concentration in micro-fermentation for 4 strains evaluated for robustness.
Figure 25B:
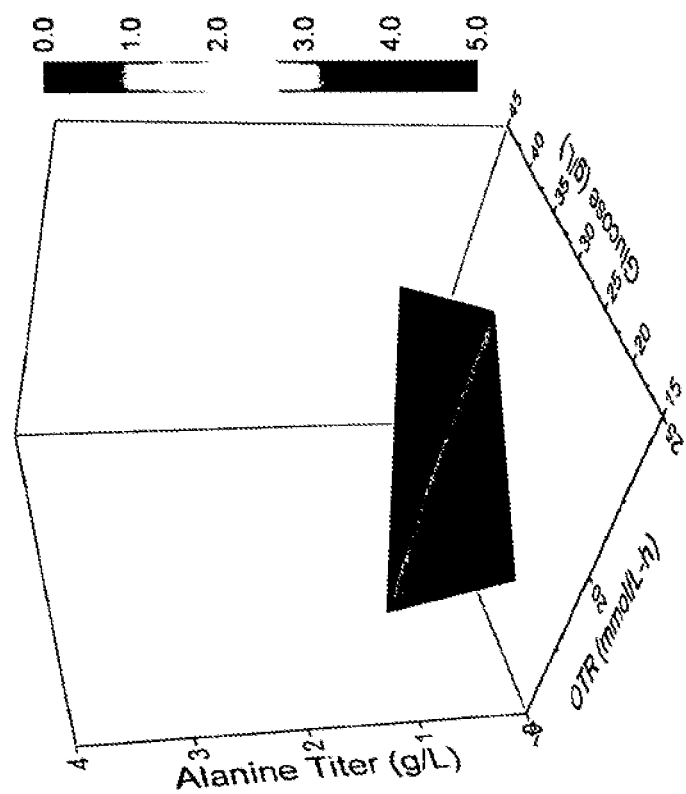
Figure 25C:
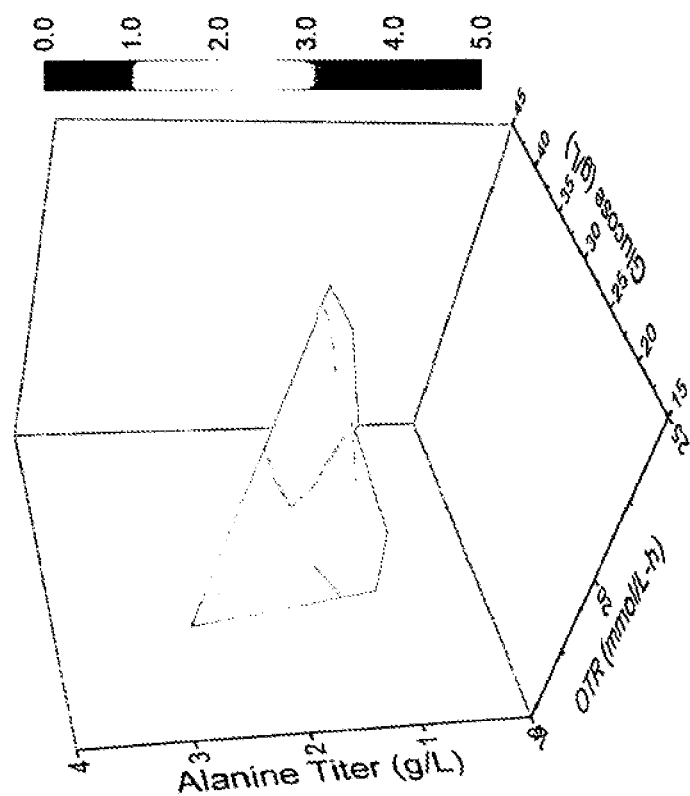
Figure 25D:
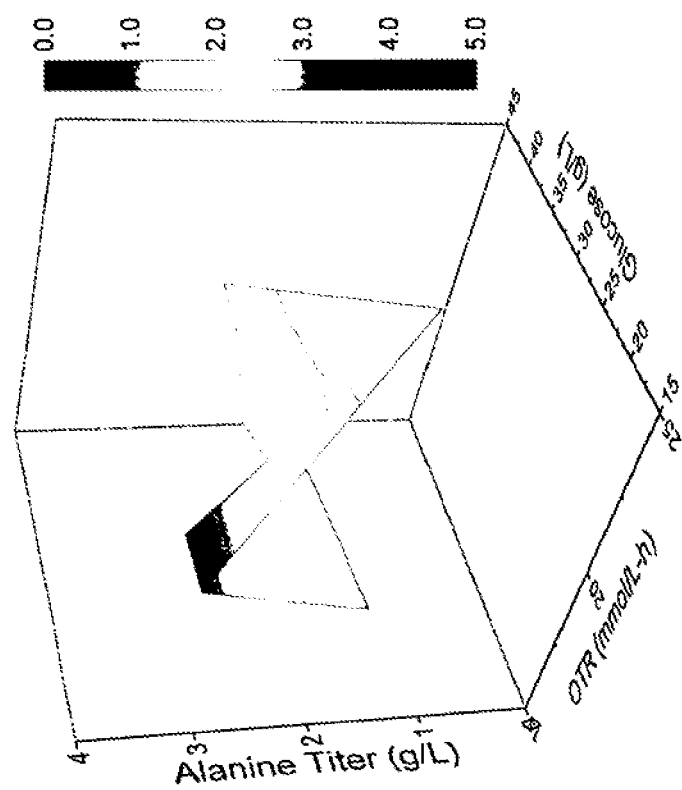
Figure 26A:
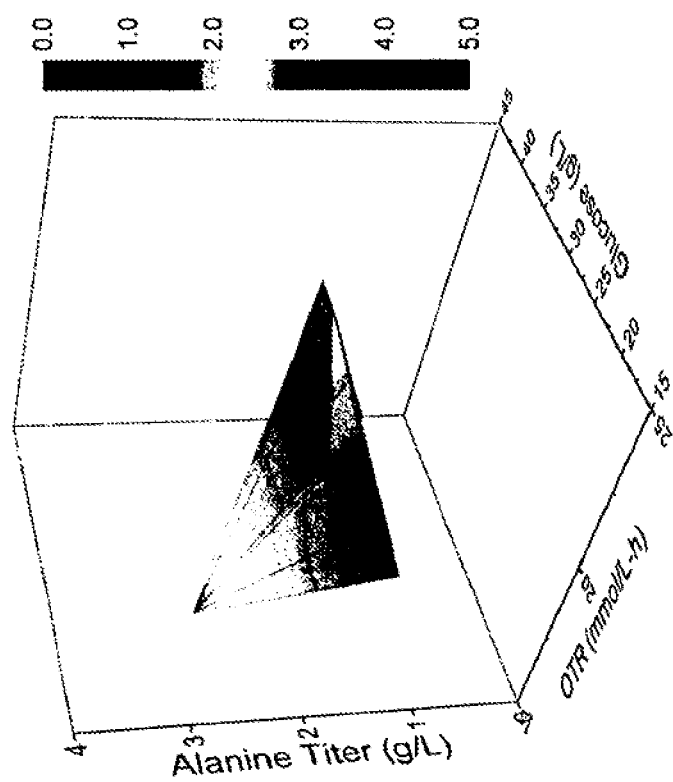
FIGS. 26A-D depict alanine production in response to different OTR and glucose concentration in micro-fermentation for 4 strains evaluated for robustness.
Figure 26B:
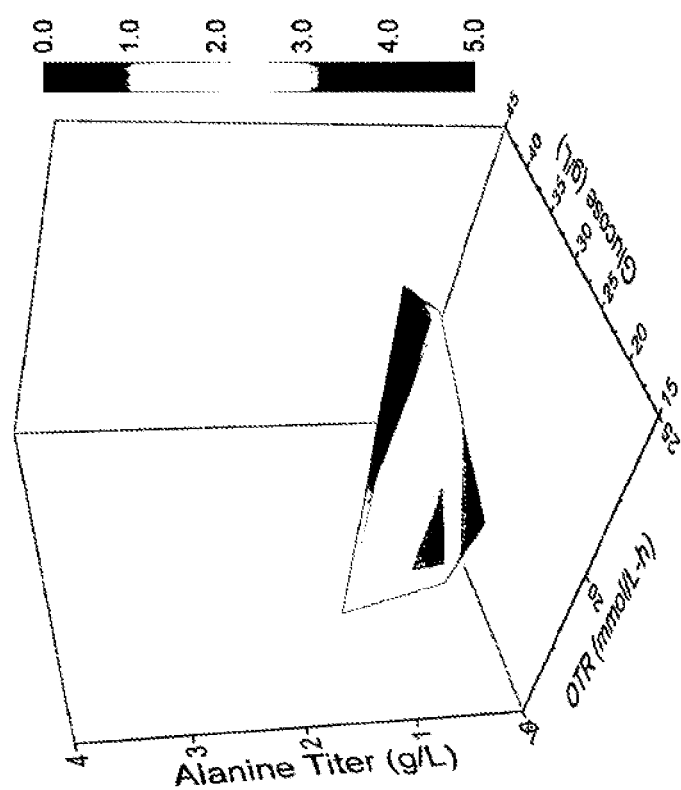
Figure 26C:
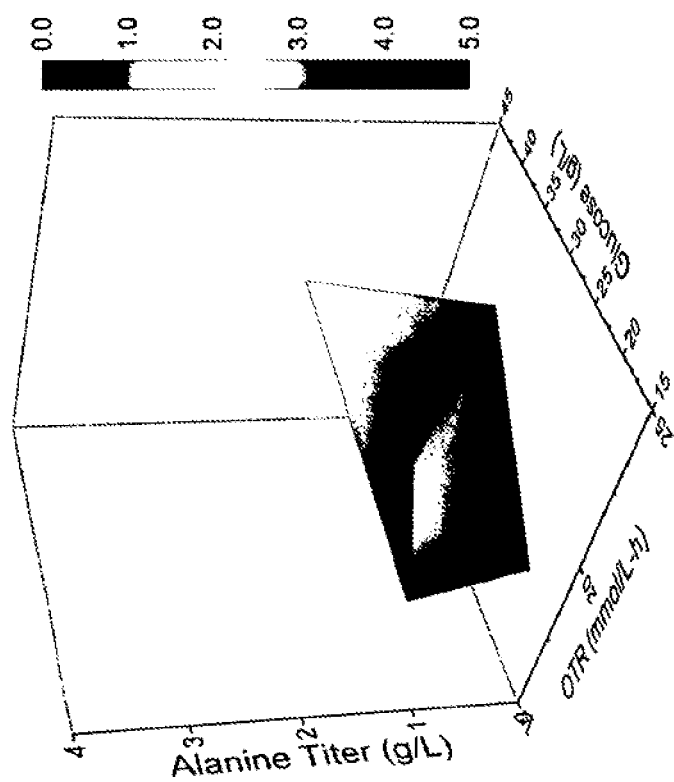
Figure 26D:
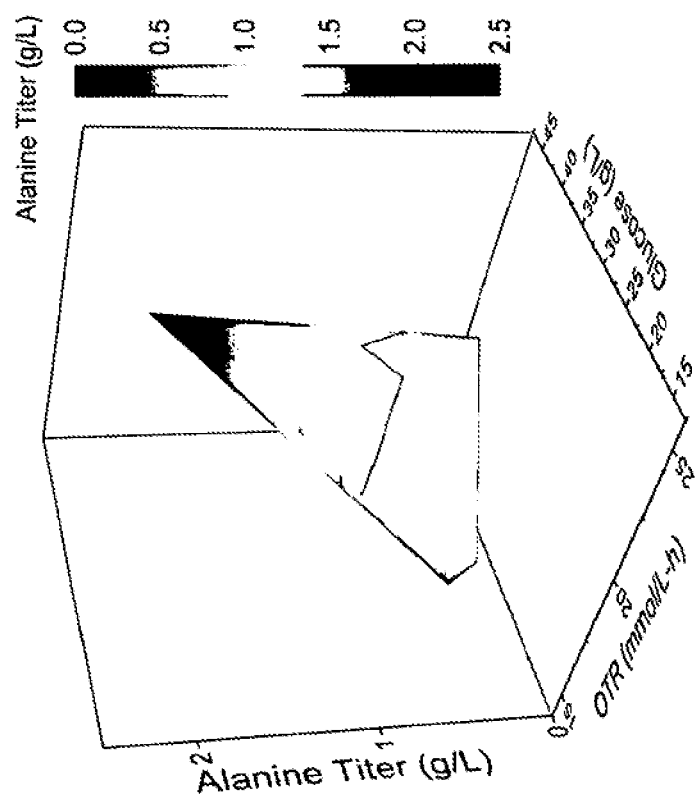
Figure 27A:
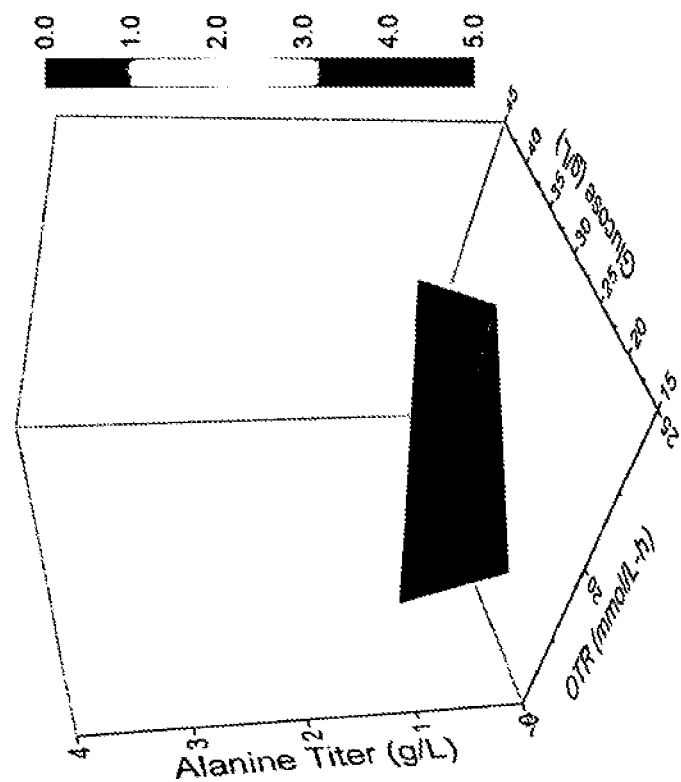
FIGS. 27A-D depict alanine production in response to different OTR and glucose concentration in micro-fermentation for 4 strains evaluated for robustness.
Figure 27B:
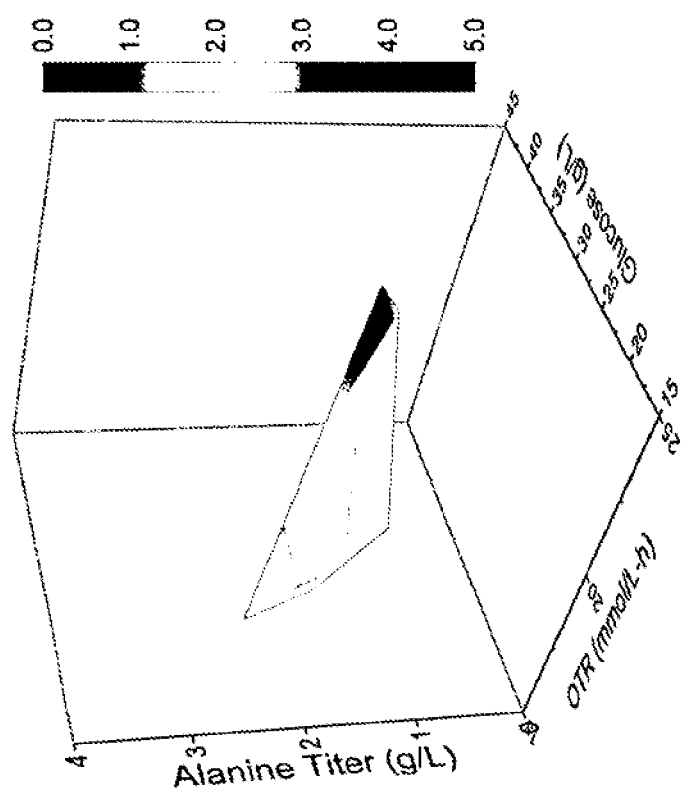
Figure 27C:
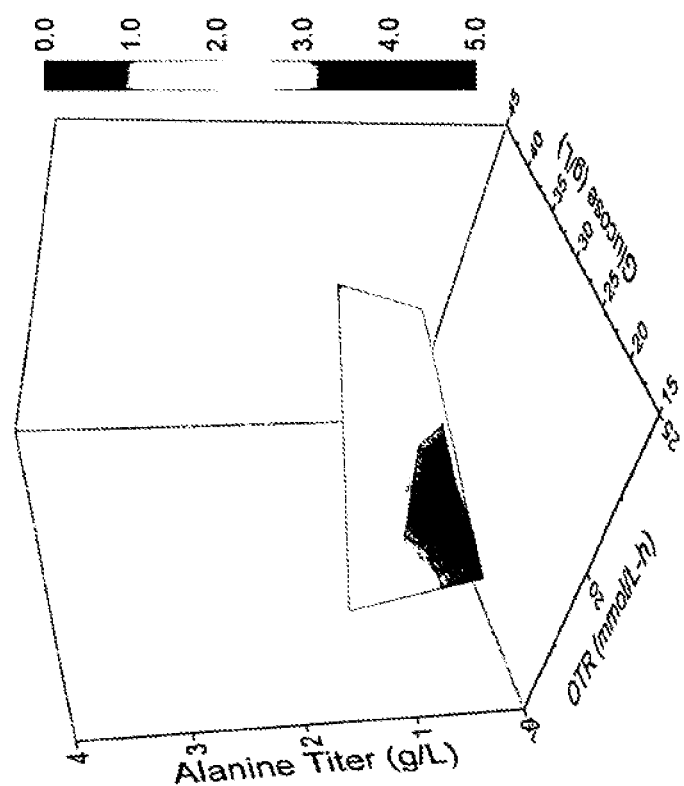
Figure 27D:
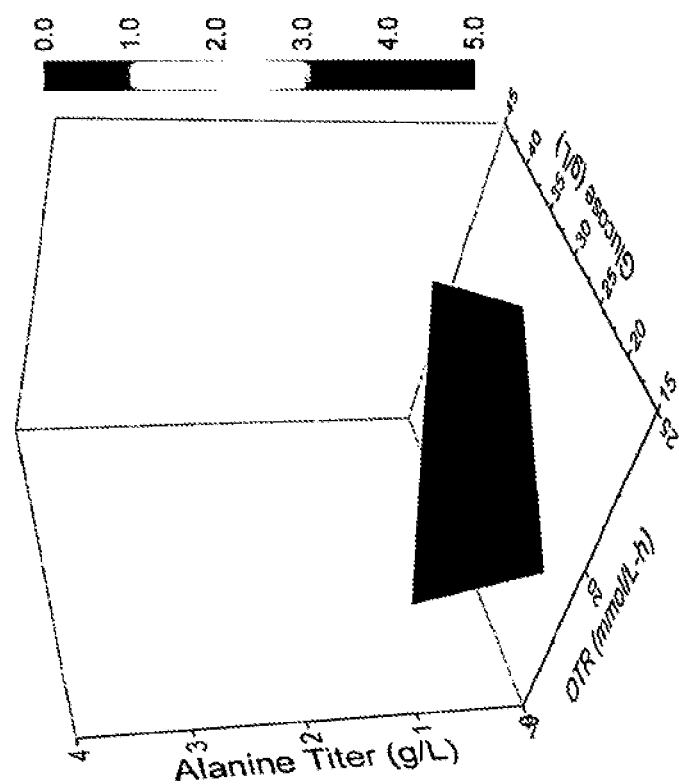
Figure 28A:
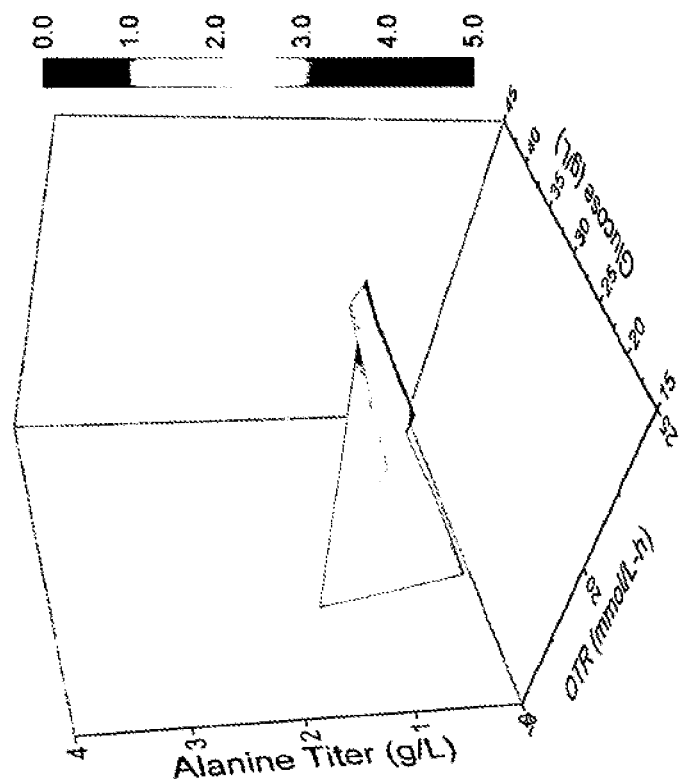
FIGS. 28A-D depict alanine production in response to different OTR and glucose concentration in micro-fermentation for 4 strains evaluated for robustness.
Figure 28B:
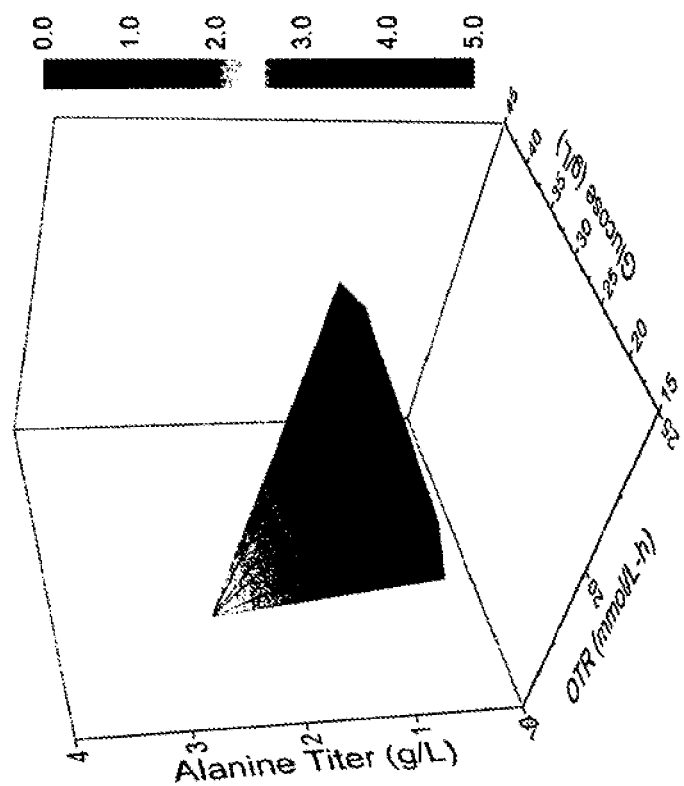
Figure 28C:
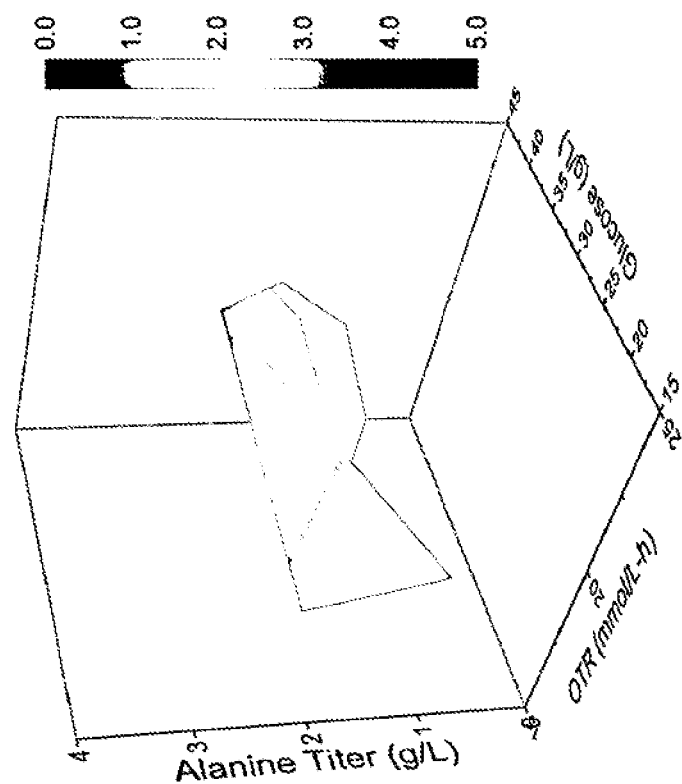
Figure 28D:
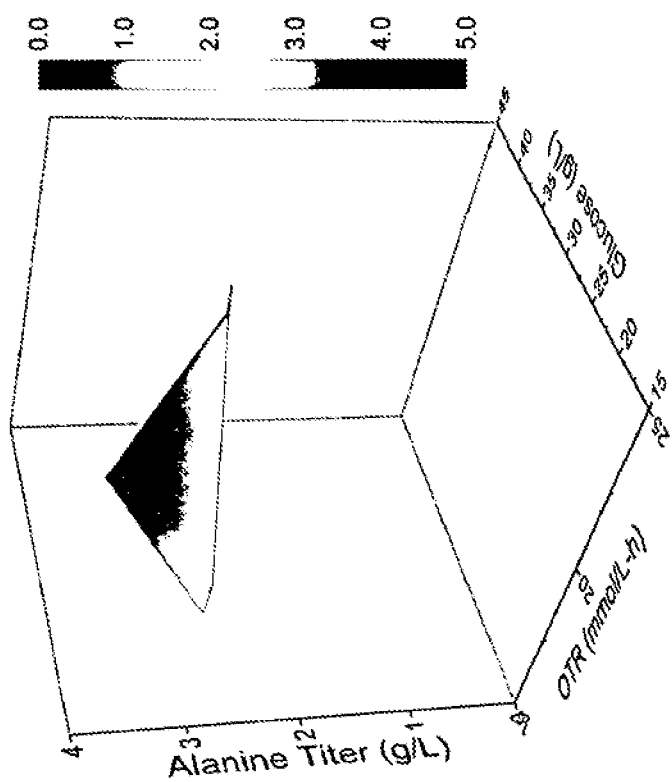
Figure 29A:
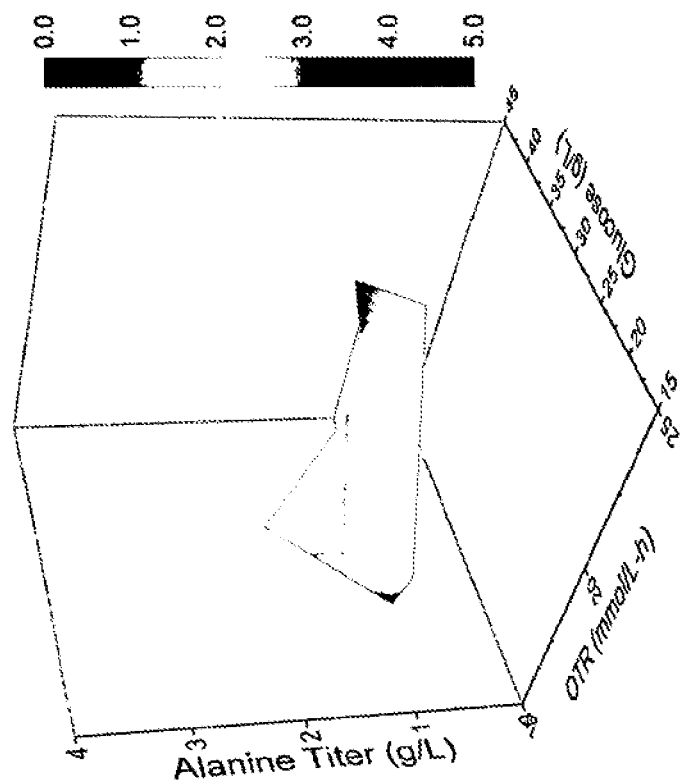
FIGS. 29A-D depict alanine production in response to different OTR and glucose concentration in micro-fermentation for 4 strains evaluated for robustness.
Figure 29B:
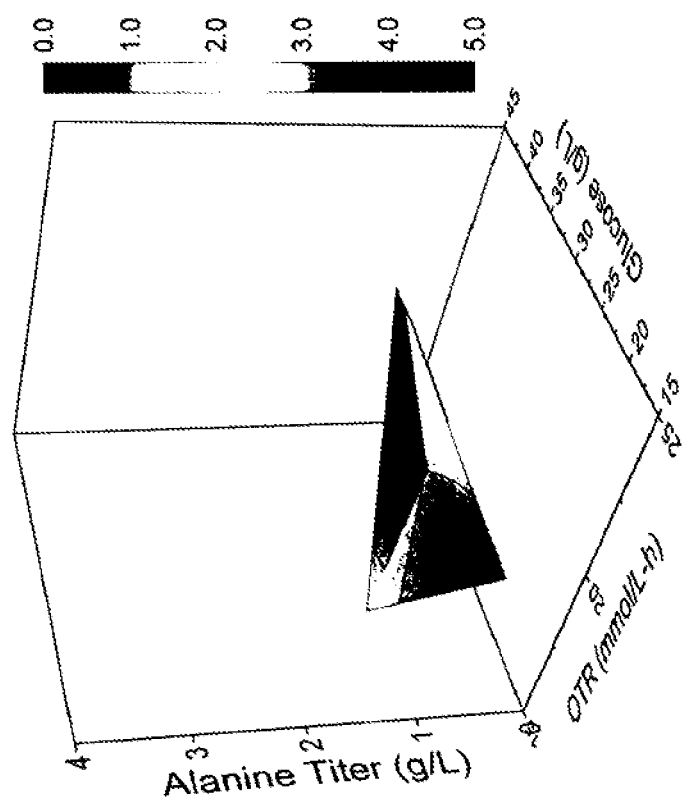
Figure 29C:
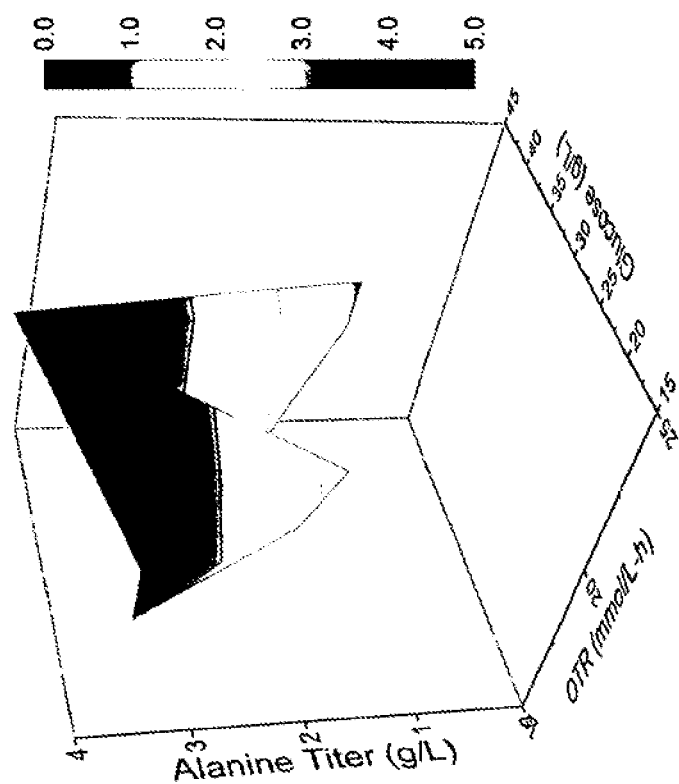
Figure 29D:
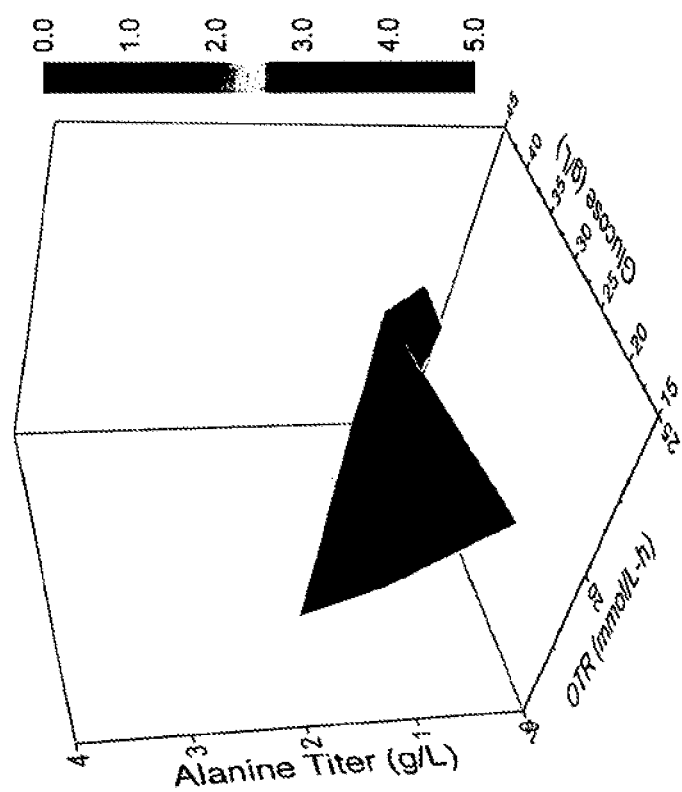
Figure 30A:
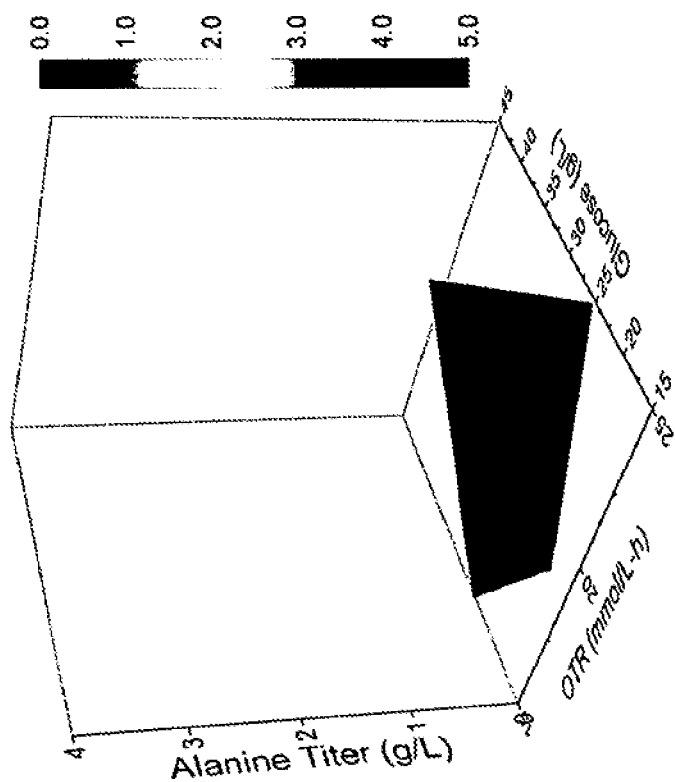
FIGS. 30A-D depict alanine production in response to different OTR and glucose concentration in micro-fermentation for 4 strains evaluated for robustness.
Figure 30B:
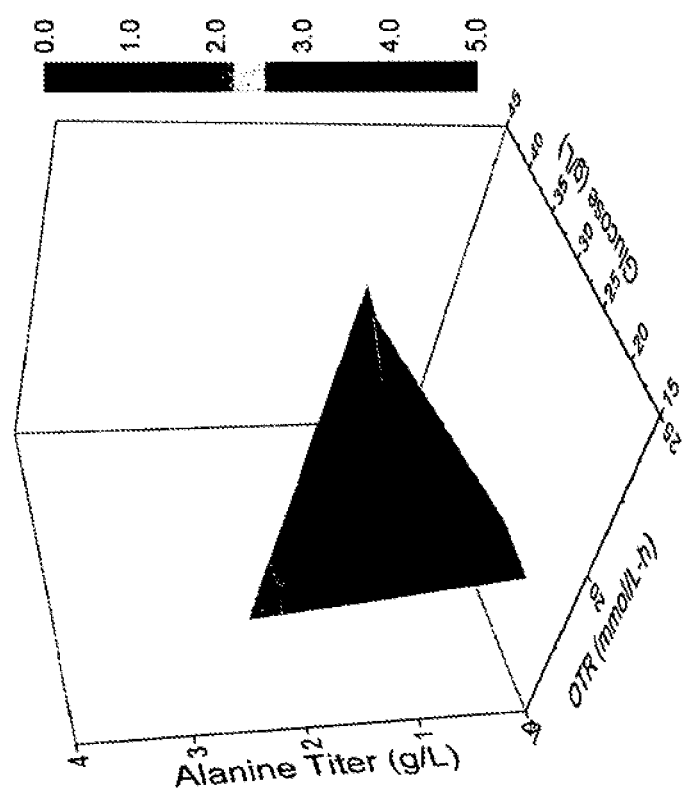
Figure 30C:
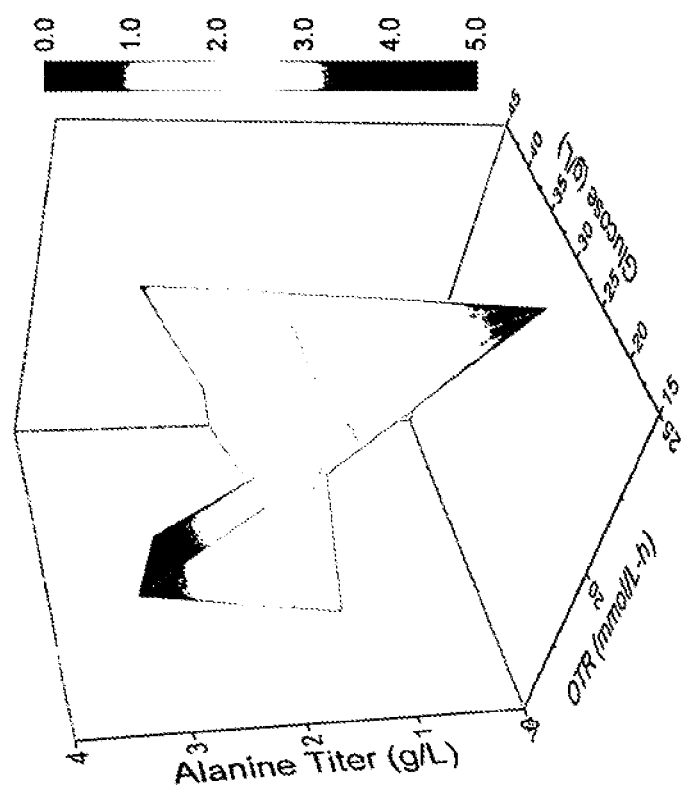
Figure 30D:
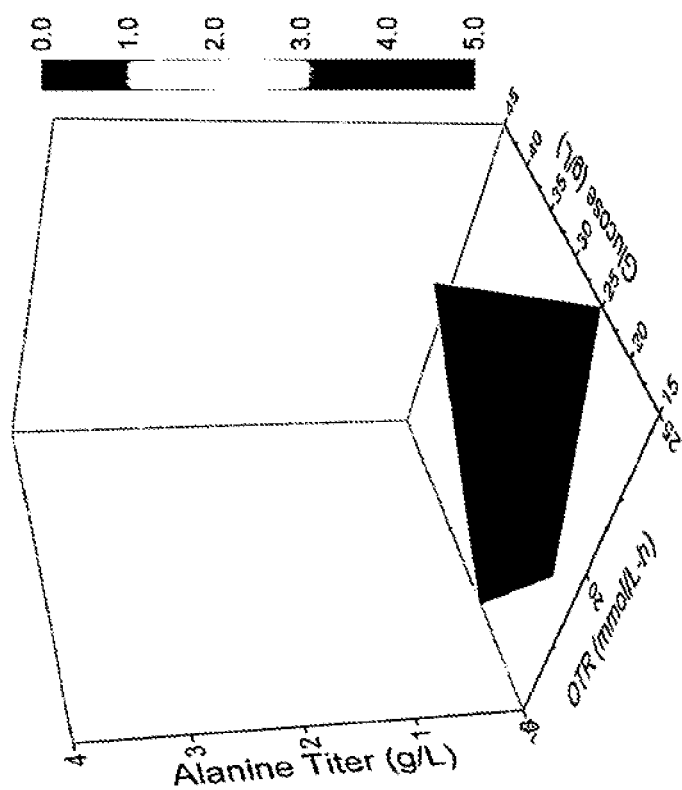
Figure 31A:
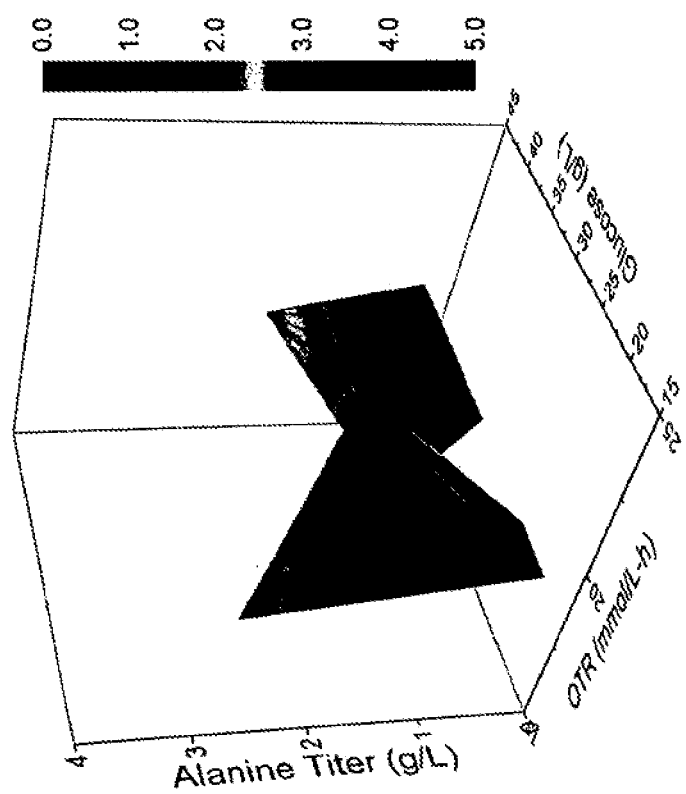
FIGS. 31A-D depict alanine production in response to different OTR and glucose concentration in micro-fermentation for 4 strains evaluated for robustness.
Figure 31B:
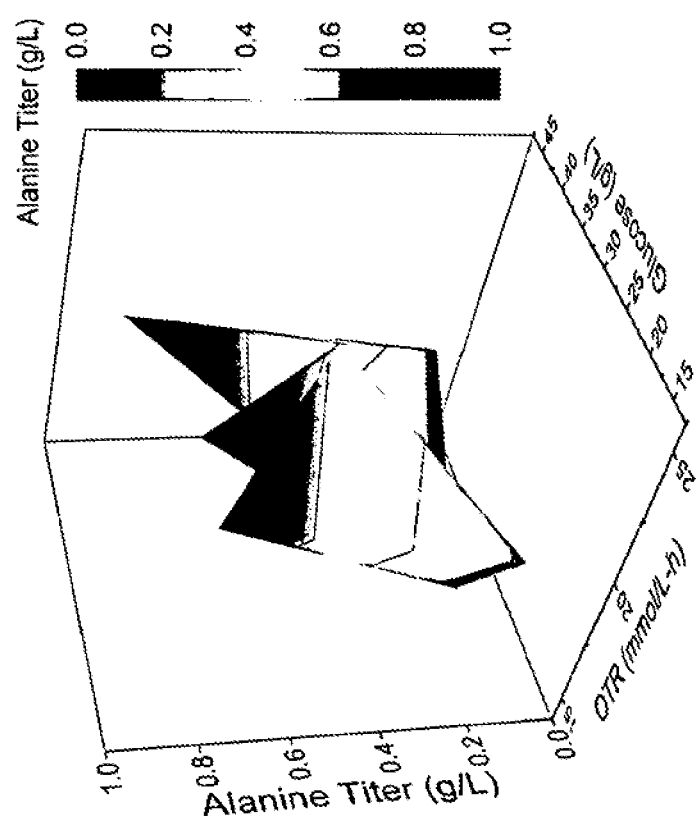
Figure 31C:
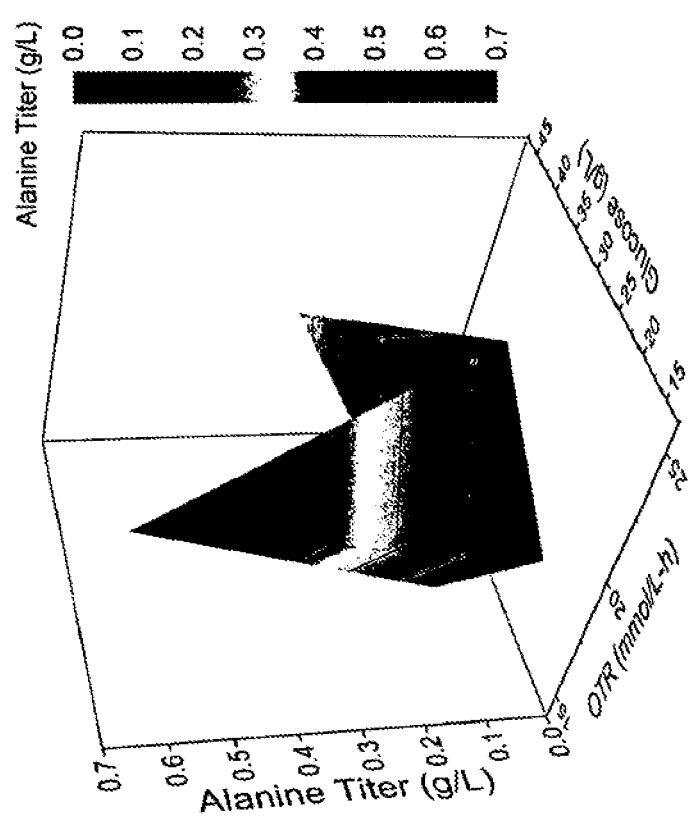
Figure 31D:
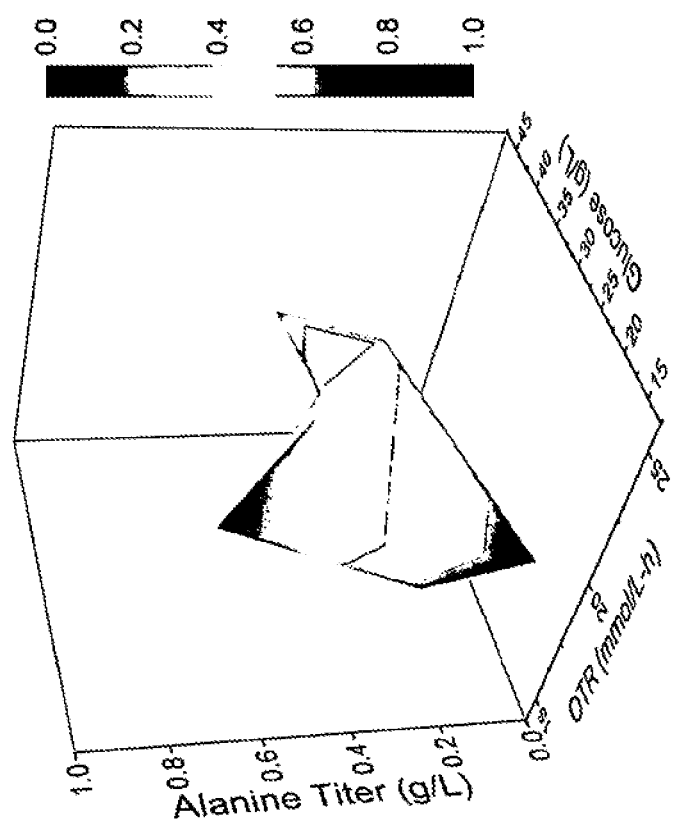

FIG. 18: Heatmap for L-alanine production by gapN/gapA strains.

FIGS. 19A-D: Alanine production in response to different OTR and glucose concentration in micro-fermentation for 4 strains evaluated for robustness.

FIGS. 20A-D: Alanine production in response to different OTR and glucose concentration in micro-fermentation for 4 strains evaluated for robustness.

FIGS. 21A-D: Alanine production in response to different OTR and glucose concentration in micro-fermentation for 4 strains evaluated for robustness.

FIGS. 22A-D: Alanine production in response to different OTR and glucose concentration in micro-fermentation for 4 strains evaluated for robustness.

FIGS. 23A-D: Alanine production in response to different OTR and glucose concentration in micro-fermentation for 4 strains evaluated for robustness.

FIGS. 24A-D: Alanine production in response to different OTR and glucose concentration in micro-fermentation for 4 strains evaluated for robustness.

FIGS. 25A-D: Alanine production in response to different OTR and glucose concentration in micro-fermentation for 4 strains evaluated for robustness.

FIGS. 26A-D: Alanine production in response to different OTR and glucose concentration in micro-fermentation for 4 strains evaluated for robustness.

FIGS. 27A-D: Alanine production in response to different OTR and glucose concentration in micro-fermentation for 4 strains evaluated for robustness.

FIGS. 28A-D: Alanine production in response to different OTR and glucose concentration in micro-fermentation for 4 strains evaluated for robustness.

FIGS. 29A-D: Alanine production in response to different OTR and glucose concentration in micro-fermentation for 4 strains evaluated for robustness.

FIGS. 30A-D: Alanine production in response to different OTR and glucose concentration in micro-fermentation for 4 strains evaluated for robustness.

FIGS. 31A-D: Alanine production in response to different OTR and glucose concentration in micro-fermentation for 4 strains evaluated for robustness.

Figure 32:
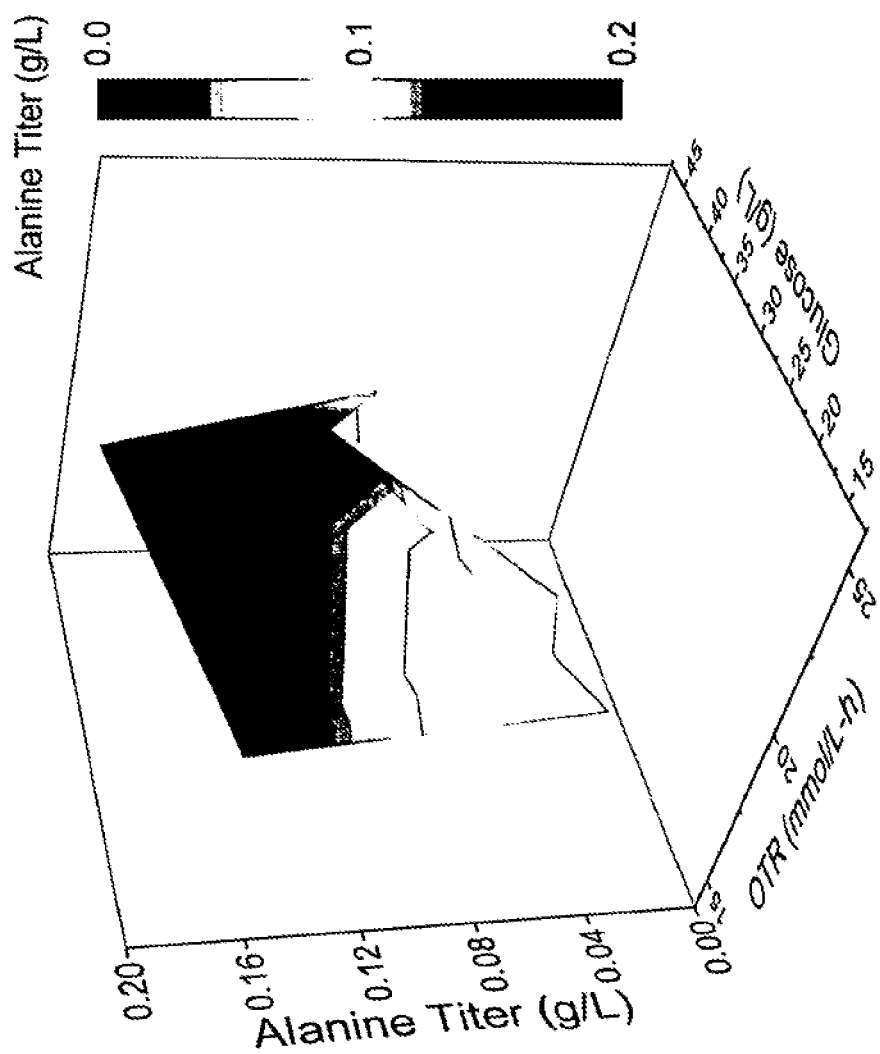
FIG. 32 depicts alanine production in response to different OTR and glucose concentration in micro-fermentation for one strain evaluated for robustness.

FIG. 32: Alanine production in response to different OTR and glucose concentration in micro-fermentation for one strain evaluated for robustness.

Figure 33B:
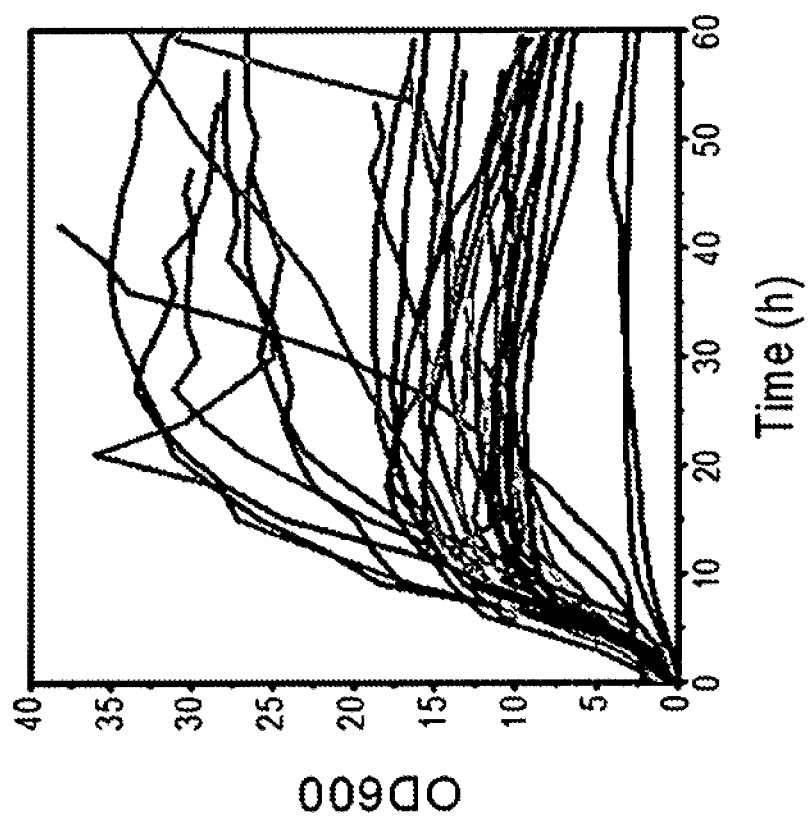

FIGS. 33A-B: Growth profile for all (FIG. 33A) valve and (FIG. 33B) growth associated strains at 1 L scale evaluated in this paper. Growth curves were synced to account for any variations in lag time. Valve strains growth curves were synced to the same mid-exponential point. Growth associated strains growth curves were synced to the same take-off point.

Figure 34:
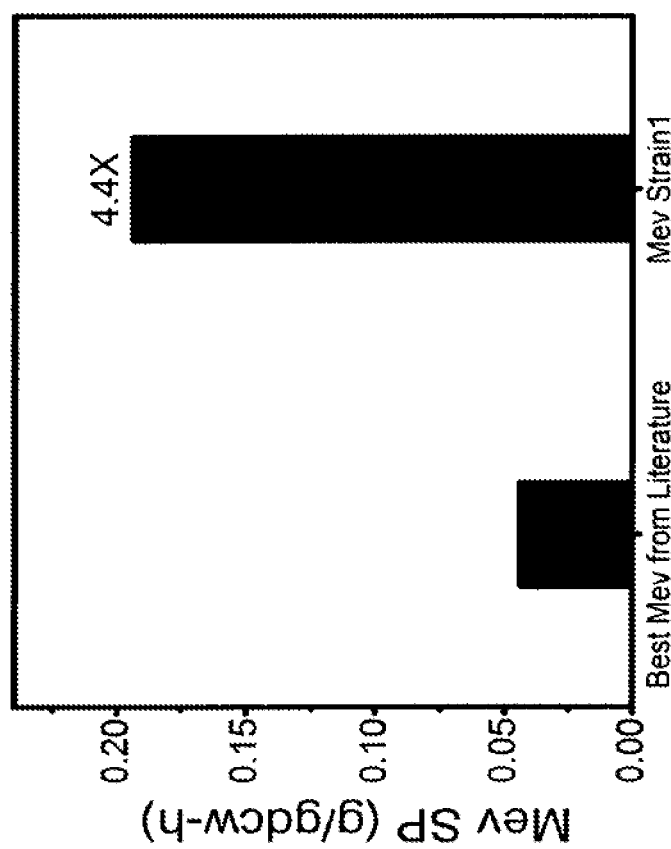
FIG. 34 depicts specific Productivity (SP) comparison for strain with highest mevalonate titer from literature and mevalonate strain 1 evaluated in this work.

FIG. 34: Specific Productivity (SP) comparison for strain with highest mevalonate titer from literature and mevalonate strain 1 evaluated in this work.

Figure 35:
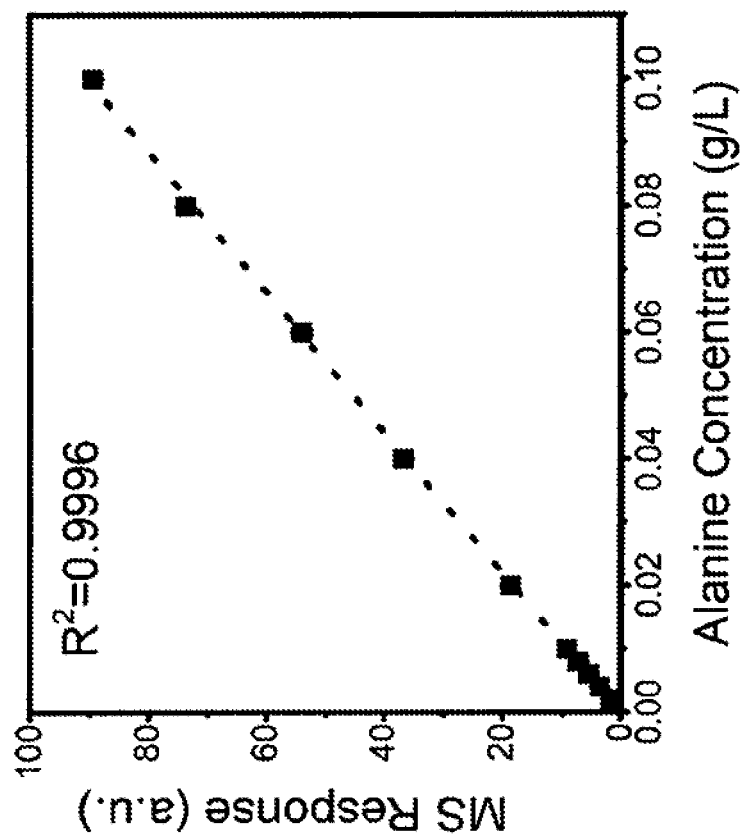
FIG. 35 depicts alanine standard curve from MS measurement. Average and standard deviation for mass spec response from triplicate standard measurement were plotted.

FIG. 35: Alanine standard curve from MS measurement. Average and standard deviation for mass spec response from triplicate standard measurement were plotted.

Figure 36B:
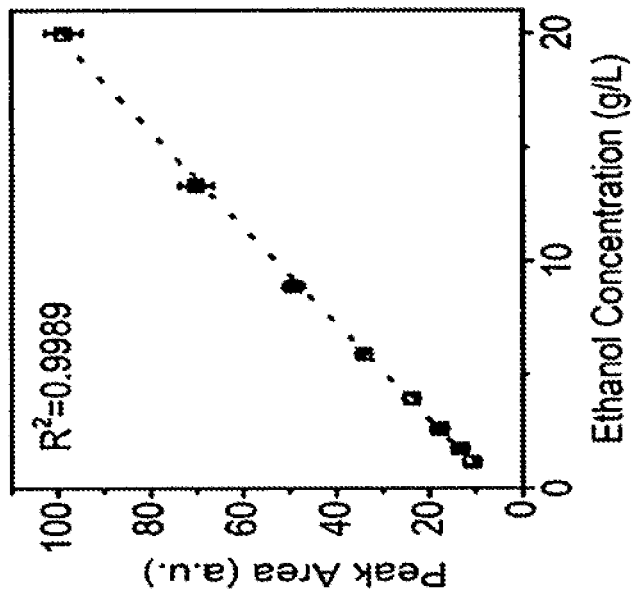
FIGS. 36A-B depict glucose and ethanol standard curves from RI measurement.
Figure 36A:
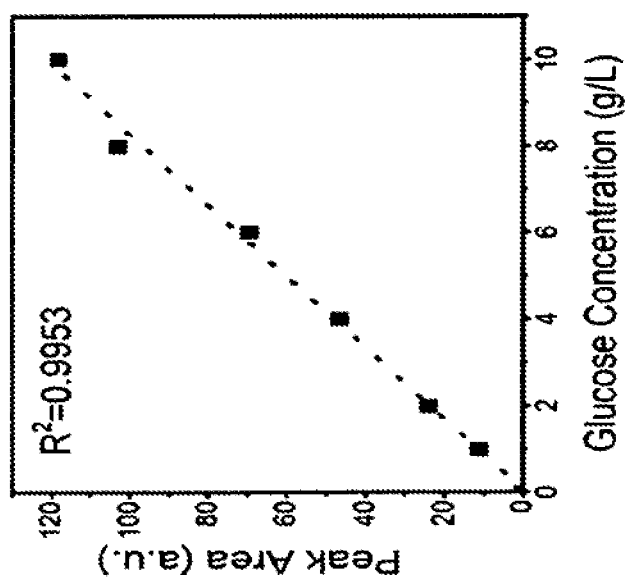

FIGS. 36A-B: Glucose (FIG. 36A) and ethanol (FIG. 36B) standard curves from RI measurement. Average and standard deviation for peak area from triplicate standard measurement were plotted.

Figure 37:
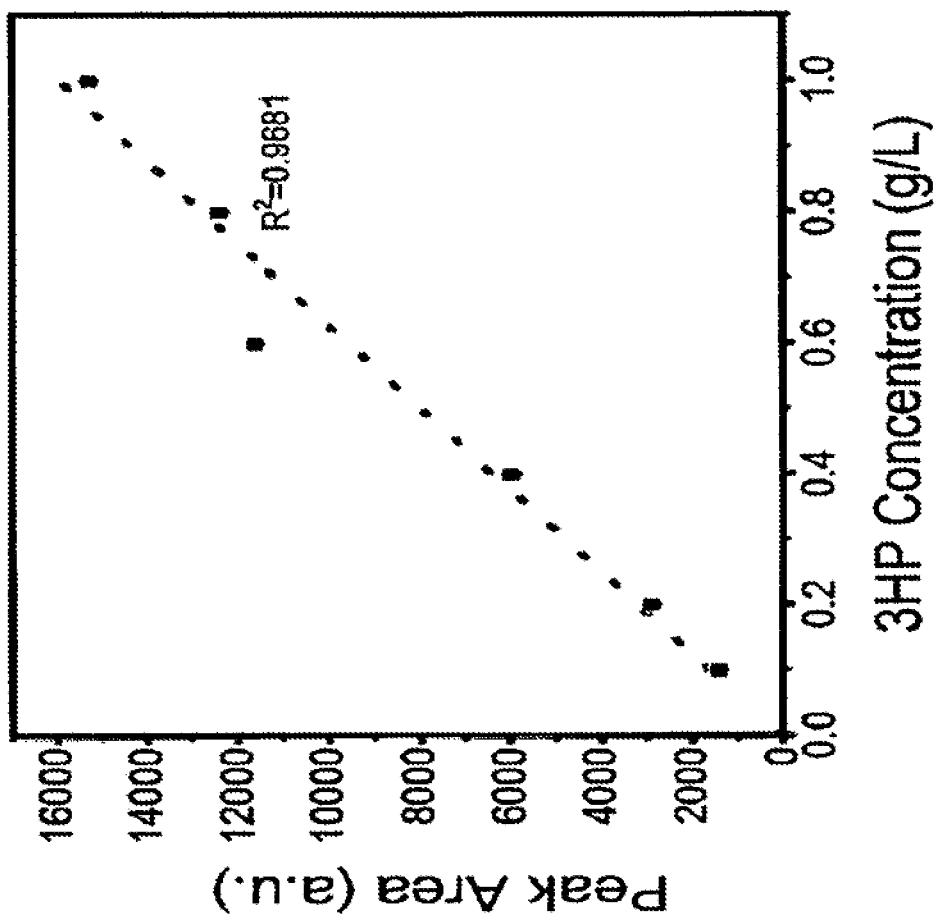
FIG. 37 depicts 3-Hydroxypropionic acid standard curve from TUV measurement.
Figure 38A:
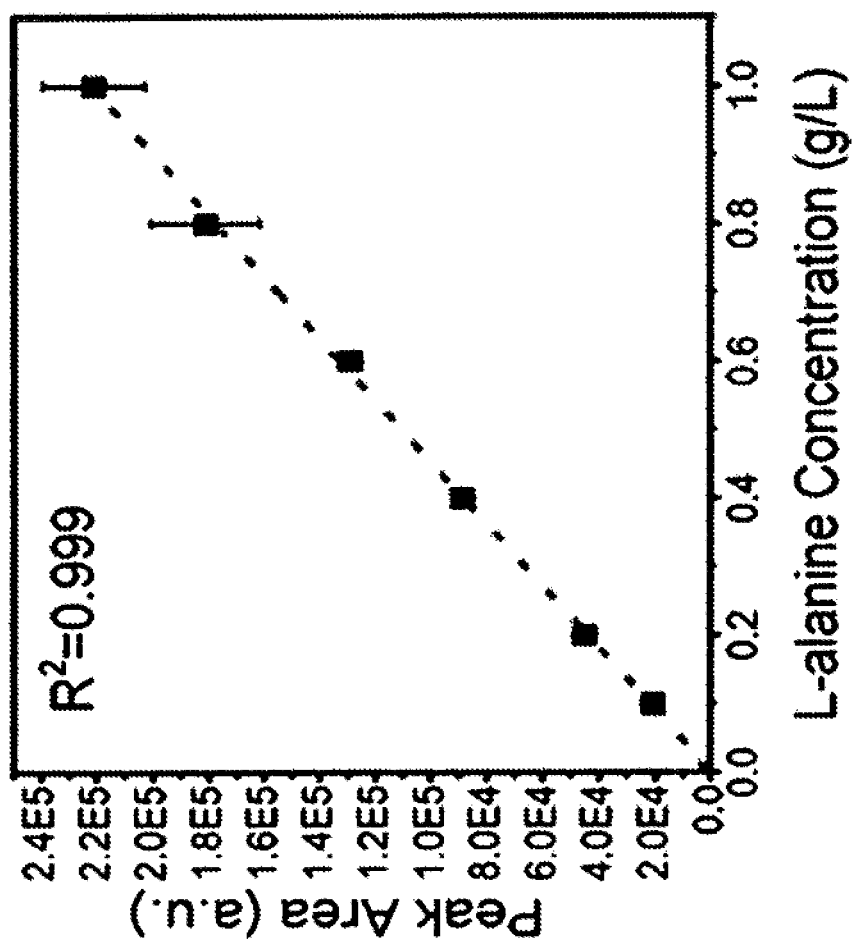
FIGS. 38A-D depict TUV standard curves for L-alanine, D-alanine, mevalonic acid, and mevalonolactone.
Figure 38B:
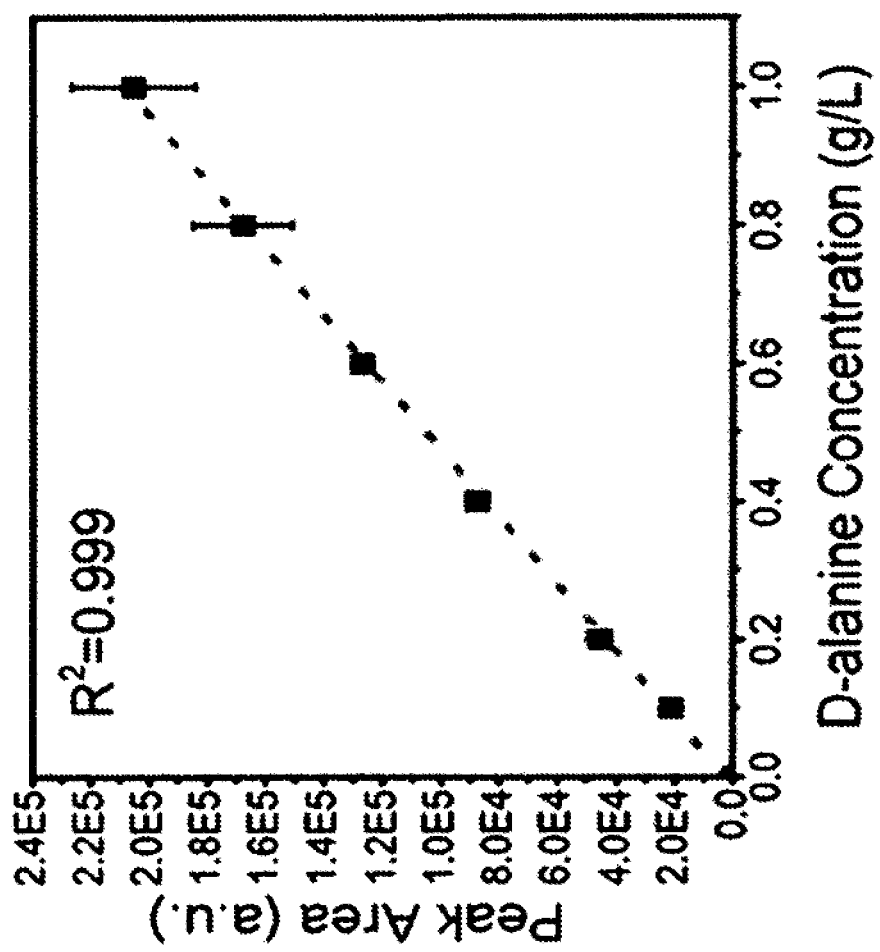
Figure 38C:
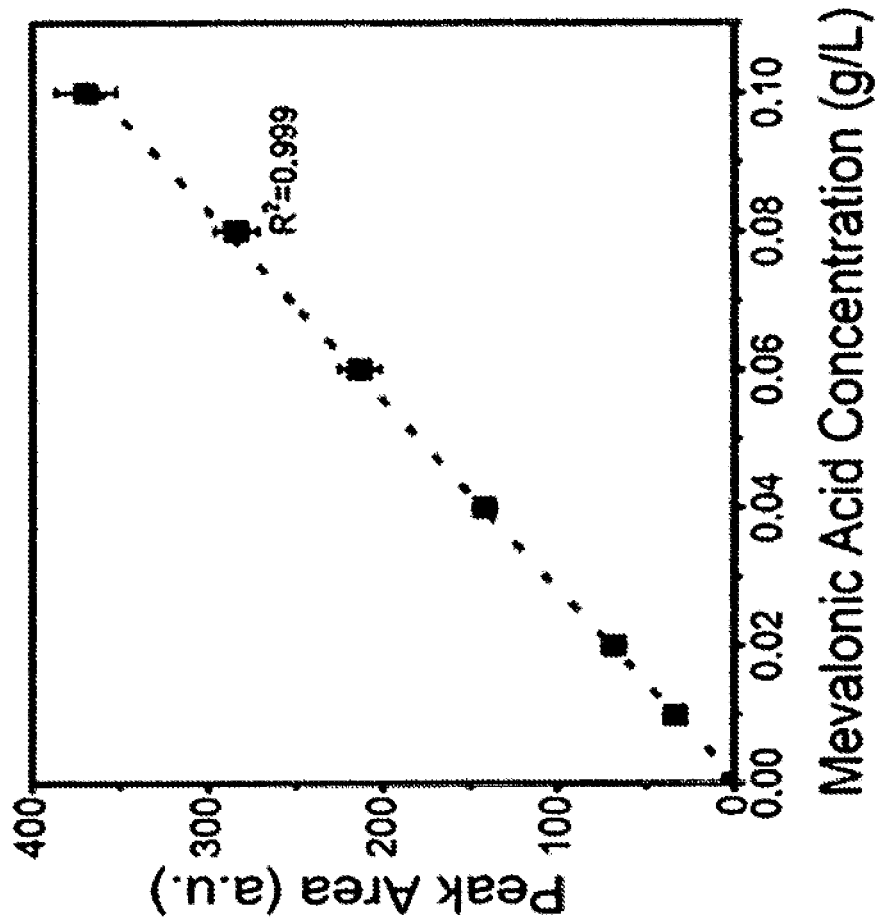
Figure 38D:
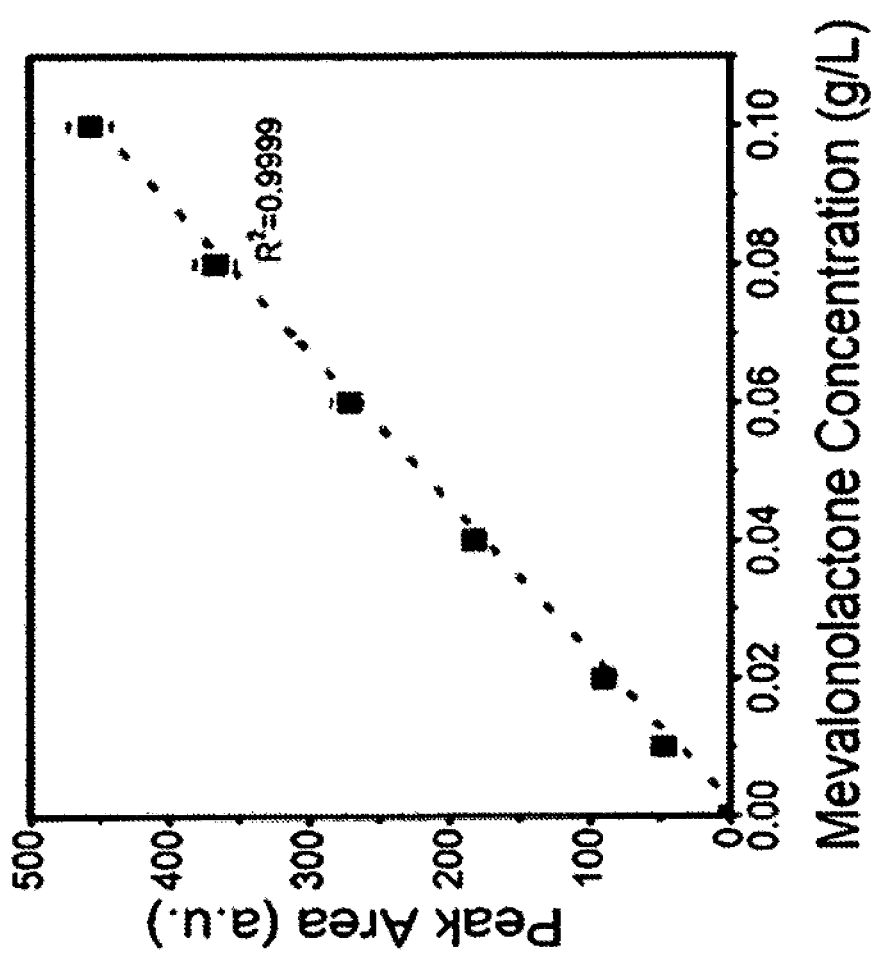

FIG. 37: 3-Hydroxypropionic acid standard curve from TUV measurement. Average and standard deviation for peak area from duplicate standard measurement were plotted.

FIGS. 38A-D: TUV standard curves for (FIG. 38A) L-alanine, (FIG. 38B) D-alanine, (FIG. 38C) mevalonic acid, and (FIG. 38D) mevalonolactone. Average and standard deviation for peak area from triplicate standard measurement were plotted.

REFERENCES

1. Cameron, D. E.; Bashor, C. J.; Collins, J. J., A brief history of synthetic biology. *Nat Rev Microbiol* 2014, 12 (5), 381-90.
2. Cheong, S.; Clomburg, J. M.; Gonzalez, R., Energy- and carbon-efficient synthesis of functionalized small molecules in bacteria using non-decarboxylative Claisen condensation reactions. *Nature biotechnology* 2016, 34 (5), 556-61.
3. Choi, S. Y.; Park, S. J.; Kim, W. J.; Yang, J. E.; Lee, H.; Shin, J.; Lee, S. Y., One-step fermentative production of poly(lactate-co-glycolate) from carbohydrates in *Escherichia coli*.
Nature biotechnology 2016, 34 (4), 435-40.
4. Jarboe, L. R.; Zhang, X.; Wang, X.; Moore, J. C.; Shanmugam, K. T.; Ingram, L. O., Metabolic engineering for production of biorenewable fuels and chemicals: contributions of synthetic biology. *Journal of biomedicine & biotechnology* 2010, 761042.
5. Lee, J. W.; Na, D.; Park, J. M.; Lee, J.; Choi, S.; Lee, S. Y., Systems metabolic engineering of microorganisms for natural and non-natural chemicals. *Nat Chem Biol* 2012, 8 (6), 536-46.
6. Dellomonaco, C.; Clomburg, J. M.; Miller, E. N.; Gonzalez, R., Engineered reversal of the beta-oxidation cycle for the synthesis of fuels and chemicals. *Nature* 2011, 476 (7360), 355-9.
7. Kim, S.; Clomburg, J. M.; Gonzalez, R., Synthesis of medium-chain length (C6-C10) fuels and chemicals via beta-oxidation reversal in *Escherichia coli*. *J Ind Microbiol Biotechnol* 2015, 42 (3), 465-75.
8. Meadows, A. L.; Hawkins, K. M.; Tsegaye, Y.; Antipov, E.; Kim, Y.; Raetz, L.; Dahl, R. H.; Tai, A.; Mahatdejkul-Meadows, T.; Xu, L.; Zhao, L.; Dasika, M. S.; Murarka, A.; Lenihan, J.; Eng, D.; Leng, J. S.; Liu, C. L.; Wenger, J. W.; Jiang, H.; Chao, L.; Westfall, P.; Lai, J.; Ganesan, S.; Jackson, P.; Mans, R.; Platt, D.; Reeves, C. D.; Saija, P. R.; Wichmann, G.; Holmes, V. F.; Benjamin, K.; Hill, P. W.; Gardner, T. S.; Tsong, A. E., Rewriting yeast central carbon metabolism for industrial isoprenoid production. *Nature* 2016, 537 (7622), 694-697.
9. Yadav, V. G.; De Mey, M.; Lim, C. G.; Ajikumar, P. K.; Stephanopoulos, G., The future of metabolic engineering and synthetic biology: towards a systematic practice. *Metab Eng* 2012, 14 (3), 233-41.
10. Brophy, J. A.; Voigt, C. A., Principles of genetic circuit design. *Nat Methods* 2014, 11 (5), 508-20.
11. Koutinas, M.; Kiparissides, A.; Pistikopoulos, E. N.; Mantalaris, A., Bioprocess systems engineering: transferring traditional process engineering principles to industrial biotechnology. *Comput Struct Biotechnol J* 2012, 3, e201210022.
12. Rodrigo, G.; Jaramillo, A., AutoBioCAD: full biodesign automation of genetic circuits. *ACS Synth Biol* 2013, 2 (5), 230-6.
13. Garst, A. D.; Bassalo, M. C.; Pines, G.; Lynch, S. A.; Halweg-Edwards, A. L.; Liu, R.; Liang, L.; Wang, Z.; Zeitoun, R.; Alexander, W. G.; Gill, R. T., Genome-wide mapping of mutations at single-nucleotide resolution for protein, metabolic and genome engineering. *Nat Biotech* 2017, 35 (1), 48-55.
14. Church, G. M.; Elowitz, M. B.; Smolke, C. D.; Voigt, C. A.; Weiss, R., Realizing the potential of synthetic biology. *Nat Rev Mol Cell Biol* 2014, 15 (4), 289-94.
15. Thomas, S.; Maynard, N. D.; Gill, J., DNA library construction using Gibson Assembly[reg]. *Nat Meth* 2015, 12 (11).
16. Goodwin, S.; McPherson, J. D.; McCombie, W. R., Coming of age: ten years of next-generation sequencing technologies. *Nat Rev Genet* 2016, 17 (6), 333-51.
17. Lynch, M. D.; Warnecke, T.; Gill, R. T., SCALEs: multiscale analysis of library enrichment. *Nat Methods* 2007, 4 (1), 87-93.
18. Zeitoun, R. I.; Garst, A. D.; Degen, G. D.; Pines, G.; Mansell, T. J.; Glebes, T. Y.; Boyle, N. R.; Gill, R. T., Multiplexed tracking of combinatorial genomic mutations in engineered cell populations. *Nat Biotechnol* 2015, 33 (6), 631-7.
19. Crook, N.; Abatemarco, J.; Sun, J.; Wagner, J. M.; Schmitz, A.; Alper, H. S., In vivo continuous evolution of genes and pathways in yeast. *Nat Commun* 2016, 7, 13051.
20. Burg, J. M., Reed, BJ., Ye, Z., Cooper, C. B., Moreb, E. A., and Lynch, M. D, Large-Scale Bioprocess Competitiveness: The Potential of Dynamic Metabolic Control in Two-Stage Fermentations. *Current Opinions in Chemical Engineering* 2016, (In Review).
21. Zhang, Y. H., Production of biofuels and biochemicals by in vitro synthetic biosystems: Opportunities and challenges. *Biotechnol Adv* 2015, 33 (7), 1467-83.
22. Dietrich, J. A.; McKee, A. E.; Keasling, J. D., High-throughput metabolic engineering: advances in small-molecule screening and selection. *Annu Rev Biochem* 2010, 79, 563-90.
23. Formenti, L. R.; Norregaard, A.; Bolic, A.; Hernandez, D. Q.; Hagemann, T.; Heins, A. L.; Larsson, H.; Mears, L.; Mauricio-Iglesias, M.; Kruhne, U.; Gernaey, K. V., Challenges in industrial fermentation technology research. *Biotechnol J* 2014, 9 (6), 727-38.
24. Levanon, S. S.; San, K. Y.; Bennett, G. N., Effect of oxygen on the *Escherichia coli* ArcA and FNR regulation systems and metabolic responses. *Biotechnol Bioeng* 2005, 89 (5), 556-64.
25. Logue, J. B.; Findlay, S. E.; Comte, J., Editorial: Microbial Responses to Environmental Changes. *Front Microbiol* 2015, 6, 1364.
26. Garcia-Ochoa, F.; Gomez, E., Bioreactor scale-up and oxygen transfer rate in microbial processes: an overview. *Biotechnol Adv* 2009, 27 (2), 153-76.
27. Waegeman, H.; Beauprez, J.; Moens, H.; Maertens, J.; De Mey, M.; Foulquie-Moreno, M. R.; Heijnen, J. J.; Charlier, D.; Soetaert, W., Effect of iclR and arcA knockouts on biomass formation and metabolic fluxes in *Escherichia coli* K12 and its implications on understanding the metabolism of *Escherichia coli* BL21 (DE3). *BMC Microbiol* 2011, 11, 70.

28. Waegeman, H.; Maertens, J.; Beauprez, J.; De Mey, M.; Soetaert, W., Effect of iclR and arcA deletions on physiology and metabolic fluxes in *Escherichia coli* BL21 (DE3). *Biotechnol Lett* 2012, 34 (2), 329-37.
29. Hemmerich, J.; Adelantado, N.; Barrigon, J. M.; Ponte, X.; Hormann, A.; Ferrer, P.; Kensy, F.; Valero, F., Comprehensive clone screening and evaluation of fed-batch strategies in a microbioreactor and lab scale stirred tank bioreactor system: application on *Pichia pastoris* producing *Rhizopus oryzae* lipase. *Microb Cell Fact* 2014, 13 (1), 36.
30. Ramirez-Vargas, R.; Vital-Jacome, M.; Camacho-Perez, E.; Hubbard, L.; Thalasso, F., Characterization of oxygen transfer in a 24-well microbioreactor system and potential respirometric applications. *J Biotechnol* 2014, 186, 58-65.
31. Huber, R.; Roth, S.; Rahmen, N.; Buchs, J., Utilizing high-throughput experimentation to enhance specific productivity of an *E. coli* T7 expression system by phosphate limitation. *BMC biotechnology* 2011, 11, 22.
32. Lynch, M. D., Into new territory: improved microbial synthesis through engineering of the essential metabolic network. *Curr Opin Biotechnol* 2016, 38, 106-11.
33. McGinness, K. E.; Baker, T. A.; Sauer, R. T., Engineering controllable protein degradation. *Mol Cell* 2006, 22 (5), 701-7.
34. Luo, M. L.; Mullis, A. S.; Leenay, R. T.; Beisel, C. L., Repurposing endogenous type I CRISPR-Cas systems for programmable gene repression. *Nucleic acids research* 2015, 43 (1), 674-81.
35. Qi, L. S.; Larson, M. H.; Gilbert, L. A.; Doudna, J. A.; Weissman, J. S.; Arkin, A. P.; Lim, W. A., Repurposing CRISPR as an RNA-guided platform for sequence-specific control of gene expression. *Cell* 2013, 152 (5), 1173-83.
36. Chubukov, V.; Sauer, U., Environmental dependence of stationary-phase metabolism in *Bacillus subtilis* and *Escherichia coli*. *Applied and environmental microbiology* 2014, 80 (9), 2901-9.
37. Santos-Beneit, F., The Pho regulon: a huge regulatory network in bacteria. *Front Microbiol* 2015, 6, 402.
38. Brouns, S. J.; Jore, M. M.; Lundgren, M.; Westra, E. R.; Slijkhuis, R. J.; Snijders, A. P.; Dickman, M. J.; Makarova, K. S.; Koonin, E. V.; van der Oost, J., Small CRISPR RNAs guide antiviral defense in prokaryotes. *Science* 2008, 321 (5891), 960-4.
39. Jian, J.; Zhang, S. Q.; Shi, Z. Y.; Wang, W.; Chen, G. Q.; Wu, Q., Production of polyhydroxyalkanoates by *Escherichia coli* mutants with defected mixed acid fermentation pathways. *Appl Microbiol Biotechnol* 2010, 87 (6), 2247-56.
40. Grunenfelder, B.; Rummel, G.; Vohradsky, J.; Roder, D.; Langen, H.; Jenal, U., Proteomic analysis of the bacterial cell cycle. *Proc Natl Acad Sci USA* 2001, 98 (8), 4681-6.
41. Hintsche, M.; Klumpp, S., Dilution and the theoretical description of growth-rate dependent gene expression. *J Biol Eng* 2013, 7 (1), 22.
42. Lerchner, A.; Jarasch, A.; Skerra, A., Engineering of alanine dehydrogenase from *Bacillus subtilis* for novel cofactor specificity. *Biotechnol Appl Biochem* 2016, 63 (5), 616-624.
43. Hori, H.; Yoneyama, H.; Tobe, R.; Ando, T.; Isogai, E.; Katsumata, R., Inducible L-alanine exporter encoded by the novel gene ygaW (alaE) in *Escherichia coli*. *Applied and environmental microbiology* 2011, 77 (12), 4027-34.
44. Davis, J. H.; Rubin, A. J.; Sauer, R. T., Design, construction and characterization of a set of insulated bacterial promoters. *Nucleic acids research* 2011, 39 (3), 1131-41.
45. Hedl, M.; Sutherlin, A.; Wilding, E. I.; Mazzulla, M.; McDevitt, D.; Lane, P.; Burgner, J. W., 2nd; Lehnbeuter, K. R.; Stauffacher, C. V.; Gwynn, M. N.; Rodwell, V. W., *Enterococcus faecalis* acetoacetyl-coenzyme A thiolase/3-hydroxy-3-methylglutaryl-coenzyme A reductase, a dual-function protein of isopentenyl diphosphate biosynthesis. *J Bacteriol* 2002, 184 (8), 2116-22.
46. Steussy, C. N.; Robison, A. D.; Tetrick, A. M.; Knight, J. T.; Rodwell, V. W.; Stauffacher, C. V.; Sutherlin, A. L., A structural limitation on enzyme activity: the case of HMG-CoA synthase. *Biochemistry* 2006, 45 (48), 14407-14.
47. Xiong, M.; Schneiderman, D. K.; Bates, F. S.; Hillmyer, M. A.; Zhang, K., Scalable production of mechanically tunable block polymers from sugar. *Proc Natl Acad Sci USA* 2014, 111 (23), 8357-62.
48. Otterstedt, K.; Larsson, C.; Bill, R. M.; Stahlberg, A.; Boles, E.; Hohmann, S.; Gustafsson, L., Switching the mode of metabolism in the yeast *Saccharomyces cerevisiae*. *EMBO Rep* 2004, 5 (5), 532-7.
49. Hubmann, G.; Guillouet, S.; Nevoigt, E., Gpd1 and Gpd2 fine-tuning for sustainable reduction of glycerol formation in *Saccharomyces cerevisiae*. *Applied and environmental microbiology* 2011, 77 (17), 5857-67.
50. Lascaris, R.; Bussemaker, H. J.; Boorsma, A.; Piper, M.; van der Spek, H.; Grivell, L.; Blom, J., Hap4p overexpression in glucose-grown *Saccharomyces cerevisiae* induces cells to enter a novel metabolic state. *Genome Biol* 2003, 4 (1), R3.
51. Mittal, N.; Babu, M. M.; Roy, N., The efficiency of mitochondrial electron transport chain is increased in the long-lived mrg19 *Saccharomyces cerevisiae*. *Aging Cell* 2009, 8 (6), 643-53.
52. Thomas, M. R.; O'Shea, E. K., An intracellular phosphate buffer filters transient fluctuations in extracellular phosphate levels. *Proc Natl Acad Sci USA* 2005, 102 (27), 9565-70.
53. Gray, J. V.; Petsko, G. A.; Johnston, G. C.; Ringe, D.; Singer, R. A.; Werner-Washburne, M., "Sleeping beauty": quiescence in *Saccharomyces cerevisiae*. *Microbiol Mol Biol Rev* 2004, 68 (2), 187-206.
54. Grilly, C.; Stricker, J.; Pang, W. L.; Bennett, M. R.; Hasty, J., A synthetic gene network for tuning protein degradation in *Saccharomyces cerevisiae*. *Mol Syst Biol* 2007, 3, 127.
55. Orth, J. D.; Thiele, I.; Palsson, B. O., What is flux balance analysis? *Nat Biotechnol* 2010, 28 (3), 245-8.
56. Yim, H.; Haselbeck, R.; Niu, W.; Pujol-Baxley, C.; Burgard, A.; Boldt, J.; Khandurina, J.; Trawick, J. D.; Osterhout, R. E.; Stephen, R.; Estadilla, J.; Teisan, S.; Schreyer, H. B.; Andrae, S.; Yang, T. H.; Lee, S. Y.; Burk, M. J.; Van Dien, S., Metabolic engineering of *Escherichia coli* for direct production of 1,4-butanediol. *Nat Chem Biol* 2011, 7 (7), 445-52.
57. Gupta, A.; Reizman, I. M.; Reisch, C. R.; Prather, K. L., Dynamic regulation of metabolic flux in engineered bacteria using a pathway-independent quorum-sensing circuit. *Nature biotechnology* 2017, 35 (3), 273-279.
58. Wang, J.; Yu, H. Q., Biosynthesis of polyhydroxybutyrate (PHB) and extracellular polymeric substances (EPS) by *Ralstonia eutropha* ATCC 17699 in batch cultures. *Appl Microbiol Biotechnol* 2007, 75 (4), 871-8.

59. Xu, P.; Qiao, K.; Ahn, W. S.; Stephanopoulos, G., Engineering *Yarrowia lipolytica* as a platform for synthesis of drop-in transportation fuels and oleochemicals. *Proc Natl Acad Sci U S A* 2016, 113 (39), 10848-53.
60. Lynch, M. D.; Warnecke, T.; Gill, R. T. Method for Producing 3-Hydroxypropionic Acid and Other Products. Sep. 8, 2011.
61. Qiao, K.; Wasylenko, T. M.; Zhou, K.; Xu, P.; Stephanopoulos, G., Lipid production in *Yarrowia lipolytica* is maximized by engineering cytosolic redox metabolism. *Nat Biotechnol* 2017.
62. Jian, J.; Zhang, S. Q.; Shi, Z. Y.; Wang, W.; Chen, G. Q.; Wu, Q., Production of polyhydroxyalkanoates by *Escherichia coli* mutants with defected mixed acid fermentation pathways. *Appl Microbiol Biotechnol* 2010, 87 (6), 2247-56.
63. Sharan, S. K.; Thomason, L. C.; Kuznetsov, S. G.; Court, D. L., Recombineering: a homologous recombination-based method of genetic engineering. *Nature protocols* 2009, 4 (2), 206-23.
64. Li, X. T.; Thomason, L. C.; Sawitzke, J. A.; Costantino, N.; Court, D. L., Positive and negative selection using the tetA-sacB cassette: recombineering and P1 transduction in *Escherichia coli*. *Nucleic acids research* 2013, 41 (22), e204.
65. Baba, T.; Ara, T.; Hasegawa, M.; Takai, Y.; Okumura, Y.; Baba, M.; Datsenko, K. A.; Tomita, M.; Wanner, B. L.; Mori, H., Construction of *Escherichia coli* K-12 in-frame, single-gene knockout mutants: the Keio collection. *Molecular systems biology* 2006, 2, 2006 0008.
66. van Dijken, J. P.; Bauer, J.; Brambilla, L.; Duboc, P.; Francois, J. M.; Gancedo, C.; Giuseppin, M. L. F.; Heijnen, J. J.; Hoare, M.; Lange, H. C.; Madden, E. A.; Niederberger, P.; Nielsen, J.; Parrou, J. L.; Petit, T.; Porro, D.; Reuss, M.; van Riel, N.; Rizzi, M.; Steensma, H. Y.; Verrips, C. T.; Vindelov, J.; Pronk, J. T., An interlaboratory comparison of physiological and genetic properties of four *Saccharomyces cerevisiae* strains. *Enzyme and Microbial Technology* 2000, 26 (9-10), 706-714.
67. Otterstedt, K.; Larsson, C.; Bill, R. M.; Stahlberg, A.; Boles, E.; Hohmann, S.; Gustafsson, L., Switching the mode of metabolism in the yeast *Saccharomyces cerevisiae*. *EMBO Rep* 2004, 5 (5), 532-7.
68. Wieczorke, R.; Krampe, S.; Weierstall, T.; Freidel, K.; Hollenberg, C. P.; Boles, E., Concurrent knock-out of at least 20 transporter genes is required to block uptake of hexoses in *Saccharomyces cerevisiae*. *FEBS Letters* 1999, 464 (3), 123-128.
69. Gietz, R. D.; Schiestl, R. H., High-efficiency yeast transformation using the LiAc/SS carrier DNA/PEG method. *Nature protocols* 2007, 2 (1), 31-4.
70. Stovicek, V.; Borodina, I.; Forster, J., CRISPR-Cas system enables fast and simple genome editing of industrial *Saccharomyces cerevisiae* strains. *Metabolic Engineering Communications* 2015, 2, 13-22.
71. Labun, K.; Montague, T. G.; Gagnon, J. A.; Thyme, S. B.; Valen, E., CHOPCHOP v2: a web tool for the next generation of CRISPR genome engineering. *Nucleic acids research* 2016, 44 (W1), W272-6.
72. Hoffman, C. S.; Winston, F., A ten-minute DNA preparation from yeast efficiently releases autonomous plasmids for transformation of *Escherichia coli*. *Gene* 1987, 57 (2-3), 267-272.
73. Luo, M. L.; Mullis, A. S.; Leenay, R. T.; Beisel, C. L., Repurposing endogenous type I CRISPR-Cas systems for programmable gene repression. *Nucleic acids research* 2015, 43 (1), 674-81.
74. Davis, J. H.; Rubin, A. J.; Sauer, R. T., Design, construction and characterization of a set of insulated bacterial promoters. *Nucleic acids research* 2011, 39 (3), 1131-41.
75. Smith, J. D.; Suresh, S.; Schlecht, U.; Wu, M.; Wagih, O.; Peltz, G.; Davis, R. W.; Steinmetz, L. M.; Parts, L.; St Onge, R. P., Quantitative CRISPR interference screens in yeast identify chemical-genetic interactions and new rules for guide RNA design. *Genome Biol* 2016, 17, 45.
76. Gilbert, L. A.; Larson, M. H.; Morsut, L.; Liu, Z.; Brar, G. A.; Torres, S. E.; Stem-Ginossar, N.; Brandman, O.; Whitehead, E. H.; Doudna, J. A.; Lim, W. A.; Weissman, J. S.; Qi, L. S., CRISPR-mediated modular RNA-guided regulation of transcription in eukaryotes. *Cell* 2013, 154 (2), 442-51.
77. Sikorski, R. S.; Hieter, P., A system of shuttle vectors and yeast host strains designed for efficient manipulation of DNA in *Saccharomyces cerevisiae*. *Genetics* 1989, 122 (1), 19-27.
78. Duetz, W. A.; Ruedi, L.; Hermann, R.; O'Connor, K.; Buchs, J.; Witholt, B., Methods for intense aeration, growth, storage, and replication of bacterial strains in microtiter plates. *Applied and environmental microbiology* 2000, 66 (6), 2641-6.
79. Duetz, W. A.; Witholt, B., Effectiveness of orbital shaking for the aeration of suspended bacterial cultures in square-deepwell microtiter plates. *Biochem Eng J* 2001, 7 (2), 113-115.
80. Lindemann, C. J.; Singh, M. M.; Ramjit, H. G.; Bell, C.; Ip, D. P., Determination of mevalonolactone in capsules by capillary gas-liquid chromatography. *J Pharm Biomed Anal* 1991, 9 (4), 311-6.
81. Keseler, I. M.; Mackie, A.; Peralta-Gil, M.; Santos-Zavaleta, A.; Gama-Castro, S.; Bonavides-Martinez, C.; Fulcher, C.; Huerta, A. M.; Kothari, A.; Krummenacker, M.; Latendresse, M.; Muniz-Rascado, L.; Ong, Q.; Paley, S.; Schroder, I.; Shearer, A. G.; Subhraveti, P.; Travers, M.; Weerasinghe, D.; Weiss, V.; Collado-Vides, J.; Gunsalus, R. P.; Paulsen, I.; Karp, P. D., EcoCyc: fusing model organism databases with systems biology. *Nucleic acids research* 2013, 41 (Database issue), D605-12.
82. Davis, J. H.; Rubin, A. J.; Sauer, R. T., Design, construction and characterization of a set of insulated bacterial promoters. *Nucleic acids research* 2011, 39 (3), 1131-41.
83. Poo, H.; Song, J. J.; Hong, S.-P.; Choi, Y.-H.; Yun, S. W.; Kim, J.-H.; Lee, S. C.; Lee, S.-G.; Sung, M. H., Novel high-level constitutive expression system, pHCE vector, for a convenient and cost-effective soluble production of human tumor necrosis factor-α. *Biotechnology Letters* 2002, 24 (14), 1185-1189.
84. Baba, T.; Ara, T.; Hasegawa, M.; Takai, Y.; Okumura, Y.; Baba, M.; Datsenko, K. A.; Tomita, M.; Wanner, B. L.; Mori, H., Construction of *Escherichia coli* K-12 in-frame, single-gene knockout mutants: the Keio collection. *Mol Syst Biol* 2006, 2, 2006 0008.
85. Jian, J.; Zhang, S. Q.; Shi, Z. Y.; Wang, W.; Chen, G. Q.; Wu, Q., Production of polyhydroxyalkanoates by *Escherichia coli* mutants with defected mixed acid fermentation pathways. *Appl Microbiol Biotechnol* 2010, 87 (6), 2247-56.
86. van Dijken, J. P.; Bauer, J.; Brambilla, L.; Duboc, P.; Francois, J. M.; Gancedo, C.; Giuseppin, M. L. F.; Heijnen, J. J.; Hoare, M.; Lange, H. C.; Madden, E. A.; Niederberger, P.; Nielsen, J.; Parrou, J. L.; Petit, T.; Porro, D.; Reuss, M.; van Riel, N.; Rizzi, M.; Steensma, H. Y.; Verrips, C. T.; Vindelov, J.; Pronk, J. T., An interlaboratory comparison of physiological and genetic properties of four *Saccharomyces cerevisiae* strains. *Enzyme and Microbial Technology* 2000, 26 (9-10), 706-714.
87. Otterstedt, K.; Larsson, C.; Bill, R. M.; Stahlberg, A.; Boles, E.; Hohmann, S.; Gustafsson, L., Switching the mode of metabolism in the yeast *Saccharomyces cerevisiae*. *EMBO Rep* 2004, 5 (5), 532-7.
88. Luo, M. L.; Mullis, A. S.; Leenay, R. T.; Beisel, C. L., Repurposing endogenous type I CRISPR-Cas systems for programmable gene repression. *Nucleic acids research* 2015, 43 (1), 674-81.
89. Wilde, R. J.; Guest, J. R., Transcript analysis of the citrate synthase and succinate dehydrogenase genes of *Escherichia coli* K12. *J Gen Microbiol* 1986, 132 (12), 3239-51.
90. Charpentier, B.; Branlant, C., The *Escherichia coli* gapA gene is transcribed by the vegetative RNA polymerase holoenzyme E sigma 70 and by the heat shock RNA polymerase E sigma 32. *Journal of Bacteriology* 1994, 176 (3), 830-839.
91. Li, X. T.; Thomason, L. C.; Sawitzke, J. A.; Costantino, N.; Court, D. L., Positive and negative selection using the tetA-sacB cassette: recombineering and P1 transduction in *Escherichia coli*. *Nucleic acids research* 2013, 41 (22), e204.
92. Duetz, W. A.; Ruedi, L.; Hermann, R.; O'Connor, K.; Buchs, J.; Witholt, B., Methods for intense aeration, growth, storage, and replication of bacterial strains in microtiter plates. *Applied and environmental microbiology* 2000, 66 (6), 2641-6.
93. Duetz, W. A.; Witholt, B., Effectiveness of orbital shaking for the aeration of suspended bacterial cultures in square-deepwell microtiter plates. *Biochem Eng J* 2001, 7 (2), 113-115.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A multi-stage fermentation bioprocess for producing mevalonate from a genetically modified *E. coli*, comprising:
   providing a genetically modified *E. coli* for producing mevalonate;
   growing the genetically modified *E. coli* in a media in a growth phase, the genetically modified *E. coli* comprising:
   i. a production pathway comprising at least one production enzyme for biosynthesis of mevalonate; and
   ii. one or more synthetic metabolic valves for reducing or eliminating flux through multiple metabolic pathways within the genetically modified *E. coli* when the synthetic metabolic valves are induced, the one or more synthetic metabolic valves comprising:
      a) at least one silencing synthetic metabolic valve that silences gene expression of two gene encoding two silenceable enzymes that are selected from fabI, gltA, ldp, zwf, or udhA gene, and
      b) at least one proteolytic synthetic metabolic valve that controls proteolysis of a fabI, gltA, ldp, zwf, or udhA enzyme;
   transitioning to a productive stationary phase, the transition comprising:
   depletion of a limiting nutrient
      inducing the one or more synthetic metabolic valves; and
      activation of the production enzyme for biosynthesis of mevalonate, and producing mevalonate.

2. The multi-stage fermentation bioprocess of claim 1, wherein the enzyme of the mevalonate production pathway is heterologous to the genetically modified *E. coli* and the heterologous enzyme is one of: an acetyl-CoA acetyltransferase, NADPH dependent HMG-CoA reductase, HMG-CoA synthase or a combination thereof.

3. The multi-stage fermentation bioprocess of claim 1, wherein the heterologous enzyme of mevalonate production is encoded by: *E. faecalis* mvaE, *E. faecalis* mvaS, *E. faecalis* mvaS(A110G), or a combination thereof.

4. The multi-stage fermentation bioprocess of claim 1, wherein the synthetic metabolic valve comprises controlled proteolysis of fabI or udhA.

5. The multi-stage fermentation bioprocess of claim 1, wherein the enzymes silenced by the silencing metabolic valve are fabI, gltA1 and gltA2 and the enzymes that are subject to enzyme degradation by the proteolytic metabolic valve are fab I, gltA, and udhA.

6. The multi-stage fermentation bioprocess of claim 1 wherein at least one silencing synthetic metabolic valve is characterized by CRISPR interference of gene expression of a gene that is a fabI, gltA, ldp, zwf, or udhA gene and expression of a CASCADE plasmid comprising an array of guide RNA genes.

7. The multi-stage fermentation bioprocess of claim 1, wherein at least one proteolytic synthetic metabolic valve is characterized by expression of the proteolytic enzyme operably linked to a or C-terminal DAS4 peptide tag and controlled proteolysis of a fabI, gltA, ldp, zwf, or udhA enzyme by the synthetic metabolic valve is selective for the tag by clpXP protease upon induction of sspB chaperone protein.

8. The multi-stage fermentation bioprocess of claim 1, wherein the genetically modified *E. coli* comprises a chromosomal gene deletion of: lactate dehydrogenase (ldhA), phosphate acetyltransferase (pta), pyruvate oxidase (poxB), pyruvateformate lyase (pflB), methylglyoxal synthase (mgsA), acetate kinase (ackA), alcohol dehydrogenase (adhE), a clpXP protease specificity enhancing factor (sspB), an ATPdependent Lon protease (Lon), an outer membrane protease (ompT), an arcA transcriptional dual regulator (arcA), or an iclR transcriptional regulator (iclR).

9. The multi-stage fermentation bioprocess of claim 1, wherein the genetically modified *E. coli* is characterized by overexpression of a gene resulting in an increase of a NADPH and/or NAD pool in the genetically modified *E. coli* during the growth phase.

10. The multi-stage fermentation bioprocess of claim 1, wherein transitioning to the productive stationary phase is further modulated by at least one of an artificial chemical inducer including tetracycline, anhydrotetracycline, lactose, isopropyl-beta-D1-thiogalactopyranoside (IPTG), arabinose, raffinose, and tryptophan or depletion of a limiting nutrient from the *E. coli* culture media.

11. The multi-stage fermentation bioprocess of claim 1, further comprising altering an environmental factor of the culture media or culture conditions effective to enhance product production, the environmental factor selected from the group consisting of: temperature of the culture media or culture conditions, pH of the culture media, nutrients of the culture media, oxygenation of the culture media, sugar concentration of the culture media, and combinations thereof.

12. The multi-stage fermentation bioprocess of claim 1, wherein transitioning to the step of entering a productive stationary phase further comprises inducing expression of the enzyme of the production pathway.

13. The multi-stage fermentation bioprocess of claim 1, wherein the genetically modified *E. coli* produces at least 0.5 grams of mevalonate per liter per hour.

14. A genetically modified *E. coli*, comprising:
   i. a production pathway comprising at least one production enzyme for biosynthesis of mevalonate, and a glycosyltransferase enzyme; and
   ii. one or more synthetic metabolic valves for reducing or eliminating flux through multiple metabolic pathways within the genetically modified *E. coli* when the one or more synthetic metabolic valves are induced, the one or more synthetic metabolic valves comprising:
      a) at least one silencing synthetic metabolic valve that silences gene expression of a two genes encoding two or more of the enzymes: fabI, gltA1 or gltA2, and
      b) at least one proteolytic synthetic metabolic valve that controls proteolysis of one or more of the proteolyzable enzymes: fabI, gltA, or udhA;
   wherein the *E. coli* produces mevalonate in a biofermentation process comprising: growing the genetically modified *E. coli* in a media in a growth phase, transitioning to a productive stationary phase, the transition comprising: depletion of a limiting nutrient: inducing the one or more synthetic metabolic valves; and activation of the production enzyme for biosynthesis of mevalonate, and the glycosyltransferase enzyme.

15. The genetically modified *E. coli* of claim 14, wherein the enzyme of the mevalonate production pathway is heterologous to the genetically modified *E. coli* and is selected from the group consisting of: *E. faecalis* mvaE, *E. faecalis* mvaS, *E. faecalis* mvaS(A110G), or a combination thereof.

16. The genetically modified *E. coli* of claim 14, wherein the proteolytic synthetic metabolic valve controls proteolysis of fabI or udhA.

* * * * *